United States Patent
Liebeschuetz et al.

(10) Patent No.: US 6,855,715 B1
(45) Date of Patent: Feb. 15, 2005

(54) SERINE PROTEASE INHIBITORS

(75) Inventors: John Walter Liebeschuetz, Macclesfield (GB); Amanda Jane Lyons, Macclesfield (GB); Christopher William Murray, Swavesey (GB); Andrew David Rimmer, Chorley (GB); Stephen Clinton Young, Heaton-Moor (GB); Nicholas Paul Camp, Bracknell (GB); Stuart Donald Jones, Macclesfield (GB); Phillip John Morgan, Congleton (GB); Simon James Richards, Bracknell (GB); William Alexander Wylie, Carrickfergus (GB); John Joseph Masters, Fishers, IN (US); Michael Robert Wiley, Indianapolis, IN (US)

(73) Assignee: Eli Lilly and Company, Indianapolis, IN (US)

( * ) Notice: Subject to any disclaimer, the term of this patent is extended or adjusted under 35 U.S.C. 154(b) by 218 days.

(21) Appl. No.: 09/926,712

(22) PCT Filed: Jun. 13, 2000

(86) PCT No.: PCT/GB00/02302

§ 371 (c)(1),
(2), (4) Date: Dec. 6, 2001

(87) PCT Pub. No.: WO00/76971

PCT Pub. Date: Dec. 21, 2000

Related U.S. Application Data

(60) Provisional application No. 60/142,064, filed on Jul. 2, 1999.

(30) Foreign Application Priority Data

Jun. 14, 1999 (GB) .............................................. 9913823
Aug. 9, 1999 (GB) .............................................. 9918741
Dec. 14, 1999 (GB) .............................................. 9929553

(51) Int. Cl.[7] ..................... A61K 31/495; C07D 241/04
(52) U.S. Cl. ..................... 514/255; 544/391; 544/372; 544/360; 514/252
(58) Field of Search ............................... 514/255, 252; 544/391, 372, 360

(56) References Cited

U.S. PATENT DOCUMENTS 5,182,284 A * 1/1993 Suzuki et al. ................. 514/80
5,346,907 A    9/1994 Kerwin et al.
5,518,735 A    5/1996 Sturzebecher et al.
5,583,146 A   12/1996 Kimball et al.
6,140,351 A   10/2000 Arnaiz et al.
6,339,087 B1 * 1/2002 Gong et al. ............ 514/252.12
6,545,055 B1   4/2003 Zhu et al.

FOREIGN PATENT DOCUMENTS

| | | |
|---|---|---|
| EP | 441226 A2 | 8/1991 |
| EP | 564924 A2 | 10/1993 |
| EP | 617032 A1 | 9/1994 |
| EP | 623596 A1 | 11/1994 |
| EP | 648780 A1 | 4/1995 |
| EP | 686642 A2 | 12/1995 |
| EP | 796866 A1 | 9/1997 |
| WO | WO 91/00725 | 1/1991 |
| WO | WO 96/12499 | 5/1996 |
| WO | WO 97/19927 | 6/1997 |
| WO | WO 97/23212 | 7/1997 |
| WO | WO97/24118 | 7/1997 |
| WO | WO 97/49404 | 12/1997 |
| WO | WO 98/47676 | 10/1998 |
| WO | WO 98/57951 | 12/1998 |
| WO | WO99/00121 | 1/1999 |
| WO | WO99/00127 | 1/1999 |
| WO | WO99/00128 | 1/1999 |
| WO | WO 99/11657 | 3/1999 |
| WO | WO 99/11658 | 3/1999 |
| WO | WO 99/25686 | 6/1999 |
| WO | WO 99/32477 | 7/1999 |
| WO | WO00/39092 | 7/2000 |
| WO | WO 00/39111 | 7/2000 |
| WO | WO 00/39117 | 7/2000 |
| WO | WO 00/39118 | 7/2000 |
| WO | WO 00/71493 | 11/2000 |
| WO | WO 00/71507 | 11/2000 |
| WO | WO 00/71508 | 11/2000 |
| WO | WO 01/05784 | 1/2001 |

* cited by examiner

Primary Examiner—Charanjit S. Aulakh
(74) Attorney, Agent, or Firm—Martin A. Hay

(57) ABSTRACT

Compounds of formula (I)

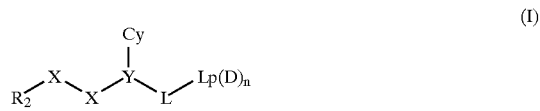

where $R_2$, each X, L, Y, Cy, Lp, D and n are as defined in the specification, are serine protease inhibitors useful as antithrombotic agents.

13 Claims, No Drawings

SERINE PROTEASE INHIBITORS

This application claims the benefit of provisional application No. 60/142,064 filed Jul. 2, 1999.

This invention relates to compounds which are inhibitors of serine proteases and to pharmaceutical compositions thereof and their use in the treatment of the human or animal body.

The serine proteases are a group of proteolytic enzymes which have a common catalytic mechanism characterized by a particularly reactive Ser residue. Examples of serine proteases include trypsin, tryptase, chymotrypsin, elastase, thrombin, plasmin, kallikrein, Complement Cl, acrosomal protease, lysosomal protease, cocoonase, α-lytic protease, protease A, protease B, serine carboxypeptidase II, subtilisin, urokinase, Factor VIIa, Factor IXa, and Factor Xa. The serine proteases have been investigated extensively over a period of several decades and the therapeutic value of inhibitors of serine proteases is well understood.

Serine protease inhibitors play a central role in the regulation of a wide variety of physiological process including coagulation, fibrinolysis, fertilization, development, malignancy, neuromuscular patterning and inflammation. It is well known that these compounds inhibit a variety of circulating proteases as well as proteases that are activated or released in tissue. It is also becoming clear that serine protease inhibitors inhibit critical cellular processes, such as adhesion, migration, free radical production and apoptosis. In addition, animal experiments indicate that intravenously administered serine protease inhibitors, variants or cells expressing serine protease inhibitors, provide a protective effect against tissue damage.

Serine protease inhibitors have also been predicted to have potential beneficial uses in the treatment of disease in a wide variety of clinical areas such as oncology, neurology, haematology, pulmonary medicine, immunology, inflammation and infectious disease.

In particular serine protease inhibitors may be beneficial in the treatment of thrombotic diseases, asthma, emphysema, cirrhosis, arthritis, carcinoma, melanoma, restenosis, atheroma, trauma, shock and reperfusion injury.

Thus for example an inhibitor of Factor Xa has value as a therapeutic agent as an anticoagulant, e.g. in the treatment and prevention of thrombotic disorders. The use of a Factor Xa inhibitor as an anticoagulant is desirable in view of the selectivity of its effect. Many-clinically approved anticoagulants have been associated with adverse events owing to the non-specific nature of their effects on the coagulation cascade.

Also, there are well-known associations of al protease inhibitor deficiency with emphysema and cirrhosis and Cl esterase inhibitor deficiency with angioedema.

It has now been found that certain aromatic compounds carrying bulky lipophilic side chains are particularly effective as inhibitors of serine proteases, especially proteases with negatively charged P1 specificity pockets, and most especially the serine proteases thrombin, and most importantly Factor Xa. The Factor Xa inhibitors of this invention are potentially useful for the prophylaxis or treatment of thrombotic disorders such as amongst others venous thrombosis, pulmonary embolism, arterial thrombosis, myocardial ischaemia, myocardial infarction, and cerebral thrombosis. They potentially have benefit in the treatment of acute vessel closure associated with thrombolytic therapy and restenosis, e.g. after transluminal coronary angioplasty or bypass grafting of the coronary or peripheral arteries and in the maintenance of vascular access patency in long term hemodialysis patients.

Factor Xa inhibitors of this invention may, with benefit, form part of a combination therapy with an anticoagulant with a different mode of action or with a thrombolytic agent.

Hence, the invention also comprises certain compounds which have been found to be inhibitors of both Factor Xa and thrombin. These compounds have excellent potential therapeutic value and may synergistically boost Fxa antithrombotic effect.

It has been reported in WO99/11658 and WO99/11657 that certain benzamidine and aminoisoquinoline derivatives carrying a bulky lipophilic side chain are excellent inhibitors of serine proteases. Unfortunately, it has since been found that benzamidine compounds of WO 99/11658 in general demonstrate poor oral bioavailability.

Surprisingly, it has now been found that certain other aromatic compounds also show inhibitory activity against serine proteases, in particular Factor Xa, despite the lack of the amidino or 1-aminoisoquinoline functionality previously believed to be crucial for activity as a factor Xa inhibitor. Many of these compounds also possess other structural features that further distinguish them from the compounds of WO99/11658 and WO99/11657.

Where compounds of the invention have been tested, they have generally demonstrated superior oral bioavailability in comparison with benzamidines disclosed in WO 99/11658. Also, it has been found that the compounds of the invention perform excellently in the prothrombin time assay (PT) when compared to aminoisoquinolines of similar factor Xa activity and structure. The PT assay is a coagulation assay and it is widely accepted that direct acting Factor Xa inhibitors which perform well in the PT assay are more likely to be good antithrombotics.

In WO99/09053 certain 2-aminobenzamide compounds are disclosed as potential motilin receptor antagonists and in U.S. Pat. No. 3,268,513 similar 2-aminobenzamide compounds are suggested as potential antibacterial agents. However, the novel compounds of the present invention have not before been suggested as potential serine protease inhibitors.

Thus viewed from an one aspect the invention provides a serine protease inhibitor compound of formula (I)

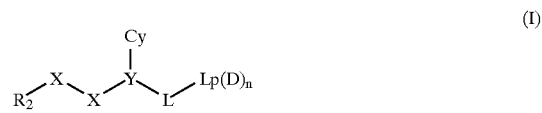

(I)

where $R_2$ represents a 5 or 6 membered aromatic carbon ring optionally interrupted by a nitrogen, oxygen or sulphur ring atom, optionally being substituted in the 3 and/or 4 position (in relation to the point of attachment of X—X) by halo, nitro, thiol, haloalkoxy, hydrazido, alkylhydrazido, amino, cyano, haloalkyl, alkylthio, alkenyl, alkynyl, acylamino, tri or difluoromethoxy, carboxy, acyloxy, MeSO$_2$— or $R_1$, or the substituents at the 3 and 4 positions taken together form a fused ring which is a 5 or 6 membered carbocyclic or heterocyclic ring optionally substituted by halo, haloalkoxy, haloalkyl, cyano, nitro, amino, hydrazido, alkylthio, alkenyl, alkynyl or $R_{1j}$, and optionally substituted in the position alpha to the X—X group (i.e. 6 position for a six membered aromatic ring etc) by amino, hydroxy, halo, alkyl, carboxy, alkoxycarbonyl, cyano, amido, aminoalkyl, alkoxy or alkylthio with the proviso that $R_2$ cannot be aminoisoquinolyl;

each X independently is a C, N, O or S atom or a CO, $CR_{1a}$, $C(R_{1a})_2$ or $NR_{1a}$ group, at least one X being C, CO, $CR_{1a}$ or $C(R_{1a})_2$;

each $R_{1a}$ independently represents hydrogen or hydroxyl, alkoxy, alkyl, aminoalkyl, hydroxyalkyl alkoxyalkyl, alkoxycarbonyl, alkylaminocarbonyl, alkoxycarbonylamino, acyloxymethoxycarbonyl or alkylamino optionally substituted by hydroxy, alkylamino, alkoxy, oxo, aryl or cycloalkyl;

$R_1$ is as defined for $R_{1a}$, provided that $R_1$ is not unsubstituted aminoalkyl;

L is an organic linker group containing 1 to 5 backbone atoms selected from C, N, O and S, or a branched alkyl or cyclic group;

Y (the α-atom) is a nitrogen atom or a $CR_{1b}$ group;

Cy is a saturated or unsaturated, mono or poly cyclic, homo or heterocyclic group, preferably containing 5 to 10 ring atoms and optionally substituted by groups $R_{3a}$ or phenyl optionally substituted by $R_{3a}$;

each $R_{3a}$ independently is $R_{1c}$, amino, halo, cyano, nitro, thiol, alkylthio, alkylsulphonyl, alkylsulphenyl, triazolyl, imidazolyl, tetrazolyl, hydrazido, alkyl imidazolyl, thiazolyl, alkyl thiazolyl, alkyl oxazolyl, oxazolyl, alkylsulphonamido, alkylaminosulphonyl, aminosulphonyl, haloalkoxy and haloalkyl;

Lp is a lipophilic organic group;

D is a hydrogen bond donor group; and n is 0, 1 or 2; and $R_{1b}$, $R_{1c}$ and $R_{1f}$ are as defined for $R_{1a}$, or a physiologically tolerable salt thereof, e.g. a halide, phosphate or sulphate salt or a salt with ammonium or an organic amine such as ethylamine or meglumine.

Compounds of formula I as defined above, but in which $R_1$ is an unsubstituted aminoalkyl group are claimed in a co-pending application.

In the compounds of the invention, where the alpha atom is carbon it preferably has the conformation that would result from construction from a D-α-aminoacid $NH_2$—$CR_{1b}$(Cy)-COOH where the $NH_2$ represents part of X—X. Likewise the fourth substituent $R_{1b}$ at an alpha carbon is preferably a methyl or hydroxymethyl group or hydrogen.

In the compounds of the invention, unless otherwise indicated, aryl groups preferably contain 5 to 10 ring atoms optionally including 1, 2 or 3 heteroatoms selected from O, N and S; alkyl, alkenyl or alkynyl groups or alkylene moieties preferably contain up to 6 carbons, e.g. $C_{1-6}$ or $C_{1-3}$; cyclic groups preferably have ring sizes of 3 to 8 atoms; and fused multicyclic groups preferably contain 8 to 16 ring atoms.

Examples of particular values for $R_{1a}$ are: hydrogen, methyl or ethyl. $R_{1a}$ is preferably a hydrogen atom.

The linker group from the $R_2$ group to the alpha atom is preferably selected from —CH=CH—, —CONH—, —CONR$_{1a}$—, —NH—CO—, —NH—CH$_2$—, —CH$_2$—NH—, —CH$_2$O—, —OCH$_2$—, —COO—, —OC=O— and —CH$_2$CH$_2$—. Preferably, the X moiety nearest to the alpha atom is an NH or O atom, most preferably a NH group. The X moiety alpha to the aromatic ring is preferably a carbon based group such as CH$_2$ or CO, preferably CO. Thus a particularly preferred linker X—X is —CONH—. In an alternative embodiment the linker is preferably a —OCH$_2$— group.

Examples of particular values for $R_{1b}$ are: hydrogen, (1–4C)alkyl, such as methyl or hydroxy(1–4C)alkyl, such as hydroxymethyl. $R_{1b}$ is preferably a hydrogen atom.

The alpha atom (Y) is preferably a CH or C(CH$_3$) group, especially CH.

The linker group from the alpha atom to the lipophilic group is preferably CO, CH$_2$NH, CONR$_{1d}$(CH$_2$)$_m$, (CH$_2$)$_m$N(R$_{1d}$)CO(CH$_2$)$_m$, (CH$_2$)$_{m+2}$, CO(CH$_2$)$_m$, (CH$_2$)$_m$CO, (CH$_2$)$_m$OC=O, (CH$_2$)$_m$O, CH=CH(CH$_2$)$_m$, SO$_2$, SO$_2$NR$_{1d}$, SO$_2$(CH$_2$)$_m$, (CH$_2$)$_m$SO$_2$ or (CH$_2$)$_m$SO$_2$NR$_{1d}$ (where each m is independently 0 or 1 and $R_{1d}$ is as defined for $R_{1a}$).

Examples of particular values for $R_{1d}$ are: hydrogen; for alkyl optionally substituted by hydroxy, alkylamino, alkoxy, oxo, aryl or cycloalkyl: (1–6C)alkyl, such as methyl or ethyl, or aryl(1–6C)alkyl, such as benzyl or phenylethyl; for aminoalkyl optionally substituted by hydroxy, alkylamino, alkoxy, oxo, aryl or cycloalkyl: (2–6C)carboxamido, such as carboxamidomethyl; for hydroxyalkyl optionally substituted by hydroxy, alkylamino, alkoxy, oxo, aryl or cycloalkyl: (1–6C)carboxyalkyl, such as carboxymethyl, carboxyethyl or carboxypropyl;

for alkoxyalkyl optionally substituted by hydroxy, alkylamino, alkoxy, oxo, aryl or cycloalkyl: (1–5C) alkoxycarbonyl(1–6C)alkyl, such as methoxycarbonylmethyl, methoxycarbonylethyl, methoxycarbonylpropyl, ethoxycarbonylmethyl, ethoxycarbonylethyl and ethoxycarbonylpropyl.

$R_{1d}$ is preferably a hydrogen atom.

The linker may be optionally branched, for example, to incorporate a polar functionality.

Examples of particular values for L are CO, CONH, CH$_2$NHCO and CONHCH$_2$.

It will be appreciated by those skilled in the art that a diverse range of organic groups are lipophilic, and that it is therefore impractical to define with precision each and every structure that may be incorporated into a serine protease inhibitor according to the invention. Accordingly, it is being assumed that the addressee of this specification will not require an exhaustive computer listing of structures of lipophilic groups, but will instead make use of the structures of lipophilic groups disclosed in the specification, especially those exemplified; the test systems described herein for identifying serine protease inhibitors; and common general knowledge of the lipophilicity, synthesis and stability of organic compounds, to obtain novel serine protease inhibitor compounds of formula (I).

The lipophilic group may be, for example, an alkyl, alkenyl, carbocyclic or heterocyclic group, or a combination of two or more such groups linked by a spiro linkage or a single or double bond or by C=O, O, S, SO, SO$_2$, CONR$_{1e}$, NR$_{1e}$—CO—, NR$_{1e}$ linkage (where $R_{1e}$ is as defined for $R_{1a}$), optionally substituted by one or more oxo or $R_3$ groups in which $R_3$ is as defined for $R_{3a}$.

By way of illustration, representative lipophilic groups include methylcyclohexyl, methylcyclohexylmethyl, methylphenylmethyl, phenylethyl, benzylpiperidinyl, benzoylpiperidinyl, bispiperidinyl and phenylpiperazinyl.

Phenylethyl is an example of a combination of an alkyl group and a carbocyclic group linked through a single bond.

Benzylpiperidinyl is an example of a combination of an alkyl group, a carbocyclic group and a heterocyclic group linked by single bonds.

Benzoylpiperidinyl is an example of a combination of a carbocyclic group and a heterocyclic group linked through C=O.

Methylcyclohexylmethyl is an example of a combination of an alkyl group (methyl) and a carbocyclic group (cyclohexyl) linked by a single bond and having a substituent $R_3$ (methyl) on cyclohexyl. It will be appreciated that this group could alternatively have been regarded as a combination of two alkyl groups and a carbocyclic group. However, in order to provide clarity, in this specification any terminal alkyl group in Lp will be treated as a substituent $R_3$.

When the lipophilic group comprises an alkyl group, this may be, for example, a (1–3C) alkyl group, such as methyl, ethyl or propyl. Preferably an alkyl group is unsubstituted.

When the lipophilic group comprises a carbocyclic group, this may be, for example, a non-aromatic or aromatic, mono or polycyclic hydrocarbon group containing up to 25, more preferably up to 10 carbon atoms. The carbocyclic group may thus be, for example, a cycloalkyl, polycycloalkyl, phenyl or naphthyl group, or a cycloalkyl group fused with a phenyl group.

Examples of particular values for a cycloalkyl group are (3–6C) cycloalkyl groups, such as cyclopentyl and cyclohexyl. A cycloalkyl group is preferably unsubstituted or substituted by one group $R_3$, preferably amino or an alkyl group, such as methyl.

Examples of particular values for a polycycloalkyl group are (6–10C) polycycloalkyl groups, such as bicycloalkyl, for example decalinyl, norbornyl or adamantyl. A polycycloalkyl group is preferably unsubstituted.

A phenyl group is preferably unsubstituted or substituted by one or two $R_3$ groups. More preferably it is substituted by one or two $R_3$ groups.

A naphthyl group is preferably unsubstituted or substituted by one $R_3$ group.

Examples of a cycloalkyl or cycloalkenyl group fused with a phenyl group are indanyl and tetrahydronaphthyl. This group is preferably unsubstituted.

When the lipophilic group comprises a heterocyclic group, this may be, for example, a non-aromatic or aromatic, mono or polycyclic group containing one or two oxygen, nitrogen or sulfur atoms in the ring system, and in total up to 25, more preferably up to 10 ring system atoms.

Examples of a heterocyclic group when it is a non-aromatic monocyclic group are azacycloalkyl groups, such as pyrrolidinyl and piperidinyl; azacycloalkenyl groups, such as pyrrolinyl; diazacycloalkyl groups, such as piperazinyl; oxacycloalkyl groups, such as tetrahydropyranyl; and thiacycloalkyl groups, such as tetrahydrothiopyranyl. A non-aromatic monocyclic group preferably contains 5, 6 or 7 ring atoms and is preferably unsubstituted or substituted by one group $R_3$, preferably alkyl, such as methyl or ethyl, or hydroxyalkyl, such as hydroxymethyl.

Examples of a heterocyclic group when it is a non-aromatic polycyclic group are bicyclic groups, such as azacycloalkyl fused with phenyl, for example dihydroindolyl, dihydroisoindolyl, tetrahydroquinolinyl and tetrahydroisoquinolinyl; and tricyclic groups, such as azacycloalkyl fused with indolyl, for example tetrahydropyrido [3,4-b] indole. This group is preferably unsubstituted.

Examples of a heterocyclic group when it is a aromatic monocyclic group are furyl, pyrrolyl, thienyl, imidazolyl, pyridyl, pyridazinyl, pyrimidinyl, pyrazinyl, oxazolyl, oxadiazolyl (such as 1,3,4-oxadiazolyl), thiadiazolyl (such as 1,3,4-thiadiazolyl) and thiazolyl. This group is preferably unsubstituted or substituted by one $R_3$.

Examples of a heterocyclic group when it is an aromatic polycyclic group are bicyclic groups such as benzofuryl, quinolinyl, isoquinolinyl and benzothienyl. This group is preferably unsubstituted or substituted by one $R_3$.

The lipophilic group preferably comprises a cycloalkyl, azacycloalkyl, diazacycloalkyl, phenyl, naphthyl, adamantyl, bicycloalkyl, mono- or diazabicycloalkyl, mono- or bicyclo heteroaromatic or a linear or branched alkyl or alkenyl group all optionally substituted by one or more groups $R_3$, or a combination of at least two such groups linked by a spiro linkage or a single or double bond or by C=O, O, S, SO, $SO_2$, $CONR_{1e}$, $NR_{1e}$, $NR_{1e}$—CO— or $NR_{1e}$ linkage (where $R_{1e}$ is as defined for $R_{1a}$).

Where Lp comprises a combination of at least two groups, it preferably comprises a combination of two or three such groups. The groups are preferably linked by a single bond, C=O, O or $NR_{1e}$.

Of particular interest are compounds of formula I in which Lp comprises an azacycloalkyl or diazacycloalkyl group of formula

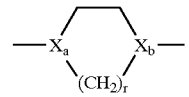

in which r is 1 or 2, one of $X_a$ and $X_b$ is N and the other is CH or N, provided that when r is 1, $X_a$ and $X_b$ are not both N.

Preferred compounds comprising this group are those in which Lp is a group of formula:

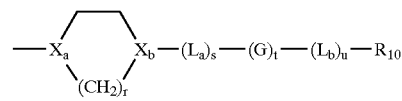

in which:
r is 1 or 2;
one of $X_a$ and $X_b$ is N and the other is CH or N provided that when r is 1, $X_a$ and $X_b$ are not both N;
s, t and u are each 0 or 1;
$L_a$ and $L_b$ are each independently selected from a single bond, C=O, O and $NR_{1e}$, in which $R_{1e}$ is hydrogen or (1–6C)alkyl;
G is (1–6C)alkanediyl; and
$R_{10}$ is (1–6C)alkyl; (3–6C)cycloalkyl which is unsubstituted or substituted by (1–6C)alkyl; indanyl; pyridyl; tetrahydropyranyl; tetrahydrothiopyranyl; phenyl which is unsubstituted or substituted by one or two $R_3$ groups; pyrrolinyl; or a group of formula

in which v is 1, 2 or 3; one of $X_c$ and $X_d$ is N and the other is CH or N, provided that when v is 1, $X_c$ and $X_d$ are not both N; and $R_{11}$ is hydrogen, (1–6C)alkyl or when $X_d$ is CH, hydroxy (1–6C) alkyl; provided that when t is 0, the sum of s and u is 1; when $X_b$ is N, $L_a$ is a bond or C=O; when $X_c$ is N, $L_b$ is a bond or C=O; when $X_b$ and $X_c$ are both N, t is 1; and when $(L_a)_s$-$(G)_t$-$(L_b)$ represents an alkyl group and $X_b$ and $X_c$ both represent N, the alkyl group contains at least two chain carbon atoms.

It will be appreciated that the provisos exclude compounds having two heteroatoms bonded directly together or separated by an alkyl group having only one carbon atom in the chain.

When $X_a$ is N, L is preferably CO or $CH_2CO$.
When $X_a$ is CH, L is preferably CONH, $CONHCH_2$ or $CH_2NHCO$.

Examples of values for G are $CH_2$, $(CH_2)_2$ and $(CH_2)_3$.
Examples of values for $R_{11}$ are hydrogen, methyl, ethyl or 2-propyl, or when $X_d$ is CH, hydroxymethyl.
Examples of particular values for $R_3$ are:—
hydrogen;
hydroxyl;
for alkoxy: methoxy or ethoxy;
for alkyl optionally substituted by hydroxy, alkylamino, alkoxy, oxo, aryl or cycloalkyl: (1–6C)alkyl, such as methyl, ethyl, propyl, 2-propyl, butyl, 2-butyl, t-butyl, pentyl, 2-pentyl or 3-pentyl, (1–6C)alkylamino(1–6C)alkyl, such as isopropylaminomethyl, dimethylaminomethyl, diethylaminomethyl or dimethylaminoethyl, or (1–6C)alkanoyl, such as acetyl;

for hydroxyalkyl optionally substituted by hydroxy, alkylamino, alkoxy, oxo, aryl or cycloalkyl; (1–6C)hydroxyalkyl, such as hydroxymethyl or hydroxyethyl, carboxy or carboxy(1–5C)alkyl;

for alkoxyalkyl: methoxymethyl;

for alkoxycarbonyl: methoxycarbonyl or ethoxycarbonyl:

for alkylaminocarbonyl: methylaminocarbonyl or dimethylaminocarbonyl;

for aminoalkyl optionally substituted by hydroxy, alkylamino, alkoxy, oxo, aryl or cycloalkyl: aminomethyl, aminocarbonyl or aminocarbonyl(1–5C)alkyl;

for alkylamino optionally substituted by hydroxy, alkylamino, alkoxy, oxo, aryl or cycloalkyl: methylamino, dimethylamino, ethylamino, formylamino or acetylamino; amino;

for halo: fluoro or chloro;

cyano;

nitro;

thiol;

for alkylthio: methylthio;

for alkylsulphonyl: methylsulphonyl, ethylsulphonyl or isopropylsulphonyl;

for alkylsulphenyl: methylsulphenyl;

for triazolyl: 1,2,4-triazol-2-yl, 1,2,4-triazol-4-yl or 1,2,3-triazol-4-yl;

for imidazolyl: 1,3-imidazol-1-yl or 1,3-imidazol-4-yl; for tetrazolyl: tetrazol-1-yl or tetrazol-5-yl;

for alkylsulphonamido: methylsulphonamido, ethylsulphonamido or propylsulphonamido;

for alkylaminosulphonyl: methylaminosulphonyl, ethylaminosulphonyl or propylaminosulphonyl;

aminosulphonyl;

for haloalkoxy: trifluoromethoxy; and for haloalkyl: trifluoromethyl or trichloromethyl.

Examples of particular values for $R_{1e}$ are hydrogen and (1–6C)alkyl, such as methyl or ethyl.

Examples of values for $R_{10}$ are:

for (1–6C)alkyl: methyl, ethyl, 2-propyl and 3-pentyl;

for (3–6C)cycloalkyl which is unsubstituted or substituted by (1–6C)alkyl: cyclopentyl, 3-methylcyclopentyl, cyclohexyl and 4-methylcyclohexyl;

for indanyl: 2-indanyl;

for pyridyl: pyrid-2-yl, pyrid-3-yl and pyrid-4-yl;

for tetrahydropyranyl: tetrahydropyran-4-yl;

for tetrahydrothiopyranyl: tetrahydrothiopyran-4-yl;

for phenyl which is unsubstituted or substituted by one or two $R_3$ groups: phenyl, 2-fluorophenyl, 3-fluorophenyl, 4-fluorophenyl, 2-(methylthio)phenyl, 2-ethylphenyl, 2-methoxyphenyl, 3-methoxyphenyl, 4-methoxyphenyl, 2-methanesulphonylphenyl, 3-methanesulphonylphenyl, 4-methanesulphonylphenyl, 4-fluoro-2-methanesulphonylphenyl, 4-amino-2-methanesulphonylphenyl, 4-amido-2-methanesulphonyl-phenyl, 4-nitro-2-methanesulphonylphenyl, 2-aminosulphonylphenyl, 2-methylaminosulphonylphenyl, 2-dimethylaminosulphonylphenyl, 2-methylsulphonylamino-phenyl, 2-carboxamidophenyl and 2-acetamidophenyl; for pyrrolinyl: pyrrolin-1-yl; and for a group of formula piperidin-1-yl, 4-methyl-piperidin-1-yl, piperidin-4-yl, 1-methylpiperidin-4-yl, 1-(2-propyl)piperidin-4-yl, pyrrolidin-1-yl; 3-methylpyrrolidin-1-yl, pyrrolidin-3-yl, 1-methyl-pyrrolidin-3-yl, 1-(2-propyl)pyrrolidin-3-yl, 1-methyl-piperazin-4-yl, 1-ethylpiperazin-4-yl, 1-(2-propyl)piperazin-4-yl, hexahydro-1,4-diazapin-1-yl and 4-methyl-hexahydro-1,4-diazapin-1-yl.

A preferred sub-group of compounds of formula I is that in which —L—Lp(D)$_n$ is q is 1 or 2;

(a) Q is a direct bond; and $R_q$ is piperidin-4-yl which may bear a $C_{1-3}$alkyl substituent at the 1-position; or $R_q$ is $NR_aR_b$ in which each of $R_a$ and $R_b$ independently is hydrogen or $C_{1-3}$alkyl; or one of $R_a$ and $R_b$ is hydrogen or methyl and the other of $R_a$ and $R_b$ is —CH$_2$—R$_c$ or —CH$_2$—R$_d$ in which $R_c$ is pyridyl or phenyl (which phenyl may bear a fluoro, chloro, methyl, CONH$_2$, SO$_2$NH$_2$, methylaminosulphonyl, dimethylaminosulphonyl, methylsulphonylamino, methoxy or methylsulphonyl substituent) and in which $R_d$ is isopropyl or cyclopentyl, or $NR_aR_b$ is pyrrolidino, piperidino, morpholino, piperazino, or tetrahydro-1,4-diazepino in which a pyrrolidino or piperidino may be a 3,4-didehydro deriviative and in which a pyrrolidino, piperidino, piperazino, or tetrahydro-1,4-diazepino may bear a methyl group at the 4-position (preferably $R_q$ is piperidin-4-yl which may bear a (1–3C)alkyl substituent at the 1-position);

(b) Q is —O— or —NH—; and $R_q$ is $R_c$ which is defined as above ($R_c$ is preferably pyrid-2-yl, pyrid-3-yl or pyrid-4-yl); or (c) Q is methylene; and $R_q$ is $NR_aR_b$ which is defined as above.

q is preferably 2.

Another sub-group of compounds is that in which —L—Lp(D)$_n$ is in which $R_r$ is —(CH$_2$)$_c$—R$_c$, —CHR$_e$R$_f$, —CH$_2$—CHR$_e$R$_f$, or $R_g$ in which c is 1 or 2 and $R_c$ is defined as above; each of $R_e$ and $R_f$ independently is hydrogen or $C_{1-3}$alkyl; or CHR$_e$R$_f$ is cyclopentyl (which may bear a methyl, ethyl or hydroxymethyl substituent at the 3- or 4-position), cyclohexyl (which may bear a methyl, ethyl or hydroxymethyl substituent at the 3- or 4-position), tetrahydropyran-4-yl, tetrahydrothiopyran-4-yl, pyrrolidin-3-yl (which may bear a 1-methyl substituent), piperidin-4-yl (which may bear a 1-methyl substituent), or indan-2-yl; and $R_g$ is 2-methylsulphonylphenyl which may bear a 4-fluoro substituent or $R_g$ is $\lambda^6$-1,1-dioxobenzo[b]thiophen-7-yl.

Preferably c is 2.

Preferably $R_c$ is pyrid-2-yl, pyrid-3-yl or pyrid-4-yl.

Another sub-group of compounds of formula I is that in which —L—Lp(D)$_n$ is

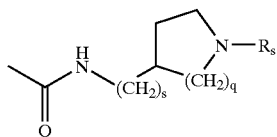

in which q is 1 or 2;

s is 0 or 1; and $R_s$ is —(CH$_2$)$_c$—R$_c$, —CHR$_e$R$_f$, or —CH$_2$—CHR$_e$R$_f$ each of which is defined as above.

Preferably s is 1.

Yet another sub-group of compounds of formula I is that in which —L—Lp(D)$_n$ is

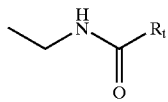

in which $R_t$ is piperidin-4-yl, piperidin-3-yl or pyrrolidin-3-yl (especially piperidin-4-yl), any of which may bear a $C_{1-3}$ alkyl substituent at the 1-position (preferably methyl, ethyl or, more preferably, 2-propyl); or $R_t$ is phenyl (which phenyl may bear a fluoro, chloro, $C_{1-4}$ alkyl, methoxy or methylsulphonyl substituent).

A further sub-group of compounds of formula I is that in which -L-Lp(D)$_n$ is

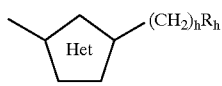

in which Het is a divalent 5 membered heteroaromatic group containing 1, 2 or 3 heteroatoms selected from O, N and S and having the two ring atoms at which it is connected separated by one ring atom;

h is 0 or 1; and $R_h$ is phenyl which may bear one or more $R_3$ substituents, for example independently selected from, for an ortho or a para substituent: $C_{1-5}$ alkyl, fluoro, chloro, difluoromethyl, trifluoromethyl, methoxy, dimethylamino, methylsulphonyl, and $C_{1-2}$ acyl, and for a meta substituent: fluoro, chloro and methyl.

Within this sub-group, a particularly preferred group of compounds is that in which -L-Lp(D)$_n$ is

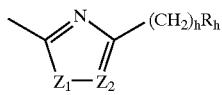

in which $R_h$ is phenyl which may bear one or two $R_3$ substituents, for example an ortho and/or a para substituent independently selected from, for an ortho: methyl, fluoro, chloro, methylsulphonyl and acetyl, and for a para substituent: methyl, fluoro, chloro, methoxy and dimethylamino;

$Z_1$ is S, $Z_2$ is CH, h is 0; or $Z_1$ is NH, $Z_2$ is N, h is 1.

Most preferably, the lipophilic group Lp is selected from

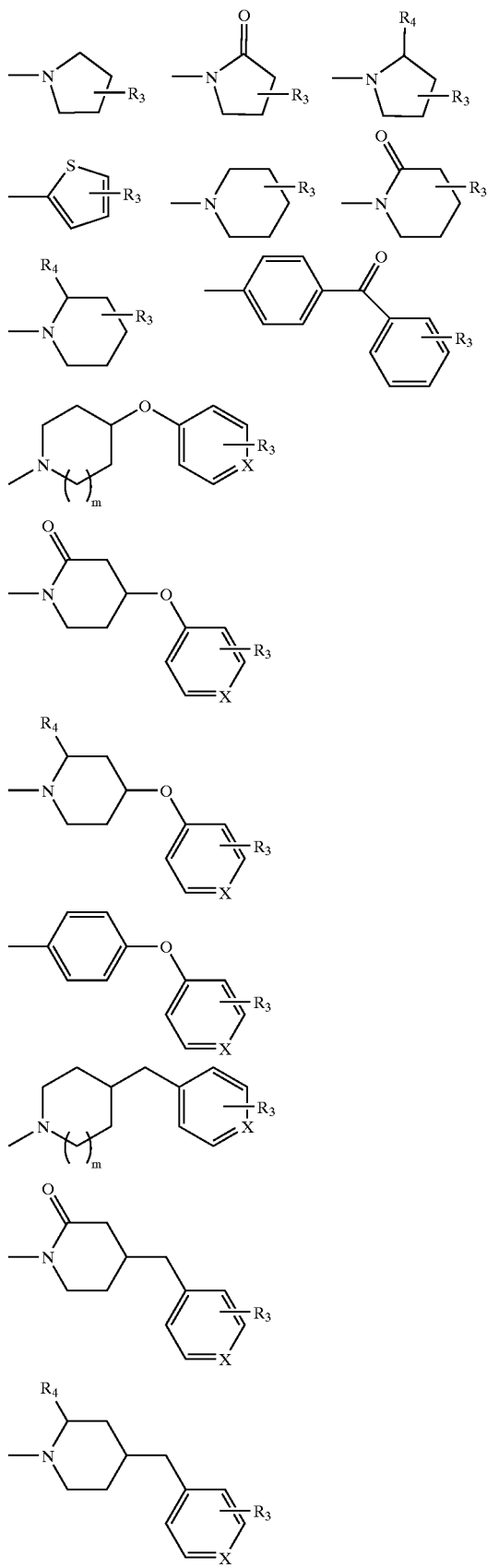

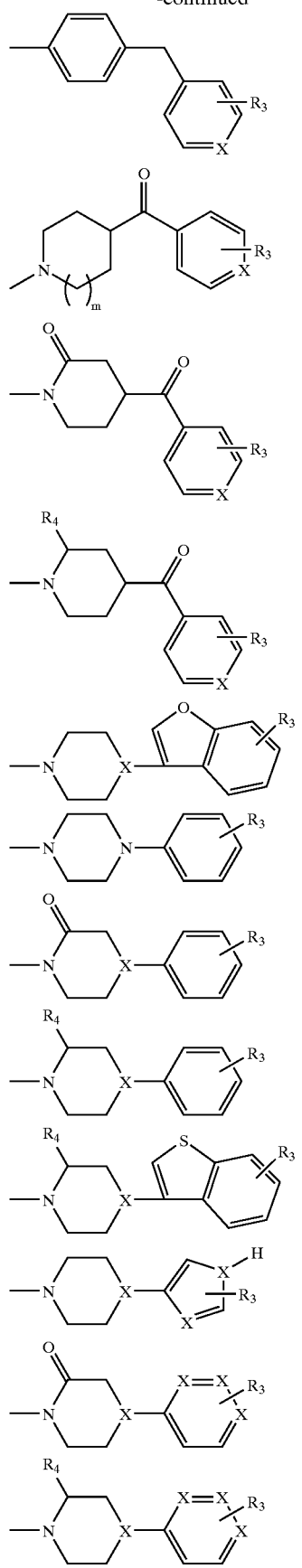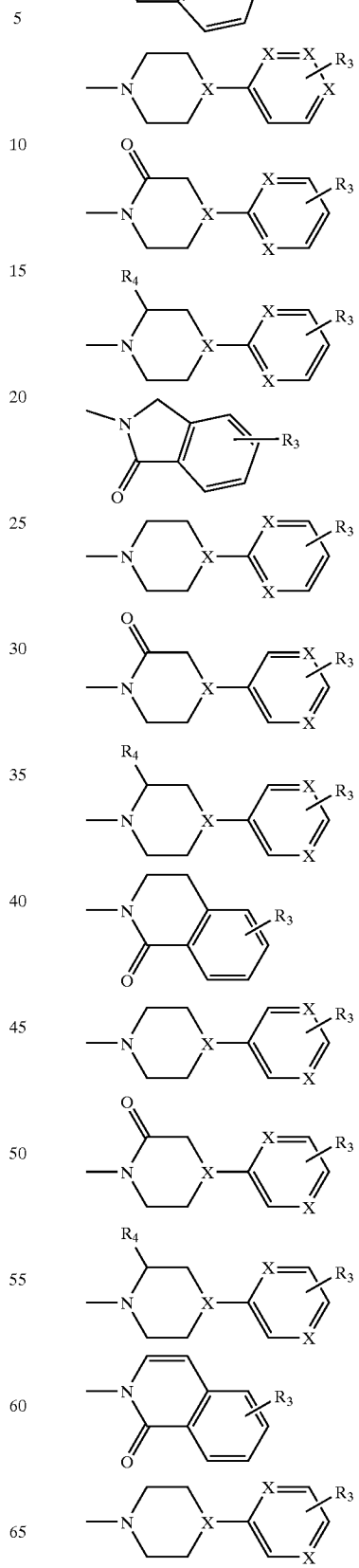

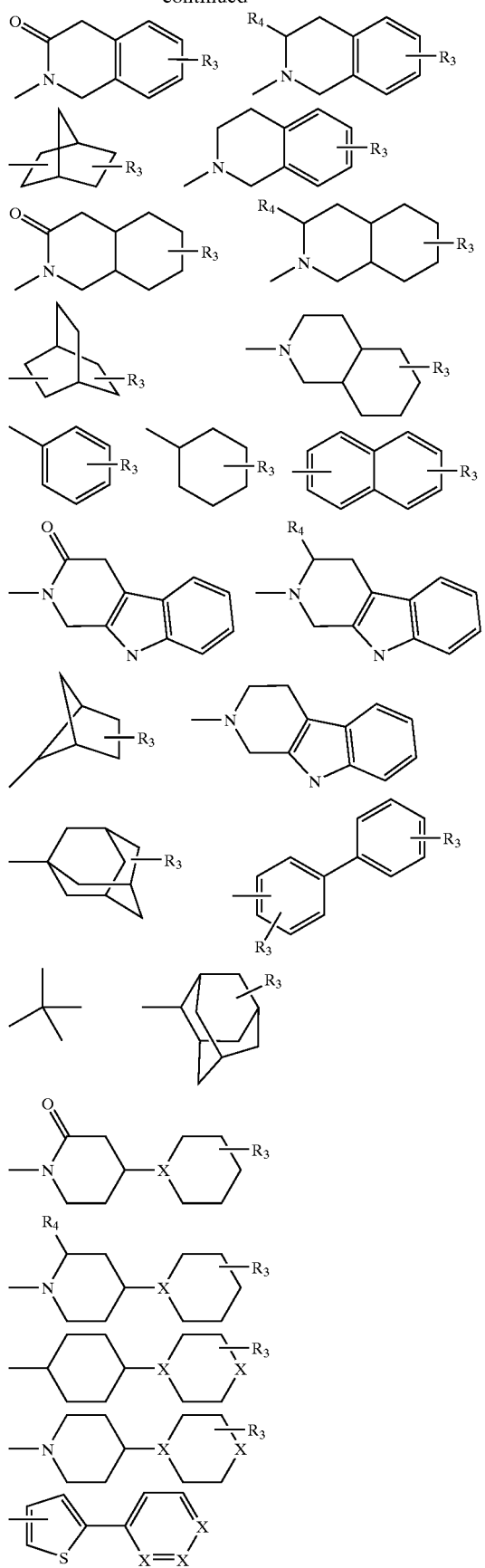
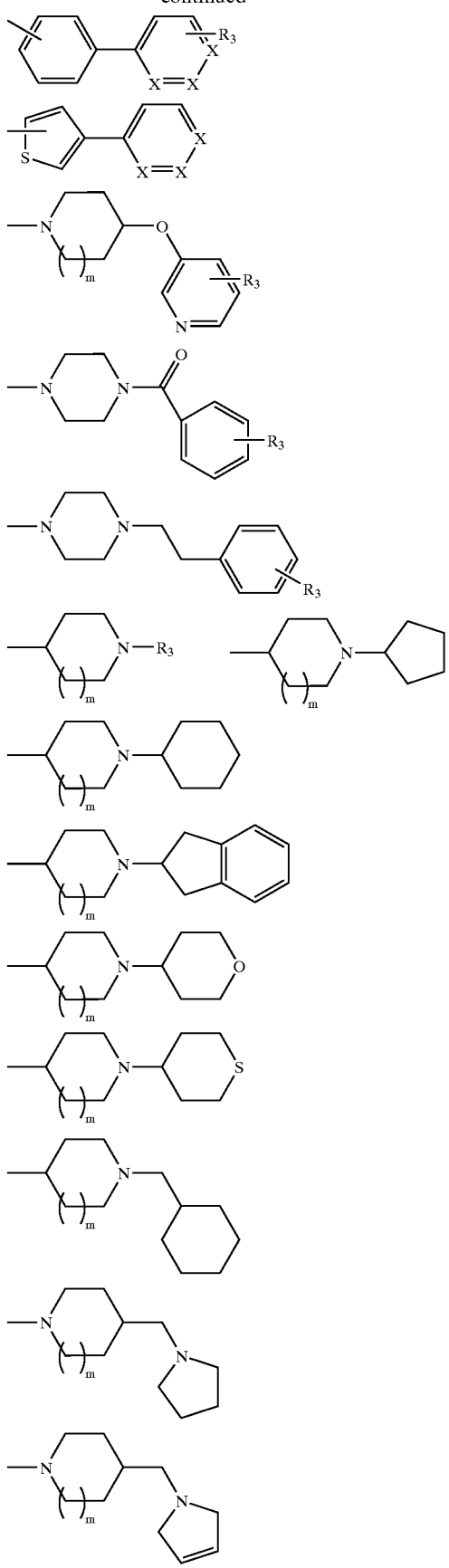

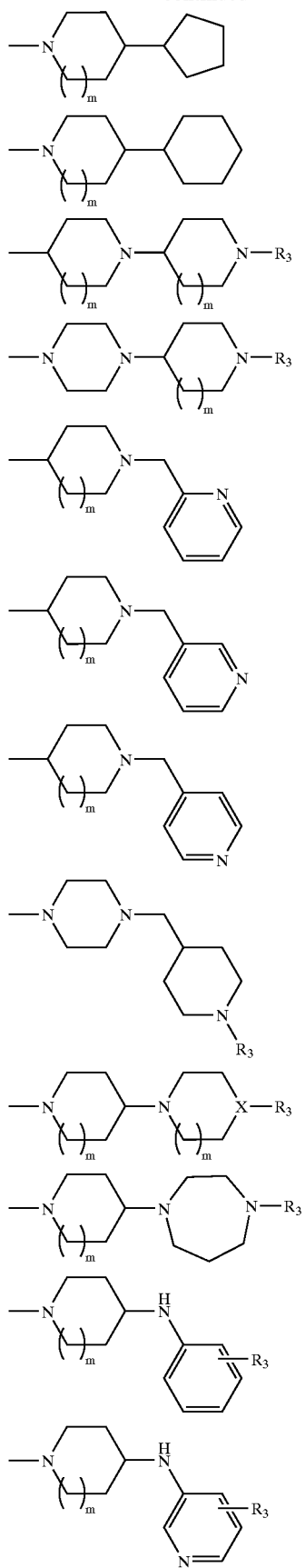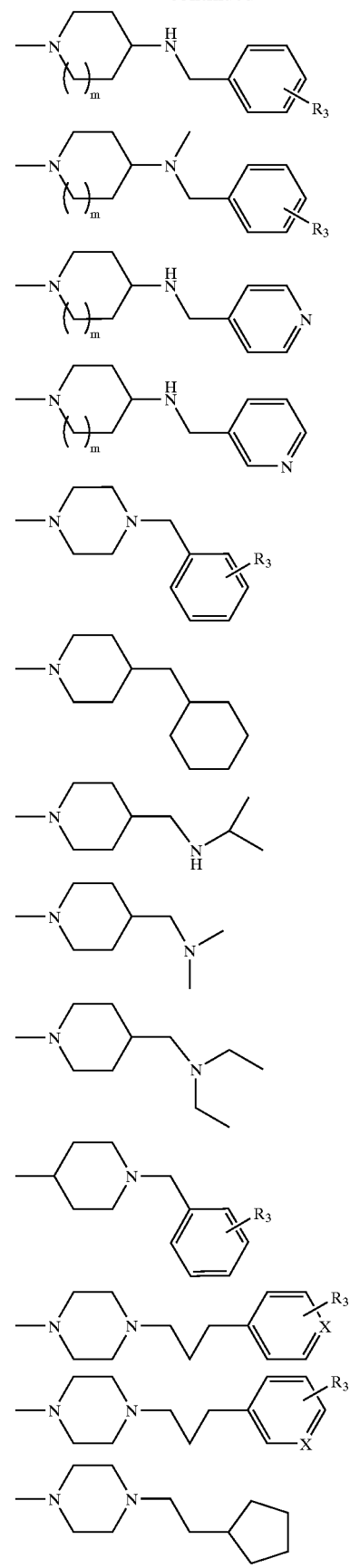

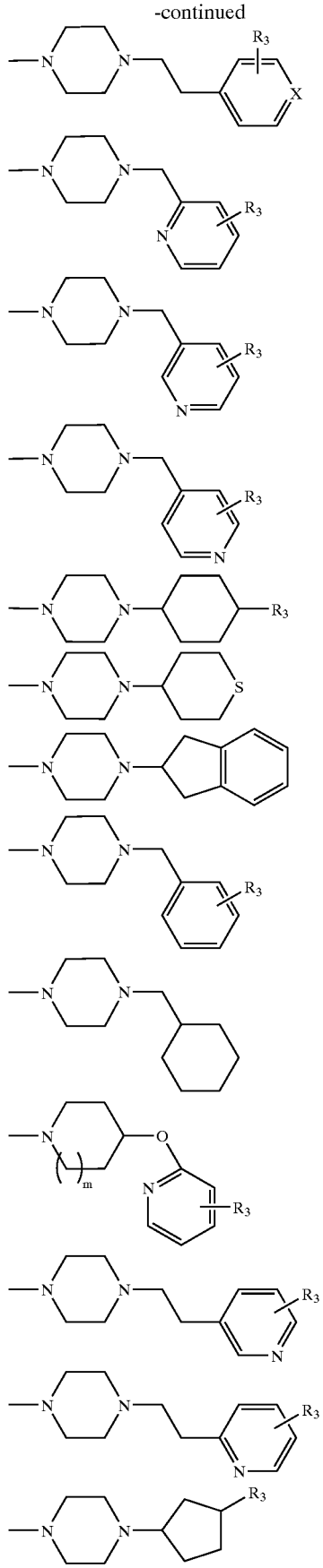

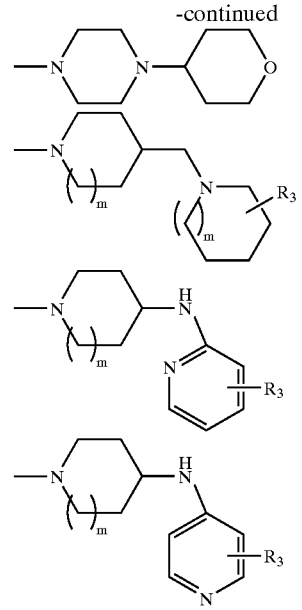

wherein R₃ is as hereinbefore defined;

m represents 0 or 1;

R₄ represents hydrogen, $(CH_2)_w COOH$ or $(CH_2)_w CONH_2$;

w represents an integer from 0 to 4; and

X represents CH or N.

Where two or more X atoms are present in a ring, preferably at least one is CH.

When R₃ is present as a substituent on an aromatic ring, it is preferably selected from hydrogen, alkylsulphonyl, aminosulphonyl, alkylaminosulphonyl, alkylaminocarbonyl, amino, amido, alkoxycarbonyl, acetylamino, chloro, fluoro, cyano, methoxy, ethoxy, nitro, hydroxy, alkylsulphonylamino, triazolyl and tetrazolyl.

When R₃ is present as a substituent on a saturated ring, it is preferably selected from hydrogen, hydroxy, amino, (1–3C)alkoxy, (1–3C)hydroxyalkyl, (1–3C)alkyl, carboxy, methoxycarbonyl and ethoxycarbonyl.

One group of lipophilic groups Lp is that of formula

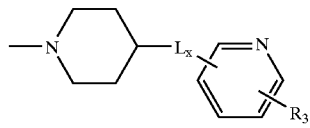

in which $L_x$ represents O or NH.

For example specific lipophilic groups include

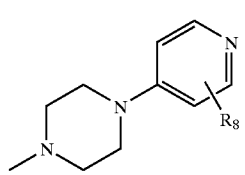

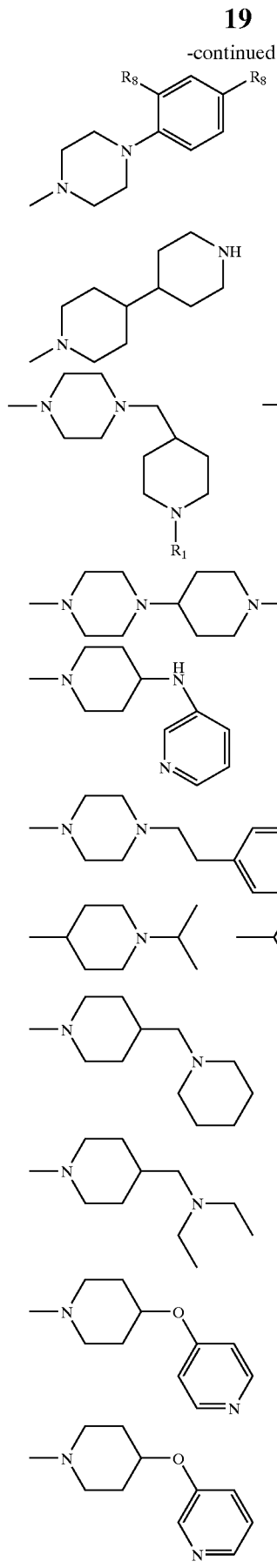

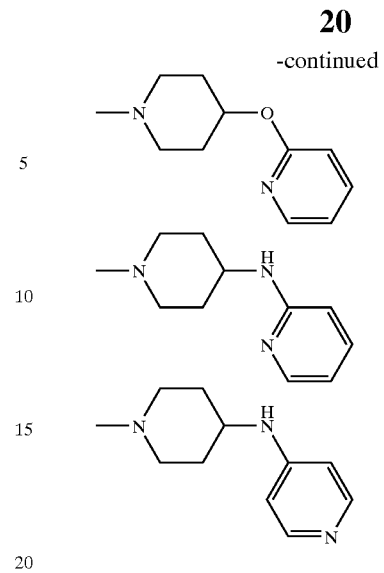

where $R_8$ is as defined for $R_3$ (preferably as defined for a substituent on an aromatic ring), especially where $R_8$ represents H, OMe, $SO_2Me$, F, cyano, amido, amino, $NO_2$, Cl or OH; and $R_1$ is hydrogen or (1–6C)alkyl (such as methyl, ethyl or 2-propyl).

Another highly preferred lipophilic group is of formula (DP)

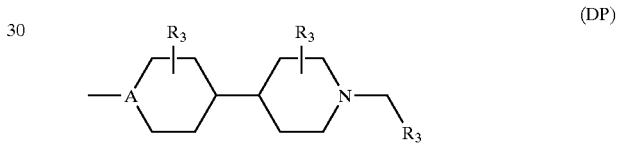

(DP)

wherein A represents N or CH (preferably N) and $R_3$ is as hereinbefore defined. When the lipophilic group is (DP) it is preferred that the group L represents CO, $CH_2$ or $SO_2$.

Also, it is preferred if the $R_3$ groups in the formula DP are hydrogen.

Hence, preferred compounds of the invention are those of formula (J)

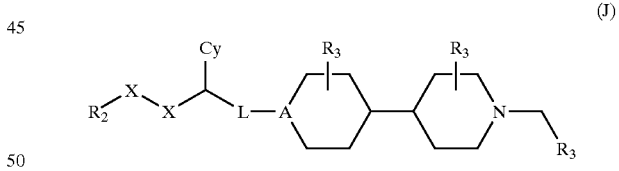

(J)

where $R_2$, X—X, and Cy are as hereinbefore defined and L represents CO, $CH_2$ or $SO_2$.

Another highly preferred lipophilic group is based on the formula (K)

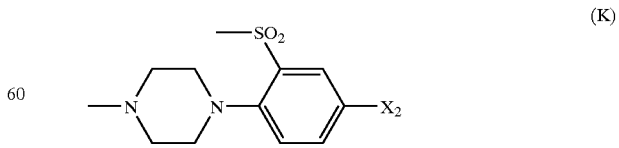

(K)

wherein $X_2$ is halo, hydrogen, amino, nitro or $CONH_2$.
Preferably $X_2$ is hydrogen or fluoro. Compounds in which the lipophilic group is based on the formula (K) or (J) have been found to perform relatively well in the prothrombin time assay, when compared with corresponding aminoisoquinolines of WO99/11657.

The hydrogen bond donor group which may be attached to the lipophilic group preferably has a nitrogen or oxygen-atom as the hydrogen bearing donor atom and conveniently is a hydroxyl group, a primary, secondary or tertiary amine, or a primary or secondary imine group (as part of an amidine or guanidine) or a saturated or unsaturated heterocyclic group containing a ring nitrogen, preferably a group containing 5 to 7 ring atoms. Where the donor atom is a ring nitrogen, the remote portion of the heterocyclic ring may be part of the lipophilic group.

The cyclic group attached to the alpha carbon is preferably an optionally $R_{3a}$ substituted phenyl, pyridyl (such as pyrid-2-yl, pyrid-3-yl or pyrid-4-yl), thienyl (such as thien-2-yl or thien-3-yl), thiazolyl (such as thiazol-2-yl, thiazol-4-yl or thiazol-5-yl), naphthyl (such as naphth-1-yl), piperidinyl (such as piperidin-4-yl) or cycloalkyl, such as a cyclohexyl group.

Examples of particular values for $R_{3a}$ are:—
hydrogen;
hydroxyl;
for alkoxy: methoxy or ethoxy;
for alkyl optionally substituted by hydroxy, alkylamino, alkoxy, oxo, aryl or cycloalkyl: alkyl, such as methyl or ethyl, or alkylaminoalkyl, such as methylaminomethyl or dimethylaminomethyl;
for hydroxyalkyl optionally substituted by hydroxy, alkylamino, alkoxy, oxo, aryl or cycloalkyl: hydroxymethyl or carboxy;
for alkoxyalkyl: methoxymethyl;
for alkoxycarbonyl: methoxycarbonyl or ethoxycarbonyl;
for alkylaminocarbonyl: methylaminocarbonyl or dimethylaminocarbonyl;
for aminoalkyl optionally substituted by hydroxy, alkylamino, alkoxy, oxo, aryl or cycloalkyl: aminomethyl, $CONH_2$ or $CH_2CONH_2$;
for alkylamino optionally substituted by hydroxy, alkylamino, alkoxy, oxo, aryl or cycloalkyl: (1–6C) alkanoylamino, such as acetylamino;
for alkoxycarbonylamino: methoxycarbonylaminno, ethoxycarbonylamino or t-butoxycarbonylamino; amino;
for halo: fluoro or chloro;
cyano;
nitro;
thiol;
for alkylthio: methylthio;
for alkylsulphonyl: methylsulphonyl or ethylsulphonyl;
for alkylsulphenyl: methylsulphenyl;
for alkylsulphonamido: methylsulphonylamido or ethylsulphonylamido;
for alkylaminosulphonyl: methylaminosulphonyl or ethylaminosulphonyl;
aminosulphonyl;
for haloalkoxy: trifluoromethoxy; and
for haloalkyl: trifluoromethyl.

Examples of particular values for $R_{1c}$ are:
hydrogen;
hydroxyl;
for alkoxy: methoxy or ethoxy;
for alkyl optionally substituted by hydroxy, alkylamino, alkoxy, oxo, aryl or cycloalkyl: alkyl, such as methyl or ethyl, or alkylaminoalkyl, such as methylaminomethyl or dimethylaminomethyl;
for hydroxyalkyl: hydroxymethyl;
for alkoxyalkyl: methoxymethyl;
for alkoxycarbonyl: methoxycabonyl or ethoxycarbonyl;
for alkylaminocarbonyl: methylaminocarbonyl or dimethylaminocarbonyl;
for alkoxycarbonylamino: methoxycarbonylamino, ethoxycarbonylamino or t-butoxycarbonylamino;
for alkylamino optionally substituted by hydroxy, alkylamino, alkoxy, oxo, aryl or cycloalkyl: (1–6C) alkanoylamino, such as acetylamino; and
for aminoalkyl substituted by hydroxy, alkylamino, alkoxy, oxo, aryl or cycloalkyl: aminomethyl, $CONH_2$ or $CH_2CONH_2$.

Preferably $R_{3a}$ is hydrogen, hydroxyl, methoxy, methyl, amino, fluoro, chloro, ethylsulphonylamino, amido or methylaminocarbonyl.

Examples of particular values for Cy are phenyl, 4-aminophenyl, 4-amidophenyl, 4-(N-methyl)amidophenyl, 4-(N,N-dimethyl)amidophenyl, 2-chlorophenyl, 2-methylphenyl, 2-fluorophenyl, 3-fluorophenyl, 4-fluorophenyl, 4-hydroxphenyl, 2-methoxyphenyl, 4-methoxyphenyl, 4-carboxyphenyl, 3-ethylsulphonylaminophenyl, thien-2-yl, thien-3-yl, thiazol-4-yl, thiazol-5-yl, 2-methylthiazol-4-yl, pyrid-2-yl, pyrid-3-yl, pyrid-4-yl, piperidin-4-yl, 1-methylpiperidin-4-yl, cyclohexyl and naphth-1-yl.

Referring to the group $R_2$, examples of a 5 or 6 membered aromatic carbon ring optionally interrupted by a nitrogen, oxygen or sulphur ring atom are phenyl; pyrrolyl, such as 2-pyrrolyl; pyridyl, such as 3-pyridyl; pyrazinyl, such as 2-pyrazinyl; furyl, such as 2-furyl; and thienyl, such as 2-thienyl or 3-thienyl. Preferably the ring is interrupted (i.e. a carbon atom is replaced) by at most one heteroatom. More preferably the ring is phenyl, 2-thienyl or 2-pyrrolyl. Most preferably, the ring is phenyl.

When the ring is phenyl, the group $R_2$ may be a group of formula

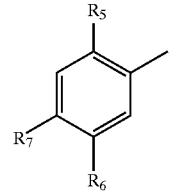

in which $R_5$ is amino, hydroxy or hydrogen, and $R_6$ and $R_7$ which may be the same or different represent halo, nitro, thiol, cyano, haloalkyl, haloalkoxy, amido, hydrazido, amino, alkylthio, alkenyl, alkynyl or $R_1$ or taken together form a 5 or 6 membered fused carbocyclic ring or 5 membered heterocyclic ring, which may itself be substituted by $R_{1j}$, amino, halo, cyano, nitro, thiol, alkylthio, haloalkyl, haloalkoxy.

When the substituents at the 3 and 4 positions taken together form a fused ring which is a 5 or 6 membered carbocyclic or heterocyclic ring, examples of the resultant bicyclic ring are naphthyl, such as 2-naphthyl; benzimidazolyl, such as benzimidazol-5-yl or benzimidazol-6-yl; isoquinolinyl, such as isoquinolin-7-yl; indolyl, such as indol-2-yl, indol-5-yl or indol-6-yl; indazolyl, such as indazol-5-yl; indazol-6-yl; 3,4-methylenedioxyphenyl; dihydroindolyl, such as 2,3-dihydroindol-6-yl; benzothiazolyl, such as benzothiazol-2-yl or benzothiazol-6-yl; benzo[b]thiophenyl, such as benzo[b]thiophen-2-yl; benzofuryl, such as benzofur-2-yl; imidazo[1,2-a]pyrimidinyl, such as imidazo[1,2-a]pyrimidin-2-yl; tetrahydroimidazo[1,2-a]pyrimidinyl, such as tetrahydroimidazo[1,2-a]pyrimidin-2-yl; and benzisoxazolyl, such as benzisoxazol-5-yl.

$R_2$ preferably represents:

(i) phenyl optionally being substituted in the 3 and/or 4 position by halo, nitro, thiol, haloalkoxy, hydrazido, alkylhydrazido, amino, cyano, haloalkyl, alkylthio, alkenyl, alkynyl, acylamino, tri or difluoromethoxy, carboxy, acyloxy, $MeSO_2$— or $R_1$, and optionally substituted at the 6 position by amino, hydroxy, halo, alkyl, carboxy, alkoxycarbonyl, cyano, amido, aminoalkyl, alkoxy or alkylthio;

(ii) naphth-2-yl optionally substituted at the 6 or 7 position by halo, haloalkoxy, haloalkyl, cyano, nitro, amino, hydrazido, alkylthio, alkenyl, alkynyl or $R_{1j}$ and optionally substituted at the 3 position by amino, hydroxy, halo, alkyl, carboxy, cyano, amido, aminoalkyl, alkoxy or alkylthio;

(iii) isoquinolin-7-yl, indol-5-yl, indol-6-yl, indazol-5-yl, indazol-6-yl, benzothiazol-6-yl or benzisoxazol-5-yl optionally substituted at the 3 position by halo, haloalkoxy, haloalkyl, cyano, nitro, amino, hydrazido, alkylthio, alkenyl, alkynyl or $R_{1j}$;

(iv) benzimidazol-5-yl or benzothiazol-6-yl optionally substituted at the 2 position by amino;

(v) thien-2-yl or thien-3-yl optionally substituted at the 4 or 5 position by halo, haloalkoxy, haloalkyl, cyano, nitro, amino, hydrazido, alkylthio, alkenyl, alkynyl or $R_1$;

(vi) 3,4-methylenedioxyphenyl, 2,3-dihydroindol-6-yl, 3,3-dichloro-2-oxo-indol-6-yl or 1-methyl-3-aminoindazol-5-yl;

(vii) benzothiazol-2-yl, imidazo[1,2-a]pyrimidin-2-yl or tetrahydroimidazo[1,2-a]pyrimidin-2-yl;

(viii) pyrazol-2-yl optionally substituted at the 6 position by halo, haloalkoxy, haloalkyl, cyano, nitro, amino, hydrazido, alkylthio, alkenyl, alkynyl or $R_1$;

(ix) pyrid-2-yl optionally substituted at the 5 position by halo, haloalkoxy, haloalkyl, cyano, nitro, amino, hydrazido, alkylthio, alkenyl, alkynyl or $R_1$;

(x) pyrid-3-yl optionally substituted at the 6 position by halo, haloalkoxy, haloalkyl, cyano, nitro, amino, hydrazido, alkylthio, alkenyl, alkynyl or $R_1$;

(xi) benzofur-2-yl optionally substituted at the 3 position by amino, hydroxy, halo, alkyl, carboxy, cyano, amido, aminoalkyl, alkoxy or alkylthio and at the 5 or 6 position by halo, haloalkoxy, haloalkyl, cyano, nitro, amino, hydrazido, alkylthio, alkenyl, alkynyl or $R_{1j}$;

(xii) indol-2-yl optionally substituted on the indole nitrogen atom by alkyl and optionally substituted at the 5 or 6 position by halo, haloalkoxy, haloalkyl, cyano, nitro, amino, hydrazido, alkylthio, alkenyl, alkynyl or $R_{1j}$;

(xiii) indol-6-yl substituted at the 5 position by amino, hydroxy, halo (such as fluoro or chloro), alkyl, carboxy, alkoxycarbonyl, cyano, amido, aminoalkyl, alkoxy or alkylthio and optionally substituted at the 3 position by halo (such as chloro), haloalkoxy, haloalkyl, cyano, nitro, amino, hydrazido, alkylthio, alkenyl, alkynyl or $R_{1j}$; or (xiv) benzo[b]thiophen-2-yl optionally substituted at the 3 position by amino, hydroxy, halo, alkyl, carboxy, cyano, amido, aminoalkyl, alkoxy or alkylthio and at the 5 or 6 position by halo, haloalkoxy, haloalkyl, cyano, nitro, amino, hydrazido, alkylthio, alkenyl, alkynyl or $R_{1j}$.

Examples of particular values for substituents that may be present on $R_2$ are:

for halo: fluoro, chloro, bromo or iodo;
nitro;
thiol;
for haloalkoxy: difluoromethoxy or trifluoromethoxy;
hydrazido;
for alkylhydrazido: methylhydrazido;
amino;
cyano;
for haloalkyl: trifluoromethyl;
for alkylthio: methylthio;
for alkenyl: vinyl;
for alkynyl: ethynyl;
for acylamino: acetylamino;
carboxy;
for acyloxy: acetoxy;
hydroxy;
for alkyl: methyl or ethyl;
amido ($CONH_2$);
for aminoalkyl: aminomethyl; and
for alkoxy: methoxy or ethoxy.

Examples of particular values for $R_1$ are:
hydrogen;
hydroxy;
for alkoxy: methoxy or ethoxy;
for alkyl optionally substituted by hydroxy, alkylamino, alkoxy, oxo, aryl or cycloalkyl: alkyl, such as methyl or ethyl, alkylaminoalkyl, such as dimethylaminomethyl, or alkanoyl, such as acetyl;
for hydroxyalkyl: hydroxymethyl;
for alkoxyalkyl: methoxymethyl;
for alkoxycarbonyl: methoxycarbonyl;
for alkylaminocarbonyl: methylaminocarbonyl;
for alkylamino: methylamino, ethylamino or dimethylamino;
for hydroxyalkyl substituted by hydroxy, alkylamino, alkoxy, oxo, aryl or cycloalkyl: carboxyl or carboxymethyl; and
for aminoalkyl substituted by hydroxy, alkylamino, alkoxy, oxo, aryl or cycloalkyl: amido ($CONH_2$) or amidomethyl.

Examples of particular values for $R_{1j}$ are:
hydrogen;
hydroxy;
for alkoxy: methoxy or ethoxy;
for alkyl optionally substituted by hydroxy, alkylamino, alkoxy, oxo, aryl or cycloalkyl: alkyl, such as methyl or ethyl, or alkanoyl, such as acetyl;
for hydroxyalkyl: hydroxymethyl;
for alkoxyalkyl: methoxymethyl;
for alkoxycarbonyl: methoxycarbonyl;
for alkylamino: methylamino, ethylamino or dimethylamino;
for hydroxyalkyl substituted by hydroxy, alkylamino, alkoxy,
oxo, aryl or cycloalkyl: carboxyl or carboxymethyl; and
for aminoalkyl substituted by hydroxy, alkylamino, alkoxy, oxo, aryl or cycloalkyl: amido ($CONH_2$) or amidomethyl.

More preferably $R_2$ represents:
(i) phenyl optionally being substituted in the 3 and/or 4 position by fluoro, chloro, bromo, iodo, nitro, difluoromethoxy, trifluoromethoxy, amino, cyano, trifluoromethyl, methylthio, vinyl, carboxy, acetoxy, $MeSO_2$—, hydroxy, methoxy, ethoxy, methyl, methoxycarbonyl, methylamino, ethylamino or amido, and optionally substituted at the 6 position by amino, hydroxy, fluoro, methoxycarbonyl, cyano or aminomethyl (preferably phenyl substituted in the 4 position by chloro, amino, vinyl, methylamino, methyl or methoxy, optionally at the 3 position with amino or hydroxy, and optionally at the 6 position with amino or hydroxy);

(ii) naphth-2-yl optionally substituted at the 6, position by hydroxy and optionally substituted at the 3 position by amino or hydroxy;

(iii) isoquinolin-7-yl, indol-5-yl, indol-6-yl, indazol-5-yl, indazol-6-yl, benzothiazol-6-yl or benzisoxazol-S-yl optionally substituted at the 3 position by chloro, bromo, amino, methyl or methoxy (preferably indol-6-yl optionally substituted at the 3 position by chloro, bromo, methyl or methoxy);

(iv) benzimidazol-5-yl or benzothiazol-6-yl optionally substituted at the 2 position by amino;

(v) thien-2-yl or thien-3-yl optionally substituted at the 4 or 5 position by methylthio, methyl or acetyl;

(vi) 3,4-methylenedioxyphenyl, 2,3-dihydroindol-6-yl, 3,3-dichloro-2-oxo-indol-6-yl or 1-methyl-3-aminoindazol-5-yl;

(vii) benzothiazol-2-yl, imidazo[1,2-a]pyrimidin-2-yl or tetrahydroimidazo[1,2-a]pyrimidin-2-yl;

(viii) pyrazol-2-yl substituted at the 5 position by methyl;

(ix) pyrid-2-yl optionally substituted at the 6 position by chloro;

(x) pyrid-3-yl optionally substituted at the 4 position by chloro;

(xi) benzofur-2-yl optionally substituted at the 3 position by chloro, methyl or methoxy, at the 5 or 6 position by methyl and at the 6 position by methoxy;

(xii) indol-2-yl optionally substituted on the indole nitrogen atom by methyl and optionally substituted at the 5 or 6 position by fluoro, chloro, bromo, methyl or methoxy;

(xiii) indol-6-yl substituted at the 5 position by chloro, fluoro or hydroxy and optionally substituted at the 3 position by chloro or methyl; or (xiv) benzo[b]thiophen-2-yl optionally substituted at the 3 position by fluoro, chloro or methyl, and optionally substituted at the 5 or 6 position by fluoro, chloro, methyl, hydroxy, or methoxy.

Examples of particular values for $R_2$ are:

(i) phenyl, 2-aminophenyl, 3-aminophenyl, 2-amino-3-fluorophenyl, 2-amino-4-fluorophenyl, 2-amino-4-chlorophenyl, 2-amino-3-bromophenyl, 2-amino-3-nitrophenyl, 2-amino-4-nitrophenyl, 3,4-dimethoxy-5-aminophenyl, 2-amino-4-methylphenyl, 2-amino-3-methylphenyl, 2-amino-3-methoxyphenyl, 3,4-diaminophenyl, 3,5-diaminophenyl, 3-amino-4-fluorophenyl, 3-amino-4-chlorophenyl, 3-amino-4-bromophenyl, 3-amino-4-hydroxyphenyl, 3-amino-4-carboxymethylphenyl, 3-amino-4-methylphenyl, 3-amino-4-methoxyphenyl, 2-fluorophenyl, 4-fluoro-3-cyanophenyl, 3-chlorophenyl, 3-chloro-4-hydroxphenyl, 3-chloro-5-hydroxyphenyl, 4-chlorophenyl, 4-chloro-2-hydroxyphenyl, 4-chloro-3-hydroxyphenyl, 4-chloro-3-methylphenyl, 4-chloro-3-methoxyphenyl, 4-bromophenyl, 4-bromo-3-methylphenyl, 4-iodophenyl, 2-cyanophenyl, 3-cyanophenyl, 4-cyanophenyl, 3-cyano-5-aminophenyl, 2-hydroxyphenyl, 2-hydroxy-4-methoxyphenyl, 3-hydroxphenyl, 3-hydroxy-4-methylphenyl, 2,4-dihydroxyphenyl, 3,4-dihydroxyphenyl, 3-hydroxy-4-methoxyphenyl, 4-difluoromethoxyphenyl, 4-trifluoromethoxphenyl, 4-trifluoromethylphenyl, 4-methylthiophenyl, 4-methoxycarbonylphenyl, 4-acetoxyphenyl, 4-methanesulfonylphenyl, 3-methylphenyl, 3-methyl-5-aminophenyl, 4-methylphenyl, 4-vinylphenyl, 4-methoxyphenyl, 4-ethoxyphenyl, 4-methoxy-3-chlorophenyl, 4-methoxy-3-methylphenyl, 3-methylaminophenyl, 4-methylaminophenyl, 4-ethylaminophenyl or 2-aminomethylphenyl;

(ii) naphth-2-yl, 3-aminonaphth-2-yl, 3-hydroxynaphth-2-yl or 6-hydroxynaphth-2-yl;

(iii) isoquinolin-7-yl, indol-5-yl, indol-6-yl, 3-chloroindol-6-yl, 3-bromoindol-6-yl, 3-methylindol-6-yl, 3-methoxyindol-6-yl, indazol-5-yl, 3-aminoindazol-5-yl, indazol-6-yl, benzothiazol-6-yl, 3-aminobenzisoxazol-5-yl;

(iv) benzimidazol-5-yl, 2-aminobenzimidazol-5-yl, or benzothiazol-6-yl;

(v) thien-2-yl, 5-methylthien-2-yl, 5-methylthio-thien-2-yl, 5-acetylthien-2-yl or thien-3-yl;

(vi) 3,4-methylenedioxyphenyl, 2,3-dihydroindol-6-yl, 3,3-dichloro-2-oxo-indol-6-yl or 1-methyl-3-aminoindazol-5-yl;

(vii) benzothiazol-2-yl, imidazo[1,2-a]pyrimidin-2-yl or tetrahydroimidazo[1,2-a]pyrimidin-2-yl;

(viii) 5-methylpyrazol-2-yl; (ix) 5-chloropyrid-2-yl;

(x) pyrid-3-yl, 6-chloropyrid-3-yl;

(xi) benzofur-2-yl, 5-chlorobenzofur-2-yl, 3-methylbenzofur-2-yl, 5-methylbenzofur-2-yl, 6-methoxybenzofur-2-yl;

(xii) indol-2-yl, 5-fluoroindol-2-yl, 5-chloroindol-2-yl, 5-methylindol-2-yl, 5-methoxindol-2-yl, 6-methoxyindol-2-yl and 1-methyl-indol-2-yl;

(xiii) 5-fluoroindol-6-yl; or (xiv) benzo[b]thiophen-2-yl, 5-chloro-benzo[b]thiophen-2-yl or 6-chlorobenzo[b]thiophen-2-yl.

In one embodiment the aromatic $R_2$ group is an optionally substituted phenyl, naphthyl, indolyl or isoindolyl group and accordingly, preferred compounds of the invention are of formula (II)

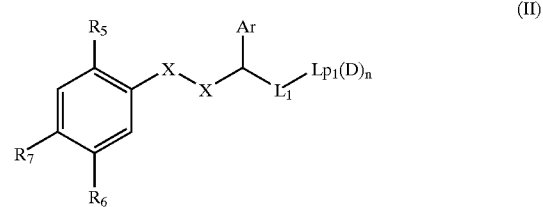

(II)

wherein $R_5$ is amino, hydroxy or hydrogen, and $R_6$ and $R_7$ which may be the same or different represent halo, nitro, thiol, cyano, haloalkyl, haloalkoxy, amido, hydrazido, amino, alkylthio, alkenyl, alkynyl or $R_1$ or taken together form a 5 or 6 membered fused carbocyclic ring or 5 membered heterocyclic ring, which may itself be substituted by $R_{1j}$, amino, halo, cyano, nitro, thiol, alkylthio, haloalkyl, haloalkoxy;

Ar is an unsubstituted or substituted aryl group, preferably phenyl;

X—X is —CONH—, —CH$_2$CH$_2$—, CH$_2$O—, —COO—, —CH$_2$NH—, —OCH$_2$— or —NHCH$_2$—, especially —CONH—;

$L_1$ is a valence bond or an organic linker group containing 1 to 4 backbone atoms selected from C, N, O and S;

$Lp_1$ is a cycloalkyl, azacycloalkyl, diazacycloalkyl, phenyl, naphthyl, adamantyl, decalinyl, bicycloalkyl, mono- or diazabicycloalkyl, mono- or bicyclo heteroaromatic or a linear or branched alkyl, alkylene, alkenyl or alkenylene group all optionally substituted by a group $R_3$, or a combination of at least two such groups linked by a spiro linkage or a single or double bond or by C=O, O, S, SO, $SO_2$, $CONR_{1e}$, $NR_{1e}$—CO—, $NR_{1e}$ linkage (for example, representative lipophilic groups include a methyl-cyclohexyl, methylcyclohexylmethyl, bispiperidinyl, methylphenylmethyl, phenylethyl, benzylpiperidinyl, benzoylpiperidinyl or phenylpiperazinyl and those as hereinbefore described);

D is a hydrogen bond donor group;

and n is 0, 1 or 2.

Suitable $R_2$ groups may be

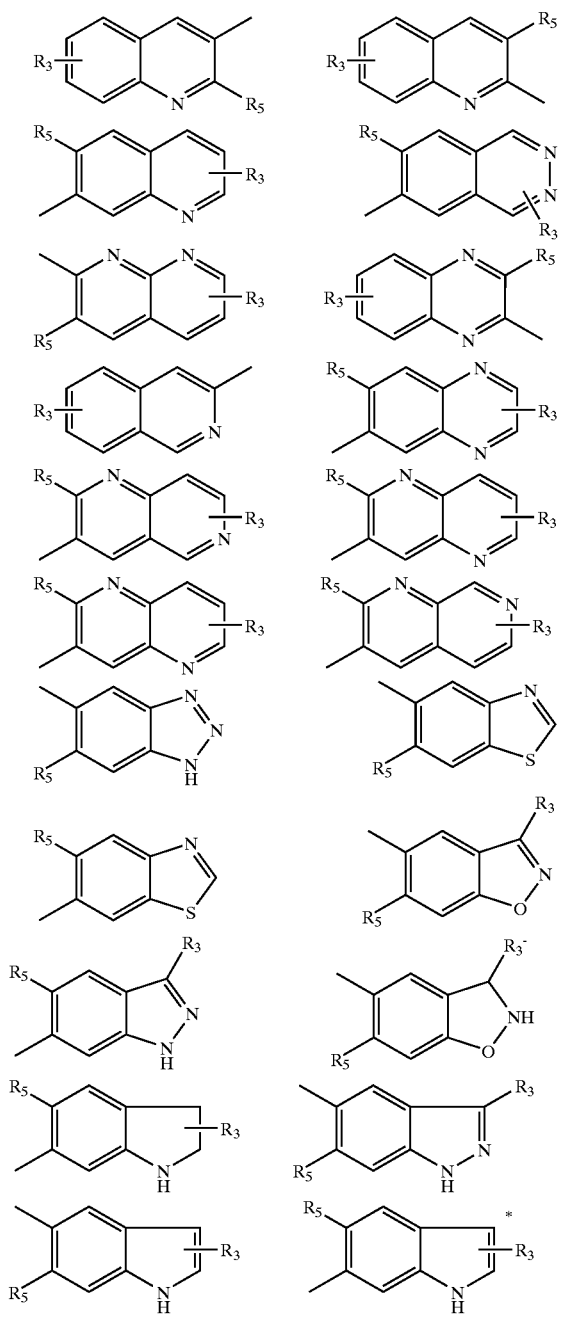

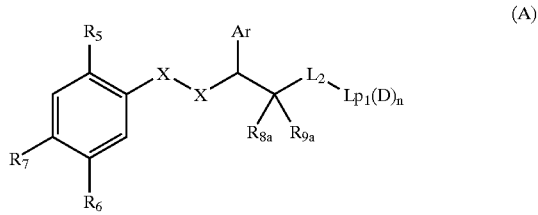

wherein $R_5$ is hydrogen, amino or hydroxy and $R_3$ (in relation to $R_2$) is halo, haloalkoxy, haloalkyl, cyano, nitro, amino, hydrazido, alkylthio, alkenyl, alkynyl or $R_{1j}$.

In a particularly favoured embodiment the $R_2$ group is an indole as marked by a * above in which $R_5$ is hydrogen and $R_3$ is a hydrogen or halogen present at the 3 position.

It is preferred that at least one of $R_6$ and $R_7$ be other than hydrogen and that $R_6$, if present, is preferably a substituent containing one or more polar hydrogens such as hydroxy, amino, alkylamino, alkylaminoalkyl, aminocarbonyl, alkylaminocarbonyl, hydrazo and alkylhydrazo; alternatively $R_6$ and $R_7$ are joined together in the formation of a naphthyl or indolyl or azaindolyl or diazaindolyl group.

It is especially preferred that $R_6$ be amino and $R_7$ be chloro, bromo, methyl, methoxy or vinyl; or that $R_6$ and $R_7$ taken together form an indolyl ring with the NH at the 6-position or taken together form a naphthyl ring.

In a further preferred embodiment the compounds of the invention are of formula (A)

(A)

[structure of formula A with $R_5$, $R_7$, $R_6$, Ar, X—X, $R_{8a}$, $R_{9a}$, $L_2$, $Lp_1(D)_n$]

(wherein $R_5$, $R_6$, $R_7$, Ar, X—X, $Lp_1$, $D_n$ are as hereinbefore defined; $L_2$ is a valence bond or an organic linker group containing 1 to 3 backbone atoms selected from C, N, O and S and $R_{8a}$ and $R_{9a}$ are hydrogen or taken together with the carbon atom to which they are attached form a carbonyl group). Again, in an alternative embodiment the phenyl derivative forming part of the $R_2$ functionality may instead be a nitrogen heterocyclic group, e.g. pyridine.

In one embodiment, $L_2$ comprises the backbone of an alpha amino acid, the lipophilic group being the side chain of the amino acid.

In one preferred embodiment $R_{8a}$ and $R_{9a}$ are hydrogen and $L_2$ is a OC=O or NHC=O group.

In a preferred embodiment, $L_2$ represents a valence bond and the lipophilic group is bound directly to a carbonyl alpha to the alpha atom via a nitrogen atom which forms part of the lipophilic group. Suitable lipophilic groups in this case therefore include piperidinyl, pyrrolidinyl and piperazinyl.

In a preferred embodiment the piperidine or piperazinyl group is further substituted by a phenyl, benzyl, phenoxy, piperidine, pyridine or benzoyl group, optionally substituted on the phenyl ring by one or more $R_3$ groups. In a more preferred embodiment a piperazine is substituted with a phenyl group substituted at the 2-position with an electron withdrawing group such as fluoro, nitro, triazolyl, cyano, alkoxycarbonyl, aminocarbonyl, aminosulphonyl, alkylaminosulphonyl and, especially preferred, alkylsulphonyl; and, at the 4-position, with hydrogen, fluoro, alkoxy or hydroxy. In another more preferred embodiment a piperidine is substituted at the 4-position with 4-piperidine which itself may be substituted on nitrogen by alkyl or aminocarbonylalkyl or alkylaminocarbonyl alkyl.

In a further embodiment, the lipophilic group has attached a group of the formula —$COOR_{1g}$ or —CON-aminoacid or ester derivative thereof (where $R_{1g}$ is as defined for $R_{1a}$).

Particularly preferred compounds are those of formula (G)

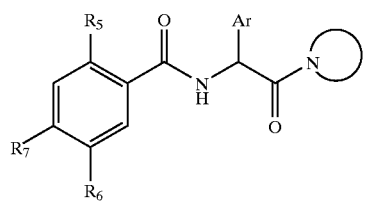

(G)

(wherein Ar, $R_6$ and $R_7$ are as hereinbefore defined, $R_5$ represents hydrogen or amino and

represents a cyclic group) or of formula (H)

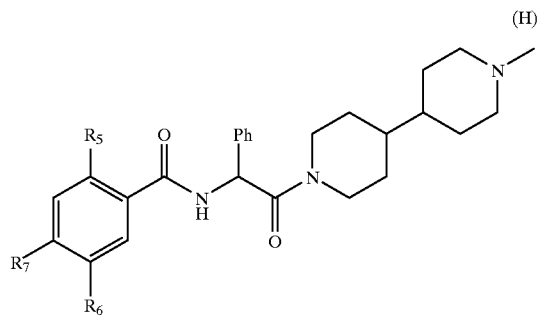

(H)

(wherein $R_6$ and $R_7$ are as hereinbefore defined, and $R_5$ represents hydrogen or amino). In a preferred embodiment $R_6$ is amino and $R_7$ a halogen, especially chlorine.

Again, in an alternative embodiment the phenyl derivative forming part of the $R_2$ functionality in formulae (G) and (H) may instead be a nitrogen heterocyclic group, e.g. pyridine, indole.

In another embodiment the group binding the alpha carbon atom to the lipophilic group comprises a heterocyclic group. Accordingly, preferred compounds of the invention also include those of formula (III)

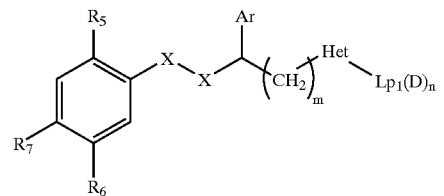

(III)

(wherein $R_5$, $R_6$, $R_7$, Ar, X—X, $Lp_1$, $D_n$ are as hereinbefore defined;

m is 0, 1 or 2;

Het is a 5 or 6-membered heterocyclic group interrupted by 1, 2 or 3 heteroatoms selected from O, N and S optionally substituted by a group $R_{3b}$ where $R_{3b}$ is as defined for $R_3$).

Again, in an alternative embodiment the phenyl derivative forming part of the $R_2$ functionality may instead be a nitrogen heterocyclic group, e.g. pyridine.

Where Het is a five membered ring, the two ring atoms at which it is connected are preferably separated by one ring atom. Where Het is a six-membered ring, the two ring atoms at which it is connected are preferably separated by one or two ring atoms. Representative heterocyclic groups include thiazole, oxazole, oxadiazole, triazole, thiadiazole or imidazole. Where the heterocyclic group is substituted by $R_{3b}$ this is preferably a COOH or $COOR_{1h}$ connected to the heterocycle via a valence bond or alkylene chain (where $R_{1h}$ is as defined for $R_{1a}$).

In a further embodiment, the lipophilic group has attached a group of the formula —$COOR_{1g}$ or —CON-aminoacid or ester derivative thereof.

In an alternative embodiment, the main aromatic $R_2$ ring in the compounds of the invention is a five membered aromatic ring leading to compounds of formula (IV) or (IVa)

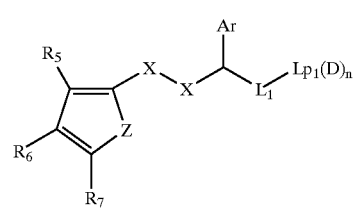

(IV)

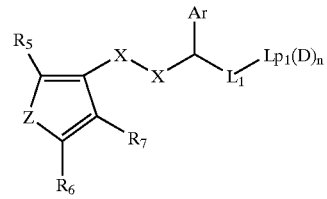

(IVa)

(wherein $R_5$, $R_6$, $R_7$, X—X, Ar, $L_1$, $Lp_1$, D and n are as hereinbefore described for formula (II) and Z represents N, O or S). It is preferred that at least one of $R_6$ and $R_7$ be other than hydrogen, or that $R_6$ and $R_7$ taken together enable the formation of an indolyl, or azaindolyl group or diazaindolyl group. Preferences for other substituents are as for formula (A) above. Examples of possible fused systems are given below.

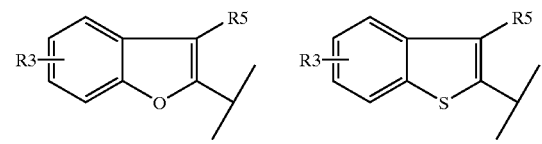
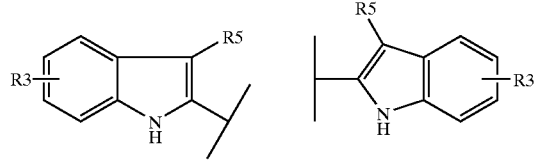
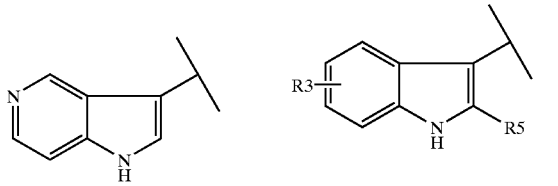
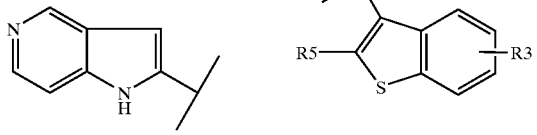
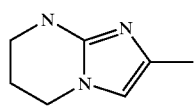

Hence in a preferred embodiment the compounds of the invention are of formula C or D

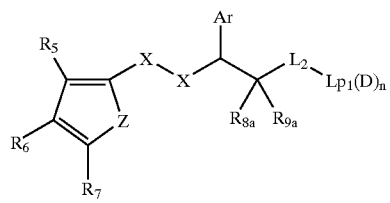
(C)

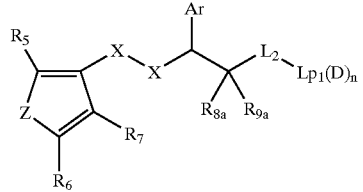
(D)

(wherein $R_5$, $R_6$, $R_7$, Ar, X—X, Z, $R_8$, $R_9$, $L_2$ $Lp_1$, $D_n$ are as hereinbefore defined)

references for Ar, X—X, $R_{8a}$, $R_{9a}$, $L_2$, $Lp_1$, $D_n$ are as for formula (A) above; or compounds of formula E or F:

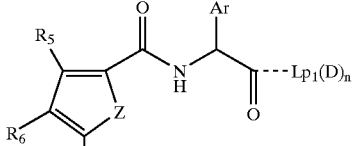
(E)

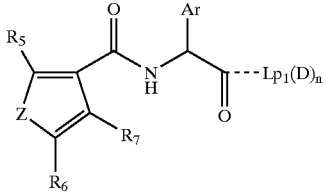
(F)

wherein $Lp_1$ is connected to the carbonyl via a nitrogen atom, $R_6$, $R_7$, Ar, Z, $Lp_1$, $D_n$ are as hereinbefore defined and $R_5$ is hydrogen or amino) preferences for Ar, $Lp_1$, $D_n$ are as for formula (A) above.

Particularly preferred are the compounds of formula I of Examples 35, 63, 66, 73, 100, 318 and 320, and physiologically tolerable salts thereof.

As previously mentioned, a number of compounds of the invention have been found to be excellent mixed inhibitors ITS in that they inhibit both the serine proteases Factor Xa and thrombin. Such mixed inhibitors are preferably based on the formula (L)

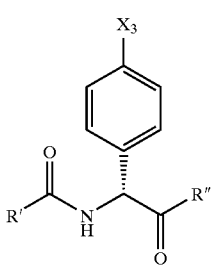
(L)

wherein R' represents

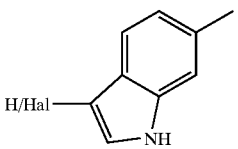 or 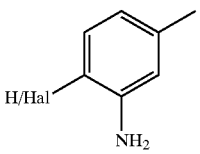

$X_3$ represents hydrogen or a polar group such as amino or $CONH_2$, especially $CONH_2$; and R" represents a cyclic group bound to the carbonyl by a nitrogen atom or an optionally substituted group of formula

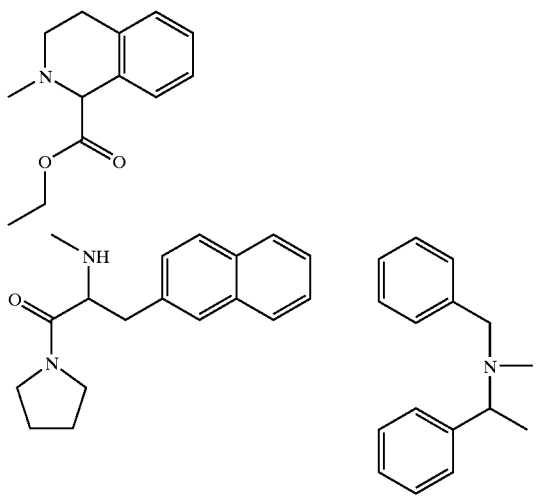

The compounds of the invention may be prepared by conventional chemical synthetic routes or by routes as illustrated by the following examples, e.g. by amide bond formation to couple the aromatic function to the alpha atom and to couple the lipophilic function to the alpha atom.

Where the alpha atom is a carbon, the cyclic group-alpha atom combination may conveniently derive from an alpha amino acid with the aromatic deriving from for example an acid derivative of a compound based on $R_2$, e.g. o-aminobenzoic acid. Amide formation from such reagents (in which any amino or hydroxyl function may if desired be protected during some or all of the synthesis steps) yields a compound of formula (V).

$$R_2\text{—CONH—CH(Cy)-COOH} \qquad (V)$$

(where Cy and $R_2$ are as defined above).

The lipophilic group (and optionally simultaneously the hydrogen bond donor) may then conveniently be introduced by reaction of a compound of formula (V) (or another analogous carboxylic acid) optionally after transformation into an activated form, e.g. an acid chloride or active ester, with a lipophilic group carrying an amine, hydroxylamine, hydrazine or hydroxyl group, e.g. to produce compounds with linkages of —CO—NR$_{1d}$—, —CO—NR$_{1d}$—O—, —CO—NR$_{1d}$—NR$_{1d}$— and —CO—O— from the alpha atom (where it is a carbon) to the lipophilic group. Cyclisation can be base induced via nucleophilic attack of the alpha atom on a leaving group on the active side chain. If necessary the amide linkage can be reduced using an appropriate reducing agent employing the necessary protection depending on whether concurrent reduction of the carboxylic acid moiety is also desired.

Alternatively a compound of formula V or another analogous carboxylic acid may be transformed into an alcohol by reaction with isobutylchloroformate and reduction with sodium borohydride.

Such an alcohol, e.g. of formula VI $$R_2\text{—CONH—CH(Cy)CH}_2\text{OH} \qquad (VI),$$

can be reacted to introduce the lipophilic group by reactions such as:

alkylation with an alkyl halide in the presence of a base;
under Mitsunobu conditions, such as reaction with diethyl azodicarboxylate/triphenylphosphine and a hydroxylated aryl compound;
by reaction with an activated carboxylic acid (e.g. an acid chloride) or with a carboxylic acid and diethylazodicarboxylate/triphenylphosphine;
by reaction with an isocyanate; and
by treatment with methanesulphonyl chloride or trifluoromethanesulphonic anhydride and reaction with an amine, or with a thiol optionally followed by oxidation, e.g. with potassium metaperiodate or hydrogen peroxide.

Alternatively, the reactions described above may be performed on a corresponding compound of formula (VI) in which $R_2$ is replaced with a protecting group, such as t-butoxycarbonyl (Boc), followed by deprotection and introduction of the group $R_2$.

In this way compounds with linkages of —CH$_2$—O—, —CH$_2$—O—CO—, —CH$_2$—O—CO—NR$_{1d}$—, —CH$_2$—NR$_{1d}$—, —CH$_2$—S—, —CH$_2$—SO— and —CH$_2$—SO$_2$— between the alpha carbon and the lipophilic group may be produced.

Alternatively the alcohol can be oxidized to form a corresponding aldehyde (e.g. by oxidation with manganese dioxide or DMSO/oxalyl chloride or DMSO/SO$_3$ or Dess-Martin reagent) which may be reacted to introduce the lipophilic group by reactions such as:

reaction with Wittig reagents or Horner-Emmons reagents, optionally followed by reduction of the resulting carbon:carbon double bond using H$_2$/Pd-carbon;
reaction with an organometallic, eg a Grignard reagent, optionally followed by reaction on the resulting hydroxyl group, such as oxidation (eg with MnO$_2$, DMSO/oxalyl chloride or Dess-Martin reagent), alkylation (eg with an alkyl halide in the presence of a base in a solvent such as DMF), arylation (eg with diethylazo dicarboxylate/triphenyl phosphine and a hydroxyaryl compound), ester formation (eg with an acid chloride or with a carboxylic acid and diethylazido dicarboxylate/triphenyl phosphine), or carbamate formation (eg with an isocyanate);
by reaction with an amine followed by reduction, e.g. with sodium cyanoborohydride;
by reaction with a hydrazine; or
by reaction with a carbazide.

In this way compounds with linkages of —CH=CR$_{1d}$—, —CH$_2$—CHR$_{1d}$—, —CHOH—, —CHR$_{1d}$—O—, —CHR$_{1d}$—O—CO—, —CHR$_{1d}$—O—CO—NR$_{1d}$—, —CO—, —CH$_2$—NR$_{1d}$—, —CH=N—NR$_{1d}$— and —CH=N—NR$_{1d}$—CO—NR$_{1d}$— between the alpha carbon and the lipophilic group may be produced.

The transformation of alcohol to amine referred to above may be used to produce an amine reagent for lipophtilic group introduction, e.g. a compound $$R_2\text{—CONH—CH(Cy)—CH}_2\text{—NR}_{1d}\text{H}.$$

Such an amine reagent may be reacted to introduce the lipophilic group, e.g. by acylation with an acid halide or activated ester, by reaction with isocyanate, by reaction with an isothiocyanate, or by reaction with a sulphonyl chloride. In this way compounds with linkages of —CH$_2$NR$_{1d}$—CO—, —CH$_2$—NR$_{1d}$—CO—NR$_1$—, —CH$_2$NR$_{1d}$—CS—NR$_{1d}$— and —CH$_2$NR$_{1d}$—SO$_2$— between the alpha carbon and the lipophilic groups may be produced.

The transformation of acid to amide referred to above may be used to produce an amide reagent for introduction of the lipophilic group, e.g. a compound $$R_2\text{—CONH—CH(Cy)—CON(R}_{1d})_2.$$

Such amides may be reacted to introduce lipophilic groups, e.g. by reaction with a haloketone (e.g. phenacyl bromide). This provides a linkage

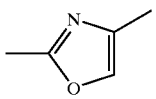

from alpha carbon to lipophilic group.

Analogously the amide may be transformed to a thioamide by reaction with Lawesson's reagent and then reacted with a haloketone to form a linkage

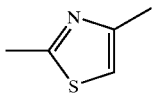

The amide reagent may likewise be transformed to a nitrile reagent by dehydration, e.g. with trifluoroacetic anhydride.

The nitrile reagent may be reacted with hydrazine then with acyl halide and then cyclized, (e.g. with trifluoroacetic anhydride) to produce a linkage

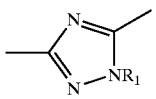

Alternatively it may be treated with hydroxylamine then reacted with acyl halide and cyclized (e.g. with trifluoroacetic anhydride) to produce a linkage

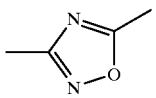

The hydrazide produced by reaction of a carboxylic acid reagent with hydrazine discussed above may likewise be used as a reagent for lipophilic group introduction, e.g. as a compound of formula

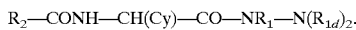

Thus the hydrazide reagent can be reacted with an acyl halide and cyclized, e.g. with trifluoroacetic anhydride to yield a linkage

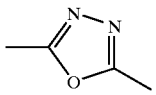

or reacted with an acyl halide or an isocyanate to yield linkages —CO—NR$_{1d}$—NR$_{1d}$—CO— and —CO—NR$_{1d}$—NR$_{1d}$—CO—NR$_{1d}$— respectively.

Alternatively the hydrazide may be transformed by reaction with Lawesson's reagent and then reacted with an acyl halide and cyclized (e.g. with trifluoroacetic anhydride) to produce the linkage

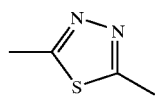

An alternative route to these compounds is to carry out any of the above chemical reactions to incorporate the lipophilic group (and optional H bond donor) into a protected intermediate such as a compound of formula (VII).

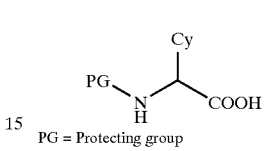

PG = Protecting group

The protecting group may then be removed before coupling of the for example o-amino benzoic acid (optionally protected).

The protection of amino and carboxylic acid groups is described in McOmie, Protecting Groups in Organic Chemistry, Plenum Press, NY, 1973, and Greene and Wuts, Protecting Groups in Organic Synthesis, 2nd. Ed., John Wiley & Sons, NY, 1991. Examples of carboxy protecting groups include $C_1$–$C_6$ alkyl groups such as methyl, ethyl, t-butyl and t-amyl; aryl($C_1$–$C_4$)alkyl groups such as benzyl, 4-nitrobenzyl, 4-methoxybenzyl, 3,4-dimethoxybenzyl, 2,4-dimethoxybenzyl, 2,4,6-trimethoxybenzyl, 2,4,6-trimethylbenzyl, benzhydryl and trityl; silyl groups such as trimethylsilyl and t-butyldimethylsilyl; and allyl groups such as allyl and 1-(trimethylsilylmethyl)prop-1-en-3-yl.

Examples of amine protecting groups (PG) include acyl groups, such as groups of formula RCO in which R represents $C_{1-6}$ alkyl, $C_{3-10}$ cycloalkyl, phenyl $C_{1-6}$ alkyl, phenyl, $C_{1-6}$ alkoxy, phenyl $C_{1-6}$ alkoxy, or a $C_{3-10}$ cycloalkoxy, wherein a phenyl group may be optionally substituted, for example by one or two of halogen, $C_1$–$C_4$ alkyl and $C_1$–$C_4$ alkoxy. Preferred amino protecting groups include benzyloxycarbonyl (CBz), t-butoxycarbonyl (Boc) and benzyl.

Compounds of the type (VII) made be prepared (for example) by one or more of the following methods.

(i) from aryl or heteroaryl aldehydes via the Strecker synthesis or modifications thereof, via Bucherer-Bergs hydantoin synthesis, or via the Ugi methodology (Isonitrile Chemistry, Ugi I. Ed.; Academic: New York, 1971; pp145–199) with removal and replacement of protecting groups;

(ii) from styrenes via Sharpless methodology (J. Am. Chem. Soc. 1998, 120, 1207–1217)

(iii) from aryl boronic acids via Petasis methodology (Tetrahedron, 1997, 53, 16463–16470) with removal and replacement of protecting groups;

(iv) from aryl and heteroaryl acetic acids—via Evan's azidation (Synthesis, 1997, 536–540) or by oximation, followed by reduction and addition of protecting groups; or (v) from existing aryl glycines by manipulation of functional groups, for example, alkylation of hydroxy groups, palladium assisted carbonylation of triflates derived from hydroxy groups and further manipulation of the carboxylic esters to give carboxylic acids by hydrolysis, carboxamides by activation of the carboxylic acid and coupling with amines, amines via Curtius reaction on the carboxylic acid or (vi) from aliphatic, carbocylic and non-aromatic heterocyclic aldehydes and ketones using a Horner-Emmons reaction with N-benzyloxycarbonyl)-α-phosphonoglycine trimethyl ester (Synthesis, 1992, 487–490).

A starting reagent for lipophilic group introduction where the alpha atom is nitrogen may be produced for example by reaction of a beta protected hydrazine (such protection to be chosen as to be compatible with the subsequent reagents to be employed) with phosgene, diphosgene, triphosgene or N,N'carbonyl duimidazole to give a reactive compound of the type:

$$PG-\underset{H}{N}-\underset{\underset{O}{\|}}{C}(Cy)-\text{Cl or imidazole}$$

PG = Protecting group

This intermediate may be used as has been described above for the carboxylic starting reagents where the alpha atom is carbon.

Removal of the protecting group by standard methods and coupling with an activated aryl carboxylic acid will give compounds of the type $$R_2-CONH-N(Cy)-L-Lp(D)_n$$

(where $R_2$, X, Y, Cy, L, Lp and D are as defined above).

Thus viewed from a further aspect the invention provides a process for the preparation of a compound according to the invention which process comprises coupling a lipophilic group to a compound of formula (VIII)

$$R_2-(X)_2-Y(Cy)-Z_1 \qquad (VIII)$$

(wherein $R_2$, X, Y and Cy are as defined above and $Z_1$ is a reactive functional group), and optionally subsequently coupling a hydrogen bond donor group to said lipophilic group.

Instead of introducing the group L-Lp(D)$_n$ as the final stage process step, the compounds of formula I may alternatively be prepared by a process in which the group $R_2$ is introduced in the final process step.

Thus viewed from another aspect the invention provides a process for the preparation of a compound according to the invention which process comprises coupling a lipophilic group to a compound of formula (IX)

$$Z_2-Y(CY)-L-Lp(D)_n \qquad (IX)$$

(wherein Y, Cy, L, Lp D, and n are as defined above and $Z_2$ is HX or a reactive functional group), or a protected derivative thereof, with a compound of formula (X)

$$R_2-Z_3$$

(wherein $R_2$ is as defined above and $Z_3$ is XH or an appropriate reactive group), or a protected derivative thereof, followed if necessary by the removal of any protecting groups.

Thus, for a compound of formula I in which X—X represents CONH, a compound of formula (IX) in which $Z_2$ is $H_2N$ may be reacted with a compounds of formula (X) in which $Z_3$ is COOH or a reactive derivative thereof, such as a acyl halide or an anhydride, for example as described in the Examples herein.

Where the lipophilic group Lp comprises more than one group, it may generally be formed by coupling these groups together at an appropriate stage in the preparation of the compound of formula I using conventional methods or as described in the Examples.

For a compound of formula I in which Lp comprises an azacycloalkyl or diazacycloalkyl group of formula $$-X_a\underset{(CH_2)_r}{\diagup\diagdown}X_b-(L_a)_s-(G)_t-(L_b)_u-R_{10}$$

in which $X_b$ is N and each of s and u is 0, alkylating the amino group of a corresponding compound in which the corresponding residue is of formula $$-X_a\underset{(CH_2)_r}{\diagup\diagdown}NH$$

using a conventional alkylating method. The alkylation may be carried out using any conventional method; however, generally preferred is a reductive alkylation using the appropriate aldehyde or ketone, for example as described in the Alkylation Methods in the Examples.

Thus, a particular starting material for the alkylation is one of formula $$R_2-CO-NH-C(Cy)-L-X_a\underset{(CH_2)_r}{\diagup\diagdown}NH$$

in which $X_a$ is N and L is CO or $X_a$ is CH and L is CONH, CONHCH$_2$ or CH$_2$NHCO.

For a compound of formula I in which Lp comprises an azacycloalkyl or diazacycloalkyl group of formula $$-X_a\underset{(CH_2)_r}{\diagup\diagdown}X_b-(L_a)_s-(G)_t-(L_b)_u-R_{10}$$

in which $R_{10}$ is a group of formula $$-X_c\underset{(CH_2)_v}{\diagup\diagdown}X_d-R_{11}$$

in which $X_d$ is N and $R_{11}$ is (1–6C)alkyl, alkylating the amino group of a corresponding compound of formula I in which $R_{11}$ is hydrogen using a conventional method. Generally preferred is a reductive alkylation using the appropriate aldehyde or ketone, for example as described in the Alkylation Methods in the Examples.

For a compound of formula I in which Lp comprises an azacycloalkyl or diazacycloalkyl group of formula $$-X_a\underset{(CH_2)_r}{\diagup\diagdown}X_b-(L_a)_s-(G)_t-(L_b)_u-R_{10}$$

in which $X_b$ is CH and $(L_a)_s-(G)_t-(L_b)_u$ is O and $R_{10}$ is phenyl or pyridyl, coupling a corresponding compound containing a group of formula

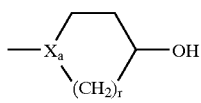

with phenols or 3-hydroxypyridine using Mitsunobu conditions, eg. DEAD (diethyl azodicarboxylate)/Ph₃P or 2-triphenylphosphonium 4,4-dimethyl-tetrahydro-1,2,5-thiadiazole to give aryloxy or 3-pyridoxy substituted piperidines or pyrrolidine. Alternatively the hydroxy group may be reacted with sodium hydride and 2-chloro or 4-chloropyridine to give 2-pyridoxy or 4-pyridoxy substituted piperidines or pyrrolidines.

For a compound of formula I in which —L—Lp(D)$_n$ is

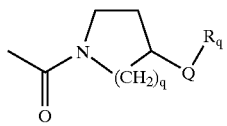

in which Q is a direct bond, reductively alkylating an amine of formula H–Q using a corresponding compound in which the corresponding residue is a ketone of formula

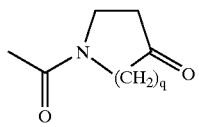

For a compound of formula I in which —L—Lp(D)$_n$ is

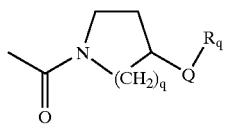

in which Q is methylene, reductively alkylating an amine of formula H—NR$_a$R$_b$ using a corresponding compound in which the corresponding residue is an aldehyde of formula

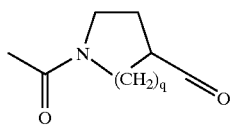

The intermediates used in the process according to the invention may generally, when not commercially available, be prepared by conventional methods or as described in the Examples herein.

For example, methyl 1-acetyl-3-formylindole-6-carboxylic acid may be converted to the 3-formate by the method of Merour et al (Synthesis, 1994, 411) and then reacted with trimethyl orthoformate to give methyl 1-acetyl-3-methoxyindole-6-carboxylate which is then hydrolysed to methyl 1-acetyl-3-methoxyindole-6-carboxylate.

5-Fluoroindole-6-carboxylic acid may be prepared from 4-fluoro-3-methoxyaniline by the following method. 4-Fluoro-3-methoxyaniline is treated with glyoxal-1,1-dimethyl acetal and then hydrogenated over Pd/C. The product is N-protected with methanesulphonyl chloride and then cyclised using titanium tetrachloride in toluene. Demethylation with BBr₃ to the phenol followed by reaction with triflic anhydride and then palladium carbonylation in methanol gives the methyl ester, which is then converted to 5-fluoro-1-methanesulphonylindole-6-carboxylic acid by hydrolysis with lithium hydroxide. This 'benzoyl' component may be reacted as previously described and deprotected by hydrolysis with sodium hydroxide at 100° C.

The intermediates disclosed herein, including the novel intermediates of formulae (V), (VI), (VII), (VIII) and (IX) are provided as further aspects of the invention.

The compounds of the invention may be administered by any convenient route, e.g. into the gastrointestinal tract (e.g. rectally or orally), the nose, lungs, musculature or vasculature or transdermally. The compounds may be administered in any convenient administrative form, e.g. tablets, powders, capsules, solutions, dispersions, suspensions, syrups, sprays, suppositories, gels, emulsions, patches etc. Such compositions may contain components conventional in pharmaceutical preparations, e.g. diluents, carriers, pH modifiers, sweeteners, bulking agents, and further active agents. Preferably the compositions will be sterile and in a solution or suspension form suitable for injection or infusion. Such compositions form a further aspect of the invention.

The following are examples of pharmaceutical compositions of compounds according to the invention.

Formulation 1
Hard gelatin capsules are prepared using the following ingredients:

|  | Quantity (mg/capsule) |
| --- | --- |
| Active Ingredient | 250 |
| Starch, dried | 200 |
| Magnesium stearate | 10 |
| Total | 460 mg |

The above ingredients are mixed and filled into hard gelatin capsules in 460 mg quantities.

Formulation 2

Tablets each containing 60 mg of active ingredient are made as follows:

| Active Ingredient | 60 mg |
| --- | --- |
| Starch | 45 mg |
| Microcrystalline cellulose | 35 mg |
| Polyvinylpyrrolidone | 4 mg |
| Sodium carboxymethyl starch | 4.5 mg |
| Magnesium stearate | 0.5 mg |
| Talc | 1 mg |
| Total | 150 mg |

The active ingredient, starch, and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50° C. and passed through a No. 18 mesh U.S. sieve. The sodium carboxymethyl starch, magnesium stearate, and talc, previously passed through a No. 60 mesh U.S. sieve, are then added to the granules which, after mixing, are compressed on a tablet machine to yield tablets each weighing 150 mg.

It is believed that the compounds of the invention will have excellent oral bioavailability.

Viewed from this aspect the invention provides a pharmaceutical composition comprising a serine protease inhibitor according to the invention together with at least one pharmaceutically acceptable carrier or excipient. The pharmaceutical composition may also optionally comprise at least one further antithrombotic and/or thrombolytic agent.

Viewed from a further aspect the invention provides the use of a serine protease inhibitor according to the invention for the manufacture of a medicament for use in a method of treatment of the human or non-human animal body (e.g. a mammalian, avian or reptilian body) to combat (i.e. treat or prevent) a condition responsive to said inhibitor.

Viewed from a further aspect the invention provides a method of treatment of the human or non-human animal body (e.g. a mammalian, avian or reptilian body) to combat a condition responsive to a serine protease inhibitor (e.g. a condition such as a thrombotic disorder responsive to a factor Xa inhibitor), said method comprising administering to said body an effective amount of a serine protease inhibitor according to the invention.

The dosage of the inhibitor compound of the invention will depend upon the nature and severity of the condition being treated, the administration route and the size and species of the patient. However in general, quantities of from 0.01 to 100 μmol/kg bodyweight will be administered.

All publications referred to herein are hereby incorporated by reference.

The invention will now be described further with reference to the following non-limiting Examples.

EXPERIMENTAL

Abbreviations used follow IUPAC-IUB nomenclature. Additional abbreviations are Hplc, high-performance liquid chromatography; DMF, dimethylformamide; DCM, dichloromethane; HAOT, 1-hydroxy-7-azabenzotriazole; HATU, [O-(7-azabenzotriazol-1-yl)-1,1,3,3-tetramethyluronium hexafluorophosphate]; Fmoc, 9-Fluorenylmethoxycarbonyl; HOBt, 1-hydroxybenzotriazole; TBTU, 2-(1H-(benzotriazol-1-yl)-1,1,3,3-tetramethyluroniumtetrafluoroborate; EDCI, 1-(3-Dimethylaminopropyl)-3-ethylcarbodiimide hydrochloride; DIPEA, diisopropylethylamine; Boc, tertiary butyloxycarbonyl; DIPCI, diisopropylcarbodiimide; DBU, 1,8-diazabicyclo [5.4.0]undec-7-ene; TEA, triethylamine; Rink linker, p-[(R, S)-α-[1-(9H-Fluoren-9-yl)methoxyformamido]-2,4-dimethoxybenzyl]phenyl acetic acid; TFA, trifluoroacetic acid; MALDI-TOF, Matrix assisted laser desorption ionisation—time of flight mass spectrometry, RT, retention time.

Amino acid derivatives, resins and coupling reagents were obtained, for example, from Novabiochem (Nottingham, UK) and other solvents and reagents from Rathburn (Walkerburn, UK) or Aldrich (Gillingham, UK) and were used without further purification. All solution concentrationsare expressed as % Vol./% Vol. unless otherwise stated.

Purification: Purification was by gradient reverse phase Hplc on a Waters Deltaprep 4000 at a flow rate of 50 ml/min. using a Deltapak C18 radial compression column (40 mm×210 mm, 10–15 mm particle size). Eluant A consisted of aqTFA (0.1%) and eluant B 90% MeCN in aq TFA(0.1%) with gradient elution (Gradient 1, 0 min. 20% B then 20% to 100% over 36 min., Gradient 2, 0 min. 5% B for 1 min. then 5% B to 20% B over 4 min., then 20% to 60% over 32 min. or Gradient 3, 0 min. 20% B then 20% to 100% over 15 min.). Fractions were analysed by analytical Hplc and MALDI-TOF before pooling those with >95% purity for lyophilisation.

Analysis: Analytical Hplc was on a Shimadzu LC6 gradient system equipped with an autosampler, a variable wavelength detector at flow rates of 0.4 ml/min. Eluents A and B as for preparative Hplc. Columns used were Techogel15 C18 (2×150 mm)(Hplc Technology), Magellan C8 column (2.1×150 mm, 5 μm particle size) and Luna C18 (2.1×150 mm, 5 μM particle size). (Phenomenex)) Purified products were further analysed by MALDI-TOF and nmr. NMR denotes an $^1$HNMR consistent with the structure was obtained Synthesis of Inhibitors Method 1: Using a solid phase strategy on a Protein Technologies, Symphony Multiple Peptide Synthesiser by attachment of bis amino compounds to Peg-trityl chloride resin: Trityl chloride resin was typically treated with greater than 2 fold excess of the di-amine in dry DCM. The resin was further modified by the attachment of acids.

Activation of Fmoc protected amino acid (2–5eq) was by TBTU/DIPEA, all couplings (minimum 120 min.) were carried out in DMF. Deprotection of the Fmoc group was achieved with 20% piperidine in DMF. In the next stage other acid substituents were added as the HOBt or HOAt esters either by activation with HBTU/HATU or HATU/EDCI with or without Boc protection of amino groups. Cleavage of the products from the resin was by treatment (30 min., ambient) with 10% triethylsilane in TFA, filtration, evaporation and trituration with diethylether Synthesis Using the Symphony Multiple Peptide Synthesiser.

The Symphony Multiple Peptide Synthesiser is charged with DMF, DCM, TBTU in DMF(450 mM), DIPEA in DMF (900 mM), 20% piperidine in DMF. Resins are held in plastic reaction vessels that allow the introduction of reagents and solvents and nitrogen for agitation or air drying.

A typical synthesis cycle on the Symphony is as follows:—

The reaction vessel containing the resin (0.1 mmol) is charged with the Fmoc protected amino acid (0.5 mol) and then this is dissolved in DMF (2.5 ml), treated with TBTU (0.56 mmol, 1.25 ml) and DIPEA (1.1 mmol, 1.25 ml) and agitated with nitrogen for 2 hours (agitation times may vary). After coupling the resin is washed with DMF (6×5 ml) then deprotected with 20% piperidine in DMF (2×5 ml for 1 min. each, then 1×5 ml for 8 min.) the resin is then washed with DMF (6×5 ml).

Example 1

1-(2-Amino-4-chlorobenzoyl-D-phenylglycinyl)-4,4'-bispiperidine 4,4-Bipiperidine dihydrochloride (4 mmol, 1 g) was dissolved in water (5 ml) and 2M sodium hydroxide solution (10 mmol, 5 ml) added. The solution was extracted with ethylacetate (2×50 ml) the combined extracts were washed with water, dried over anhydrous sodium carbonate, filtered and evaporated to give the 4,4 bipiperidine (0.35 g) as a white solid. The 4,4 bipiperidine was dissolved in dry DMF (2 ml) and added to Peg-tritylchloride resin (0.95 mmol/g, 1.5 g) pre swollen in dry DCM (10 ml). After 2 h the resin was washed with DCM (6×5 ml), DMF (6×5 ml) and DCM (6×5 ml). The resin was then air dried to allow aliquots to be taken.

The 4,4 bipiperidine trityl resin (0.1 mmol) was treated with Fmoc-D-Phenylglycine (0.5 mmol, 187 mg), DMF (2.5 ml), TBTU in DMF (1.25 ml of a 450 mM solution) and DIPEA in DMF (1.25 ml of a 900 mM solution). The mixture was agitated with nitrogen for 2 hours. Deprotection and washing as above.

A solution of 4-chloroanthranilic acid (87 mg 0.5 mmole) in dry dimethylformamide (DMF) was treated successively with HOAt (102 mg 0.75 mmole) and EDCI (115 mg 0.6 mmole) and stirred at room temperature for 10 min. The mixture was transferred to the reaction vessel on the Symphony and agitated for 2 hours with nitrogen. The resin was washed with DMF (6×5 ml), DCM (6×5 ml) and air dried. The product was cleaved from the resin with 10% triethylsilane in TFA (10 ml) for 30 minutes, the resin filtered off and the TFA solution evaporated to dryness and triturated with diethyl ether to give the crude product. The crude product was dissolved in water (10 ml), filtered and purified by preparative reverse phase Hplc.

$^1$H nmr (CD$_3$CN) 7.30 (6H, m); 6.60 (1H, s); 6.55 (1H, d); 5.85 (1H, s); 4.40 (1H, m); 3.75 (1H, m); 2.30–2.95 (6H, m); 1.60 (4H, m); 1.10 (6H, m)

MS TOF 456 (M+1$^+$).

Hplc (Magellan C8, Gradient 3, water/acetonitrile/TFA) rt 11.77 min.

Example 2
1-(2-Amino-5-bromobenzoyl-D-phenylglycinyl)-4,4'-bispiperidine $^1$H nmr (CD$_3$CN) 7.30 (7H, m); 6.50 (1H, d); 5.85 (1H, s); 4.40 (1H, m); 3.75 (1H, m); 2.30–2.95 (6H, m); 1.60 (4H, m); 1.10 (6H, m)

MS TOF 500 (M+1$^+$).

Hplc (Magellan C8, Gradient 3, water/acetonitrile/TFA) rt 11.31 min.

Example 3
1-(2-Amino-4-methylbenzoyl-D-phenylglycinyl)-4,4'-bispiperidine $^1$H nmr (CD$_3$CN) 7.30 (6H, m); 6.50 (1H, s); 6.45 (1H, d); 5.80 (1H, s); 4.40 (1H, m); 3.75 (1H, m); 2.30–2.95 (6H, m); 2.05 (3H, s); 1.60 (4H, m); 1.10 (6H, m)

MS TOF 436 (M+1$^+$).

Hplc (Magellan C8, Gradient 3, water/acetonitrile/TFA) rt 9.22 min.

Example 4
1-(2-Amino-5-methylbenzoyl-D-phenylglycinyl)-4,4'-bispiperidine $^1$H nmr (CD$_3$CN) 7.30 (7H, m); 6.50 (1H, d); 5.85 (1H, s); 4.40 (1H, m); 3.75 (1H, m); 2.30–2.95 (6H, m); 1.60 (4H, m); 1.10 (6H, m).

MS TOF 436 (M+1$^+$).

Hplc (Magellan C8, Gradient 3, water/acetonitrile/TFA) rt 8.74 min.

Example 5
1-(2-Amino-5-methoxybenzoyl-D-phenylglycinyl)-4,4'-bispiperidine $^1$H nmr (CD$_3$CN) 7.55 (6H, m); 7.30 (1H, d); 6.95 (1H, m); 6.15 (1H, s); 4.40 (1H, m); 3.75 (1H, m); 3.60 (3H, s); 2.30–2.95 (6H, m); 2.20 (3H, s); 1.60 (4H, m); 1.10 (6H, m)

MS TOF 452 (M+1$^+$).

Hplc (Magellan C8, Gradient 3, water/acetonitrile/TFA) rt 8.20 min.

Example 6
1-(3-Methylbenzoyl-D-phenylglycinyl)-4,4'-bispiperidine $^1$H nmr (CD$_3$CN) 7.40 (2H, m); 7.30 (7H, m); 5.85 (1H, s); 4.40 (1H, m); 3.75 (1H, m); 2.30–2.95 (6H, m); 2.20 (3H, s); 1.60 (4H, m); 1.10 (6H, m)

MS TOF 421 (M+1$^+$).

Hplc (Magellan C8, Gradient 3, water/acetonitrile/TFA) rt 10.68 min.

Example 7
1-(4-Methylbenzoyl-D-phenylglycinyl)-4,4'-bispiperidine $^1$H nmr (CD$_3$CN) 7.55 (2H, m); 7.30 (5H, m); 7.10 (2H, m); 5.85 (1H, s); 4.40 (1H, m); 3.75 (1H, m); 2.30–2.95 (6H, m); 2.20 (3H, s); 1.60 (4H, m); 1.10 (6H, m)

MS TOF 420 (M+1$^+$).

Hplc (Magellan C8, Gradient 3, water/acetonitrile/TFA) rt 10.61 min.

Example 8
1-(3-Amino-2-naphthoyl-D-phenylglycinyl)-4,4'-bispiperidine $^1$H nmr (CD$_3$CN) 7.90 (1H, d); 7.60 (1H, d); 7.40 (1H, m); 7.30 (6H, m); 7.05 (1H, m); 6.90 (1H, s); 5.85 (1H, s); 4.40 (1H, m); 3.75 (1H, m); 2.30–2.95 (6H, m); 1.60 (4H, m); 1.10 (6H, m)

MS TOF 471 (M+1$^+$).

Hplc (Magellan C8, Gradient 3, water/acetonitrile/TFA) rt 9.87 min.

Example 9
1-(3-Aminobenzoyl-D-phenylglycinyl)-4,4'-bispiperidine

MS TOF 421 (M+1$^+$).

Hplc (Magellan C8, Gradient 3, water/acetonitrile/TFA) rt 9.06 min.

Example 10
1-(2-Aminobenzoyl-D-phenylglycinyl)-4,4'-bipiperidine

MS TOF 421 (M+1$^+$).

Hplc (Magellan C8, Gradient 3, water/acetonitrile/TFA) rt 9.00 min.

Example 11
1-(2-Amino-4-fluorobenzoyl-D-phenylglycinyl)-4,4'-bispiperidine

MS TOF 440 (M+1$^+$).

Hplc (Magellan C8, Gradient 3, water/acetonitrile/TFA) rt 9.23 min.

Example 12
1-(2-Amino-5-fluorobenzoyl-D-phenylglycinyl)-4,4'-bispiperidine

MS TOF 440 (M+1$^+$).

Hplc (Magellan C8, Gradient 3, water/acetonitrile/TFA) rt 9.14 min.

Example 13
1-(2-Amino-4-nitrobenzoyl-D-phenylglycinyl)-4,4'-bispiperidine

MS TOF 467 (M+1$^+$).

Hplc (Magellan C8, Gradient 3, water/acetonitrile/TFA) rt 10.59 min.

Example 14
1-(2-Amino-5-nitrobenzoyl-D-phenylglycinyl)-4,4'-bispiperidine

MS TOF (M+1$^+$).

Hplc (Magellan C8, Gradient 3, water/acetonitrile/TFA) rt 10.57 min.

Example 15
1-(2-Amino-4,5-dimethoxybenzoyl-D-phenylglycinyl)-4,4'-bispiperidine

MS TOF 481 (M+1$^+$).

Hplc (Magellan C8, Gradient 3, water/acetonitrile/TFA) rt 11.67 min.

Example 16
1-(Benzoyl-D-phenylglycinyl)-4,4'bispiperidine
MS TOF 407 (M+1$^+$).
Hplc (Magellan C8, Gradient 3, water/acetonitrile/TFA) rt 9.88 min.

Example 17
1-(4-Chlorobenzoyl-D-phenylglycinyl)-4,4'-bispiperidine
MS TOF 441 (M+1$^+$).
Hplc (Magellan C8, Gradient 3, water/acetonitrile/TFA) rt 10.89 min.

Example 18
1-(2-Hydroxybenzoyl-D-phenylglycinyl)-4,4'-bispiperidine
MS TOF 423 (M+1$^+$).
Hplc (Magellan C8, Gradient 3, water/acetonitrile/TFA) rt 8.97 min.

Method 2: By solution phase strategy: Typically an activated amino acid was treated with an amine (primary or secondary) or alcohol (1eq.). Activation of the protected amino acid (Boc or Cbz protection) was by HATU/DIPEA (1:2) by TBTU/DIPEA (1:2), by HOBt or HOAt and a carbodiimide (EDCI or DCC), or by diethyl cyanophosphonate and triethylamine or DIPEA, all couplings (minimum 120 min.) were carried out in DMF without or without dichloromethane as co-solvent. After an aqueous work up the deprotection of the Boc group was achieved with TFA. Other acid substituents were added as the HOBt or HOAt esters either by activation with HBTU/HATU, EDC or DIPCI with or without Boc protection of amino groups. The final products were purified by preparative reverse phase Hplc.

Examples 19–126

The compounds of Examples 19–126 were prepared by the method described below, but using the appropriate starting materials.

Boc D-phenylglycine (251 mg, 1 mmol.) was dissolved in DMF (3 ml) with HATU (380 mg., 1 mmol.) and DIPEA (350 µl., 2 mmol.). To this mixture was added 4-methylbenzylamine (121 mg., 1 mmol.) and DIPEA (170 µl., 1 mmol.). The mixture was stirred overnight. The mixture was then taken up into ethylacetate and washed with water, sodium carbonate solution, water, 10% hydrochloric acid solution and water. The ethylacetate was evaporated without drying and treated immediately with TFA for 30 min. The TFA was then evaporated to dryness and the product triturated with diethylether. TEA (1 ml) was added and evaporated to dryness. A solution of 3-hydroxymethylbenzoic acid (76 mg, 0.5 mmole) in dry dimethylformamide (DMF) was treated with TBTU (161 mg., 0.5 mmol.) and DIPEA (1.5 mmol.). The mixture was then added to the D-phenylglycine-4-methylbenzylamide (0.5 mmol.) and stirred overnight. The crude product was dissolved in water/acetonitrile (20 ml), filtered and purified by preparative Hplc to yield pure product.

$^1$H nmr (CD$_3$CN) 7.75 (1H, m); 7.65 (2H, m); 7.30 (7H, broad m); 6.80 (3H, m); 5.40 (1H, s); 4.45 (2H, s); 4.10 (2H, m); 2.10 (3H, s).

MS TOF 389 (M+1$^+$).

Hplc (Magellan C8, Gradient 3, water/acetonitrile/TFA) rt 13.51 min.

Compounds made by the above method:—

Example 19
1-(2-Aminobenzoyl-D-phenylglycinyl)-4-(4-fluoro-2-methylsulphonylphenyl)piperazine
$^1$H nmr (DMSO) 7.65 (3H, m); 7.45 (1H, m); 7.35 (5H, m); 7.15 (1H, m); 6.65 (1H, d); 6.55 (1H, m); 6.05 (1H, s); 3.15 (3H, s); 3.00–2.00 (8H, m).
MS TOF 511 (M+1$^+$).
Hplc (Magellan C8, Gradient 3, water/acetonitrile/TFA) rt 13.43 min.

Example 20
1-(2-Amino-4-chlorobenzoyl-D-phenylglycinyl)-4-(4-fluoro-2-methylsulphonylphenyl)piperazine
$^1$H nmr (DMSO) 7.55 (3H, m); 7.45 (1H, m); 7.35 (5H, m); 7.15 (1H, m); 6.75 (1H, s); 6.55 (1H, d); 6.05 (1H, s) 3.15 (3H, s); 3.00–2.00 (8H, m).
MS TOF 546 (M+1$^+$).
Hplc (Magellan C8, Gradient 3, water/acetonitrile/TFA) rt 15.18 min.

Example 21
1-(2-Amino-5-fluorobenzoyl-D-phenylglycinyl)-4-(4-fluoro-2-methylsulphonylphenyl)piperazine
$^1$H nmr (CDCl$_3$) 7.75 (1H, m); 7.60 (1H, m); 7.25 (6H, m); 7.15 (6H, m); 6.90 (1H, m); 6.75 (1H, m); 5.85 (1H, s); 3.15 (3H, s); 3.00–2.00 (8H, m).
MS TOF 529 (M+1$^+$).
Hplc (Magellan C8, Gradient 3, water/acetonitrile/TFA) rt 13.87 min.

Example 22
1-(2-Amino-4-methylbenzoyl-D-phonylglycinyl)-4-(4-fluoro-2-methylsulphonylphenyl)piperazine
$^1$H nmr (DMSO) 7.55 (3H, m); 7.45 (2H, m); 7.35 (5H, m); 6.65 (1H, m); 6.35 (1H, d); 6.05 (1H, s); 3.15 (3H, s); 3.00–2.00 (8H, m) 2.15 (3H, s);.
MS TOF 525 (M+1$^+$).
Hplc (Magellan C8, Gradient 3, water/acetonitrile/TFA) rt 13.12 min.

Example 23
1-(2-Amino-5-methylbenzoyl-D-phenylglycinyl)-4-(4-fluoro-2-methylsulphonylphenyl)piperazine
$^1$H nmr (CDCl$_3$) 7.75 (1H, m); 7.60 (1H, m); 7.25 (6H, m); 7.15 (1H, m); 6.90 (1H, m); 6.75 (1H, m); 5.85 (1H, s); 3.15 (3H, s); 3.00–2.00 (8H, m) 2.30 (3H, s).
MS TOF 525 (M+1$^+$).
Hplc (Magellan C8, Gradient 3, water/acetonitrile/TFA) rt 12.84 min.

Example 24
1-(2-Amino-4-nitrobenzoyl-D-phenylglycinyl)-4-(4-fluoro-2-methylsulphonylphenyl)piperazine
$^1$H nmr (CDCl$_3$) 7.75 (2H, m); 7.55 (1H, m); 7.35 (7H, m); 7.25 (1H, m); 5.80 (1H, s); 3.15 (3H, s); 3.00–2.00 (8H, m). MS TOF 556 (M+1$^+$).
Hplc (Magellan C8, Gradient 3, water/acetonitrile/TFA) rt 15.35 min.

Example 25
1-(2-Amino-5-nitrobenzoyl-D-phenylglycinyl)-4-(4-fluoro-2-methylsulphonylphenyl)piperazine
$^1$H nmr (CDCl$_3$) 8.25 (1H, d); 7.85 (1H, m); 7.55 (1H, m); 7.25 (7H, m); 7.05 (1H, m); 5.80 (1H, s); 3.15 (3H, s); 3.00–2.00 (8H, m).
MS TOF 556 (M+1$^+$).
Hplc (Magellan C8, Gradient 3, water/acetonitrile/TFA) rt 15.08 min.

Example 26
1-(2-Amino-5-cyanobenzoyl-D-phenylglycinyl)-4-(4-fluoro-2-methylsulphonylphenyl)piperazine $^1$H nmr (CD$_3$CN) 7.65 (4H, m); 7.25 (6H, m); 6.65 (1H, d); 5.80 (1H, s); 3.15 (3H, s); 3.00–2.00 (8H, m).

MS TOF 536 (M+1$^+$).

Hplc (Magellan C8, Gradient 3, water/acetonitrile/TFA) rt 14.89 min.

Example 27
1-(2,5-Diaminobenzoyl-D-phenylglycinyl)-4-(4-fluoro-2-methylsulphonylphenyl)piperazine $^1$H nmr (CDCl$_3$) 7.70 (1H, d); 7.45 (7H, m); 6.85 (1H, s); 6.55 (1H, m); 6.55 (1H, m); 5.90 (1H, s); 3.15 (3H, s); 3.00–2.00 (8H, m).

MS TOF 526 (M+1$^+$).

Hplc (Magellan C8, Gradient 3, water/acetonitrile/TFA) rt 11.82 ml.

Example 28
1-(2-Amino-4,5-dimethoxybenzoyl-D-phenylglycinyl)-4-(4-fluoro-2-methylsulphonylphenyl)piperazine $^1$H nmr (CD$_3$CN) 7.65 (2H, m); 7.35 (2H, m); 7.25 (5H, m); 6.75 (1H, d); 6.15 (1H, d); 5.80 (1H, s); 3.60 (3H, s); 3.50 (3H, s); 3.15 (3H, s); 3.00–2.00 (8H, m).

MS TOF 571 (M+1$^+$).

Hplc (Magellan C8, Gradient 3, water/acetonitrile/TFA) rt 12.84 min.

Example 29
1-(Benzoyl-D-phenylglycinyl)-4-(4-fluoro-2-methylsulphonylphenyl)piperazine $^1$H nmr (CD$_3$CN) 7.75 (2H, m); 7.70 (1H, m); 7.40 (10H, m); 6.05 (1H, s); 3.15 (3H, s); 3.00–2.00 (8H, m).

MS TOF 496 (M+1$^+$).

Hplc (Magellan C8, Gradient 3, water/acetonitrile/TFA) rt 12.84 min.

Example 30
1-(3-Aminobenzoyl-D-phenylglycinyl)-4-(4-fluoro-2-methylsulphonylphenyl)piperazine $^1$H nmr (CD$_3$CN) 7.85 (1H, m); 7.60 (1H, m); 7.50 (2H, m); 7.30 (7H, m); 7.05 (1H, d); 6.05 (1H, s); 3.15 (3H, s); 3.00–2.00 (8H, m).

MS TOF 511 (M+1$^+$).

Hplc (Magellan C8, Gradient 3, water/acetonitrile/TFA) rt 11.32 min.

Example 31
1-(4-Aminobenzoyl-D-phenylglycinyl)-4-(4-fluoro-2-methylsulphonylphenyl)piperazine $^1$H nmr (CDCl$_3$) 7.95 (1H, d); 7.80–7.45 (10H, broad m); 7.35 (1H, d); 6.20 (1H, s); 3.15 (3H, s); 3.00–2.00 (8H, m).

MS TOF 511 (M+1$^+$).

Hplc (Magellan C8, Gradient 3, water/acetonitrile/TFA) rt 12.05 min.

Example 32
1-(3,4 Diaminobenzoyl-D-phenylglycinyl)-4-(4-fluoro-2-methylsulphonylphenyl)piperazine $^1$H nmr (CDCl$_3$) 7.75 (1H, d); 7.40–7.15 (9H, broad m); 6.55 (1H, d); 6.00 (1H, s); 3.15 (3H, s); 3.00–2.00 (8H, m).

MS TOF 540 (M+1$^+$).

Hplc (Magellan C8, Gradient 3, water/acetonitrile/TFA) rt 11.30 min.

Example 33
1-(3-Chlorobenzoyl-D-phenylglycinyl)-4-(4-fluoro-2-methylsulphonylphenyl)piperazine $^1$H nmr (CD$_3$CN) 7.85 (1H, m); 7.80 (1H, s); 7.60 (2H, m); 7.30 (8H, m); 6.00 (1H, s); 3.20 (3H, s); 3.00–2.00 (8H, m).

MS TOF 531 (M+1$^+$).

Hplc (Magellan C8, Gradient 3, water/acetonitrile/TFA) rt 15.40 min.

Example 34
1-(4-Chlorobenzoyl-D-phenylglycinyl)-4-(4-fluoro-2-methylsulphonylphenyl)piperazine $^1$H nmr (CD$_3$CN) 7.95 (1H, m); 7.75 (2H, m); 7.60 (1H, m); 7.40 (8H, m); 6.05 (1H, s); 3.25 (3H, s); 3.00–2.00 (8H, m).

MS TOF 531 (M+1$^+$).

Hplc (Magellan C8, Gradient 3, water/acetonitrile/TFA) rt 16.54 min.

Example 35
1-(3-Amino-4-chlorobenzoyl-D-phenylglycinyl)-4-(4-fluoro-2-methylsulphonylphenyl)piperazine $^1$H nmr (CDCl$_3$) 8.05 (1H, m); 7.80 (1H, m); 7.70 (1H, s); 7.20–7.60 (8H, broad m); 6.05 (1H, s); 3.25 (3H, s); 3.00–2.00 (8H, m).

MS TOF 546 (M+1$^+$).

Hplc (Magellan C8, Gradient 3, water/acetonitrile/TFA) rt 14.53 min.

Example 36
1-(4-Bromobenzoyl-D-phenylglycinyl)-4-(4-fluoro-2-methylsulphonylphenyl)piperazine $^1$H nmr (CD$_3$CN) 7.85 (1H, m); 7.65 (2H, m); 7.60 (2H, d); 7.45 (2H, d); 7.30 (5H, m); 6.00 (1H, s); 3.20 (3H, s); 3.00–2.00 (8H, m).

MS TOF 576 (M+1$^+$).

Hplc (Magellan C8, Gradient 3, water/acetonitrile/TFA) rt 15.94 min.

Example 37
1-(4-Iodobenzoyl-D-phenylglycinyl)-4-(4-fluoro-2-methylsulphonylphenyl)piperazine $^1$H nmr (CD$_3$CN)); 7.75 (2H, m); 7.65 (1H, m 7.55 (2H, d); 7.45 (2H, d); 7.30 (5H, m); 5.95 (1H, s); 3.20 (3H, s); 3.00–2.00 (8H, m).

MS TOF 622 (M+1$^+$).

Hplc (Magellan C8, Gradient 3, water/acetonitrile/TFA) rt 15.96 min.

Example 38
1-(3-Amino-4-methylbenzoyl-D-phenylglycinyl)-4-(4-fluoro-2-methylsulphonylphenyl)piperazine $^1$H nmr (CDCl$_3$) 7.95 (1H, s); 7.60 (1H, d); 7.45 (1H, d); 7.40–7.15 (8H, broad m); 6.00 (1H, s); 3.15 (3H, s); 3.00–2.50 (8H, m) 2.20 (3H, s).

MS TOF 525 (M+1$^+$).

Hplc (Magellan C8, Gradient 3, water/acetonitrile/TFA) rt 11.71 min.

Example 39
1-(4-Methoxybenzoyl-D-phenylglycinyl)-4-(4-fluoro-2-methylsulphonylphenyl)piperazine $^1$H nmr (CD$_3$CN) 7.85 (2H, d); 7.65 (1H, m), 7.50 (2H, m); 7.40 (5H, m); 6.80 (2H, d); 6.00 (1H, s); 3.80 (3H, s); 3.20 (3H, s); 3.00–2.00 (8H, m).

MS TOF 526 (M+1$^+$).

Hplc (Magellan C8, Gradient 3, water/acetonitrile/TFA) rt 14.63 min.

Example 40
1-(3-Amino-4-methoxybenzoyl-D-phenylglycinyl)-4-(4-fluoro-2-methylsulphonylphenyl)piperazine $^1$H nmr (CDCl$_3$) 7.90 (1H, m); 7.75 (1H, d); 7.60 (2H, m); 7.40–7.15 (6H, broad m); 7.45 (1H, d); 6.10 (1H, s); 3.95 (3H, s); 3.35 (3H, s); 3.00–2.50 (8H, m).

MS TOF 541 (M+1$^+$).

Hplc (Magellan C8, Gradient 3, water/acetonitrile/TFA) rt 11.78 min.

Example 41
1-(3,4-Dihydroxybenzoyl-D-phenylglycinyl)-4-(4-fluoro-2-methylsulphonylphenyl)piperazine $^1$H nmr (CDCl$_3$) 7.55 (1H, m); 7.45 (1H, d); 7.25 (2H, m); 7.15 (5H, m); 7.00 (1H, d); 6.60 (1H, d); 5.80 (1H, s); 3.05 (3H, s); 3.00–2.50 (8H, m).

MS TOF 541 (M+1$^+$).

Hplc (Magellan C8, Gradient 3, water/acetonitrile/TFA) rt 11.78 min.

Example 42
1-(Naphth-2-oyl-D-phenylglycinyl)-4-(4-fluoro-2-methylsulphonylphenyl)piperazine $^1$H nmr (CDCl$_3$) 8.35 (1H, s); 8.00 (1H, d); 7.85 (5H, m); 7.45 (4H, m); 7.25 (4H, m); 6.10 (1H, s); 3.20 (3H, s); 3.00–2.50 (8H, m).

MS TOF 546 (M+1$^+$).

Hplc (Magellan C8, Gradient 3, water/acetonitrile/TFA) rt 16.66 min.

Example 43
1-(3-Aminonaphth-2-oyl-D-phenylglycinyl)-4-(4-fluoro-2-methylsulphonylphenyl)piperazine $^1$H nmr (CDCl$_3$) 8.15 (1H, d); 8.00 (1H, s); 7.75 (2H, m); 7.65 (1H, d); 7.30–7.60 (9H, m); 6.10 (1H, s); 3.25 (3H, s); 3.00–2.50 (8H, m).

MS TOF 561 (M+1$^+$).

Hplc (Magellan C8, Gradient 3, water/acetonitrile/TFA) rt 13.90 min.

Example 44
1-(Thiophene-3-carbonyl-D-phenylglycinyl)-4-(4-fluoro-2-methylsulphonylphenyl)piperazine $^1$H nmr (CDCl$_3$) 8.15 (1H, s); 7.95 (1H, m); 7.85 (1H, m); 7.60 (8H, m); 6.30 (1H, s); 3.45 (3H, s); 2.00–2.50 (8H, m).

MS TOF 502 (M+1$^+$).

Hplc (Magellan C8, Gradient 3, water/acetonitrile/TFA) rt 14.28 min.

Example 45
1-(Thiophene-2-carbonyl-D-phenylglycinyl)-4-(4-fluoro-2-methylsulphonylphenyl)piperazine $^1$H nmr (CDCl$_3$) 7.65 (2H, m); 7.45 (1H, s); 7.30 (2H, m); 7.20 (5H, m); 6.95 (1H, m); 6.00 (1H, s); 3.05 (3H, s); 3.00–2.50 (8H, m).

MS TOF 502 (M+1$^+$).

Hplc (Magellan C8, Gradient 3, water/acetonitrile/TFA) rt 14.52 min.

Example 46
1-(5-Methylthiophene-2-carbonyl-D-phenylglycinyl)-4-(4-fluoro-2-methylsulphonylphenyl)piperazine $^1$H nmr (CDCl$_3$) 7.70 (1H, m); 7.45 (2H, m); 7.35 (6H, m); 6.65 (1H, m); 6.00 (1H, s); 3.05 (3H, s); 3.00–2.50 (8H, m) 2.45 (3H, s).

MS TOF 516 (M+1$^+$).

Hplc (Magellan C8, Gradient 3, water/acetonitrile/TFA) rt 14.98 min.

Example 47
1-(Isoquinolin-7-carbonyl-D-phenylglycinyl)-4-(4-fluoro-2-methylsulphonylphenyl)piperazine $^1$H nmr (CD$_3$CN) 9.50 (1H, s); 8.75 (1H, s); 8.55 (1H, d); 8.30 (1H, d); 8.10 (2H, m); 7.65 (1H, m); 7.45 (2H, m); 7.35 (5H, m); 6.10 (1H, s); 3.20 (3H, s); 3.00–2.50 (8H, m).

MS TOF 547 (M+1$^+$).

Hplc (Magellan C8, Gradient 3, water/acetonitrile/TFA) rt 11.39 min.

Example 48
1-(Pyridin-3-carbonyl-D-phenylglycinyl)-4-(4-fluoro-2-methylsulphonylphenyl)piperazine $^1$H nmr (CD$_3$CN) 9.00 (1H, s); 8.70 (1H, d); 8.35 (1H, d); 8.10 (1H, m); 7.65 (2H, m); 7.45 (1H, m); 7.30 (5H, m); 6.00 (1H, s); 3.20 (3H, s); 3.00–2.50 (8H, m).

MS TOF 497 (M+1$^+$).

Hplc (Magellan C8, Gradient 3, water/acetonitrile/TFA) rt 11.99 min.

Example 49
1-(Indol-6-carbonyl-D-phenylglycinyl)-4-(4-fluoro-2-methylsulphonylphenyl)piperazine $^1$H nmr (CD$_3$CN) 7.95 (2H, m); 7.60 (2H, m); 7.50 (3H, m) 7.35 (5H, m); 6.45 (1H, s); 6.05 (1H, s); 3.25 (3H, s); 3.00–2.50 (8H, m).

MS TOF 535 (M+1$^+$).

Hplc (Magellan C8, Gradient 3, water/acetonitrile/TFA) rt 15.44 min.

Example 50
1-(2,5-Diaminobenzoyl-D-phenylglycinyl)-4-(4-fluoro-2-methylsulphonylphenyl)piperazine

MS TOF 526 (M+1$^+$).

Hplc (Magellan C8, Gradient 3, water/acetonitrile/TFA) rt 11.89 min.

Example 51
1-(4-Methylaminobenzoyl-D-phenylglycinyl)-4-(4-fluoro-2-methylsulphonylphenyl)piperazine $^1$H nmr (CD$_3$CN) 7.65 (3H, m); 7.50 (2H, m); 7.35 (5H, m); 6.60 (2H, d); 6.05 (1H, s); 3.30 (3H, s); 3.00–2.50 (8H, m); 2.80 (3H, s).

MS TOF 525 (M+1$^+$).

Hplc (Magellan C8, Gradient 3, water/acetonitrile/TFA) rt 13.17 min.

Example 52
1-(3-Methyl-4-chlorobenzoyl-D-phenylglycinyl)-4-(4-fluoro-2-methylsulphonylphenyl)piperazine $^1$H nmr (CD$_3$CN) 7.90 (1H, s); 7.85 (1H, s); 7.80 (1H, s); 7.55 (6H, m); 6.25 (1H, s); 3.45 (3H, s); 3.00–2.50 (8H, m); 2.60 (3H, s).

MS TOF 545 (M+1$^+$).

Hplc (Magellan C8, Gradient 3, water/acetonitrile/TFA) rt 16.39 min.

Example 53
1-(4-Vinylbenzoyl-D-phenylglycinyl)-4-(4-fluoro-2-methylsulphonylphenyl)piperazine $^1$H nmr (CD$_3$CN) 7.75 (2H, d); 7.60 (1H, m); 7.45 (4H, m); 7.35 (5H, m); 6.75 (1H, m); 6.05 (1H, s); 5.90 (1H, d); 5.30 (1H, d); 3.00–2.50 (8H, m); 2.80 (3H, s).

MS TOF 522 (M+1$^+$).

Hplc (Magellan C8, Gradient 3, water/acetonitrile/TFA) rt 15.45 min.

Example 54
1-(3-Amino-4-hydroxybenzoyl-D-phenylglycinyl)-4-(4-fluoro-2-methylsulphonylphenyl)piperazine $^1$H nmr (CD$_3$CN) 7.60 (1H, m); 7.50–7.10 (9H, m); 7.35 (1H, d); 5.95 (1H, s); 3.25 (3H, s); 3.00–2.50 (8H, m).

MS TOF 527 (M+1$^+$).

Hplc (Magellan C8, Gradient 2, water/acetonitrile/TFA) rt 15.46 min.

Example 55
1-(4-Methylthiobenzoyl-D-phenylglycinyl)-4-(4-fluoro-2-methylsulphonylphenyl)piperazine $^1$H nmr (CD$_3$CN) 7.85 (2H, d); 7.80 (1H, m); 7.60 (2H, m); 7.50 (5H, m); 7.40 (2H, d); 6.15 (1H, s); 3.40 (3H, s); 3.10–2.70 (5H, m); 2.60 (3H, s).

MS TOF 542 (M+1$^+$).

Hplc (Magellan C8, Gradient 3, water/acetonitrile/TFA) rt 16.67 min.

Example 56
1-(3-Carboxamidobenzoyl-D-phenylglycinyl)-4-(4-fluoro-2-methylsulphonylphenyl)piperazine $^1$H nmr (CD$_3$CN) 8.25 (1H, s); 7.95 (2H, d); 7.70 (1H, m); 7.55 (3H, m); 7.40 (5H, m); 6.05 (1H, s); 3.30 (3H, s); 3.00–2.50 (8H, m).

MS TOF 539 (M+1$^+$).

Hplc (Magellan C8, Gradient 3, water/acetonitrile/TFA) rt 12.83 min.

Example 57
1-(3-Amino-4-methylbenzoyl-D-phenylglycinyl)-4-(4-fluoro-2-methylsulphonylphenyl)piperazine $^1$H nmr (CD$_3$CN) 7.90 (1H, d); 7.70 (1H, m); 7.55 (2H, m); 7.45 (5H, m); 7.20 (1H, s); 6.95 (1H, d); 6.05 (1H, s); 3.80 (3H, s); 3.30 (3H, s); 3.00–2.50 (8H, m).

MS TOF 569 (M+1$^+$).

Hplc (Magellan C8, Gradient 3, water/acetonitrile/TFA) rt 14.49 min.

Example 58
1-(3-Methyl-4-bromobenzoyl-D-phenylglycinyl)-4-(4-fluoro-2-methylsulphonylphenyl)piperazine $^1$H nmr (CD$_3$CN) 7.65 (3H, m); 7.45 (3H, m); 7.30 (5H, m); 6.00 (1H, s); 3.25 (3H, s); 3.00–2.50 (8H, m); 2.40 (3H, s).

MS TOF 589 (M+1$^+$).

Hplc (Magellan C8, Gradient 3, water/acetonitrile/TFA) rt 16.67 min.

Example 59
1-(4-Ethoxybenzoyl-D-phenylglycinyl)-4-(4-fluoro-2-methyleulphonylphenyl)piperazine $^1$H nmr (CD$_3$CN) 7.75 (2H, d); 7.60 (1H, m); 7.50 (2H, m); 7.35 (5H, m); 6.85 (2H, d); 6.00 (1H, s); 4.00 (2H, m); 3.20 (3H, s); 3.00–2.50 (8H, m); 1.30 (3H, t).

MS TOF 540 (M+1$^+$).

Hplc (Magellan C8, Gradient 3, water/acetonitrile/TFA) rt 16.58 min.

Example 60
1-(Indol-S-carbonyl-D-phenylglycinyl)-4-(4-fluoro-2-methylsulphonylphenyl)piperazine $^1$H nmr (CD$_3$CN) 8.15 (1H, s); 7.95 (2H, d); 7.65 (2H, m); 7.60–7.35 (7H, m); 6.60 (1H, s); 6.10 (1H, s); 3.30 (3H, s); 3.00–2.60 (8H, m).

MS TOF 535 (M+1$^+$). Hplc (Magellan C8, Gradient 3, water/acetonitrile/TFA) rt 13.88 min.

Example 61
1-(Benzimidazo-5-carbonyl-D-phenylglycinyl)-4-(4-fluoro-2-methylsulphonylphenyl)piperazine $^1$H nmr (CD$_3$CN) 8.75 (1H, s); 8.25 (1H, s); 7.75 (2H, m); 7.60 (1H, m); 7.50 (2H, m); 7.35 (5H, m); 6.60 (2H, d); 6.05 (1H, s); 3.30 (3H, s); 3.00–2.50 (8H, m).

MS TOF 536 (M+1$^+$).

Hplc (Magellan C8, Gradient 3, water/acetonitrile/TFA) rt 10.08 min.

Example 62
1-(3-Aminobenzoyl-D-phonylglycinyl)-1'-methyl-4,4'-bispiperidine $^1$H nmr (CD$_3$CN) a mixture of conformers only one recorded here 7.65 (1H, m); 7.35 (5H, m); 7.05 (1H, m); 6.95 (2H, m); 5.85 (1H, s); 4.45 (1H, m); 3.85 (1H, m); 3.30 (2H, m); 2.90–2.40 (8H, m); 2.55 (3H, s); 1.60 (2H, m); 1.30 (2H, m); 1.00 (2H, m).

MS TOF 435 (M+1$^+$). Hplc (Magellan C8, Gradient 3, water/acetonitrile/TFA) rt 7.65 min.

Example 63
1-(3-Amino-4-chlorobenzoyl-D-phenylglycinyl)-1'-methyl-4,4'-bispiperidine $^1$H nmr (CD$_3$CN) a mixture of conformers only one recorded here 7.75 (1H, m); 7.30 (5H, m); 7.20 (1H, m); 6.95 (1H, m); 5.85 (1H, s); 4.45 (1H, m); 3.85 (1H, m); 3.30 (2H, m); 2.90–2.40 (8H, m); 2.55 (3H, s); 1.60 (2H, m); 1.30 (2H, m); 1.00 (2H, m).

MS TOF 469 (M+1$^+$).

Hplc (Magellan C8, Gradient 3, water/acetonitrile/TFA) rt 9.58 min.

Example 64
1-(3-Amino-4-methylbenzoyl-D-phenylglycinyl)-1'-methyl-4,4'-bispiperidine $^1$H nmr (CD$_3$CN) a mixture of conformers only one recorded here 7.75 (1H, m); 7.35 (5H, m); 7.05 (2H, m); 5.85 (1H, s); 4.45 (1H, m); 3.85 (1H, m); 3.30 (2H, m); 2.90–2.40 (8H, m); 2.65 (3H, S); 2.15 (3H, s); 1.60 (2H, m); 1.30 (2H, m); 1.00 (2H, m).

MS TOF 449 (M+1$^+$).

Hplc (Magellan C8, Gradient 3, water/acetonitrile/TFA) rt 8.03 min

Example 65
1-(3-Aminonaphth-2-oyl-D-phenylglycinyl)-1'-methyl-4,4'-bispiperidine $^1$H nmr (CD$_3$CN) a mixture of conformers only one recorded here 7.95 (1H, m); 7.65 (1H, d); 7.45 (2H, m); 7.30 (5H, m); 7.15 (1H, m); 6.95 (1H, s) 5.95 (1H, s); 4.45 (1H, m); 3.85 (1H, m); 3.30 (2H, m); 2.90–2.40 (8H, m); 2.65 (3H, s); 1.60 (2H, m); 1.30 (2H, m); 1.00 (2H, m).

MS TOF 485 (M+1$^+$).

Hplc (Magellan C8, Gradient 3, water/acetonitrile/TFA) rt 9.94 min.

Example 66
1-(Indol-6-carbonyl-D-phenylglycinyl)-1'-methyl-4,4'-bispiperidine $^1$H nmr (CD$_3$CN) a mixture of conformers only one recorded here 7.78 (2H, s); 7.50 (1H, d); 7.25(7H, m); 6.34 (1H, s); 6.82 (1H, s); 4.40 (1H, m); 3.83 (1H, m); 3.35 (2H, t); 2.9–2.4 (8H, m) and 2.65 (3H, s) masked by water in solvent; 1.60 (2H, m); 1.40 (2H, m); 1.08 (2H, m).

MS TOF 459 (M+1$^+$).

Hplc (Luna2 C18, Gradient 3, water/acetonitrile/TFA rt 10.01 min.

Example 67
1-(3-Amino-4-fluorobenzoyl-D-phenylglycinyl)-1'-methyl-4,4'-bispiperidine $^1$H nmr (d$_4$ methanol) a mixture of conformers only one recorded here 7.4 (6H, m); 7.1 (1H, m); 7.0 (1H, t); 6.0 (1H, s); 4.63 (1H, m); 4.02 (1H, m); 3.30 (2H, m); 2.90–2.40 (8M, m); 2.65 (3H, s); 1.60 (2H, m); 1.30 (2H, m); 1.00 (2H, m).

MS TOF 453 (M+1$^+$).

Hplc (Symmetry C8, Gradient 3, water/acetonitrile/TFA) rt 5.03 min.

Example 68
1-(3-Amino-4-bromobenzoyl-D-phenylglycinyl)-1'-methyl-4,4'-bispiperidine $^1$H nmr (CD$_3$CN) a mixture of conformers only one recorded here 7.75 (1H, m); 7.35 (5H, m); 7.05 (1H, m); 6.80 (1H, m); 5.85 (1H, s); 4.45 (1H, m); 3.85 (1H, m); 3.30 (2H, m); 2.90–2.40 (8H, m) and 2.65 (3H, s) masked by water in solvent; 1.60 (2H, m); 1.30 (2H, m); 1.00 (2H, m).

MS TOF 513 and 515 (M+1$^+$).

(Symmetry C8, Gradient 3, water/acetonitrile/TFA) rt 5.70 min.

Example 69
1-(3-Amino-4-methoxybenzoyl-D-phenylglycinyl)-1'-methyl-4,4'-bispiperidine $^1$H nmr (CD$_3$CN) a mixture of conformers only one recorded here 7.70 (1H, m); 7.30 (5H, m); 7.0 (2H, m); 6.72 (1H, d); 5.80 (1H, s); 4.45 (1H, m); 3.85(1H, m); 3.70(3H, s); 3.30 (2H, m); 2.9–2.4 (8H, m) masked by water in solvent, 1.60 (2H, m); 1.30 (2H, m); 1.00 (2H, m).

MS TOF 465 (M+1$^+$).

Hplc (Luna2 C18, Gradient 3, water/acetonitrile/TFA) rt 7.55 min.

Example 70
1-(4-(Methylamino)benzoyl-D-phenylglycinyl)-1'-methyl-4,4'-bispiperidine $^1$H nmr (CD$_3$CN) a mixture of conformers only one recorded here 7.70 (3H, m); 7.35 (5H, m); 6.60 (2H, d); 5.90 (1H, s); 4.45 (1H, m); 3.85(1H, m); 3.40 (2H, m); 2.9–2.4 (8H, m); 2.70 (3H, s); 1.60 (2H, m); 1.30 (2H, m); 1.00 (2H, m).

MS TOF 465 (M+1$^+$).

Hplc (Luna2 C18, Gradient 3, water/acetonitrile/TFA) rt 8.52 min.

Example 71
1-(4-Ethylaminobenzoyl-D-phenylglycinyl)-4-(4-fluoro-2-methylsulphonylphenyl)piperazine 1H nmr (CD3CN) 7.65 (3H, m); 7.45 (2H, m); 7.35 (5H, m); 6.60 (2H, d); 6.00 (1H, s); 3.20 (3H, s); 3.10 (2H, q); 3.00–2.50 (8H, m); 1.15 (3H, t).

MS TOF 539 (M+1+).

Hplc (Magellan C8, Gradient 3, water/acetonitrile/TFA) rt 12.57 min.

Example 72
1-(3-Methylaminobenzoyl-D-phenylglycinyl)-4-(4-fluoro-2-methylsulphonylphenyl)piperazine 1H nmr (CD3CN) 7.75 (1H, d); 7.60 (1H, d); 7.35 (7H, m); 7.15 (1H, t); 7.00 (1H, m); 6.70 (1H, d); 6.00 (1H, s); 3.20 (3H, s); 3.00–2.50 (8H, m); 2.70 (3H, s).

MS TOF 525 (M+1+).

Hplc (Magellan C8, Gradient 3, water/acetonitrile/TFA) rt 12.07 min.

Example 73
1-(4-Chloro-3-aminobenzoyl-D-phenylglycinyl)-4-(2-methylsulphonylphenyl)piperazine 1H nmr (CD3CN) 7.95 (1H, d); 7.60 (1H, m); 7.45 (10H, m); 7.00 (1H, d); 6.00 (1H, s); 3.25 (3H, s); 3.00–2.50 (8H, m).

MS TOF 527 (M+1+).

Hplc (Magellan C8, Gradient 3, water/acetonitrile/TFA) rt 13.56 min.

Example 74
1-(4-Trifluoromethoxybenzoyl-D-phenylglycinyl)-4-(4-fluoro-2-methylsulphonylphenyl)piperazine 1H nmr (CD3CN) 7.85 (3H, m); 7.65 (1H, d); 7.45 (2H, m); 7.35 (6H, m); 6.00 (1H, s); 3.25 (3H, s); 3.00–2.50 (8H, m).

MS TOF 580 (M+1+).

Hplc (Magellan C8, Gradient 3, water/acetonitrile/TFA) rt 16.01 min.

Example 75
1-(4-Difluoromethoxybenzoyl-D-phenylglycinyl)-4-(4-fluoro-2-methylsulphonylphenyl)piperazine 1H nmr (CD3CN) 7.85 (3H, m); 7.45 (2H, d); 7.30 (5H, m); 7.15 (2H, d); 6.80 (1H, t); 6.00 (1H, s); 3.20 (3H, s); 3.00–2.50 (8H, m).

MS TOF 562 (M+1+).

Hplc (Magellan C8, Gradient 3, water/acetonitrile/TFA) rt 14.99 min.

Example 76
1-(4-Trifluoramethylbenzoyl-D-phenylglycinyl)-N-(4-fluoro-2-methylsulphonylphenyl)piperazine 1H nmr (CD3CN) 7.85 (2H, d); 7.70 (2H, d); 7.45 (2H, m); 7.35 (6H, m); 6.00 (1H, s); 3.20 (3H, s); 3.00–2.50 (8H, m)

MS TOF 564 (M+1+).

Hplc (Magellan C8, Gradient 3, water/acetonitrile/TFA) rt 15.00 min.

Example 77
1-(Indol-3-carbonyl-D-phenylglycinyl)-4-(4-fluoro-2-methylsulphonylphenyl)piperazine 1H nmr (CD3CN) 8.05 (1H, s); 7.85 (1H, d); 7.70 (1H, m); 7.50 (2H, m); 7.35 (6H, m); 7.20 (2H, m); 6.15 (1H, s); 3.20 (3H, s); 3.00–2.50 (8H, m).

MS TOF 535 (M+1+).

Hplc (Magellan C8, Gradient 3, water/acetonitrile/TFA) rt 14.25 min.

Example 78
1-(4-Chloro-3-aminobenzoyl-L-phenylglycinyl)-4-(4-fluoro-2-methylsulphonylphenyl)piperazine 1H nmr (CD3CN) 7.75 (1H, d); 7.60 (1H, d); 7.45 (8H, m); 6.90 (1H, d); 5.95 (1H, s); 3.20 (3H, s); 3.00–2.50 (8H, m).

MS TOF 545 (M+1+).

Hplc (Magellan C8, Gradient 3, water/acetonitrile/TFA) rt 14.53 min.

Example 79
1-(2-Carboxybenzoyl-D-phenylglycinyl)-4-(4-fluoro-2-methylsulphonylphenyl)piperazine 1H nmr (CD3CN) 7.75 (1H, d); 7.60 (1H, d); 7.50 (1H, d); 7.25–7.50 (9H, m); 6.00 (1H, s); 3.20 (3H, s); 3.00–2.50 (8H, m).

MS TOF 540 (M+1+).

Hplc (Magellan C8, Gradient 3, water/acetonitrile/TFA) rt 12.19 min.

Example 80
1-(2-Fluorobenzoyl-D-phenylglycinyl)-4-(4-fluoro-2-methylsulphonylphenyl)piperazine 1H nmr (CD3CN) 7.85 (1H, m); 7.60 (1H, d); 7.25–7.50 (10H, m); 6.00 (1H, s); 3.20 (3H, s); 3.00–2.50 (8H, m).

MS TOF 514 (M+1+).

Hplc (Magellan C8, Gradient 3, water/acetonitrile/TFA) rt 13.29 min.

Example 81
1-(3-Bromoindol-6-carbonyl-D-phenylglycinyl)-4-(4-fluoro-2-methylsulphonylphenyl)piperazine 1H nmr (CD3CN) 7.85 (2H, m); 7.70–7.20 (10H, m); 6.05 (1H, s); 3.20 (3H, s); 3.00–2.50 (8H, m).

MS TOF 614 (M+1+).

Hplc (Magellan C8, Gradient 3, water/acetonitrile/TFA) rt 16.16 min.

Example 82
1-(3-Chloroindol-6-carbonyl-D-phenylglycinyl)-4-(4-fluoro-2-methylsulphonylphenyl)piperazine 1H nmr (CD3CN) 7.95 (2H, m); 7.70–7.30 (10H, m); 6.05 (1H, s); 3.25 (3H, s); 3.00–2.50 (8H, m).

MS TOF 570 (M+1+).

Hplc (Magellan C8, Gradient 3, water/acetonitrile/TFA) rt 16.18 min.

Example 83
1-(2-Cyanobenzoyl-D-phenylglycinyl)-4-(4-fluoro-2-methylsulphonylphenyl)piperazine 1H nmr (CD3CN) 7.25–7.80 (12H, m); 6.05 (1H, s); 3.25 (3H, s); 3.00–2.50 (8H, m).

MS TOF 521 (M+1+).

Hplc (Magellan C8, Gradient 3, water/acetonitrile/TFA) rt 14.85 min.

Example 84
1-(2-Aminomethylbenzoyl-D-phenylglycinyl)-4-(4-fluoro-2-methylsulphonylphenyl)piperazine 1H nmr (CD3CN) 7.95 (2H, m); 7.80–7.35 (10H, m); 6.15 (1H, s); 4.30 (2H, s); 3.15 (3H, s); 3.00–2.50 (8H, m).

MS TOF 525 (M+1+).

Hplc (Magellan C8, Gradient 3, water/acetonitrile/TFA) rt 12.21 min.

Example 85
1-(4-Carboxy-3-aminobenzoyl-D-phenylglycinyl)-4-(4-fluoro-2-methylsulphonylphenyl)piperazine 1H nmr (CD3CN) 7.75 (1H, d); 7.60 (1H, d); 7.45 (7H, m); 7.15 (1H, s); 6.85 (1H, d); 5.95 (1H, s); 3.25 (3H, s); 3.00–2.50 (8H, m).

MS TOF 554 (M+1+).

Hplc (Magellan C8, Gradient 3, water/acetonitrile/TFA) rt 13.00 min.

Example 86
1-(1H-Indazol-6-carbonyl-D-phenylglycinyl)-4-(4-fluoro-2-methylsulphonylphenyl)piperazine 1H nmr (CD3CN) 8.05 (2H, m); 7.85 (1H, d); 7.70 (1H, d); 7.55 (2H, m); 7.45 (5H, m); 5.95 (1H, s); 3.30 (3H, s); 3.00–2.50 (8H, m).

MS TOF 545 (M+1+).

Hplc (Magellan C8, Gradient 3, water/acetonitrile/TFA) rt 13.44 min.

Example 87
1-(4-Methylcarboxybenzoyl-D-phenylglycinyl)-4-(4-fluoro-2-methylsulphonylphenyl)piperazine 1H nmr (CD3CN) 7.95 (2H, m); 7.80 (2H, m); 7.45 (2H, m); 7.35 (6H, m); 6.00 (1H, s); 3.90 (3H, s); 3.20 (3H, s); 3.00–2.50 (8H, m).

MS TOF 554 (M+1+).

Hplc (Magellan C8, Gradient 3, water/acetonitrile/TFA) rt 14.90 min.

Example 88
1-(4-Acetoxybenzoyl-D-phenylglycinyl)-4-(4-fluoro-2-methylsulphonylphenyl)piperazine 1H nmr (CD3CN) 7.75 (3H, m); 7.60 (1H, d); 7.45 (2H, m); 7.35 (5H, m); 7.10 (2H, d); 6.00 (1H, s); 3.20 (3H, s); 3.00–2.50 (8H, m); 2.20 (3H, s).

MS TOF 554 (M+1+).

Hplc (Magellan C8, Gradient 3, water/acetonitrile/TFA) rt 14.53 min.

Example 89
1-(5-Methylpyrazin-2-carbonyl-D-phenylglycinyl)-4-(4-fluoro-2-methylsulphonylphenyl)piperazine 1H nmr (CD3CN) 8.90 (1H, s); 8.35 (1H, s); 7.55 (1H, m); 7.40 (2H, m); 7.25 (5H, m); 5.85 (1H, s); 3.10 (3H, s); 3.00–2.50 (8H, m); 2.40 (3H, s).

MS TOF 512 (M+1+).

Hplc (Magellan C8, Gradient 3, water/acetonitrile/TFA) rt 14.17 min.

Example 90
1-(1,3-Benzodioxol-5-carbonyl-D-phenylglycinyl)-4-(4-fluoro-2-methylsulphonylphenyl)piperazine 1H nmr (CD3CN) 7.55 (2H, m); 7.35 (2H, m); 7.25 (6H, m); 6.70 (1H, d); 5.85 (2H, s); 5.80 (1H, s); 3.10 (3H, s); 3.00–2.50 (8H, m).

MS TOF 540 (M+1+).

Hplc (Magellan C8, Gradient 3, water/acetonitrile/TFA) rt 14.28 min.

Example 91
1-(4-(Methylsulphonyl)benzoyl-D-phenylglycinyl)-4-(4-fluoro-2-methylsulphonylphenyl)piperazine 1H nmr (CD3CN) 7.95 (3H, m); 7.60 (1H, m); 7.50 (2H, m); 7.35 (6H, m); 6.05 (1H, s); 3.25 (3H, s); 3.10 (3H, s); 3.00–2.50 (8H, m).

MS TOF 574 (M+1+).

Hplc (Magellan C8, Gradient 3, water/acetonitrile/TFA) rt 13.62 min.

Example 92
1-(2,3-Dichloroindol-6-carbonyl-D-phenylglycinyl)-4-(4-fluoro-2-methylsulphonylphenyl)piperazine 1H nmr (CD3CN) 7.90 (1H, d); 7.85 (1H, s); 7.55 (2H, m); 7.40 (2H, m); 7.25 (5H, m); 6.05 (1H, s); 3.30 (3H, s); 3.00–2.50 (8H, m); 2.40 (3H, s).

MS TOF 614 (M+1+).

Hplc (Magellan C8, Gradient 3, water/acetonitrile/TFA) rt 16.35 min.

Example 93
1-(3-Chloro-2-oxo-(1H) indol-6-carbonyl-D-phenylglycinyl)-4-(4-fluoro-2-methylsulphonylphenyl)piperazine 1H nmr (CD3CN) 7.90 (1H, d); 7.55 (1H, m); 7.25–7.50 (9H, m); 5.95 (1H, s); 5.20 (1H, s); 3.20 (3H, s); 3.00–2.50 (8H, m).

MS TOF 585 (M+1+).

Hplc (Magellan C8, Gradient 3, water/acetonitrile/TFA) rt 14.38 min.

Example 94
1-(3,3-Dichloro-2-oxo-(1H) indol-6-carbonyl-D-phenylglycinyl)-4-(4-fluoro-2-methylsulphonylphenyl)-piperazine 1H nmr (CD3CN) 7.90 (1H, d); 7.65 (2H, m); 7.55 (1H, m); 7.45 (2H, m); 7.35 (5H, m); 5.95 (1H, s); 3.25 (3H, s); 3.00–2.50 (8H, m).

MS TOF 619 (M+1+).

Hplc (Magellan C8, Gradient 3, water/acetonitrile/TFA) rt 15.13 min.

Example 95
1-(3-Methylindol-6-carbonyl-D-phenylglycinyl)-1'-methyl-4,4-bispiperidine 1H nmr (CD3CN) a mixture of conformers only one recorded here 7.85 (2H, m); 7.40 (3H, m); 7.30 (3H, m); 7.05 (1H, s) 5.95 (1H, s); 4.55 (1H, m); 3.85 (1H, m); 3.30 (2H, m); 2.90–2.40 (8H, m); 2.55 (3H, s); 2.20 (3H, s); 1.60 (2H, m); 1.30 (2H, m); 1.00 (2H, m).

MS TOF 473 (M+1+).

Hplc (Magellan C8, Gradient 3, water/acetonitrile/TFA) rt 12.40 min.

Example 96
1-(2,3-Dihydroindol-6-carbonyl-D-phenylglycinyl)-1'-methyl-4,4'-bispiperidine 1H nmr (CD3CN) a mixture of conformers only one recorded here 7.75 (1H, m); 7.30 (7H, m); 5.85 (1H, s); 4.45 (1H, m); 3.85 (1H, m); 3.65 (2H, t); 3.30 (2H, m); 3.10 (2H, t); 2.90–2.40 (8H, m); 2.55 (3H, s); 1.60 (2H, m); 1.30 (2H, m); 1.00 (2H, m).

MS TOF 461 (M+1+).

Hplc (Magellan C8, Gradient 3, water/acetonitrile/TFA) rt 8.68 min.

Example 97
1-(1H-indazol-6-carbonyl-D-phenylglycinyl)-1'-methyl-4,4'-bispiperidine 1H nmr (CD3CN) a mixture of conformers only one recorded here 7.95 (1H, m); 7.85 (2H, m); 7.65 (1H, m); 7.45 (2H, m); 7.30 (3H, m); 5.95 (1H, s); 4.55 (1H, m); 3.95 (1H, m); 3.30 (2H, m); 2.90–2.40 (8H, m); 2.55 (3H, s); 1.60 (2H, m); 1.30 (2H, m); 1.00 (2H, m).

MS TOF 460 (M+1+).

Hplc (Magellan C8, Gradient 3, water/acetonitrile/TFA) rt 9.72 min.

Example 98
1-(Benzimidazol-5-carbonyl-D-phenylglycinyl)-1'-methyl-4,4'-bispiperidine 1H nmr (CD3CN) a mixture of conformers only one recorded here. 8.05 (1H, s); 7.90 (1H, m); 7.75 (2H, m); 7.30 (5H, m); 5.95 (1H, s); 4.45 (1H, m); 3.85 (1H, m); 3.30 (2H, m); 2.90–2.40 (8H, m); 2.75 (3H, s); 1.60 (2H, m); 1.30 (2H, m); 1.00 (2H, m).

MS TOF 460 (M+1+).

Hplc (Magellan C8, Gradient 3, water/acetonitrile/TFA) rt 8.80 min.

Example 99
1-(Benzthiazol-6-carbonyl-D-phenylglycinyl)-1'-methyl-4,4'-bispiperidine 1H nmr (CD3CN) a mixture of conformers only one recorded here 8.40 (1H, s); 7.95 (3H, m); 7.30 (5H, m); 5.85 (1H, s); 4.45 (1H, m); 3.85 (1H, m); 3.30 (2H, m); 2.90–2.40 (8H, m); 2.65 (3H, s); 1.60 (2H, m); 1.30 (2H, m); 1.00 (2H, m).

MS TOF 477 (M+1+).

Hplc (Magellan C8, Gradient 3, water/acetonitrile/TFA) rt 9.58 min.

Example 100
1-(3-Chloroindol-6-carbonyl-D-phenylglycinyl)-1'-methyl-4,4'-bispiperidine 1H nmr (CD3CN) a mixture of conformers only one recorded here 7.85 (2H, m); 7.30 (7H, m); 5.85 (1H, s); 4.45 (1H, m); 3.85 (1H, m); 3.30 (2H, m); 2.90–2.40 (8H, m); 2.65 (3H, s); 1.60 (2H, m); 1.30 (2H, m); 1.00 (2H, m).

MS TOF 493 (M+1+).

Hplc (Magellan C8, Gradient 3, water/acetonitrile/TFA) rt 12.22 min.

Example 101
1-(3-Bromoindol-6-carbonyl-D-phenylglycinyl)-1'-methyl-4,4'-bispiperidine 1H nmr (CD3CN) a mixture of conformers only one recorded here 7.85 (2H, m); 7.30 (7H, m); 5.85 (1H, s); 4.45 (1H, m); 3.85 (1H, m); 3.30 (2H, m); 2.90–2.40 (8H, m); 2.65 (3H, s); 1.60 (2H, m); 1.30 (2H, m); 1.00 (2H, m).

MS TOF 539 (M+1+).

Hplc (Magellan C8, Gradient 3, water/acetonitrile/TFA) rt 12.45 min.

Example 102
1-(3-Amino-4-chlorobenzoyl-L-phenylglycinyl)-1'-methyl-4,4'-bispiperidine 1H nmr (CDCl3) a mixture of conformers only one recorded here 7.65 (1H, m); 7.30 (6H, m); 7.00 (1H, m); 5.85 (1H, s); 4.65 (1H, m); 3.80 (1H, m); 3.55 (2H, m); 2.90–2.40 (8H, m); 2.65 (3H, s); 1.60 (2H, m); 1.30 (2H, m); 1.00 (2H, m).

MS TOF 469 (M+1+). Hplc (Magellan C8, Gradient 3, water/acetonitrile/TFA) rt 10.71 min.

Example 103
1-(4-Vinylbenzoyl-D-phenylglycinyl)-1'-methyl-4,4'-bispiperidine 1H nmr (CD3CN) a mixture of conformers only one recorded here 7.85 (1H, m); 7.70 (2H, m); 7.40 (6H, m); 6.75 (1H, m); 6.00 (1H, s); 5.85 (1H, d); 5.50 (1H, d); 4.55 (1H, m); 3.95 (1H, m); 3.30 (2H, m); 2.90–2.40 (8H, m); 2.65 (3H, s); 1.60 (2H, m); 1.30 (2H, m); 1.00 (2H, m).

MS TOF 446 (M+1+).

Hplc (Magellan C8, Gradient 3, water/acetonitrile/TFA) rt 11.21 min.

Example 104
1-(3-Amino-4-chlorobenzoyl-D-phenylglycinyl)-4-(4-amino-2-methylsulphonylphenyl)piperazine 1H nmr (CD3CN) 7.55 (1H, m); 7.45 (3H, m); 7.35 (5H, m); 7.10 (1H, d); 6.90 (1H, d); 6.10 (1H, s); 3.20 (3H, s); 3.00–2.50 (8H, m).

MS TOF 542 (M+1+).

Hplc (Magellan C8, Gradient 3, water/acetonitrile/TFA) rt 12.02 min.

Example 105
1-(3-Aminobenzoyl-D-phenylglycinyl)-4-(4-amino-2-methylsulphonylphenyl)piperazine 1H nmr (CD3CN) 7.55 (2H, m); 7.45 (3H, m); 7.35 (5H, m); 7.10 (1H, d); 6.90 (1H, d); 6.10 (1H, s); 3.10 (3H, s); 3.00–2.50 (8H, m).

MS TOF 508 (M+1+).

Hplc (Magellan C8, Gradient 3, water/acetonitrile/TFA) rt 9.35 min.

Example 106
1-(3-Amino-4-chlorobenzoyl-D-phenylglycinyl)-4-(4-carboxamido-2-methylsulphonylphenyl)piperazine 1H nmr (CD3CN) 8.05 (1H, d); 7.80 (1H, m); 7.35–7.60 (8H, m); 7.10 (1H, d); 6.10 (1H, s); 3.25 (3H, s); 3.00–2.50 (8H, m).

MS TOF 570 (M+1+). Hplc (Magellan C8, Gradient 3, water/acetonitrile/TFA) rt 12.24 min.

Example 107
1-(3-Amino-4-chlorobenzoyl-D-phenylglycinyl)-4-(4-nitro-2-methylsulphonylphenyl)piperazine 1H nmr (CD3CN) 8.70 (1H. s); 8.45 (1H, d); 7.55 (1H, m); 7.45 (5H, m); 7.30 (2H, m); 7.10 (1H, d); 6.10 (1H, s); 3.40 (3H, s); 3.00–2.50 (8H, m).

MS TOF 572 (M+1+).

Hplc (Magellan C8, Gradient 3, water/acetonitrile/TFA) rt 14.25 min.

Example 108
1-(3-Amino-4-chlorobenzoyl-D-4-aminophenylglycinyl)-4-(4-fluoro-2-methylsulphonylphenyl)piperazine 1H nmr (CD3CN) 7.65 (1H, d); 7.45 (4H, m); 7.25 (2H, m); 7.15 (2H, d); 7.05 (1H, d); 6.10 (1H, s); 3.20 (3H, s); 3.00–2.50 (8H, m).

MS TOF 560 (M+1+).

Hplc (Magellan C8, Gradient 3, water/acetonitrile/TFA) rt 11.90 min.

Example 109
1-(3-Amino-4-chlorobenzoyl-D-4-carboxamidophenyl-glycinyl)-4-(4-fluoro-2-methylsulphonylphenyl)piperazine
1H nmr (CD3CN) 7.70 (2H, d); 7.55 (1H, d); 7.45 (2H, d); 7.25 (2H, m); 7.20 (2H, d); 6.90 (1H, d); 6.10 (1H, s); 3.20 (3H, s); 3.00–2.50 (8H, m).

MS TOF 588 (M+1+).

Hplc (Magellan C8, Gradient 3, water/acetonitrile/TFA) rt 12.18 min.

Example 110
1-(3-Amino-4-chlorobenzoyl-D-4-(methylcarboxamido)phenylglycinyl)-4-(4-fluoro-2-methylsulphonylphenyl)piperazine 1H nmr (CD3CN) 7.70 (2H, d); 7.55 (1H, d); 7.45 (2H, d); 7.25 (2H, m); 7.20 (2H, d); 6.90 (1H, d); 6.10 (1H, s); 3.20 (3H, s); 2.70 (3H, s); 3.00–2.50 (8H, m). MS TOF 602 (M+1+).

Hplc (Magellan C8, Gradient 3, water/acetonitrile/TFA) rt 12.70 min.

Example 111
3-Amino-4-chlorobenzoyl-D-phenylglycine 4-methylbenzylamide 1H nmr (CD3CN) 7.55 (1H, m); 7.35 (7H, m); 7.00 (4H, m); 5.45 (1H, s); 4.25 (2H, m); 2.20 (3H, s).

MS TOF 408 (M+1+).

Hplc (Magellan C8, Gradient 3, water/acetonitrile/TFA) rt 14.61 min.

Example 112
3-Amino-4-chlorobenzoyl-D-4-carboxamidophenylglycine R,S-2-methylcyclohexylamide 1H nmr (CD3CN) mixture of isomers only one recorded here 7.75 (2H, d); 7.60 (2H, m); 7.30 (2H, m); 7.10 (1H, d); 5.55 (1H, s); 3.90 (1H, m); 3.25 (1H, m); 1.00–2.00 (8H, m) 0.50 (3H, m).

MS TOF 443 (M+1+).

Hplc (Magellan C8, Gradient 3, water/acetonitrile/TFA) rt 9.18 min

Example 113
3-Amino-4-chlorobenzoyl-D-4-carboxamidophenylglycine 2-indanamide

MS TOF 463 (M+1+).

Hplc (Magellan C8, Gradient 3, water/acetonitrile/TFA) rt 12.58 min.

Example 114
3-Amino-4-chlorobenzoyl-D-4-carboxamidophenylglycine (S)—N-benzyl-alpha-methylbenzylamide

MS TOF 541 (M+1+).

Hplc (Magellan C8, Gradient 3, water/acetonitrile/TFA) rt 15.34 min.

Example 115
3-Amino-4-chlorobenzoyl-D-4-carboxamidophenylglycine 1-(S)-1-naphthylethylamide

MS TOF 5013 (M+1+).

Hplc (Magellan C8, Gradient 3, water/acetonitrile/TFA) rt 14.00 min.

Example 116
3-Amino-4-chlorobenzoyl-D-4-carboxamidophenylglycine 3-(1-(R,S)-hydroxyethyl)benzamide

MS TOF 443 (M+1+).

Hplc (Magellan C8, Gradient 3, water/acetonitrile/TFA) rt 11.81 min.

Example 117
3-Amino-4-chlorobenzoyl-D-phenylglycine cis,trans-2-aminocyclohexylamide

MS TOF 401 (M+1+).

Hplc (Magellan C8, Gradient 3, water/acetonitrile/TFA) rt 11.00 min.

Example 118
1-(3-Amino-4-chlorobenzoyl-D,L-(4-piperidinyl)glycinyl)-4-(4-fluoro-2-methylsulphonylphenyl)piperazine

MS TOF 552 (M+1+).

Hplc (Magellan C8, Gradient 3, water/acetonitrile/TFA) rt 11.00 min.

Example 119
1-(3-Amino-4-chlorobenzoyl-D,L-(4-N-methylpiperidinyl)-glycinyl)-4-(4-fluoro-2-methylsulphonylphenyl)piperazine

MS TOF 566 (M+1+).

Hplc (Magellan C8, Gradient 3, water/acetonitrile/TFA) rt 10.83 min.

Example 120
1-(3-Amino-4-chlorobenzoyl-D,L-(4-N-trifluoroacetyl-piperidinyl)glycinyl)-4-(4-fluoro-2-methylsulphonylphenyl)piperazine

MS TOF 649 (M+1+).

Hplc (Magellan C8, Gradient 3, water/acetonitrile/TFA) rt 12.63 min.

Example 121
3-Amino-4-chlorobenzoyl-D-phenylglycine (2-chloro-5-carboxamido)benzenesulphonamide MS TOF 521 (M+1+). Hplc (Magellan C8, Gradient 3, water/acetonitrile/TFA) rt 10.23 min.

Example 122
1-(4-Cyanobenzoyl-D-phenylglycinyl)-1'-methyl-4,4'-bispiperidine

MS TOF 445 (M+1+).

Hplc (Magellan C8, Gradient 3, water/acetonitrile/TFA) rt 10.13 min.

Example 123
1-(3-Cyanobenzoyl-D-phenylglycinyl)-1'-methyl-4,4'-bispiperidine

MS TOF 445 (M+1+).

Hplc (Magellan C8, Gradient 3, water/acetonitrile/TFA) rt 10.23 min.

Example 124
1-(4-Chlorobenzoyl-D-phenylglycinyl)-4-(4-pyridyl)-piperazine

MS TOF 435 (M+1+).

Hplc (Magellan C8, Gradient 3, water/acetonitrile/TFA) rt 12.11 min.

Example 125
1-(4-Methoxybenzyl-D-phenylglycinyl)-4-(4-fluoro-2-methylsulphonylphenyl)piperazine

MS TOF 512 (M+1+).

Hplc (Magellan C8, Gradient 3, water/acetonitrile/TFA) rt 11.91 min.

Example 126
1-N-(3-Amino-4-chlorobenzoyl)-2-N-(4-methoxybenzoyl)-1,2-diamino-1-phenylethane 1H nmr (CD3OH) 7.45 (2H, m); 7.35 (3H, m); 7.20 (2H, m); 7.10 (3H, m); 6.75 (2H, d); 4.80 (1H, m); 4.25 (2H, m); 3.70 (3H, s).

MS TOF 424 (M+1+).

Hplc (Magellan C8, Gradient 3, water/acetonitrile/TFA) rt 14.05 min.

Examples 127 to 136
Preparation of Starting Materials
4-methoxybenzoyl-D-phenylglycinyl-R,S-3-hydroxypyrrolidine D-phenylglycinyl-R,S-3-hydroxypyrrolidine (3.42 g, 15.5 mmol) was dissolved in dichloromethane (100 ml) and placed under argon. Triethylamine (2.27 ml, 16.28 mmol) was added followed by 4-methoxybenzoyl chloride (2.78 g, 16.3 mmol) and the mixture stirred at room temperature for 3.5 h. The organic solution was washed with 0.5% hydrochloric acid (50 ml), sat. sodium bicarbonate solution (50 ml) and brine (50 ml). The organic solution was dried (MgSO$_4$) and evaporated to an off-white solid, 4-methoxybenzoyl-D-phenylglycinyl-R,S-3-hydroxypyrrolidine, (5.49 g, 100%)

Hplc (Luna C18, Gradient3, water/acetonitrile/TFA), rt, 11.7 min.

LCMS M+1 355 Nmr.
4-methoxybenzoyl-D-phenylglycinyl-4-hydroxypiperidine

By a similar method D-phenylglycinyl-4-hydroxypiperidine was converted to 4-methoxybenzoyl-D-phenylglycinyl-4-hydroxypiperidine.

Hplc (Luna C18, Gradient3, water/acetonitrile/TFA), rt, 11.9 min.

LCMS M+1 369 Nmr.

Example 127
1-(4-Methoxybenzoyl-D-phenylglycinyl)-3-(R,S)-(2-fluorophenoxy)pyrrolidine To a solution of 4-methoxybenzoyl-D-phenylglycinyl-R,S-3-hydroxypyrrolidine (400 mg, 1.13 mmol) in benzene (10 ml) at 10° C. was added 2-triphenylphosphonium 4,4-dimethyl-tetrahydro-1,2,5-thiadiazolidine 1,1-dioxide (Reference: J. Castro et al. J. org. Chem. 1994, 59, 2289–2291) (696 mg, 1.69 mmol) and 3-methoxyphenol (210 mg) and the mixture allowed to warm to room temperature overnight. The reaction mixture was diluted with ether (30 ml) and washed with dilute sodium bicarbonate solution. The organic solution was dried (MgSO$_4$) and concentrated. The residue was purified by by reverse phase preparative chromatography to give 1-(4-methoxybenzoyl-D-phenylglycinyl)-3-(R,S)-(3-methoxyphenoxy)pyrrolidine.

Hplc (Luna C18, Gradient3, water/acetonitrile/TFA), rt, 11.75 min.

LCMS M+1 461 Nmr (mixture of diastereomers).

Example 128
1-(4-Methoxybenzoyl-D-phenylglycinyl)-3-(R,S)-(3-methoxyphenoxy)pyrrolidine From 4-methoxybenzoyl-D-phenylglycinyl-R,S-3-hydroxypyrrolidine and 3-methoxyphenol:

Hplc (Luna C18, Gradient3, water/acetonitrile/TFA), rt, 11.75 min.

LCMS M+1 461 Nmr (mixture of diastereomers).

Example 129
1-(4-methoxybenzoyl-D-phenylglycinyl)-4-(3-methoxyphenoxy)piperidine From 4-methoxybenzoyl-D-phenylglycinyl-4-hydroxypiperidine and 3-methoxyphenol:

Hplc (Luna C18, Gradient3, water/acetonitrile/TFA), rt, 16.09 min

LCMS M+1 475. Nmr

Example 130
1-(4-methoxybenzoyl-D-phenylglycinyl)-4-(4-methoxyphenoxy)piperidine From 4-methoxybenzoyl-D-phenylglycinyl-4-hydroxypiperidine and 4-methoxyphenol:

Hplc (Luna C18, Gradient3, water/acetonitrile/TFA), rt, 15.8 min.

LCMS M+1 475. Nmr.

Example 131
1-(4-methoxybenzoyl-D-phenylglycinyl)-4-(3-fluorophenoxy)piperidine From 4-methoxybenzoyl-D-phenylglycinyl-4-hydroxypiperidine and 3-fluorophenol:

Hplc (Luna C18, Gradient3, water/acetonitrile/TFA), rt, 12.75 min.

LCMS M+1 463 Nmr

Example 132
1-(4-methoxybenzoyl-D-phenylglycinyl)-4-(2-methanesulfonylphenoxy)piperidine From 4-methoxybenzoyl-D-phenylglycinyl-4-hydroxypiperidine and 2-methanesulphonylphenol:

Hplc (Luna C18, Gradient3, water/acetonitrile/TFA), rt, 10.8 min.

LCMS M+1 523 Nmr.

Example 133
1-(4-methoxybenzoyl-D-phenylglycinyl)-4-(2-methylmercaptophenoxy)piperidine From 4-methoxybenzoyl-D-phenylglycinyl-4-hydroxypiperidine and 2-methylmercaptophenol:

Hplc (Luna C18, Gradient3, water/acetonitrile/TFA), rt, 12.7 min
LCMS M+1 491 Nmr.

Example 134
1-(4-methoxybenzoyl-D-phenylglycinyl)-4-(2-fluorophenoxy)piperidine
From 4-methoxybenzoyl-D-phenylglycinyl-4-hydroxypiperidine and 2-fluorophenol:
Hplc (Luna C18, Gradient3, water/acetonitrile/TFA), rt, 15.8 min.
LCMS M+1 463 Nmr.

Example 135
1-(4-methoxybenzoyl-D-phenylglycinyl)-4-(phenoxy)piperidine
From 4-methoxybenzoyl-D-phenylglycinyl-4-hydroxypiperidine and phenol:
Hplc (Luna C18, Gradient3, water/acetonitrile/TFA), rt, 16.8 min.
LCMS M+1 445.

Example 136
1-(4-methoxybenzoyl-D-phenylglycinyl)-4-(3-pyridoxy)piperidine
From 4-methoxybenzoyl-D-phenylglycinyl-4-hydroxypiperidine and 3-hydroxypyridine:
Hplc (Luna C18, Gradient3, water/acetonitrile/TFA), rt, 11.4 min.
LCMS M+1 446 Nmr.

Example 137
1-(4-methoxybenzoyl-D-phenylglycinyl)-4-(4-fluorophenoxy)piperidine
To a solution of triphenylphosphine (285 mg, 1.09 mmol) in dry THF (5 ml) under argon at −15° C. was added slowly (<−10° C.) diethyl azodicarboxylate (DEAD) (20 mg, 1.19 mmol) and the solution stirred at <−10° C. for 5 min. To this mixture was added a solution of 4-methoxybenzoyl-D-phenylglycinyl-4-hydroxypiperidine (400 mg, 1.08 mmol) and 4-fluorophenol (122 mg, 1.09 mmol) in dry THF (5 ml) over 5 min at <−10° C. The reaction was warmed to room temperature and monitored by tlc (SiO$_2$—ethyl acetate). The reaction mixture was poured into water (5 ml) and extracted with dichloromethane (100 ml). The organic solution was washed with sat. sodium bicarbonate (50 ml) and 0.5% hydrochloric acid (50 ml), dried (MgSO$_4$) and concentrated and the residue purified by flash chromatography, (SiO$_2$-30% ethyl acetate in hexane to give 1-(4-methoxybenzoyl-D-phenylglycinyl)-4-(4-fluorophenoxy)piperidine, (107 mg, 21%)
Hplc (Luna C18, Gradient3, water/acetonitrile/TFA), rt, 16.0 min.
LCMS M+1 463. Nmr.

Examples 138 to 142
Preparation of Starting Materials
Benzyloxycarbonyl-D-phenylglycinyl-R,S-3-hydroxypyrrolidine
Benzyloxycarbonyl-D-phenylglycine (18.01 g, 63.1 mmol) and R,S-3-hydroxypyrrolidinol (5.0 g, 57.4 mmol) were suspended in dimethylformamide (300 ml). HOAt (8.61 g, 63.1 mmol) was added, the mixture stirred for 3 min. and then EDCI (12.1 g 63.1 mmol) was added with stirring and the mixture left overnight. The orange solution was concentrated in vacuo and the residue taken up in ethyl acetate (300 ml). The organic solution was washed with sat. sodium bicarbonate (2×100 ml), 0.5% aqueous hydrochloric acid (50 ml) and brine (100 ml). The organic solution was dried (MgSO$_4$) and evaporated in vacuo to give an orange solid. Flash chromatography (SiO$_2$ 1:1 dichloromethane: ethyl acetate gave benzyloxycarbonyl-D-phenylglycinyl-R, S-3-hydroxypyrrolidine, (11.4 g, 56%).
Hplc (Luna C18, Gradient3, water/acetonitrile/TFA), rt, 12.7 min
LCMS M+1 355 Nmr.
Benzyloxycarbonyl-D-phenylglycinyl-4-hydroxypiperidine
By a similar method using benzyloxycarbonyl-D-phenylglycine and 4-hydroxypiperidine, benzyloxycarbonyl-D-phenylglycinyl-4-hydroxypiperidine was prepared.
Hplc (Luna C18, Gradient3, water/acetonitrile/TFA), rt, 11.9 min
LCMS M+1 369 Nmr.
D-Phenylglycinyl-R,S-3-hydroxypyrrolidine
Benzyloxycarbonyl-D-phenylglycinyl-R,S-3-hydroxypyrrolidine, (5.49 g, 15.5 mmol) was dissolved in ethanol (120 ml) and Pd/C (10%, 100 mg) added. The mixture was hydrogenated at atmospheric pressure until complete by tlc (SiO$_2$ ethyl acetate—starting material Rf. 0.6, product 0.05). The catalyst was filtered off through celite and concentrated in vacuo to give D-phenylglycinyl-R,S-3-hydroxypyrrolidine as a yellow oil, (3.54 g, 16.1 mmol).
D-Phenylglycinyl-4-hydroxypiperidine
By a similar method benzyloxycarbonyl-D-phenylglycinyl-4-hydroxypiperidine was converted to D-phenylglycinyl-4-hydroxypiperidine.
Benzyloxycarbonyl-D-phenylglycinyl-4-(3-pyridoxy)piperidine
To a solution of benzyloxycarbonyl-D-phenylglycinyl-4-hydroxypiperidine (500 mg, 1.36 mmol), 3-hydroxypyridine (129 mg, 1.36 mmol) and triphenylphosphine (356 mg, 1.36 mmol) in dry THF (20 ml) at 0° C., was slowly added diethyl azodicarboxylate (259 mg, 1.19 mmol) and the mixture stirred for 1 h at 0° C. and then 16 h at room temperature. Water (5 ml) was added and the mixture extracted with ethyl acetate (2×10 ml). The organic solution was washed with water and brine, dried (MgSO$_4$) and concentrated to an oil which was purified by flash chromatography, (SiO$_2$—hexane/ethyl acetate 1:1) to give benzyloxycarbonyl-D-phenylglycinyl-4-(3-pyridoxy)piperidine, (490 mg 65%-contaminated with triphenylphosphine).
Benzyloxycarbonyl-D-phonylglycinyl-R,S-3-(3-pyridoxy)-pyrrolidine
A solution of benzyloxycarbonyl-D-phenylglycinyl-R,S-3-hydroxypyrrolidine (2.0 g, 8.64 mmol), 2-triphenylphosphonium 4,4-dimethyl-tetrahydro-1,2,5-thiadiazolidine 1,1-dioxide (Reference: J. Castro et al. J. Org. Chem. 1994, 59, 2289–2291) (3.479 g, 8.47 mmol) and 3-hydroxypyridine (0.805 g, 8.47 mmol) in benzene (30 ml) was stirred at room temperature for 18 h. The mixture was poured onto ether (50 ml) and the organic solution was washed with sat. sodium bicarbonate (2×50 ml). The product was extracted into 5% hydrochloric acid which was then basified (pH8) with 2M sodium hydroxide solution and extracted with ether (3×100 ml). The organic solution was dried (MgSO$_4$) and evaporated to give benzyloxycarbonyl-D-phenylglycinyl-R,S-3-(3-pyridoxy)pyrrolidine.
D-Phenylglycinyl-4-(3-pyridoxy)piperidine
Benzyloxycarbonyl-D-phenylglycinyl-4-(3-pyridoxy) piperidine (1.18 g 2.64 mmol) was dissolved in ethanol (120 ml) containing Pd/C 10% (100 mg) and acetic acid (0.3 ml) and hydrogenated at atmospheric pressure for 8 h—(incomplete by tlc). The catalyst was removed by filtration and the solution evaporated to an oil. The oil was re-hydrogenated as before. The catalyst was removed by filtration and the solvent evaporated in vacuo to an oil which was taken up in dilute hydrochloric acid. The aqueous solution was washed with dichloromethane and then basified with solid sodium bicarbonate. Extraction with chloroform, drying ($MgSO_4$) and evaporation of the solvent in vacuo gave D-phenylglycinyl-4-(3-pyridoxy)piperidine, (331 mg 40%). Nmr D-phenylglycinyl-R,S-3-(3-pyridoxy)pyrrolidine In a similar manner D-phenylglycinyl-R,S-3-(3-pyridoxy)pyrrolidine was prepared from benzyloxycarbonyl-D-phenylglycinyl-R,S-3-(3-pyridoxy)pyrrolidine by hydrogenation over Pd/C in ethanol. Nmr.

Example 138
1-(Indole-6-carbonyl-D-phenylglycinyl)-4-(3-pyridoxy)piperidine

A mixture of EDCI (169 mg 0.88 mmol), HOAt (120 mg 0.88 mmol) and indole-6-carboxylic acid (142 mg 0.88 mmol) in DMF (5 ml) was stirred for 2 min and then added to a solution of D-phenylglycinyl-4-(3-pyridoxy)piperidine (229 mg 0.735 mmol) and triethylamine (89 mg 0.88 mmol) in DMF (20 ml). The mixture was stirred at room temperature for 3 h and excess solvent removed in vacuo. The residue was taken up in ethyl acetate (150 ml) and washed with sat. sodium bicarbonate (50 ml). The solution was dried ($MgSO_4$), evaporated and the residue purified by flash chromatography ($SiO_2$ ethyl acetate: methanol 0%–5%) to give 1-(indole-6-carbonyl-D-phenylglycinyl)-4-(3-pyridoxy)piperidine (122 mg 41%)

Hplc (Luna C18, Gradient3, water/acetonitrile/TFA), rt, 10.8 min.

LCMS M+1 455 Nmr.

The following were prepared in a similar manner:

Example 139
1-(3-Chloroindole-6-carbonyl-D-phenylglycinyl)-4-(3-pyridoxy)piperidine From D-phenylglycinyl-4-(3-pyridoxy)piperidine and 3-chloro-6-indolecarboxylic acid:

Hplc (Luna C18, Gradient3, water/acetonitrile/TFA), rt 11.95 min

LMCS M+1 489 Nmr.

Example 140
1-(Indole-6-carbonyl-D-phenylglycinyl)-3-(R,S)-(3-pyridoxy)pyrrolidine From D-phenylglycinyl-R,S-3-(3-pyridoxy)pyrrolidine and 6-indolecarboxylic acid.

Hplc (Luna C18, Gradient3, water/acetonitrile/TFA), rt, 6.4 min.

LCMS M+1 441 Nmr (mixture of diastereomers).

Example 141
1-(3-Chloroindole-6-carbonyl-D-phenylglycinyl)-3-(R,S)-(3-pyridoxy)pyrrolidine From D-phenylglycinyl-R,S-3-(3-pyridoxy)pyrrolidine and 3-chloro-6-indolecarboxylic acid.

Hplc (Luna C18, Gradient3, water/acetonitrile/TFA), rt, 7.2 min.

LCMS M+1 475 Nmr (mixture of diastereomers).

Example 142
1-(3-Methylindole-6-carbonyl-D-phenylglycinyl)-3-(R,S)-(3-pyridoxy)pyrrolidine From D-phenylglycinyl-R,S-3-(3-pyridoxy)pyrrolidine and 3-methyl-6-indolecarboxylic acid.

Hplc (Luna C18, Gradient3, water/acetonitrile/TFA), rt, 6.84 and 7.0 min.

LCMS M+1 455 Nmr (mixture of diastereomers).

Example 143
(R)-2-(1'-(3-Chloroindole-6-carboxamido)benzyl)-4-methoxyphenyl-1,3-thiazole
(R)-2-(1'-benzyloxycarbonylamidobenzyl)-4-methoxyphenyl-1,3-thiazole To a solution of benzyloxycarbonyl-D-phenylglycine thioamide (1 g, 3.33 mmol.) in acetone (25 ml) was added α-bromo-4-methoxyacetophenone (0.76 g, 3.32 mmol) and the mixture stirred at room temperature for 30 min. Chloroform (25 ml) and sat. aqueous sodium hydrogen carbonate (30 ml) were added and the organic solution separated, dried ($MgSO_4$) and evaporated in vacuo. The residue was dissolved in dichloromethane (30 ml) and pyridine (0.5 ml, 6.18 mmol) and trifluoroacetic anhydride (0.5 ml, 3.54 mmol) were added. The mixture was stirred at room temperature until complete by tlc ($SiO_2$ dichloromethane-1 h.), washed with 5% hydrochloric acid, dried ($MgSO_4$) and evaporated in vacuo. Flash chromatography of the residue (0.87 g). ($SiO_2$-dichloromethane) gave (R)-2-(1'-benzyloxycarbonylamidobenzyl)-4-methoxyphenyl-1,3-thiazole (0.74 g 1.72 mmol. 52%).

Nmr: $CDCl_3$ 7.85(2H, d), 7.3–7.5 (11H, m), 6.95 (2H, d), 6.44 (0.5H, bd), 6.16 (0.5H, bd), 5.02–5.22 2H, m), 3.83 (3H, m).

(R)-2-(1'-aminobenzyl)-4-methoxyphenyl-1,3-thiazole (R)-2-(1'-Benzyloxycarbonylamidobenzyl)-4-methoxyphenyl-1,3-thiazole (0.70 g, 1.63 mmol) was dissolved in acetic acid (50 ml) and HBr in acetic acid (25 ml) added. The mixture was heated in a 50° C. oil bath for 2 h when no starting material remained by tlc ($SiO_2$ 30% ether in dichloromethane). The mixture was evaporated in vacuo, basified with sat. aqueous sodium hydrogen carbonate and extracted with ethyl acetate (×3). The organic solution was dried ($MgSO_4$) and evaporated in vacuo. Flash chromatography ($SiO_2$ dichloromethane then 30% ether in dichloromethane) gave (R)-2-(1'-aminobenzyl)-4-methoxyphenyl-1,3-thiazole (172 mg, 36%)

Nmr: $CDCl_3$ 7.7 (2H, d), 7.5 (2H, d), 7.17–7.4 (3H, m), 6.85 (2H, d), 3.76 (3H, s).

(R)-2-(1'-(3-Chloroindole-6-carboxamido)benzyl)-4-methoxyphenyl-1,3-thiazole (R)-2-(1'-Aminobenzyl)-4-methoxyphenyl-1,3-thiazole (80 mg, 0.27 mmol) was coupled to 3-chloroindolecarboxylic acid using EDC/HOAt to give: (R)-2-(1'-(3-Chloroindole-6-carboxamido)benzyl)-4-methoxyphenyl-1,3-thiazole (49%)

Hplc (Luna C18 Gradient3) rt 17.2 min.

LCMS M+1 474. Nmr.

Examples 144 to 147

The compounds of Examples 144 to 147 were prepared by coupling to the appropriate carboxylic acid to D-phenylglycinyl-4,4'-(1'-methylbispiperidine) using EDC and HOAt as described previously.

Example 144
1-(4-Methylbenzoyl-D-phenylglycinyl)-1'-methyl-4,4-bispiperidine Hplc (Luna C18 Gradient3) rt 11.2 min.

LCMS M+1 434. Nmr.

Example 145
1-(4-Chlorobenzoyl-D-phenylglycinyl)-1'-methyl-4,4'-bispiperidine
Hplc (Luna C18 Gradient3) rt 11.5 min.
LCMS M+1 454. Nmr.

Example 146
1-(4-Methoxybenzoyl-D-phenylglycinyl)-1'-methyl-4,4'-bispiperidine
Hplc (Luna C18 Gradient3) rt 11.1 min.
LCMS M+1 450. Nmr.

Example 147
1-(3,4-Methylenedioxybenzoyl-D-phenylglycinyl)-1'-methyl-4,4'-bispiperidine
Hplc (Luna C18 Gradient3) rt 10.65 min.
LCMS M+1 464. Nmr.

Example 148
1-(Indole-6-carbonyl-D-phenylglycinyl)-1'-isopropyl-4,4'-bispiperidine
Benzyloxycarbonyl-D-phenylglycinyl-4,4'-(1'-bispiperidine)
Benzyloxycarbonyl-D-phenylglycinyl-1'-isopropyl-4,4'-bispiperidine
D-phenylglycinyl-1'-isopropyl-4,4'-bispiperidine
1-(Indole-6-carbonyl-D-phenylglycinyl)-1'-isopropyl-4,4'-bispiperidine
Prepared by coupling the appropriate carboxylic acid to D-phenylglycinyl-4,4'-(1'-(2"-propyl)bispiperidine).
Hplc (Luna C18 Gradient3) rt 11.46 min.
LCMS M+1 487. Nmr.

Examples 149 to 154

The compounds of Examples 149 to 154 were prepared by coupling Boc-D-4-carboxamidophenylglycine to the appropriate amine with EDCI/HOAt, deprotection with TFA/DCM and coupling to 3-amino-4-chlorobenzoic acid with EDCI/HOAt as previously described.

Example 149
2-(3-Amino-4-chlorobenzoyl-D-4-carboxamidophenyl-glycinyl)-1,2,3,4-tetrahydroisoquinoline
Hplc (Luna C18 Gradient3) rt 13.15 min.
LCMS M+1 463. Nmr.

Example 150
1-(3-Amino-4-chlorobenzoyl-D-4-carboxamidophenyl-glycinyl)-4-benzylpiperazine
Hplc (Luna C18 Gradient3) rt 11.4 min.
LCMS M+1 512. Nmr.

Example 151
1-(3-Amino-4-chlorobenzoyl-D-4-carboxamidophenyl-glycinyl)-4-(2-methylthiophenyl)piperazine
Hplc (Luna C18 Gradient3) rt 14.3 min.
LCMS M+1 539. Nmr.

Example 152
1-(3-Amino-4-chlorobenzoyl-D-4-carboxamidophenyl-glycinyl)-4-(2-phenylethyl)piperazine
Hplc (Luna C18 Gradient3) rt 11.1 min.
LCMS M+1 521. Nmr.

Example 153
1-(3-Amino-4-chlorobenzoyl-D-4-carboxamidophenyl-glycinyl)-4-benzoylpiperidine
Hplc (Luna C18 Gradient3) rt 12.8 min.
LCMS M+1 520. Nmr.

Example 154
1-(3-Amino-4-chlorobenzoyl-D-4-carboxamidophenyl-glycinyl)-4-(2-ethylphenyl)piperazine
Hplc (Luna C18 Gradient3) rt 13.9 min.
LCMS M+1 521. Nmr.

Example 155
1-(3-Methoxyindole-6-carbonyl-D-phenylglycinyl)-1'-methyl-4,4'-bispiperidine
Methyl 1-acetyl-3-formylindole-6-carboxylate
A suspension of methyl 3-formylindole-6-carboxylate (1 g, 4.93 mmol) in acetic anhydride (10 ml) was refluxed for 2 h.
The acetic anhydride was removed under reduced pressure to afford a pinkish solid (1.2 g, 100%) that was used without further purification. $^1$H NMR (CDCl$_3$) 2.7 (3H, s), 3.9 (3H, s), 8.05 (1H, d), 8.15 (1H, s), 8.25 (1H, d), 9.0 (1H, s), 10.1 (1H, s);
LCMS M+H 246.
Methyl 1-acetyl-2,3-dihydroindol-3-one-6-carboxylate
This was prepared from methyl 1-acetyl-3-formylindole-6-carboxylate (1.03 g, 4.20 mmol) using the method of Merour et al. (*Synthesis*, 1994, 411) to yield the formate (680 mg).
The formate was dissolved in THF (50 ml) and treated with sat. NaHCO$_3$ solution (10 ml). After 15 min. the reaction mixture was extracted with ethyl acetate, washed with water, dried and concentrated to give the ketone (574 mg).
$^1$H NMR (CDCl$_3$) 2.3 (3H, br.), 3.9 (3H, s), 4.3 (2H, s), 7.75 (1H, d), 7.85 (1H, d), 9.1 (1H, br.);
LCMS M+H 234.
Methyl 1-acetyl-3-methoxyindole-6-carboxylate
Methyl 1-acetyl-2,3-dihydroindol-3-one-6-carboxylate (233 mg, 1 mmol), trimethyl orthoformate (10 ml) and p-toluene sulphonic acid (20 mg) were heated under reflux for 3 h. in methanol (10 ml). The reaction mixture was concentrated under reduced pressure, poured into water and extracted with chloroform. After drying and evaporation, the product was purified by prep hplc;
$^1$H NMR (CD$_3$CN) 2.56 (3H, s), 3.93 (3H, s), 3.97 (3H, a), 7.25 (1H, s), 7.62 (1H, d), 7.90 (1H, d), 9.0 (1H, br.);
LCMS M+H 248.
3-Methoxyindole-6-carboxylic acid
To a solution of methyl 1-acetyl-3-methoxyindole-6-carboxylate (74 mg, 0.3 mmol) in THF (10 ml) and water (2 ml) was added lithium hydroxide hydrate (63 mg, 1.5 mmol). The reaction mixture was warmed to 50° C. and stirred for 3 h. The THF was removed under reduced pressure and the pH of the aqueous phase adjusted to 3. Extraction of the aqueous layer with ethyl acetate, drying and concentration gave the acid (50 mg, 87%);
$^1$H NMR (CD$_3$CN) 3.75 (3H, s), 3.97 (3H, s), 6.9 (1H, 9), 7.45 (1H, d), 7.55 (1H, d), 8.2 (1H, s);
LCMS M+H 192.
1-(3-Methoxyindole-6-carbonyl-D-phenylglycinyl)-4,4'-(1'-methylbispiperidine)
Prepared by coupling to D-phenylglycinyl-4,4'-(1'-methylbispiperidine) using EDC and HOAt as described previously.
Hplc (Luna C18, Gradient3) rt 8.35 min.
LCMS M+1 489 Nmr.

Example 156
1-(3-Amino-4-chlorobenzoyl-D-cyclohexylglycinyl)-4-(4-fluoro-2-methylsulfonylphenyl)-piperazine Hplc (Luna C18, Gradient3, water/acetonitrile/TFA) rt 15.37 min.

LCMS M+1 551.

Example 157
1-(3-Amino-4-chlorobenzoyl-D,L-1-napthylglycinyl)-4-(4-fluoro-2-methylsulfonylphenyl)-piperazine Hplc (Luna C18, Gradient3, water/acetonitrile/TFA) rt 15.69 min.

LCMS M+1 595.

Example 158
1-(3-Chloroindole-6-carbonyl-D,L-(2-methylthiazol-4-yl) glycinyl)-1'-methyl-4,4'-bispiperidine Ethyl Oximinoacetoacetate This was prepared from ethyl acetoacetate (10.00 g) using the method of Fischer (organic Synthesis Coll. Vol. 3, 513–516) to yield the titled compound (12.45 g);

$^1$H NMR (CDCl$_3$) 1.25 (3H, t), 2.35 (3H, s), 4.3 (2H, q), 8.8 (1H, br.).

Ethyl-γ-chloro-α-oximinoacetoacetate

This was prepared from ethyl oximinoacetoacetate (1.73 g) using the method of Hatanaka et al. (*Journal of Medicinal Chemistry*, 1973, 16(9), 978–984) to yield the titled compound (1.44 g);

$^1$H NMR (CDCl$_3$) 1.25 (3H, t), 4.3 (2H, q), 4.55 (2H, s), 9.45 (1H, s), contains 20% starting material by NMR.

Ethyl-α-oximino-2-methylthiazole-4-acetate

This was prepared from ethyl-γ-chloro-α-oximinoacetoacetate (1.44 g) using the method of Hatanaka et al. (*Journal of Medicinal Chemistry*, 1973, 16(9), 978–984) to yield the titled compound (0.64 g);

$^1$H NMR (CDCl$_3$) 1.35 (3H, t), 2.7 (3H, s), 4.35 (2H, q), 8.2 (1H, s).

D,L-(2-methylthiazol-4-yl)glycine ethyl ester

This was prepared from ethyl-α-oximino-2-methylthiazole-4-acetate (0.62 g) using the method of Hatanaka et al. (*Journal of Medicinal Chemistry*, 1973, 16(9), 978–984) to yield the titled compound (0.40 g);

$^1$H NMR (CDCl$_3$) 1.15 (3H, t), 1.95 (2H, br.), 2.6 (3H, 8), 4.15 (2H, m), 4.65 (1H, s), 6.95 (1H, s).

N-Boc-D,L-(2-methylthiazol-4-yl)glycine ethyl ester

To a solution of D,L-(2-methylthiazol-4-yl)glycine ethyl ester (0.397 g, 1.982 mmol) in tetrahydrofuran (20 cm$^3$), was added di-tert-butyldicarbonate (0.475 g, 2.180 mmol) and triethylamine (0.304 cm$^3$, 2.180 mmol). This was allowed to stir for 1 hour and the solution concentrated in vacuo. The oil was taken up in ethyl acetate (c.a. 50 cm$^3$) washed with 0.5% hydrochloric acid solution (c.a. 20 cm$^3$), and saturated sodium bicarbonate solution (c.a. 20 cm$^3$). This was then dried over magnesium sulphate and concentrated in vacuo to yield a yellow oil (0.654 g, 2.177 mmol) [~100% yield]; $^1$H NMR (CDCl$_3$) 1.1 (3H, s), 1.35 (9H, s), 2.6 (3H, s), 4.15 (3H, m), 5.3 (1H, d), 5.7 (1H, s), 7.0 (1H, s).

N-Boc-D,L-(2-methylthiazol-4-yl)glycine

To a solution of N-Boc-D,L-(2-methylthiazol-4-yl)glycine ethyl ester (0.595 g, 1.982 mmol) in methanol (c.a. 15 cm$^3$), was added 2M sodium hydroxide (1.98 cm$^3$, 3.964 mmol), and allowed to stir for 30 minutes. The solution was concentrated in vacuo and taken up in water (c.a. 50 cm$^3$). The aqueous solution was washed with ethyl acetate (c.a. 30 cm$^3$), and then acidified to pH 2 with 5% hydrochloric acid solution (c.a. 50 cm$^3$). The product was extracted with ethyl acetate (c.a. 3×60 cm$^3$), dried over magnesium sulphate, and concentrated in vacuo to yield a pale yellow oil (0.645 g, 2.368 mmol) [~100% yield];

$^1$H NMR (CDCl$_3$) 1.35 (9H, s), 2.6 (3H, s), 5.4 (1H, d), 5.9 (1H, s), 7.1 (1H, s).

1-(N-Boc-D,L-(2-methylthiazol-4-yl)glycinyl) 1'-methyl-4,4'-bispiperidine

Prepared by coupling N-Boc-D,L-(2-methylthiazol-4-yl)-glycine to 4,4'-(1'-methylbispiperidine) di-HCl salt using EDC and HOAt as described previously;

$^1$H NMR (CDCl$_3$) 0.5–1.3 (10H, br.), 1.35 (9H, s), 1.4–1.85 (6H, br.), 2.2 (3H, d), 2.6 (3H, s), 3.75–4.0 (1H, br.), 4.55 (3H, br.), 5.7 (1H, d), 6.1 (1H, d), 6.95 (1H, d).

1-(D,L-(2-Methylthiazol-4-yl)glycinyl)-1'-methyl-4,4'-bispiperidine

Prepared from 1-(N-Boc-D,L-(2-methylthiazol-4-yl) glycinyl)1'-methyl-4,4'-bispiperidine using DCM/TFA deprotection as described previously;

$^1$H NMR (CDCl$_3$) 0.9–1.8 (12H, br.), 2.4–2.3 (2H, br.), 2.45 (3H, br.), 2.6 (3H, s), 3.1–3.4 (3H, br.), 4.6 (1H, br.), 4.95 (1H, s), 6.85 (1H, d).

1-(3-Chloroindole-6-carbonyl-D,L-(2-Methylthiazol-4-yl) glycinyl)-1'-methyl-4,4'-bispiperidine Prepared by coupling 1-(D,L-(2-methylthiazol-4-yl)-glycinyl)-1'-methyl-4,4'-bispiperidine to 3-chloroindole-6-carboxylic acid using EDC and HOAt as described previously;

$^1$H NMR (CDCl$_3$) 0.5–1.9 (12H, br.), 2.4 (2H, br.), 2.55 (3H, s), 2.65 (3H, s), 3.5 (2H, br.), 4.1 (1H, br.), 4.55 (1H, br.), 6.15 (1H, d), 7.15 (1H, d), 7.5 (2H, br.), 7.8–8.1 (2H, br.), 8.9–9.25 (1H, br.), 12.2–12.6 (1H, br. d);

HPLC (Luna C18, Gradient3) rt 8.75 min.;

LCMS M+1 514.

Example 159
1-(3-Chloroindole-6-carbonyl-D,L-4-(thiazolylglycinyl)-1'-methyl-4,4'-bispiperidine Ethyl-α-oximino-thiazole-4-acetate To a 2 necked r.b. flask (100 cm$^3$) with ethanol thermometer, concentrated sulphuric acid (25 cm$^3$) was added and cooled to 0° C. with stirring. To this solution, was added the ethyl-α-oximino-2-aminothiazole-4-acetate (5.00 g, 23.231 mmol). Water (10 cm$^3$) was then added and cooled to −10° C. A solution of sodium nitrite (1.683 g, 24.393 mmol) in water (5 cm$^3$) was then added slowly over an hour keeping the temperature below −5° C.

To a separate r.b. flask (500 cm$^3$), water (180 cm$^3$) was added and cooled to 3° C. The reaction solution was poured on to the cold water with stirring and then cooled to −5° C. To this solution, 50% hypophosphoric acid (90 cm$^3$) was added dropwise over 10 minutes keeping the temperature at −5° C. The solution was allowed to warm to room temperature and stirred overnight. The product was extracted with diethyl ether (c.a. 3×150 cm$^3$) and washed with water. The ether layer was concentrated in vacuo and treated to flash chromatography (50% ethyl acetate/n-hexane) to yield a orange oil upon concentration in vacuo (0.60 g, 3.00 mmol) [13% yield];

$^1$H NMR (CDCl$_3$) 1.35 (3H, m), 4.35 (2H, m), 8.4 (1H, s), 8.9 (1H, s), 14.4 (1H, s).

D,L-4-thiazolylglycine ethyl ester

This was prepared from ethyl-α-oximino-thiazole-4-acetate (0.60 g) using the method of Hatanaka et al. (*Journal of Medicinal Chemistry*, 1973, 16(9), 978–984) to yield the titled compound (0.46 g);

$^1$H NMR (CDCl$_3$) 1.25 (3H, t), 1.8–2.3 (2H, br.), 4.1 (2H, m), 4.75 (1H, s), 7.25 (1H, d), 8.7 (1H, d).

N-Boc-D,L-4-thiazolylglycine ethyl ester

To a solution of D,L-4-thiazolylglycine ethyl ester (0.460 g, 2.470 mmol) in tetrahydrofuran (20 cm$^3$), was added di-tert-butyldicarbonate (0.530 g, 2.470 mmol) and triethylamine (0.344 cm$^3$, 2.470 mmol). This was allowed to stir for 1 hour and the solution concentrated in vacua. The oil was taken up in ethyl acetate (c.a. 50 cm$^3$) washed with 0.5% hydrochloric acid solution (c.a. 20 cm$^3$) and saturated sodium bicarbonate solution (c.a. 20 cm$^3$). This was then dried over magnesium sulphate and concentrated in vacuo to yield an orange oil (0.709 g, 2.477 mmol) [~100% yield;

$^1$H NMR (CDCl$_3$) 1.15 (3H, t), 1.35 (9H, s), 4.1 (2H, m), 5.45 (1H, d), 5.75 (1H, d), 7.3 (1H, d), 8.7 (1H, d).

N-Boc-D, L-4-thiazolylglycine

To a solution of N-Boc-D,L-4-thiazolylglycine ethyl ester (0.700 g, 2.470 mmol) in methanol (c.a. 15 cm$^3$), was added 2M sodium hydroxide (2.47 cm$^3$, 4.940 mmol) and allowed to stir for 90 minutes. The solution was concentrated in vacuo and taken up in water (c.a. 20 cm$^3$). The aqueous solution was washed with ethyl acetate (c.a. 20 cm$^3$), and then acidified to pH 2 with 5% hydrochloric acid solution (c.a. 50 cm$^3$). The product was extracted with ethyl acetate (c.a. 3×30 cm$^3$), dried over magnesium sulphate, and concentrated in vacuo to yield a pale yellow oil (0.582 g, 2.254 mmol) [91% yield];

$^1$H NMR (CDCl$_3$) 1.35 (9H, s), 5.5 (1H, d), 5.8 (1H, d), 7.35 (1H, d), 8.75 (1H, d), 9.8–10.2 (1H, br.).

1-(N-Boc-D,L-4-thiazolylglycinyl)-1'-methyl-4,4'-bispiperidine

Prepared by coupling N-Boc-D,L-4-thiazolylglycine to 4,4'-(1'-methylbispiperidine) di-HCl salt using EDC and HOAt as described previously;

$^1$H NMR (CDCl$_3$) 0.8–1.25 (10H, br.), 1.35 (9H, m), 1.7 (6H, br.), 2.0 (6H, m), 2.4 (3H, br.), 3.1 (2H, br.), 3.7 (1H, d), 4.6 (1H, d), 5.8 (1H, d), 6.0 (1H, br., 7.25 (1H, 1H, br.), 8.65 (1H, m).

1-(D,L-4-Thiazolylglycinyl)-1'-methyl-4,4'-bispiperidine

Prepared from 1-(N-Boc-D,L-4-thiazolylglycinyl)-1'-methyl-4,4'-bispiperidine using DCM/TFA deprotection as described previously. The product was purified by prep HPLC; LCMS M+1 323.

1-(3-Chloroindole-6-carbonyl-D,L-thiazol-4-ylglycinyl-1'-methyl-4,4'-bispiperidine Prepared by coupling 1-(D,L-4-Thiazolylglycinyl)-1'-methyl-4,4'-bispiperidine to 3-chloroindole-6-carboxylic acid using EDC and HOAt as described previously;

$^1$H NMR (CD$_3$CN) 0.5–2.0 (10H, br.), 2.5 (2H, m), 2.8 (3H, br.), 3.1 (2H, m), 3.5 (2H, br.), 4.2 (1H, d), 4.6 (1H, d), 6.4 (1H, m), 7.5 (1H, br.), 7.8 (2H, br.), 8.15 (2H, br.), 9.05 (1H, br.), 9.9 (1H, br.);

HPLC (Luna C18, Gradient3) rt 6.69 min;

LCMS M+1 500.

Preparation of Starting Materials:

Boc-R-4-(carboxymethyl)phenylglycine

R-4-Hydroxyphenylglycine methyl ester hydrochloride.

To a dry 250 ml three necked round bottom flask, equipped with a low temperature thermometer, a septum for nitrogen coverage and another for introduction of thionyl chloride by syringe, was added R-4-hydroxyphenylglycine (12.5 g) and dry methanol (24 ml). The mixture was stirred (magnetic stirrer) and cooled to an internal temperature of −20° C. using cardice/acetone. Using a syringe, thionyl chloride was added dropwise to the cooled mixture over a period of 10 min. (Care: the reaction of thionyl chloride with methanol is very exothermic and rate of addition should be such that the thionyl chloride is efficiently stirred into the mixture and that the temperature does not rise above −20° C. Once the addition was complete the mixture was allowed to warm to room temperature overnight (16–18 hr). Dry ether (150 ml) was added and the white ppt. that formed was filtered off, washed with a little more ether and dried.

Yield 15.5 g 95%. Nmr.

Boc-R-4-Hydroxyphenylglycine methyl ester hydrochloride

To a stirred mixture of R-4-hydroxyphenylglycine methyl ester hydrochloride 14 g and sodium bicarbonate 11.7 g in tetrahydrofuran (THF) 150 ml and water 50 ml, was added in one portion, di-t-butyl dicarbonate 15.9 g. The mixture was stirred rapidly to allow thorough mixing for 4 h. Hexane (75 ml) was added and the organic layer separated and washed with sat. sodium bicarbonate solution, then brine and then dried with magnesium sulphate. The drying agents was filtered off and washed with a little THF and evaporated to dryness, finishing with a high vacuum pump to remove the last traces of di-t-butyl dicarbonate.

Yield 19.7 g 96%. Nmr.

Boc-R-4-(trifluoromethanesulphonyloxy)phenylglycine methyl ester hydrochloride

To a stirred solution of Boc-R-4-hydroxyphenylglycine methyl ester 19 g in dichloromethane 400 ml was added 2,6-lutidine 9.44 ml and 4-dimethylaminopyridine 1.65 g and the mixture cooled in an ice bath. Trifluoromethananesulphonic anhydride 13.74 ml was added over a period of 5 min and then the reaction left to warm to room temperature over 4 h. The organic solution was washed with water, 2×150 ml, 1N HCl 2×150 ml and the saturated sodium bicarbonate 150 ml. The organics were dried with magnesium sulphate and then evaporated to and oil. The mixture was purified using flash chromatography (SiO$_2$ 250 g eluting with 1:1 hexane/dichloromethane and then neat dichloromethane). Pure product fractions were combined and evaporated, finishing with a high vacuum pump to remove all traces of solvent, to give a white solid, 19 g 77%. Nmr.

Boc-R-4-(carboxymethyl)phenylglycine methyl ester.

Boc-R-4-trifluoromethanesulphonyloxyphenylglycine methyl ester (15 g), methanol (32.6 ml), bis-1,3-diphenylphosphinylpropane (448 mg), palladium (II) acetate (255 mg), triethylamine (10.2 ml) and dimethylformamide (72 ml) were placed in the glass liner of the Parr reactor and the reactor assembled. The vessel was pressurised to ~10 psi with nitrogen and the gas released (repeated five times to remove all oxygen from the system). Carbon monoxide gas was then carefully introduced (use extreme care—the gas cylinder is pressurised to far beyond the bursting disc pressure of the Parr, ideally use a pressure regulator to reduce the pressure to ~100 psi) to ~20 psi and released three times (into the back of a fume hood). Carbon monoxide was then added to ~100 psi and the stirrer started. The vessel was slowly heated to 65° C. internal temperature and then stirred at 65° C. overnight. (At the early stages more carbon monoxide was added to maintain ~100 psi) A sample was removed after 18 h and examined by tlc. When complete, the reaction was cooled to ~30° C., the gas released and the vessel flushed five times with nitrogen as before. The reaction mixture was partitioned between ethyl acetate and water and the organic layer washed with 1M hydrochloric acid and then saturated sodium bicarbonate. The solution was dried with MgSO$_4$ and evaporated. Flash chromatography of the resulting oil gave the product, pure by tlc, 10.6 g 90%. Nmr.

Boc-R-4-(carboxymethyl)phenylglycine.

To a solution of Boc-R-4-carboxymethylphenylglycine methyl ester 692 mg in THF 10 ml was added a solution of lithium hydroxide hydrate 90 mg in water 7 ml. The mixture immediately became cloudy and over 15 min cleared. After 30 min, tlc showed the reaction to be complete. Ethyl acetate 20 ml and water 20 ml were added and the aqueous layer separated. The aqueous solution was acidified with 2M hydrochloric acid and extracted with ethyl acetate (3×20 ml). The organic solution was then washed with water×2 and brine×2, dried with MgSO$_4$ and evaporated to give the mono-ester (650 mg, 0.98 t), pure by tlc. Nmr.

Boc-R-4-(carboxybenzyl)phenylglycine methyl ester

By the same method as described above, using 27.6 g of Boc-R-4-trifluoromethanesulphonyloxyphenylglycine methyl ester and benzyl alcohol to give the Boc-D-4-(carboxybenzyl)phenylglycine methyl ester 18.7 g pure, 70% plus a further 6 g of impure material (the major contaminant is benzyl alcohol). Nmr.

Boc-R-4-(carboxamido)phenylglycine Methyl Ester

Boc-R-4-(carboxy)phenylglycine Methyl Ester

Boc-R-4-(carboxybenzyl)phenylglycine methyl ester (500 mg) was dissolved in THF containing Pd/C 10% (100 mg) and hydrogenated at 1atm for 2 h. Removal of the catalyst by filtration and evaporation of solvent gave Boc-R-4-(carboxy)phenylglycine methyl ester (330 mg, 87%). Nmr.

Boc-R-4-(carboxamido)phenylglycine methyl ester

To a solution of Boc-R-4-(carboxy)phenylglycine methyl ester (3.5 g) in DMF 30 ml was added EDCI (2.60 g 1.36 mmol) and HOBt (1.4 g 10.4 mmol) and the mixture stirred for 10 min before cooling in a ice bath and bubbling in ammonia gas for 5 min. The mixture was stirred for 2 h at room temperature ansd then diluted with ethyl acetate and washed with water. The aqueous solution was extracted with a little ethyl acetate and the combined organics washed with brine. The organic solution was evaporated to an oil which was purified by flash chromatography (SiO$_2$—dichloromethane/ethyl acetate 0–25%) to give Boc-R-4-(carboxamido)phenylglycine methyl ester (1.7 g 48%). Nmr.

Boc-R-4-(methylcarboxamido)phenylglycine methyl ester

Was prepared by a similar method to that described above. Nmr.

Boc-R-4-Hetoxyphenylglycine.

Boc-R-4-hydroxyphenylglycine methyl ester was converted to Boc-R-4-methoxyphenylglycine using the alkylation method described by Basak et al. (Tetrahedron Lett. 1998, 39 (27), 4883–4886) followed by hydrolysis of the methyl ester with lithium hydroxide in aqueous THF. Nmr.

Boc-D,L-2-chlorophenylglycine

2-Chlorobenzaldehyde (20 mmol., 2.252 ml) and 2,4 dimethoxybenzylamine (20 mmol., 3.004 ml) were added together and stirred for 2 hours. DCM (5 ml) was added and any water separated and removed tert-Butyl isonitrile (20 mmol., 2.262 ml) was added and stirred for 10 mins followed by acetic acid (20 mmol., 1.145 ml). Stirring was continued for 3 days. The reaction mixture was then treated with TFA (30 ml) and triethylsilane (5 ml). After 3 hours the mixture was evaporated to dryness, 6M HCl (100 ml) added and the whole refluxed overnight at 130° C., stirring rapidly. The mixture was allowed to cool and extracted with EtOAc (50 ml×2) the aqueous fraction was evaporated to dryness and treated with 2M NaOH solution. The mixture was extracted with EtOAc (50 ml×2) excess boc anhydride (5.2 g) in dioxan (20 ml) was added to the aqueous fraction and stirred overnight. The mixture was extracted with diethyl ether (100 ml×2) acidified to pH 1 (cHCl) and extracted with EtOAc (50 ml×2). The combined organic fractions were washed with water and evaporated to dryness under high vacuo The product Boc-2-chloro phenylglycine (4.252 g, 74.5%)

$^1$H nmr (CD3CN/D2O) 7.3 (4H, m); 5.5 (1H, s); 1.3 (9H, s).

MS 286 (M+1).

By a similar method the following amino acids were obtained.

Boc-D,L-3-fluorophenylglycine $^1$H nmr (CD$_3$CN/D2O) 7.3 (1H, m), 7.1(3H, m); 5.2 (1H, s); 1.3 (9H, s).

MS 270 (M+1)

Boc-D,L-4-fluorophnylglycine $^1$H nmr (CD3CN/D2O) 7.3 (2H, m); 6.9 (2H, m), 5.0 (1H, s); 1.3 (9H, s).

MS 270 (M+1).

Boc-D,L-2-methylphenylglycine, $^1$H nmr (CD3CN/D2O) 7.3 (4H, m); 5.5 (1H, s); 2.5 (3H, s); 1.3 (9H, s).

MS 266 (M+1)

Boc-D,L-3-thienylglycine $^1$H nmr (CD3CN/D2O) 7.5 (2H, m); 7.1 (1H, d); 5.3 (1H, s); 1.3 (9H, s).

MS 258 (M+1).

Boc-D,L-2-fluorophenylglycine

Was obtained by treating D,L-2-fluorophenylglycine (Aldrich) with Boc anhydride (1.1 eq) and 2M NaOH (1 eq) in Ethanol. Aqueous work up as described above yielded the protected amino acid. Nmr.

These protected aminoacids were then coupled with first an amine and then, after removal of the Boc protecting group, with a carboxylic acid by method 2 to give the following inhibitor examples:

Example 160

1-(4 Methoxybenzoyl-D,L-3-thienylglycinyl) 4-(2-methylsulfonylphenyl)-piperazine Hplc (Luna C18, Gradient3, water/acetonitrile/TFA) rt 10.18

LCMS M+1 514. Nmr.

Example 161

1-(Indol-6-carbonyl-D,L-3-thienylglycinyl) 4-(2-methylsulfonylphenyl)-piperazine Hplc (Luna C18, Gradient3, water/acetonitrile/TFA) rt 10.44

LCMS M+1 523. Nmr.

Example 162

1-(4 Methoxybenzoyl-D,L-3-fluorophenylglycinyl) 4-(2-methylsulfonylphonyl)-piperazine Hplc (Luna C18, Gradient3, water/acetonitrile/TFA) rt 10.61

LCMS M+1 526. Nmr.

Example 163

1-(Indol-6-carbonyl-D,L-3-fluorophenylglycinyl) 4-(2-methylsulfonylphenyl)-piperazine Hplc (Luna C18, Gradient3, water/acetonitrile/TFA) rt 10.88

LCMS M+1 535. Nmr.

Example 164

1-(4 Methoxybenzoyl-D,L-4-fluorophenylglycinyl) 4-(2-methylsulfonylphenyl)-piperazine Hplc (Luna C18, Gradient3, water/acetonitrile/TFA) rt 10.52

LCMS M+1 526. Nmr.

Example 165
1-(Indol-6-carbonyl-D,L-4-fluorophenylglycinyl) 4-(2-methylsulfonylphenyl)-piperazine Hplc (Luna C18, Gradient3, water/acetonitrile/TFA) rt 10.92

LCMS M+1 535. Nmr.

Example 166
1-(4 Methoxybenzoyl-D,L-2-chlorophenylglycinyl) 4-(2-methylsulfonylphenyl)-piperazine Hplc (Luna C18, Gradient3, water/acetonitrile/TFA) rt 10.82

LCMS M+1 542 Nmr.

Example 167
1-(Indol-6-carbonyl-D,L-2-chlorophenylglycinyl) 4-(2-methylsulfonylphenyl)-piperazine Hplc (Luna C18, Gradient3, water/acetonitrile/TFA) rt 10.63

LCMS M+1 551 Nmr.

Example 168
1-(4 Methoxybenzoyl-D,L-2-methylphenylglycinyl) 4-(2-methylsulfonylphenyl)-piperazine Hplc (Luna C18, Gradient3, water/acetonitrile/TFA) rt 10.69

LCMS M+1 522 Nmr.

Example 169
1-(Indol-6-carbonyl-D,L-2-methylphenylglycinyl) 4-(2-methylsulfonylphenyl)-piperazine Hplc (Luna C18, Gradient3, water/acetonitrile/TFA) rt 10.76

LCMS M+1 531 Nmr.

Example 170
1-(Indol-6-carbonyl-D-2-fluorophenylglycinyl) 4-(4-fluoro-2-methylsulfonylphenyl)-piperazine Hplc (Luna 2 C18 3u water/acetonitrile/TFA, gradient =5–100% MeCN over 7 min) rt 10.92

LCMS M+1 553 Nmr.

Example 171
1-(Indol-6-carbonyl-D-(4-carboxyphenylglycinyl)-(4-(1-methylpiperidin-4-yl)piperazine)

By coupling of Boc-D-4-carboxymethylphenylglycine with 1-(4-(1-methylpiperidin-4-yl)piperazine) using HOAt and EDCI, followed by deprotection (TFA), coupling to indol-6-carboxylic acid using HOAt and EDCI followed by hydrolysis of the methyl ester with lithium hydroxide.

Hplc (Luna C18, Gradient3, water/acetonitrile/TFA), rt, 6.05 min.

LCMS M+1 504 Nmr.

Example 172
1-(Indol-6-carbonyl-D-phenylglycinyl)-4-(4-hydroxyphenyl)piperazine By coupling of Boc-D-phenylglycine with 1-(4-hydroxyphenyl)piperazine using HOAt and EDCI, followed by deprotection (TFA) and coupling to indol-6-carboxylic acid using HOAt and EDCI.

Hplc (Symmetry C8, Gradient3, water/acetonitrile/TFA), rt, 6.0 min.

LCMS M+1 455 Nmr.

Example 173
1-(3-Chloroindol-6-carbonyl-D-phenylglycinyl)-4-(4-hydroxyphenyl)piperazine By coupling of Boc-D-phenylglycine with 1-(4-hydroxyphenyl)piperazine using HOAt and EDCI, followed by deprotection (TFA) and coupling to 3-chloroindol-6-carboxylic acid using HOAt and EDCI.

Hplc (Symmetry C8, Gradient3, water/acetonitrile/TFA), rt, 6.55 min.

LCMS M+1 489 Nmr.

Example 174
1-(4-methoxybenzoyl-D-4-methoxyphenylglycinyl)-4-(2-methylsulphonylphenyl)piperazine By coupling of Boc-D-4-methoxyphenylglycine with-(2-methylsulphonylphenyl)piperazine using HOAt and EDCI, followed by deprotection (TFA) and coupling to 4-methoxybenzoic acid using HOAt and EDCI.

Hplc (Luna C18, Gradient3, water/acetonitrile/TFA), rt, 10.4 min.

LCMS M+1 538 Nmr.

Example 175
1-(5-Fluoroindole-6-carbonyl-D-phenylglycinyl)-1-methyl-4,4'-bispiperidine.

N-(2,2-Dimethoxyethyl)-4-fluoro-3-methoxyaniline

To a solution of 4-fluoro-3-methoxyaniline (0.98 g 6.9 mmol) in ethanol (20 ml) was added glyoxal 1,1-dimethyl acetal (0.89 g 8.27 mmol). Pd/C 5% (50 mg) was added and the mixture hydrogenated. Removal of the catalyst by filtration and evaporation of solvent in vacuo gave N-(2,2-dimethoxyethyl)-4-fluoro-3-methoxyaniline 1.6 g NMR LCMS M+1 (less MeO) 199

N-(2,2-Dimethoxyethyl)-N-methanesulphonyl-4-fluoro-3-methoxyaniline

N-(2,2-dimethoxyethyl)-4-fluoro-3-methoxyaniline (1.46 g, 6.37 mmol) in dichloromethane (20 ml) was treated with pyridine (0.5 g 6.37 mmol) and methanesulphonyl chloride (766 mg, 6.69 mmol) and the mixture stirred until the reaction was complete by tlc. Aqueous work up and removal of solvent in vacuo gave N-(2,2-dimethoxyethyl)-N-methanesulphonyl-4-fluoro-3-methoxyaniline 1.91 g

NMR.

5-Fluoro-1-methanesulphonyl-6-methoxyindole

To a solution of N-(2,2-dimethoxyethyl)-N-methanesulphonyl-4-fluoro-3-methoxyaniline (1.91 g, 0.65 mmol) in dry toluene at 0° C. under argon, was added slowly a solution of TiCl$_4$ (0.173 g, 0.911 mmol) in dry toluene (10 ml). The solution was then heated to 70° C. for 1 h. cooled and poured onto ice/sat. sod. bicarbonate solution (20 ml). The organic layer was separated, washed with sat. sod. bicarbonate solution, 0.5% hydrochloric acid (2×20 ml) and water (2×20 ml). The solution was dried (MgSO$_4$) and evaporated in vacuo to give 5-fluoro-1-methanesulphonyl-6-methoxyindole ((0.102 g)

NMR.

5-Fluoro-6-hydroxy-1-methanesulphonylindole

To a solution of 5-fluoro-1-methanesulphonyl-6-methoxyindole (0.10 g 0.41 mmol) in dry dichloromethane (3 ml) at −10° C. was added a solution of BBr$_3$ (1M in dichloromethane, 1.23 ml) over one minute. The reacture was warmed to room temperature and stirred for 2 h and then poured onto ice/1M hydrochloric acid (10 ml). After stirring for 15 min the mixture was extracted with ethyl acetate (1×50 ml, 2×20 ml), dried (MgSO$_4$) and evaporated in vacuo to give 5-fluoro-6-hydroxy-1-methanesulphonylindole (70 mg)

NMR.

5-Fluoro-1-methanesulphonyl-6-trifluoromethanesulphonyloxyindole

To a solution of 5-fluoro-6-hydroxy-1-methanesulphonylindole (0.57 mg, 2.49 mmol) in dry dichloromethane (20 ml) at 0° C. was added pyridine (0.24 ml, 2.99 mmol) and then trifluoromethanesulphonic anhydride (0.50 ml, 2.99 mmol) and the mixture stirred for 2 h. The reaction mixture was washed with 0.5% hydrochloric acid (2×50 ml), sodium bicarbonate solution (2×50 ml) and water (50 ml), dried (MgSO$_4$) and filtered through a short pad of silica. Evaporation of solvent in vacuo gave 5-fluoro-1-methanesulphonyl-6-trifluoromethanesulphonyloxy-indole, (0.67 g)

NMR.

Methyl 5-fluoro-1-methanesulphonyl-indol-6-carboxylate,

To a solution of 5-fluoro-1-methanesulphonyl-6-trifluoromethanesulphonyloxy-indole, (0.70 g 1.94 mmol) was added, Pd (II) acetate (14 mg), bis 1,3-diphenylphosphinylpropane (24 mg), dimethylformamide (4 ml) and methanol (2 ml) and triethylamine (0.54 ml) and the mixture stirred for 2 min. Carbon monoxide gas was bubbled in for 15 min and then the mixture was heated to 75° C. under an atmosphere of carbon monoxide and stirred overnight.

After cooling to room temperature the mixture was poured into ethyl acetate (80 ml) and washed with 1M hydrochloric acid (50 ml), sat. sod. bicarbonate (50 ml) and water (50 ml).

Drying (MgSO$_4$), evaporation of solvent gave crude product (0.53 g). Purification of a portion (225 mg) by flash chromatography (SiO$_2$ 25% ethyl acetate in hexane) gave methyl 5-fluoro-1-methanesulphonyl-indol-6-carboxylate, (173 mg)

NMR.

5-fluoro-1-methanesulphonyl-indol-6 carboxylic acid

To a solution of methyl 5-fluoro-1-methanesulphonyl-indol-6-carboxylate (173 mg) in THF (15 ml) and water (2 ml) was added 2M lithium hydroxide solution (3 equiv) and the mixture heated to 50° C. for 2 h. and then allowed to cool overnight.

The solution was concentrated in vacuo, diluted with 2M sodium hydroxide solution (10 ml) and washed with ethyl acetate. The aqueous solution was acidified to pH3 with conc. hydrochloric acid and extracted with ethyl acetate (3×30 ml). The organic solution was evaporated in vacuo to give 5-fluoro-1-methanesulphonyl-indol-6-carboxylic acid (164 mg)-(circa 80% pure)

NMR.

1-(5-fluoro-1-methanesulphonyl-indol-6-carbonyl-D-phenylglycinyl- 4,4'-(1'-methylbispiperidine)

5-fluoro-1-methanesulphonyl-indol-6-carboxylic acid (164 mg) was coupled to D-phenylglycinyl-4,4'-(1'-methylbispiperidine) using EDCI/HOAt as previously described to give 1-(5-fluoro-1-methanesulphonyl-indol-6-carbonyl-D-phenylglycinyl- 4,4'-(1'-methylbispiperidine) (111 mg)-(~70% pure)

NMR.

1-(5-fluoroindol-6-carbonyl-D-phenylglycinyl-4,4'-(1'-methylbispiperidine)

1-(5-fluoro-1-methanesulphonyl-indol-6-carbonyl-D-phenylglycinyl- 4,4'-(1'-methylbispiperidine) (111 mg-~70% pure) was refluxed in ethanol (5 ml) and sodium hydroxide solution (34 mg in 0.34 ml) for 2.25 h. The mixture was evaporated to dryness, taken up in water (10 ml) and extracted with chloroform (60 ml). The organic solution was dried (MgSO$_4$) and evaporated in vacuo and the residue purified by Prep Hplc. To give 1-(5-fluoroindol-6-carbonyl-D-phenylglycinyl- 4,4'-(1'-methylbispiperidine) (19 mg)

Hplc (Luna C18 Gradient 3) rt 11.37 min.
LCMS M+1 477
NMR.

Example 176

1-(4-Methoxybenzoyl-D-phenylglycinyl)-4-(2-pyridoxy)piperidinamide 1-t-Butoxycarbonyl-4-(2-pyridoxy)piperidine 1-t-Butoxycarbonyl-4-piperidinol (5.0 g 24.88 mmol) in dry dimethylformamide (60 ml) was treated with sodium hydride (60% 2.99 g 74.75 mmol) at room temperature under argon and then with 2-chloropyridine hydrochloride (4.1 g 27.33 mmol). Then mixture was heated at 80° C. overnight. After cooling the reaction was carefully quenched with water (5 ml) and then diluted with more water (20 ml) and extracted with ethyl acetate (30 ml). The organic solution was washed with sat. sodium bicarbonate, dried (MgSO$_4$) and evaporated to give 1-t-butoxycarbonyl-4-(2-pyridoxy)piperidine (4.96 g 72%).

4-(2-pyridoxy)piperidine dihydrochloride 1-t-Butoxycarbonyl-4-(2-pyridoxy)piperidine (6.5 g) was treated with a solution of hydrogen chloride in ethyl acetate (110 ml) for 7 h and the mixture evaporated to give 4-(2-pyridoxy)piperidine dihydrochloride, (7.4 g 90%)

1-(Benzyoxycarbonyl-D-phenylglycinyl)-4-(2-pyridoxy)piperidinamide

Benzyloxycarbonyl-D-phenylglycine (3.75 g 13.14 mmol) was coupled to 4-(2-pyridoxy)piperidine dihydrochloride (3.0 g 11.94 mmol) using EDCI (2.52 g 13.14 g), HOAt (1.79 g 13.13 mmol) and triethylamine (3.63 g 35.87 mmol) to give, after work up with ethyl acetate and sodium bicarbonate solution, 1-(benzyoxycarbonyl-D-phenylglycinyl)-4-(2-pyridoxy)piperidinamide, (4.9 g 92%)

1-D-phenylglycinyl-4-(2-pyridoxy)piperidinamide 1-(Benzyoxycarbonyl-D-phenylglycinyl)-4-(2-pyridoxy)piperidinamide (400 mg) was hydrogenated in ethanol with 5% Pd/C overnight. Removal of catalyst and evaporation of solvent gave 1-D-phenylglycinyl-4-(2-pyridoxy)piperidinamide (162 mg 58%)

Using a similar method and the appropriate starting materials the following intermediates were also prepared:
1-(D-phenylglycinyl)-4-(4-pyridoxy)piperidinamide
1-(D-phenylglycinyl)-3-R,S-(4-pyridoxy)pyrrolidinamide
1-(D-phenylglycinyl)-3-R,S-(2-pyridoxy)pyrrolidinamide
1-(4-Methoxybenzoyl-D-phenylglycinyl)-4-(2-pyridoxy)piperidinamide 1-D-phenylglycinyl-4-(2-pyridoxy)piperidinamide (162 mg 0.52 mmol) was treated with triethylamine (58 mg 0.573 mmol) and p-anisoyl chloride (93 mg 0.545 mmol) in dry dichloromethane for 1 h. The reaction mixture was washed with sodium bicarbonate solution and brine, dried (MgSO$_4$) and evaporated to an oil. Flash chromatography gave the product 1-(4-Methoxybenzoyl-D-phenylglycinyl)-4-(2-pyridoxy)piperidinamide, (60 mg 26%).

Hplc (Luna C18, Gradient3, water/acetonitrile/TFA), rt, 8.94 min.
LCMS M+Na 468
Nmr.

By a similar method the following compounds were prepared:

Example 177

1-(Indol-6-carbonyl-D-phenylglycinyl)-4-(2-pyridoxy)piperidinamide

By the coupling of indol-6-carboxylic acid and 1-D-phenylglycinyl-4-(2-pyridoxy)piperidinamide using EDCI and HOAt.

LCMS M+1 455
Nmr.

Example 178
1-(3-Chloroindol-6-carbonyl-D-phenylglycinyl)-4-(2-pyridoxy)piperidinamide By the coupling of 3-chloroindol-6-carboxylic acid and 1-D-phenylglycinyl- 4-(2-pyridoxy)piperidinamide using EDCI and HOAt.

Hplc (Luna C18, Gradient3, water/acetonitrile/TFA), rt, 10.29 min.

LCMS M+1 489
Nmr.

Example 179
1-(3-Chloroindol-6-carbonyl-D-phenylglycinyl)-4-(4-pyridoxy)piperidinamide By the coupling of 3-chloroindol-6-carboxylic acid and 1-D-phenylglycinyl- 4-(4-pyridoxy)piperidinamide using EDCI and HOAt.

Hplc (Luna C18, Gradient3, water/acetonitrile/TFA), rt, 8.16 min.

LCMS M+1 489
Nmr.

Example 180
1-(4-Methoxybenzoyl-D-phenylglycinyl)-4-(4-pyridoxy)piperidinamide By the coupling of p-anisoyl chloride and 1-D-phenylglycinyl-4-(4-pyridoxy)piperidinamide in dichloromethane with triethylamine Hplc (Luna C18, Gradient3, water/acetonitrile/TFA), rt, 7.0 min.

LCMS M+1 446
Nmr.

Example 181
1-(Indol-6-carbonyl-D-phenylglycinyl)-4-(4-pyridoxy)piperidinamide By the coupling of indol-6-carboxylic acid and 1-D-phenylglycinyl- 4-(4-pyridoxy)piperidinamide with EDCI and HOAt.

Hplc (Luna C18, Gradient3, water/acetonitrile/TFA), rt, 7.08 min.

LCMS M+1 455
Nmr.

Example 182
1-(4-Methoxybenzoyl-D-phenylglycinyl)-3-R,S-(4-pyridoxy)pyrrolidinamide By the coupling of p-anisoyl chloride and 1-(D-phenylglycinyl)-3-R,S-(4-pyridoxy) pyrrolidinamide in dichloromethane with triethylamine LCMS M+1 432
Nmr.

Example 183
1-(Indol-6-carbonyl-D-phenylglycinyl)-3-R,S-(4-pyridoxy)pyrrolidinamide By the coupling indol-6-carboxylic acid and 1-(D-phenylglycinyl)-3-R,S-(4-pyridoxy)pyrrolidinamide with EDCI and HOAt.

LCMS M+1 441
Nmr.

Example 184
1-(3-Chloroindol-6-carbonyl-D-phenylglycinyl)-3-R,S-(4-pyridoxy)pyrrolidinamide By the coupling 3-chloroindol-6-carboxylic acid and 1-(D-phenylglycinyl)-3-R,S-(4-pyridoxy)pyrrolidinamide with EDCI and HOAt.

LCMS M+1 475
Nmr.

Example 185
1-(4-Methoxybenzoyl-D-phenylglycinyl)-3-R,S-(2-pyridoxy)pyrrolidinamide By the coupling of p-anisoyl chloride and 1-(D-phenylglycinyl)-3-R,S-(2-pyridoxy)pyrrolidinamide in dichloromethane with triethylamine LCMS M+1 432
Nmr.

Example 186
1-(3-Chloroindol-6-carbonyl-D-phenylglycinyl)-3-R,S-(2-pyridoxy)pyrrolidinamide By the coupling 3-chloroindol-6-carboxylic acid and 1-(D-phenylglycinyl)-3-R,S-(2-pyridoxy)pyrrolidinamide with EDCI and HOAt.

LCMS M+1 475
Nmr.

Example 187
1-(Indol-6-carbonyl-D-phenylglycinyl)-3-R,S-(2-pyridoxy)pyrrolidinamide By the coupling indol-6-carboxylic acid and 1-(D-phenylglycinyl)-3-R,S-(2-pyridoxy)pyrrolidinamide with EDCI and HOAt.

LCMS M+1 441
Nmr.

Example 188
1-(4-methoxybenzoyl-D-4-hydroxyphenylglycinyl)-4-(2-methylsulphonylphenyl)piperazine By coupling of Boc-D-4-hydroxyphenylglycine with-(2-methylsulphonylphenyl)piperazine using HOAT and EDCI, followed by deprotection (TFA) and coupling to 4-methoxybenzoic acid using HOAt and EDCI.

Hplc (Luna C18, Gradient3, water/acetonitrile/TFA), rt, 9.1 min.

LCMS M+1 524
Nmr.

Example 189
1-(Indol-6-carbonyl-D-4-hydroxyphenylglycinyl)-4-(2-methylsulphonylphenyl)piperazine By coupling of Boc-D-4-hydroxyphenylglycine with-(2-methylsulphonylphenyl)piperazine using HOAt and EDCI, followed by deprotection (TFA) and coupling to 6-indole carboxylic acid using HOAt and EDCI.

Hplc (Luna C18, Gradient3, water/acetonitrile/TFA), rt, 9.0 min.

LCMS M+1 533
Nmr.

Example 190
1-(Indol-6-carbonyl-D-4-hydroxyphenylglycinyl)-1'-methyl-4,4'-bispiperidine By coupling of Boc-D-4-hydroxyphenylglycine with 4,4'-(1-methylbispiperidine) di-HCl salt using HOAt and EDCI, followed by deprotection (TFA) and coupling to 6-indole carboxylic acid using HOAt and EDCI.

Hplc (Luna C18, Gradient3, water/acetonitrile/TFA), rt, 6.8 min.

LCMS M+1 475
Nmr.

Example 191
1-(3-Chloroindol-6-carbonyl-D-4-hydroxyphenylglycinyl)-1'-methyl-4,4'-bispiperidine By coupling of Boc-D-4-hydroxyphenylglycine with 4,4'-(1'-methylbispiperidine) di-HCl salt using HOAt and EDCI, followed by deprotection (TFA) and coupling to 3-chloroindole-6-carboxylic acid using HOAt and EDCI.

Hplc (Luna C18, Gradient3, water/acetonitrile/TFA), rt, 7.3 min.
LCMS M+1 509
Nmr.

In the following examples the following additional abbreviations and meanings are included: CI-MS, chemical ionization mass spectrum; DMSO, dimethyl sulfoxide (perdeuterated if for NMR); EtOAc, ethyl acetate; EtOH, ethanol; IS-MS, ion spray mass spectrum; RPHPLC, reverse phase HPLC; SCX, strong cation exchange resin; THF, tetrahydrofuran; TLC, thin layer chromatography with $R_f$ as relative mobility;

Reagents were obtained from a variety of commercial sources.

IR means an infrared spectrum was obtained. $^1$NMR, 1H-NMR, or 1H NMR means a proton magnetic resonance spectrum was obtained.

In general in this specification, "D-" or "R-" in the name of a product indicates the product was made beginning with a chiral starting material, for example D-phenylglycine; however, racemization may have occurred, and the enantiomeric purity may not have been determined.

Examples 201–210
Preparation of Starting Materials
4-[(Benzyloxycarbonyl-D-phenylglycinyl)aminomethyl]-1-Boc-piperidine Using Coupling Method C, benzyloxycarbonyl-D-phenylglycine (10.4 g, 36.5 mmol) and 4-aminomethyl-1-Boc-piperidine (7.3 g, 36.5 mmol) afforded, after purification by column chromatography (SiO$_2$: 4:1 to 3:2 hexanes:EtOAc), 10.2 g (58%) of the title compound.
$^1$NMR
IS-MS, m/e 482 (M+1).

4-[(D-Phenylglycinyl)aminomethyl]-1-Boc-piperidine
(Deprotection Method C) A solution of 4-[(benzyloxycarbonyl-D-phenylglycinyl)aminomethyl]-1-Boc-piperidine (9.00 g, 18.7 mmol) and 10% palladium on carbon (2.34 g) in EtOAc (80 mL):EtOH (200 mL) was placed under an atmosphere of hydrogen gas (balloon). After 16 h, the mixture was filtered and concentrated affording 6.31 g (98%) of the title compound, which was used without further purification.
$^1$NMR
IS-MS, m/e 348 (M+1).

4-[(4-Methoxybenzoyl-D-phenylglycinyl)aminomethyl]-1-Boc-piperidine
(Acylation Method C) A solution of 4-[(D-phenylglycinyl)aminomethyl]-1-Boc-piperidine (2.38 g, 6.88 mmol) and pyridine (8 mL) in methylene chloride was treated with 4-methoxybenzoyl chloride (1.76 g, 10.3 mmol) in methylene chloride (prepared by treatment of 4-methoxy benzoic acid with excess oxalyl chloride in methylene chloride followed by concentration). After 2 days, the mixture was partitioned between water and methylene chloride. The organic extracts were washed with 1 N HCl, water, 1 N NaOH and brine, and concentrated. The residue was purified by column chromatography (SiO$_2$: 1:1 to 1:3 hexanes;EtOAc), affording 2.33 g (71%) of the title compound.
$^1$NMR
IS-MS, m/e 482 (M+1).
Analysis for $C_{27}H_{35}N_3O_5$:
Calcd: C, 67.3; H, 7.3; N, 8.7;
Found: C, 67.4; H, 7.4; N, 8.7.

4-[(4-Methoxybenzoyl-D-phenylglycinyl)aminomethyl]-piperidine

Using Deprotection Method D, 4-[(4-methoxybenzoyl-D-phenylglycinyl)aminomethyl]-1-Boc-piperidine (2.38 g) afforded 1.56 g (82%) of 4-[(4-methoxybenzoyl-D-phenylglycinyl)aminomethyl]piperidine.
$^1$NMR
IS-MS, m/e 382 (M+1).

General Procedure: Unless otherwise indicated, the product of Examples 201–210 was prepared from 4-[(4-methoxybenzoyl-D-phenylglycinyl)aminomethyl]piperidine and the indicated aldehyde or ketone using Alkylation Method D.

Example 201
4-[(4-Methoxybenzoyl-D-phenylglycinyl)aminomethyl]-1-isopropylpiperidine 4-[(4-Methoxybenzoyl-D-phenylglycinyl)aminomethyl]piperidine (0.10 g, 0.26 mmol) and acetone afforded 89 mg (81%) of the title compound.
$^1$NMR
IS-MS, m/e 424 (M+1)
Analysis for $C_{25}H_{33}N_3O_3$:
Calcd: C, 70.9; H, 7.9; N, 9.9;
Found: C, 70.8; H, 7.8; N, 9.9.

Example 202
4-[(4-Methoxybenzoyl-D-phenylglycinyl)aminomethyl]-1-(3-pentyl)piperidine 4-[(4-Methoxybenzoyl-D-phenylglycinyl)aminomethyl]piperidine (0.10 g, 0.26 mmol) and 3-pentanone afforded 57 mg (49%) of the title compound.
$^1$NMR
IS-MS, m/e 452 (M+1)

Example 203
4-[(4-Methoxybenzoyl-D-phenylglycinyl)aminomethyl]-1-(2-indanyl)piperidine 4-[(4-Methoxybenzoyl-D-phenylglycinyl)aminomethyl]piperidine (0.10 g, 0.26 mmol) and 2-indanone afforded 91 mg (78%) of the title compound.
$^1$NMR
IS-MS, m/e 498 (M+1)
Analysis for $C_{25}H_{33}N_3O_3$:
Calcd: C, 74.8; H, 7.1; N, 8.4;
Found: C, 74.5; H, 7.0; N, 7.9.

Example 204
4-[(4-Methoxybenzoyl-D-phenylglycinyl)aminomethyl]-1-cyclopentylpiperidine 4-[(4-Methoxybenzoyl-D-phenylglycinyl)aminomethyl]piperidine (0.10 g, 0.26 mmol) and cyclopentanone afforded 101 mg (86%) of the title compound.
$^1$NMR
IS-MS, m/e 450 (M+1).

Example 205
4-[(4-Methoxybenzoyl-D-phenylglycinyl)aminomethyl]-1-(cyclohexylmethyl)piperidine 4-[(4-Methoxybenzoyl-D-phenylglycinyl)aminomethyl]piperidine (0.10 g, 0.26 mmol) and cyclohexanecarboxaldehyde afforded 98 mg (79%) of the title compound.
$^1$NMR
IS-MS, m/e 478 (M+1).

Example 206
4-[(4-Methoxybenzoyl-D-phenylglycinyl)aminomethyl]-1-cyclohexylpiperidine 4-[(4-methoxybenzoyl-D-phenylglycinyl)aminomethyl]piperidine (0.10 g, 0.26 mmol) and cyclohexanone afforded 95 mg (79%) of the title compound.
$^1$NMR
IS-MS, m/e 464 (M+1).

Example 207
4-[(4-Methoxybenzoyl-D-phenylglycinyl)aminomethyl]-1-(tetrahydropyran-4-yl)piperidine 4-[(4-methoxybenzoyl-D-phenylglycinyl)aminomethyl]piperidine (0.10 g, 0.26 mmol) and tetrahydro-4H-pyran-4-one afforded 78 mg (65%) of the title compound.
$^1$NMR
IS-MS, m/e 466 (M+1).

Example 208
4-[(4-Methoxybenzoyl-D-phenylglycinyl)aminomethyl]-1-(tetrahydrothiopyran-4-yl)piperidine 4-[4-Methoxybenzoyl-D-phenylglycinyl)aminomethyl]piperidine (0.10 g, 0.26 mmol) and tetrahydro-4H-thiopyran-4-one afforded 63 mg (50%) of the title compound.
$^1$NMR
IS-MS, m/e 482 (M+1).

Example 209
4-[(4-Methoxybenzoyl-D-phenylglycinyl)aminomethyl]-1-methylpiperidine 4-[(4-Methoxybenzoyl-D-phenylglycinyl)aminomethyl]piperidine (60 mg, 0.16 mmol) and paraformaldehyde afforded 59 mg (93%) of the title compound.
$^1$NMR
IS-MS, m/e 396 (M+1).

Example 210
4-[(4-Methoxybenzoyl-D-phenylglycinyl)aminomethyl]-1-ethyl-piperidine 4-[(4-Methoxybenzoyl-D-phenylglycinyl)aminomethyl]piperidine (60 mg, 0.16 mmol) and acetaldehyde afforded 23 mg (35%) of the title compound.
$^1$NMR
IS-MS, m/e 410 (M+1).

Examples 211–213
Preparation of Starting Materials
4-[(Indole-6-carbonyl-D-phenylglycinyl)aminomethyl]-1-Boc-piperidine Using Coupling Method C, 4-[(D-phenylglycinyl)aminomethyl]-1-Boc-piperidine (2.5 g, 6.8 mmol) and indole-6-carboxylic acid (1.2 g, 7.6 mmol) afforded, after purification by column chromatography (SiO$_2$: 2:3 hexanes:EtOAc to EtOAc), 2.57 g (83%) of the title compound.
$^1$NMR
IS-MS, m/e 491 (M+1).
4-[(Indole-6-carbonyl-D-phenylglycinyl)aminomethyl]piperidine Using Deprotection Method D, 4-[(indole-6-carbonyl-D-phenylglycinyl)aminomethyl]-1-Boc piperidine (1.6 g, 3.3 mmol) afforded 4-[(indole-6-carbonyl-D-phenylglycinyl)aminomethyl]piperidine (1.27 g, 79%).
$^1$NMR
IS-MS, m/e 391 (M+1).
General Procedure: Unless otherwise indicated, the product of Examples 211–213 was prepared from 4-[(indole-6-carbonyl-D-phenylglycinyl)aminomethyl]piperidine and the indicated aldehyde or ketone using Alkylation Method D.

Example 211
4-[(Indole-6-carbonyl-D-phenylglycinyl)aminomethyl]-1-isopropylpiperidine 4-[(Indole-6-carbonyl-D-phenylglycinyl)aminomethyl]piperidine (0.10 g, 0.26 mmol) and acetone afforded 16 mg (14%) of the title compound.
$^1$NMR
IS-MS, m/e 433 (M+1).

Example 212
4-[(Indole-6-carbonyl-D-phenylglycinyl)aminomethyl]-1-cyclopentylpiperidine 4-[(Indole-6-carbonyl-D-phenylglycinyl)aminomethyl]piperidine (0.10 g, 0.26 mmol) and cyclohexanone afforded 19 mg (16%) of the title compound.
$^1$NMR
IS-MS, m/e 459 (M+1).

Example 213
4-[(Indole-6-carbonyl-D-phenylglycinyl)aminomethyl]-1-cyclohexylmethylpiperidine 4[(Indole-6-carbonyl-D-phenylglycinyl)aminomethyl]piperidine (0.10 g, 0.2.6 mmol) and cyclohexanecarboxaldehyde afforded 14 mg (11%) of the title compound.
$^1$NMR
IS-MS, m/e 487 (M+1).

Examples 214–217
Preparation of Starting Materials
4-[(Benzyloxycarbonyl-D-phenylglycinyl)]-1-Boc-piperidine Using Coupling Method C, D-phenylglycine (6.10 g, 21.4 mmol) and 4-amino-1-Boc-piperidine (4.27 g, 21.4 mmol) afforded, after purification by column chromatography (SiO$_2$:7:3 hexanes:EtOAc), 8.44 g (841) of the title compound.
$^1$NMR
IS-MS, m/e 468 (M+1)
Analysis for C$_{26}$H$_{33}$N$_3$O$_5$:
Calcd: C, 66.3; H, 7.1; N, 9.0;
Found: C, 66.5; H, 7.1; N, 9.0.
4-[(D-phenylglycinyl)amino]-1-Boc-piperidine Using Deprotection Method C, 4-[(benzyloxycarbonyl-D-phenylglycinyl)amino]-1-Boc-piperidine (8.0 g, 17 mmol) afforded 6.1 g (90%) of the title compound, which was used without further purification.
$^1$NMR
IS-MS, m/e 334 (M+1).
4-[(4-Methoxybenzoyl-D-phenylglycinyl)amino]-1-Boc-piperidine Using Acylation Method C, 4-[(D-phenylglycinyl)amino]-1-Boc piperidine (2.23 g, 6.7 mmol) afforded, after purification by column chromatography (SiO$_2$: 1:1 hexanes EtOAc), 2.44 g (78%) of the title compound.
$^1$NMR
IS-MS, m/e 468 (M+1).
4-[(4-Methoxybenzoyl-D-phenylglycinyl)amino]piperidine Using Deprotection Method D, 4-[(4-methoxybenzoyl-D-phenylglycinyl)amino]-1-Boc-piperidine (2.32 g) afforded 1.53 g (84%) of 4-[(4-methoxybenzoyl-D-phenylglycinyl)-amino]piperidine.
$^1$NMR
IS-MS, m/e 368 (M+1).
General Procedure: Unless otherwise indicated, the product of Examples 214–217 was prepared from 4-[(4- methoxybenzoyl-D-phenylglycinyl)amino]piperidine and the indicated aldehyde or ketone using Alkylation Method D.

Example 214
4-[(4-Methoxybenzoyl-D-phenylglycinyl)aminomethyl]-1-(3-pentyl)piperidine 4-[(4-Methoxybenzoyl-D-phenylglycinyl)amino]piperidine (0.11 g, 0.3 mmol) and 3-pentanone afforded 81 mg (62%) of the title compound.
$^1$NMR
IS-MS, m/e 438 (M+1).

Example 215
4-[(4-Methoxybenzoyl-D-phenylglycinyl)amino]-1-(2-indanyl)-piperidine 4-[(4-Methoxybenzoyl-D-phenylglycinyl)amino]piperidine (0.11 g, 0.3 mmol) and 2-indanone afforded 121 mg (83%) of the title compound.
$^1$NMR
IS-MS, m/e 484 (M+1).

Example 216
4-[(4-Methoxybenzoyl-D-phenylglycinyl)amino]-1-cyclopentylpiperidine 4-[(4-Methoxybenzoyl-D-phenylglycinyl)amino]piperidine (0.11 g, 0.3 mmol) and cyclopentanone afforded 103 mg (79%) of the title compound.
$^1$NMR
IS-MS, m/e 436 (M+1).

Example 217
4-[(4-Methoxybenzoyl-D-phenylglycinyl)amino]-1-cyclohexylpiperidine 4-[(4-Methoxybenzoyl-D-phenylglycinyl)amino]piperidine (0.11 g, 0.3 mmol) and 2-cyclohexanone afforded 112 mg (83%) of the title compound.
$^1$NMR
IS-MS, m/e 450 (M+1).

Examples 218–220
Preparation of Starting Materials
4-[(Indole-6-carbonyl-D-phenylglycinyl)amino]-1-Boc-piperidine Using Acylation Method C, 4-[(D-phenylglycinyl)amino]-1-Boc-piperidine (2.24 g, 6.15 mmol) and indole-6-carboxylic acid afforded 4-[(indole-6-carbonyl-D-phenylglycinyl)amino]-1-Boc-piperidine (2.66 g, 82%).
$^1$NMR
IS-MS, m/e 477 (M+1).
4-[(Indole-6-carbonyl-D-phenylglycinyl)amino]piperidine Using Deprotection Method C, 4-[(indole-6-carbonyl-D-phenylglycinyl)amino]-1-Boc-piperidine (1.2 g, 2.5 mmol) afforded 4-[(indole-6-carbonyl-D-phenylglycinyl)amino]-piperidine (0.81 g, 83%).
$^1$NMR
IS-MS, m/e 377 (M+1).
General Procedure: Unless otherwise indicated, the product of Examples 218–220 was prepared from 4-[(indole-6-carbonyl-D-phenylglycinyl)amino]piperidine and the indicated aldehyde or ketone using Alkylation Method D.

Example 218
4-[(Indole-6-carbonyl-D-phenylglycinyl)amino]-1-isopropylpiperidine 4-[(Indole-6-carbonyl-D-phenylglycinyl)amino]piperidine (0.10 g, 0.27 mmol) and acetone afforded 21 mg (19%) of the title compound.
$^1$NMR
IS-MS, m/e 419 (M+1).

Example 219
4-[(Indole-6-carbonyl-D-phenylglycinyl)amino]-1-cyclopentylpiperidine 4-[(Indole-6-carbonyl-D-phenylglycinyl)amino]piperidine (0.10 g, 0.27 mmol) and cyclopentanone afforded 28 mg (24%) of the title compound.
$^1$NMR
IS-MS, m/e 445 (M+1).

Example 220
4-[(Indole-6-carbonyl-D-phenylglycinyl)amino]-1-(cyclohexylmethyl)piperidine 4-[(Indole-6-carbonyl-D-phenylglycinyl)amino]piperidine (0.10 g, 0.27 mmol) and cyclohexanecarboxaldehyde afforded 17 mg (14%) of the title compound.
$^1$NMR
IS-MS, m/e 473 (M+1).

Examples 221–246
Preparation of Starting Materials
1-Methyl-4,4'-bispiperidine hydrobromide dihydrobromide A solution of 4,4'-bipyridine (34.2 g, 100 mmol) in acetone was treated with methyl p-toluenesulfonate. After 3 days, the salt (28 g, 80%) was isolated by filtration. The salt (44.0 g) was then treated with 10% Pd/C in acetic acid (400 mL) and hydrogen gas (4.1 bar) at 60° C. After 16 h, the mixture was concentrated, the residue was dissolved in acetone, and then treated with hydrogen bromide in acetic acid. The resulting salt (36 g, 86%) was isolated by filtration as a dihydrobromide.
$^1$NMR
1-(D-Phenylglycinyl)-1'-methyl-4,4'-bispiperidine Using Coupling Method A, benzyloxycarbonyl-D-phenylglycine (16 g, 56 mmol) and 1-methyl-4,4'-bispiperidine dihydrobromide (17.2 g, 50 mmol) afforded, after treatment of the crude acylation product with HBr (150 mL) and acetic acid (150 mL) at 60° C. for 6 h, 8.4 g (54%) of the title compound.
$^1$NMR
IS-MS, m/e 316 (M+1)
Analysis for $C_{19}H_{29}N_3O$:
Calcd: C, 72.3; H, 9.3; N, 13.3;
Found: C, 71.9; H, 9.2; N, 13.1.
General Procedure: Unless otherwise indicated, the product of Examples 221–246 (or a protected derivative thereof) was prepared from 1-(D-phenylglycinyl)-1'-methyl-4,4'-bispiperidine and the indicated acid using procedures similar to Acylation Method C.
Removal of Protecting Group; Where a protecting group was present in the acylation procedure, the procedure for its removal is described.

Example 221
1-(4-Methoxy-3-methylbenzoyl-D-phenylglycinyl)-1'-methyl-4,4'-bispiperidine 1-(D-Phenylglycinyl)-1'-methyl-4,4'-bispiperidine (200 mg, 0.64 mmol) and 4-methoxy-3-methylbenzoic acid (116 mg, 0.70 mmol) afforded 159 mg (54%) of the title compound.
$^1$NMR
IS-MS, m/e 464 (M+1).
Analysis for $C_{25}H_{33}N_3O_3 \cdot 0.35H_2O$:
Calcd: C, 71.6; H, 8.1; N, 8.9;
Found: C, 71.5; H, 7.8; N, 9.0.

Example 222
1-(5-Methylthiothiophene-2-carbonyl-D-phenylglycinyl]-1'-methyl-4,4'-bispiperidine 1-(D-Phenylglycinyl)-1'-methyl-4,4'-bispiperidine (200 mg, 0.64 mmol) and 5-methylthiothiophene-2-carboxylic acid (120 mg, 0.70 mmol) afforded 190 mg (63%) of the title compound.

$^1$NMR

IS-MS, m/e 472 (M+1).

Example 223
1-(3-Chloro-4-methoxybenzoyl-D-phenylglycinyl)-1'-methyl-4,4'-bispiperidine 1-(D-Phenylglycinyl)-1'-methyl-4,4'-bispiperidine (200 mg, 0.64 mmol) and 3-chloro-4-methoxybenzoic acid (130 mg, 0.70 mmol) afforded 182 mg (59%) of the title compound.

$^1$NMR

IS-MS, m/e 484 (M+1).

Example 224
1-(5-Methoxybenzofuran-2-carbonyl-D-phenylglycinyl)-1'-methyl-4,4'-bispiperidine 1-(D-Phenylglycinyl)-1'-methyl-4,4'-bispiperidine (200 mg, 0.64 mmol) and 5-methoxybenzofuran-2-carboxylic acid (135 mg, 0.70 mmol) afforded 298 mg (96%) of the title compound.

$^1$NMR

IS-MS, m/e 490 (M+1).

Analysis for $C_{29}H_{35}N_3O_4$:

Calcd: C, 71.1; H. 7.2; N, 8.6;

Found: C, 71.5; H, 7.4; N, 8.8.

Example 225
1-(5-Acetylthiophene-2-carbonyl-D-phenylglycinyl)-1'-methyl-4,4'-bispiperidine 1-(D-Phenylglycinyl)-1'-methyl-4,4'-bispiperidine (200 mg, 0.64 mmol) and 5-acetylthiophene-2-carboxylic acid (119 mg, 0.70 mmol) afforded 245 mg (83%) of the title compound.

$^1$NMR

IS-MS, m/e 468 (M+1).

Analysis for $C_{26}H_{33}N_3O_3S$:

Calcd: C, 66.8; H, 7.1; N, 9.0;

Found: C, 66.5; H, 7.1; N, 9.0.

Example 226
1-(4-Chloro-3-methylbenzoyl-D-phenylglycinyl)-1'-methyl-4,4'-bispiperidine 1-(D-Phenylglycinyl)-1'-methyl-4,4'-bispiperidine (315 mg, 1.00 mmol) and 4-chloro-3-methylbenzoic acid (171 mg, 1.00 mmol) afforded 240 mg (51%) of the title compound.

$^1$NMR

IS-MS, m/e 468 (M+1).

Analysis for $C_{26}H_{33}N_3O_3S$:

Calcd; C, 69.3; H, 7.3; N, 9.0;

Found: C, 68.9; H, 7.2; N, 8.9.

Example 227
1-(5-Methylindole-2-carbonyl-D-phenylglycinyl)-1'-methyl-4,4'-bispiperidine 1-(D-Phenylglycinyl)-1'-methyl-4,4'-bispiperidine (315 mg, 1.00 mmol) and 5-methylindole-2-carboxylic acid (263 mg, 1.50 mmol) afforded 240 mg (51%) of the title compound.

$^1$NMR

IS-MS, m/e 473 (M+1).

Example 228
1-(5-Methoxyindole-2-carbonyl-D-phenylglycinyl)-1'-methyl-4,4'-bispiperidine 1-(D-Phenylglycinyl)-1'-methyl-4,4'-bispiperidine (315 mg, 1.00 mmol) and 5-methoxyindole-2-carboxylic acid (1.50 mmol) afforded 77 mg (16%) of the title compound.

$^1$NMR

IS-MS, m/e 489 (M+1).

Analysis for $C_{26}H_{33}N_3O_3S$:

Calcd: C, 69.3; H, 7.3; N, 9.0;

Found: C, 68.9; H, 7.2; N, 8.9.

Example 229
1-(Benzothiazole-2-carbonyl-D-phenylglycinyl)-1'-methyl-4,4'-bispiperidine 1-(D-Phenylglycinyl)-1'-methyl-4,4'-bispiperidine (315 mg, 1.00 mmol) and benzothiazole-2-carboxylic acid (200 mg, 1.12 mmol) afforded 180 mg (16%) of the title compound.

$^1$NMR

IS-MS, m/e 477 (M−1).

Example 230
1-(5-Fluoroindole-2-carbonyl-D-phenylglycinyl)-1-methyl-4,4'-bispiperidine 1-(D-Phenylglycinyl)-1'-methyl-4,4'-bispiperidine (315 mg, 1.00 mmol) and 5-fluoroindole-2-carboxylic acid (280 mg, 1.50 mmol) afforded 80 mg (17%) of the title compound.

$^1$NMR

IS-MS, m/e 477 (M+1).

Analysis for $C_{28}H_{33}FN_4O_2 \cdot H_2O$:

Calcd: C, 68.0; H, 7.1; N, 11.3;

Found: C, 68.0; H, 6.7; N, 11.1.

Example 231
1-(Napthalene-2-carbonyl-D-phenylglycinyl)-1'-methyl-4,4'-bispiperidine 1-(D-Phenylglycinyl)-1'-methyl-4,4'-bispiperidine (315 mg, 1.00 mmol) and napthalene-2-carboxylic acid (220 mg, 1.28 mmol) afforded 160 mg (38%) of the title compound.

$^1$NMR

IS-MS, m/e 470 (M+1).

Analysis for $C_{30}H_{35}N_3O_2 \cdot 0.5\ H_2O$:

Calcd: C, 75.3; H, 7.6; N, 8.8;

Found: C, 75.6; H, 7.4; N, 8.9.

Example 232
1-(6-Methoxyindole-2-carbonyl-D-phenylglycinyl)-1'-methyl-4,4'-bispiperidine Using Coupling Method C, 1-(D-phenylglycinyl)-1'-methyl-4,4'-bispiperidine (315 mg, 1.00 mmol) and 6-methoxyindole-2-carboxylic acid (191 mg, 1.00 mmol) afforded 200 mg (41%) of the title compound.

$^1$NMR

IS-MS, m/e 489 (M+1).

Analysis for $C_{29}H_{36}N_4O_3 \cdot 0.5\ H_2O$:

Calcd: C, 70.0; H, 7.5; N, 11.3;

Found: C, 69.3; H, 7.5; N, 11.1.

Example 233
1-(5-Chloroindole-2-carbonyl-D-phenylglycinyl)-1'-methyl-4,4'-bispiperidine Using Coupling Method A, 1-(D-phenylglycinyl)-1'-methyl-4,4'-bispiperidine (315 mg, 1.00 mmol) and 5-chloroindole-2-carboxylic acid (230 mg, 1.15 mmol) afforded 220 mg (45%) of the title compound.

¹NMR
IS-MS, m/e 493 (M+1).
Analysis for $C_{28}H_{33}ClN_4O_2 \cdot 0.75H_2O$:
Calcd: C, 66.4; H, 6.9; N, 11.1;
Found: C, 66.8; H, 6.6; N, 10.9.

Example 234
1-(3-Hydroxybenzoyl-D-phenylglycinyl)-1'-methyl-4,4'-bispiperidine 1-(D-Phenylglycinyl)-1'-methyl-4,4'-bispiperidine (200 mg, 0.635 mmol) and 3-benzyloxybenzoic acid (158 mg, 0.698 mmol) afforded 100 mg (30%) of 1-(3-benzyloxybenzoyl-D-phenyl1 glycinyl)-1'-methyl-4,4'-bispiperidine. A solution of this material and 10% Pd/C in 3 mL of EtOH was treated with hydrogen gas (1 atm). After 16 h, the mixture was filtered, concentrated, and the residue triturated with EtOAc, affording 27 mg (32%) of the title compound.
¹NMR
IS-MS, m/e 436 (M+1).

Example 235
1-(3-Hydroxy-4-methylbenzoyl-D-phenylglycinyl)-1'-methyl-4,4'-bispiperidine 1-(D-Phenylglycinyl)-1'-methyl-4,4'-bispiperidine (200 mg, 0.635 mmol) and 3-acetoxy-4-methylbenzoic acid (135 mg, 0.698 mmol) afforded, after treatment of the crude acylation mixture with methanolic potassium carbonate and purification by column chromatography (4% to 6% 2 N $NH_3$ in methanol:—methylene chloride), 132 mg (46%) of the title compound.
¹NMR
IS-MS, m/e 450 (M+1).
Analysis for $C_{27}H_{35}N_3O_3 \cdot 0.5H_2O$:
Calcd: C, 71.4; H, 7.9; N, 9.3;
Found: C, 71.4; H, 7.9; N, 9.2.

The protected starting acid for the above procedure was prepared as follows:
3-Acetoxy-4-methylbenzoic acid A solution of 3-hydroxy-4-methylbenzoic acid (3.0 g, 19.7 mmol) in acetic anhydride (5.6 mL) was treated with sulfuric acid (0.03 mL), heated to 70° C., cooled and diluted with water. The resulting solid was collected by filtration yielding 1.14 g (30%) of the title compound, which was used without further purification.
¹NMR.

Example 236
1-(2-Hydroxybenzoyl-D-phenylglycinyl)-1'-methyl-4,4'-bispiperidine 1-(D-Phenylglycinyl)-1'-methyl-4,4'-bispiperidine (200 mg, 0.635 mmol) and 2-acetoxybenzoic acid (125 mg, 0.698 mmol; prepared using methods substantially equivalent to those described for 3-acetoxy-4-methylbenzoic acid) afforded, after treatment of the crude acylation mixture with methanolic potassium carbonate and purification by column chromatography, 100 mg (36%) of the title compound.
¹NMR
IS-MS, m/e 436 (M+1).

Example 237
1-(4-Chloro-3-hydroxybenzoyl-D-phenylglycinyl)-1'-methyl-4,4'-bispiperidine 1-(D-Phenylglycinyl)-1'-methyl-4,4'-bispiperidine (200 mg, 0.635 mmol) and 4-chloro-3-acetoxybenzoic acid (150 mg, 0.698 mmol; prepared using methods substantially equivalent to those described for 3-acetoxy-4-methylbenzoic acid) afforded, after treatment of the crude acylation mixture with methanolic potassium carbonate and purification by column chromatography, 110 mg (37%) of the title compound.
¹NMR
IS-MS, m/e 470 (M+1).

Example 238
1-(4-Chloro-2-hydroxybenzoyl-D-phenylglycinyl)-1'-methyl-4,4'-bispiperidine 1-(D-Phenylglycinyl)-1'-methyl-4,4'-bispiperidine (200 mg, 0.635 mmol) and 4-chloro-2-acetoxybenzoic acid (150 mg, 0.698 mmol; prepared using methods substantially equivalent to those described for 3-acetoxy-4-methylbenzoic acid) afforded, after treatment of the crude acylation mixture with methanolic potassium carbonate and purification by radial chromatography, 60 mg (20%) of the title compound.
¹NMR
IS-MS, m/e 470 (M+1).

Example 239
1-(4-Chloro-3-methoxybenzoyl-D-phenylglycinyl)-1'-methyl-4,4'-bispiperidine 1-(D-Phenylglycinyl)-1'-methyl-4,4'-bispiperidine (200 mg, 0.635 mmol) and 4-chloro-2-methoxybenzoic acid (130 mg, 0.698 mmol) afforded, after purification by column chromatography, 120 mg (39%) of the title compound.
¹NMR
IS-MS, m/e 484 (M+1).
Analysis for $C_{27}H_{34}ClN_3O_3$:
Calcd: C, 67.0; H, 7.1; N, 8.7;
Found: C, 66.8; H, 7.1; N, 8.8.

Example 240
1-(3-Hydroxy-4-methoxybenzoyl-D-phenylglycinyl)-1'-methyl-4,4'-bispiperidine 1-(D-Phenylglycinyl)-1'-methyl-4,4'-bispiperidine (200 mg, 0.635 mmol) and 3-acetoxy-4-methoxybenzoic acid (146 mg, 0.698 mmol; prepared using methods substantially equivalent to those described for 3-acetoxy-4-methylbenzoic acid) afforded, after treatment of the crude acylation mixture with methanolic potassium carbonate and purification by column chromatography, 52 mg (18%) of the title compound.
¹NMR
IS-MS, m/e 466 (M+1).

Example 241
1-(2,4-Dihydroxybenzoyl-D-phenylglycinyl)-1'-methyl-4,4'-bispiperidine 1-(D-Phenylglycinyl)-1'-methyl-4,4'-bispiperidine (200 mg, 0.635 mmol) and 2,4-diacetoxybenzoic acid (167 mg, 0.698 mmol; prepared using methods substantially equivalent to those described for 3-acetoxy-4-methylbenzoic acid) afforded, after treatment of the crude acylation mixture with methanolic potassium carbonate and purification by column chromatography, 145 mg (50%) of the title compound.
¹NMR
IS-MS, m/e 452 (M+1).
Analysis for $C_{26}H_{33}N_3O_4 \cdot 0.75 H_2O$:
Calcd: C, 67.2; H, 7.5; N, 9.0;
Found: C, 67.3; H, 7.2; N, 9.3.

Example 242
1-(2-Hydroxy-4-methoxybenzoyl-D-phenylglycinyl)-1'-methyl-4,4'-bispiperidine 1-(D-Phenylglycinyl)-1'-methyl-4,4'-bispiperidine (200 mg, 0.635 mmol) and 2-acetoxy-4-methoxybenzoic acid (146 mg, 0.698 mmol; prepared using methods substantially equivalent to those described for 3-acetoxy-4-methylbenzoic acid) afforded, after treatment of the crude acylation mixture with methanolic potassium carbonate and purification by ion exchange chromatography (Varian, SCX), 118 mg (40%) of the title compound.
$^1$NMR
IS-MS, m/e 466 (M+1).
Analysis for $C_{27}H_{35}N_3O_4 \cdot 0.50$ $H_2O$:
Calcd: C, 68.3; H, 7.7; N, 8.9;
Found: C, 68.2; H, 7.4; N, 9.1.

Example 243
1-(5-Chloro-2-hydroxybenzoyl-D-phenylglycinyl)-1'-methyl-4,4'-bispiperidine 1-(D-Phenylglycinyl)-1'-methyl-4,4'-bispiperidine (200 mg, 0.635 mmol) and 2-acetoxy-5-chlorobenzoic acid (150 mg, 0.698 mmol; prepared using methods substantially equivalent to those described for 3-acetoxy-4-methylbenzoic acid) afforded, after treatment of the crude acylation mixture with methanolic potassium carbonate and purification by ion exchange chromatography (Varian, SCX), 100 mg (33%) of the title compound
$^1$NMR
IS-MS, m/e 471 (M+1).
Analysis for $C_{26}H_{32}ClN_3O_3 \cdot 0.25$ $H_2O$:
Calcd: C, 65.8; H, 6.9; N, 8.9;
Found: C, 65.9; H, 7.0; N, 9.2.

Example 244
1-(3-Chloro-4-hydroxybenzoyl-D-phenylglycinyl)-1'-methyl-4,4'-bispiperidine 1-(D-Phenylglycinyl)-1-methyl-4,4'-bispiperidine (315 mg, 1.00 mmol) and 4-acetoxy-3-chlorobenzoic acid (321 mg, 1.50 mmol; prepared using methods substantially equivalent to those described for 3-acetoxy-4-methylbenzoic acid) afforded, after treatment of the acylation mixture with methanolic potassium carbonate, 50 mg (27%) of the title compound.
$^1$NMR
IS-MS, m/e 470 (M+I).
Analysis for $C_{26}H_{32}ClN_3O_3 \cdot 1.0$ $H_2O$:
Calcd: C, 64.0; H, 7.0; N, 8.6;
Found: C, 63.7; H, 7.0; N, 8.7.

Example 245
1-(3-Hydroxynaphthalene-2-carbonyl-D-phenylglycinyl)-1'-methyl-4,4'-bispiperidine 1-(D-Phenylglycinyl)-1'-methyl-4,4'-bispiperidine (315 mg, 1.00 mmol) and 3-acetoxynaphthalene-2-carboxylic acid (300 mg, 1.30 mmol; prepared using methods substantially equivalent to those described for 3-acetoxy-4-methylbenzoic acid) afforded, after treatment of the acylation product with methanolic potassium carbonate, 128 mg (38%) of the title compound.
$^1$NMR
IS-MS, m/e 486 (M+1).

Example 246
1-(6-Hydroxynaphthalene-2-carbonyl-D-phenylglycinyl)-1'-methyl-4,4'-bispiperidine
1-(D-Phenylglycinyl)-1'-methyl-4,4'-bispiperidine (315 mg, 1.00 mmol) and 6-acetoxynaphthalene-2-carboxylic acid (300 mg, 1.30 mmol; prepared using methods substantially equivalent to those described for 3-acetoxy-4-methylbenzoic acid) afforded, after treatment of the acylation product with methanolic potassium carbonate, 210 mg (43%) of the title compound.
$^1$NMR
IS-MS, m/e 486 (M+1).
Analysis for $C_{30}H_{35}N_3O_3 \cdot 1.0$ $H_2O$:
Calcd: C, 71.6; H, 7.4; N, 8.3;
Found: C, 71.5; H, 7.3; N, 8.3.

Examples 247–251
Preparation of Starting Materials
1-(Benzyloxycarbonyl-D-phenylglycinyl)piperidine-4-methanol
Using Coupling Method C, benzyloxycarbonyl-D-phenylglycine (8.41 g, 29.5 mmol) and 4-piperidinemethanol (3.85 g, 37.4 mmol) afforded 10.2 g (93%) of the title compound.
$^1$NMR
1-(D-Phenylglycinyl)piperidine-4-methanol
Using Deprotection Method C, 1-(benzyloxycarbonyl-D-phenylglycinyl)piperidine-4-methanol (3.93 g, 29.5 mmol) and 10% palladium on carbon (1.30 g) afforded 2.31 g (88%) of the title compound.
$^1$NMR
IS-MS, m/e 249 (M+1).
1-(4-Methoxybenzoyl-D-phenylglycinyl)piperidine-4-methanol
Using methods substantially equivalent Acylation Method C described prior to Example 201, 1-(D-phenylglycinyl)piperidine-4-methanol (1.23 g, 4.96 mmol) and p-anisoyl chloride (0.888 g, 5;21 mmol) afforded, after purification by column chromatography ($SiO_2$: 1:1 to 1:9 hexanes:EtOAc), 1.26 g (66%) of the title compound.
$^1$NMR
IS-MS, m/e 383 (M+1).
1-(4-Methoxybenzoyl-D-phenylglycinyl)piperidine-4-carboxaldehyde
A solution of 1-(4-methoxybenzoyl-D-phenylglycinyl)piperidine-4-methanol (0.800 g, 2.08 mmol) and N-methylmorpholine oxide (0.366 g, 3.13 mmol) in methylene chloride (15 mL) was treated with tetrapropylammonium perruthenate (TPAP, 2 mg). After 14 h, the mixture was treated with additional TPAP (5 mg). After 20 h, the mixture was treated with additional TPAP (5 mg). After 32 h, the mixture was loaded directly onto a column and purified by column chromatography ($SiO_2$: 1:1 to 1:4 hexanes:EtOAc) affording 0.286 g (36%) of the title compound.
$^1$NMR
IS-MS, m/e 381 (M+1).
General Procedure: Unless otherwise indicated, the product of Examples 247–251 was obtained from the indicated amine and 1-(4-methoxybenzoyl-D-phenylglycinyl)piperidine-4-carboxaldehyde using Alkylation Method D.

Example 247
1-[(4-Methoxybenzoyl-D-phenylglycinyl)]-4-[(isopropylamino)methyl]piperidine hydrochloride
1-(4-Methoxybenzoyl-D-phenylglycinyl)piperidine-4-carboxaldehyde (0.050 g, 0.131 mmol) and isopropylamine afforded, after treatment of the isolated product with excess hydrochloric acid in methanol and concentration, 37 mg of the title compound as a hydrochloride salt.
$^1$NMR
IS-MS, m/e 424 (M+1).

Example 248
1-(4-Methoxybenzoyl-D-phenylglycinyl)-4-(dimethylamino)-methyl]piperidine
1-(4-Methoxybenzoyl-D-phenylglycinyl)piperidine-4-carboxaldehyde (0.050 g, 0.131 mmol) and dimethylamine afforded 25 mg (47%) of the title compound.

¹NMR
IS-MS, m/e 410 (M+1).

Example 249
1-[(4-Methoxybenzoyl-D-phenylglycinyl)]-4-[(N,N-diethylamino)methyl]piperidine hydrochloride 1-(4-Methoxybenzoyl-D-phenylglycinyl)piperidine-4-carboxaldehyde (0.050 g, 0.131 mmol) and diethylamine afforded, after treatment of isolated product with excess hydrochloric acid in methanol and concentration, 42 mg of the title compound as a hydrochloride salt.

¹NMR
IS-MS, m/e 438 (M+1).

Example 250
1-[(4-Methoxybenzoyl-D-phenylglycinyl)]-4-[(1-pyrrolidinyl)methyl]piperidine 1-(4-Methoxybenzoyl-D-phenylglycinyl)piperidine-4-carboxaldehyde (0.050 g, 0.131 mmol) and pyrrolidine afforded 27 mg (47%) of the title compound.

¹NMR
IS-MS, m/e 436 (M+1).

Example 251
1-[(4-Methoxybenzoyl-D-phenylglycinyl)]-4-[(3-pyrrolin-1-yl)methyl]piperidine hydrochloride 1-(4-Methoxybenzoyl-D-phenylglycinyl)piperidine-4-carboxaldehyde (0.050 g, 0.131 mmol) and 3-pyrroline afforded, after treatment of isolated product with excess hydrochloric acid in methanol and concentration, 43 mg of the title compound as a hydrochloride salt.

¹NMR
IS-MS, m/e 434 (M+1).

Examples 252 to 253
Preparation of Starting Materials
4-[(Benzyloxycarbonyl-D-phenylglycinyl)aminomethyl]-piperidine Using Deprotection Method D, 4-[(benzyloxycarbonyl-D-phenylglycinyl) aminomethyl]-1-Boc piperidine (2.70 g, 5.61 mmol) afforded 1.56 g (73%) of the title compound.

¹NMR
IS-MS, m/e 382 (M+1).
4-[(Benzyloxycarbonyl-D-phenylglycinyl)aminomethyl]-1-cyclopentylpiperidine Using Alkylation Method D, 4-[(benzyloxycarbonyl-D-phenylglycinyl)aminomethyl]piperidine (1.50 g, 3.93 mmol) and cyclopentanone afforded 3.48 g (91%) of the title compound.

¹NMR
IS-MS, m/e 450 (M+1).
4-[(D-Phenylglycinyl)aminomethyl]-1-cyclopentylpiperidine Using a deprotection procedure similar to that described above for preparation of 1-(D-phenylglycinyl)-1'-methyl-4,4'-bispiperidine, 4-[(benzyloxycarbonyl-D-phenylglycinyl)aminomethyl]-1-cyclopentylpiperidine (1.70 g, 3.78 mmol) afforded 0.75 g (63%) of the title compound.

¹NMR
IS-MS, m/e 316 (M+1).

General Procedure: Using Coupling Method A, 4-[(D-phenylglycinyl) aminomethyl]-1-cyclopentylpiperidine was coupled with the indicated acid.

Example 252
4-[(5-Chloroindole-2-carbonyl-D-phenylglycinyl)aminomethyl]-1-cyclopentylpiperidine 4-[(D-Phenylglycinyl)aminomethyl]-1-cyclopentylpiperidine (0.100 g, 0.317 mmol) and 5-chloroindole-2-carboxylic acid (0.075 g, 0.38 mmol) afforded 156 mg (98%) of the title compound.

¹NMR
IS-MS, m/e 493 (M+1).

Example 253
4-[(3-Methylindole-6-carbonyl-D-phenylglycinyl)aminomethyl]-1-cyclopentylpiperidine 4-[(D-Phenylglycinyl)aminomethyl]-1-cyclopentylpiperidine (0.100 g, 0.317 mmol) and 3-methylindole-6-carboxylic acid (0.067 g, 0.38 mmol) afforded 137 mg (91%) of the title compound.

¹NMR
IS-MS, m/e 473 (M+1).

Particular Analytical Methods for Examples 254–276:

HPLC Analysis (Method A): Dynamax (trademark) C18, 60Å column. The elution system consisted of a linear gradient from 90:10(95% $H_2O$, $CH_3CN$)/(95% $CH_3CN$, $H_2O$) to (95% $CH_3CN$, $H_2O$) over 20 min, followed by (95% $CH_3CN$, $H_2O$) isocratic elution over 15 min. The flow rate was 1 mL/min. UV Detection was performed at 254 nm unless otherwise noted.

HPLC Analysis (Method B): Microsorb-MV (trademark) C8 (4.6×250 mm) column. The elution system consisted of a linear gradient from 95:5 (2.5% TFA in $H_2O$):(2.5% TFA in acetonitrile) to 0:100 (2.5% TFA in $H_2O$):(2.5% TFA in acetonitrile) over 25 min at 30° C. and a flow rate of 1 mL/min. UV Detection was performed at 254 nm unless otherwise noted.

HPLC Analysis (Method C): Dynamax (trademark), C18, 60Å column. The elution system consisted of a linear gradient from 95:5 (0.2% TFA in $H_2O$)/(0.2% TFA in $CH_3CN$) to 5:95 (0.2% TFA in $H_2O$)/(0.2% TFA in $CH_3CN$) over 20 min, followed by (0.2% TFA in $CH_3CN$) isocratic elution over 15 min. The flow rate was 1 mL/min. UV Detection was performed at 254 nm unless otherwise noted.

HPLC Analysis (Method D): Waters Symmetry (trademark), C18 (4.6×250 mm) column. The elution system consisted of a linear gradient from 95:5 (0.2% TFA in $H_2O$)/(0.2% TFA in $CH_3CN$) to 5:95 (0.2% TFA in $H_2O$)/ (0.2% TFA in $CH_3CN$) over min, followed by (0.2% TFA in $CH_3CN$) isocratic over 15 min. The flow rate was 1 mL/min. UV Detection was performed at 254 nm unless otherwise noted.

HPLC Analysis (Method E): Microsorb-MV C18 (4.6× 250 mm) column. The elution system consisted of a linear gradient from 90:10 (2.5% TFA in $H_2O$):(2.5% TFA in acetonitrile) to 10:90 (2.5% TFA in $H_2O$):(2.5% TFA in acetonitrile) over 25 min at 30° C. and a flow rate of 1 mL/min. UV Detection was performed at 254 nm unless otherwise noted.

API-MS (atmospheric pressure chemical ionization mass spectra) were obtained on a PESciex (trademark) API 150EX with a heated nebulizer and nitrogen as the reagent gas in positive ion mode.

Examples 254 to 257
Preparation of Starting Materials
(R)-(−)-Boc-phenylglycinol: Di-tert-butyl dicarbonate (232.4 g, 1.06 mol) was added to a well stirred, ice bath cooled mixture of (R)-(−)-2-phenylglycinol (121.7 g, 0.887 mol), potassium carbonate (171.7 g, 1.24 mol), 1,4-dioxane (1 L), and water (1 L). The temperature rose from 5° C. 11° C. during the addition. The reaction was allowed to stir overnight. The reaction was diluted with water (1 L), and cooled in ice-water. The resultant precipitate was collected by vacuum filtration, washed with water, air dried, and vacuum dried at 40° C. overnight to afford 201.7 g (95%) as a white solid.

1H-NMR(CDCl$_3$)
TLC R$_f$=0.45 (83% CH$_2$Cl$_2$, EtOAc).

(R)-(-)-[2-[(Methylsulphonyl)oxy]-1-phenylethyl]carbamic acid 1,1-dimethylethyl ester The sulphonate was prepared from the above alcohol according to *J. Med. Chem.* 1994, 37, 1819.
1H-NMR(CDCl$_3$)
TLC R$_f$=0.45 (95% CH$_2$Cl$_2$, EtOAc)

(R)-2-[(Butoxycarbonyl) amino]-2-phenylethyl azide

The azide was prepared form the above sulphonate according to *J. Med. Chem.* 1994, 37, 1819.
1H-NMR(CDCl$_3$)
TLC R$_f$=0.85 (95% CH$_2$Cl$_2$, EtOAc).

(R)-2-(4-Methoxybenzoylamino)-2-phenylethyl azide (R)-2-[(Butoxycarbonyl)amino]-2-phenylethyl azide (47.8 g, 0.182 mole) was added to trifluoroacetic acid (500 mL) with stirring and ice-water bath cooling. The cooling bath was removed, the reaction was allowed to stir 1 h, and the solvent was removed in vacuo at 35° C. water bath temperature. The residue was co-evaporated with toluene to give a weight of 75.0 g. The residue was dissolved in 1,4-dioxane (500 mL) and water (500 mL), with ice-water bath cooling, and then potassium carbonate (113.5 g, 0.82 mol), and anisoyl chloride (37.3 g, 0.219 mol) were added.

Another portion of 1,4-dioxane (300 mL) was added to facilitate stirring. After stirring over the weekend, water (1 L) was added. The mixture was cooled to -15° C., and vacuum filtered to collect a white solid. The solid was washed with water, air dried, and then dried under vacuum at 50° C. for 4 h to afford 46.3 g (86%).
1H-NMR(CDCl$_3$)
TLC R$_f$ 0.85 (83% CH$_2$Cl$_2$, EtOAc).

(R)-2-(4-Methoxybenzoylamino)-2-phenylethylamine (R)-2-(4-methoxybenzoylamino)-2-phenylethyl azide (46.3 g) was combined with 10% palladium on carbon in THF (400 mL), methanol (100 mL) and was stirred under a hydrogen atmosphere. Analysis by TLC (70% methylene chloride, ethyl acetate) indicated absence of starting material after stirring overnight. The solution was filtered through diatomaceous earth, rinsed with THF, and evaporated. The resulting solid was recrystallized with ethyl acetate, and dried under vacuum at 60° C. for 1 h to afford 35.4 g (84%) of a white crystalline solid.
1H-NMR(CDCl$_3$)
TLC R$_f$=0.17 (90% CH$_2$Cl$_2$, 9% Methanol, 1% NH$_4$OH).

Examples 254–257 were prepared from (R)-2-(4-methoxybenzoylamino)-2-phenylethylamine and the indicated acid chloride using the acylation method described in Example 254 (Acylation Method A).

Example 254

(R)-N-[2-(4-Methoxybenzoylamino)-2-phenylethyl]-4-methylbenzamide (Acylation Method A) p-Toluoyl chloride (0.22 mL, 1.6 mmol) was added via syringe to a 15° C. stirring mixture of (R)-2-(4-methoxybenzoylamino)-2-phenylethylamine (0.40 g, 1.48 mmol), potassium carbonate (0.27 g, 1.9 mmol), 1,4-dioxane (8 mL), and water (4 mL). TLC analysis (80% methylene chloride, 18% methanol, 2% ammonium hydroxide) indicated reaction completion within 1 h. The solution was diluted with water, and the precipitated solid was collected by vacuum filtration. The precipitate was recrystallized from methanol and dried under vacuum at 50° C. overnight to afford the title compound (0.42 g, 72%) as a white solid.
1H-NMR (DMSO)
IS-MS, m/e=389(M+1)
Analysis for C$_{24}$H$_{24}$N$_2$O$_3$:
Calcd: C, 74.21; H, 6.23; N, 7.21;
Found: C, 73.82; H, 6.32; N, 7.04.
HPLC Analysis (Method A): 99.3%, RT: 21.35 min.
Melting Point: 230–238° C.

Example 255

(R)-N-[2-(4-Methoxybenzoylamino)-2-phenylethyl]-4-ethylbenzamide

Prepared from 4-ethylbenzoyl chloride (84%).
1H-NMR (DMSO)
IS-MS, m/e=403 (M+1)
Analysis for C$_{25}$H$_{26}$N$_2$O$_3$:
Calcd: C, 74.60; H, 6.51; N, 6.96;
Found: C, 74.25; H, 6.63; N, 6.83.
HPLC Analysis (Method A): 95.4%, RT=22.62 min.
Melting Point: 222–229° C.

Example 256

(R)-N-[2-(4-Methoxybenzoylamino)-2-phenylethyl]-4-isopropylbenzamide

Prepared from 4-isopropylbenzoyl chloride (40%).
1H-NMR (DMSO)
IS-MS, m/e=417 (M+1)
Analysis for C$_{26}$H$_{28}$N$_2$O$_3$:
Calcd: C, 74.97; H, 6.78; N, 6.73;
Found: C, 74.61; H, 6.78; N, 6.61.
HPLC Analysis (Method A): 98.4%, RT=23.77 min.
Melting Point: 239–244° C.

Example 257

(R)-N-[2-(4-Methoxybenzoylamino)-2-phenylethyl]-4-tert-butylbenzamide

Prepared from 4-tert-butylbenzoyl chloride (89%).
1H-NMR (DMSO)
IS-MS, m/e=431 (M+1)
Analysis for C$_{27}$H$_{30}$N$_2$O$_3$·0.25H$_2$O:
Calcd: C, 74.54; H, 7.07; N, 6.44;
Found: C, 74.39; H, 7.13; N, 6.34.
HPLC Analysis (Method A): 96.4%, RT=25.04 min.
Melting Point=171–175° C.

Examples 258 to 266
Preparation of Starting Materials
(R)-N-[2-(4-Methoxybenzoylamino)-2-phenylethyl]-1-tert-butoxycarbonylpiperidine-4-carboxamide.

N-Boc-iso-nipecotic acid (2.13 g, 9.5 mmol) followed by (R)-2-(4-methoxybenzoylamino)-2-phenylethylamine (2.34 g, 8.7 mmol) were added at 2° C. to a stirring mixture of EDCI (2.5 g, 13.0 mmol), and HOBt (1.64 g, 12.1 mmol) in DMF (50 mL). Triethylamine (1.8 mL, 13.0 mmol) was added dropwise. The reaction was allowed to warm to room temperature, with stirring overnight. Water (100 mL) was added, and the aqueous mixture was extracted with ethyl acetate (2×200 mL). The extracts were combined, and THF (200 mL) was added. Next, the organic layers were washed with water (5×70 mL), aqueous NaHCO$_3$ (70 mL), and brine (100 mL). The organic layer was dried over Na$_2$SO$_4$, filtered, and evaporated. The crude residue (4.2 g, 100%), was recrystallized from ethyl acetate and hexanes to afford 2.9 g (71%) of a white solid.
1H-NMR (DMSO)
IS-MS, m/e=482 (M+1)
Analysis for C$_{27}$H$_{30}$N$_2$O$_3$:
Calcd: C, 67.34; H, 7.33; N, 8.73;
Found: C, 67.34; H, 7.46; N, 8.66.
HPLC Analysis (Method A): 98.8%, RT=20.72 min.

(R)-N-[2-(4-Methoxybenzoylamino)-2-phenylethyl] piperidine-4-carboxamide trifluoroacetate (Deprotection Method A) Trifluoroacetic acid was added to a stirring suspension of (R)-N-[2-(4-methoxybenzoylamino)-2-phenylethyl]-1-tert-butoxycarbonylpiperidine-4-carboxamide (2.0 g, 4.2 mmol), methylene chloride (20 mL), and anisole (0.5 g, 4.6 mmol) at room temperature. A solution was obtained and bubbling was observed. After 1 h, the reaction mixture was evaporated at 40° C. The residue was taken up in warm methanol, and to this stirring solution was added ether to precipitate the product. The precipitate was collected by vacuum filtration, washed with ethyl acetate, then dried under vacuum at 60° C. overnight to afford 1.9 g (92%) of a white solid 1H-NMR(DMSO)
IS-MS, m/e=382 (M+1)
Analysis for $C_{24}H_{28}F_3N_3O_5$:
Calcd: C, 58.18; H, 5.70; N, 8.48;
Found: C, 58.19; H, 5.78; N, 8.27.
HPLC Analysis (Method C): >99%, RT=20.40 min.

Except as otherwise noted, Examples 258–266 were prepared from (R)-N-[2-(4-methoxybenzoylamino)-2-phenylethyl]-piperidine-4-carboxamide trifluoroacetate and the indicated aldehyde or ketone using the reductive alkylation method described in Example 258 (Alkylation Method A).

Example 258
(R)-N-[2-(4-Methoxybenzoylamino)-2-phenylethyl]-1-isopropylpiperidine-4-carboxamide (Alkylation Method A) (R)-N-[2-(4-Methoxybenzoylamino)-2-phenylethyl]piperidine-4-carboxamide trifluoroacetate (0.50 g, 1.0 mmol), acetone (4.5 mL, 61 mmol), acetic acid (0.28 mL, 4.9 mmol), and sodium cyanoborohydride (0.32 g, 5.1 mmol) were combined in methanol, and stirred. After 4 h, TLC (79% $CH_2Cl_2$, 19% methanol, 1% $NH_4OH$) indicated reaction completion. The solution was diluted with methanol (100 mL), and passed through H+ form ion exchange resin (Varian SCX cartridge, Catalog #1225–6035) washed with methanol, and then with 2 M $NH_3$ in methanol to collect the product. The product was recrystallized from methanol and ether to afford 0.30 g (70%) of a white crystalline solid 1H-NMR (DMSO)
IS-MS, m/e=424 (M+1)
Analysis for $C_{25}H_{33}N_3O_3 \cdot 0.75H_2O$:
Calcd: C, 68.70; H, 7.96; N, 9.61;
Found: C, 68.73; H, 7.68; N, 9.29.
HPLC Analysis (Method C): >99% RT=18.19 min.

Examples 259–262 were purified by passing a solution through a silica gel column, eluting with 200:10:1 methylene chloride, methanol, and concentrated ammonium hydroxide.

Example 259
(R)-N-[2-(4-Methoxybenzoylamino)-2-phenylethyl]-1-cyclopentylpiperidine-4-carboxamide Prepared from cyclopentanone (44%).
1H-NMR (DMSO)
IS-MS, m/e=450 (M+1)
Analysis for $C_{27}H_{35}N_3O_3 \cdot 0.25H_2O$:
Calcd: C, 71.42; H, 7.88; N, 9.25;
Found: C, 71.21; H, 7.93; N, 9.18.
HPLC Analysis (Method C): >99%, RT=18.84 min.
Melting Point=253–257° C.

Example 260
(R)-N-[2-(4-Methoxybenzoylamino)-2-phenylethyl]-1-cyclohexylpiperidine-4-carboxamide Prepared from cyclohexanone (65%).
1H-NMR (DMSO)
IS-MS, m/e=464 (M+1)
Analysis for $C_{28}H_{37}N_3O_3 \cdot 1.0H_2O$:
Calcd: C, 69.83; H, 8.16; N, 8.72;
Found: C, 69.64; H, 7.84; N, 8.90.
HPLC Analysis (Method C): >99%, RT=19.13 min.
Melting Point=239–243° C.

Example 261
(R)-N-[2-(4-Methoxybenzoylamino)-2-phenylethyl]-1-ethylpiperidine-4-carboxamide Prepared from acetaldehyde (36%).
1H-NMR (DMSO)
IS-MS, m/e 410 (M+1)
Analysis for $C_{24}H_{31}N_3O_3$:
Calcd: C, 70.39; H, 7.63; N, 10.26;
Found: C, 70.06; H, 7.67; N, 10.00.
HPLC Analysis (Method D): 96.9%, RT=16.04 min.
Melting Point=245–251° C.

Example 262
(R)-N-[2-(4-Methoxybenzoylamino)-2-phenylethyl]-1-(1-methylpiperidin-4-yl)piperidine-4-carboxamide Prepared from 1-methylpiperid-4-one (27%).
1H-NMR (DMSO)
IS-MS, m/e 479 (M+1)
Analysis for $C_{28}H_{38}N_4O_3 \cdot 0.25H_2O$:
Calcd: C, 69.61; H, 8.03; N, 11.60;
Found: C, 69.72; H, 8.11; N, 11.48.
HPLC Analysis (Method D): 97.0%, RT=15.42 min.
Melting Point=252–259° C.
(No example for Examples 263–264.)

Examples 265–266 were purified by passing a solution through a silica gel column, eluting with 200:10:1 methylene chloride, methanol, and concentrated ammonium hydroxide.

Example 265
(R)-N-[2-(4-Methoxybenzoylamino)-2-phenylethyl]-1-(3-pyridinylmethyl)piperidine-4-carboxamide Prepared from pyridine-3-carboxaldehyde (68%).
1H-NMR (DMSO)
CI-MS, m/e=473 (M+1)
HPLC Analysis (Method D): 92.7%, RT=15.39 min.

Example 266
(R)-N-[2-(4-Methoxybenzoylamino)-2-phenylethyl]-1-(4-pyridinylmethyl)piperidine-4-carboxamide Prepared from pyridine-4-carboxaldehyde (63%).
1H-NMR (DMSO)
CI-MS, m/e=473 (M+1)
HPLC Analysis (Method D): 89.2%, RT=15.33 min.

Example 267
1-(4-Methoxybenzoyl-D-phenylglycinyl)-4-(4-piperidinylmethyl)piperazine trifluoroacetate 1-[D-(+)-Benzyloxycarbonylphenylglycinyl]-(4-tert-butoxy-carbonyl)piperazine.
(Coupling Method A) D-(+)-Benzyloxycarbonylphenylglycine (58.0 g, 203 mmol) and 1-Boc-piperazine (41.7 g, 224 mmol) were dissolved in DMF (1 L) and cooled to approximately −15° C. in an ice-methanol bath. Diethyl cyanophosphonate (37.0 mL, 244 mmol) was slowly added to the mixture. Triethylamine (59.4 mL, 426 mmol) was added dropwise to the solution. The mixture was stirred at −15° C. for 2 h and was allowed to gradually warm to room temperature overnight. The mixture was diluted with ethyl acetate and water. The layers were separated, and the water layer extracted with ethyl acetate. The organic layers were combined, washed with 10% citric acid (2×500 mL) and brine, dried ($Na_2SO_4$), filtered and concentrated under vacuum. The crude product was filtered through a plug of silica gel (1.2 kg) using 1:1 hexanes:ethyl acetate as eluent to provide 1-[D-(+)-benzyloxycarbonylphenylglycinyl]-4-(tert-butoxycarbonyl)piperazine (69.9 g, 76%) as a colorless oil.

1H-NMR($CDCl_3$)
API-MS, m/e=454 (M+1)
1-[D-(+)-Phenylglycinyl]-4-(tert-butoxycarbonyl)piperazine 1-[D-(+)-Benzyloxycarbonylphenylglycinyl]-4-(tert-butoxy carbonyl)piperazine (69.5 g, 153 mmol) was dissolved in ethanol (500 mL). The mixture was degassed with nitrogen and Pd/C (6.8 g) was added. Hydrogen was bubbled through the mixture for 1 h, and it was maintained under a hydrogen atmosphere for 16 h. The Pd/C was removed by filtration through cellulose powder. The filter cake was rinsed with ethanol and ethyl acetate. The filtrate was concentrated under vacuum to give 1-[D-(+)-phenylglycinyl]-4-(tert-butoxycarbonyl)piperazine (45.3 g, 93%) as a light yellow solid.

1H-NMR($CDCl_3$)
API-MS, m/e=320 (M+1)
1-(4-Methoxybenzoyl-D-phenylglycinyl)-4-(tert-butoxycarbonyl)piperazine
(Acylation Method B) 1-[D-(+)-phenylglycinyl]-4-(tert-butoxycarbonyl)piperazine (42.0 g, 131.5 mmol) was dissolved in 1,4-dioxane (420 mL) and water (210 mL) and was cooled to 10° C. Potassium carbonate (36.4 g, 263 mmol) was added, followed by p-anisoyl chloride (24.7 g, 144 mmol). The mixture was stirred at room temperature overnight. The mixture was diluted with water and ethyl acetate. The layers were separated, and the water layer extracted with ethyl acetate. The organic layers were combined, washed with brine, dried, filtered and concentrated to provide 1-(4-methoxybenzoyl-D-phenylglycinyl)-(4-tert-butoxycarbonyl)piperazine (58.7 g, 98%) as an off-white solid.

1H-NMR($CDCl_3$)
API-MS, m/e=454 (M+1)
1-(4-Methoxybenzoyl-D-phenylglycinyl)piperazine trifluoroacetate 1-(4-Methoxybenzoyl-D-phenylglycinyl)-(4-tert-butoxycarbonyl)piperazine (20.0 g, 44.1 mmol) was dissolved in dichloromethane (50 mL) and anisole (20 mL). To this vigorously stirred mixture was added trifluoroacetic acid (50 mL) The mixture was stirred for 25 min at room temperature. The solvents were removed under vacuum. The residue was triturated in ether and sonicated for 60 min. The solid was collected by filtration and dried in a vacuum pistol overnight to provide 1-(4-methoxybenzoyl-D-phenylglycinyl)piperazine trifluoroacetate (18.2 g, 88%) as a light yellow solid.

1H-NMR($CD_3OD$)
API-MS, m/e=354 (M+1)
1-Boc-isonipecotic acid

Isonipecotic acid (15.0 g, 116 mmol) was dissolved in THF (300 mL), water (150 mL) and 6 N NaOH (40 mL). Di-tert-butyl dicarbonate (26.6 g, 122 mmol) was added and the mixture stirred overnight. The mixture was diluted with water and ethyl acetate, and the layers separated. The water layers were extracted with ethyl acetate, and the organic layers discarded. The water layer was diluted with $KHSO_4$ (2 N, pH~4) and extracted with ethyl acetate. The organic layer was washed with brine, dried ($Na_2SO_4$), filtered and concentrated to provide 1-Boc-isonipecotic acid (23.9 g, 90%) as a white solid.

1H-NMR ($CDCl_3$)
API-MS, m/e=230 (M+1)
1-Boc-piperidine-4-methanol

1-Boc-isonipecotic acid (10.0 g, 214 mmol) was dissolved in THF (400 mL) and cooled to 0° C. A solution of $BH_3$-THF (180 mL, 1 N in THF, 180 mmol) was added slowly. The mixture stirred for 1 h at 0° C. and was allowed to warm to room temperature for 12 h. The mixture was carefully quenched with water and diluted with ethyl acetate. The water layer was extracted with ethyl acetate. The organic layers were combined, washed with brine, dried ($Na_2SO_4$), filtered and concentrated to provide 1-Boc-piperidine-4-methanol (7.98 g, 85%) as a white solid.

1H-NMR($CDCl_3$)
API-MS, m/e=220 (M+1)
1-Boc-piperidine-4-carboxaldehyde

Dimethyl sulfoxide (3.5 mL, 48.7 mmol) was dissolved in dichloromethane (100 mL) and was cooled to −78° C. Oxalyl chloride (3.65 mL, 41.8 mmol) was added. The mixture stirred for 30 min. To this solution was added a solution of 1-Boc-piperidine-4-methanol (7.5 g, 34.8 mmol) in dichloromethane (15 mL), and the mixture stirred for 1 h. Triethylamine (9.7 mL, 69.6 mmol) was added slowly and the mixture stirred at −78° C. for 30 min and warmed to room temperature over the course of 1 h. The mixture was diluted with water and the layers separated. The water layer was extracted with dichloromethane and the organic layers combined, dried ($Na_2SO_4$), filtered and concentrated to provide 1-Boc-piperidine-4-carboxaldehyde (6.75 g, 91%) as a yellow oil.

1H-NMR($CDCl_3$)
API-MS, m/e=214 (M+1)
1-(4-Methoxybenzoyl-D-phenylglycinyl)-4-(1-Boc-piperidin-4-ylmethyl)piperazine
(Alkylation Method B) Using Alkylation Method A, except using sodium triacetoxyborohydride in 1,2-dichloroethane, 1-(4-methoxybenzoyl-D-phenylglycinyl)-4-(1-Boc-piperidin-4-ylmethyl)piperazine was prepared from 1-(4-methoxybenzoyl-D-phenylglycinyl)piperazine trifluoroacetate and 1-Boc-piperidine-4-carboxaldehyde (85%).

1H-NMR($CDCl_3$)
1-(4-Methoxybenzoyl-D-phenylglycinyl)-4-(4-piperidinyl-methyl)piperazine trifluoroacetate.

Using Deprotection Method A, the title compound was prepared from 1-(4-methoxybenzoyl-D-phenylglycinyl)-4-(1-Boc-piperidin-4-ylmethyl)piperazine (90%).

Melting Point=70–72° C. with decomposition
IR(KBr)
1H-NMR($CD_3OD$)
API-MS, m/e=451 (M+1)
Analysis for $C_{26}H_{34}N_4O_3 \cdot 2.5TFA \cdot 0.4H_2O$:
Calcd: C, 50.12; H, 5.06; N, 7.54;
Found: C, 49.81; H, 5.33; N, 7.39.
HPLC Analysis (Method B): 97.1% RT=14.3 min.

Examples 268 to 272

Unless otherwise indicated, using Alkylation Method A or B, the title compounds were prepared from 1-(4-methoxybenzoyl-D-phenylglycinyl)-4-(4-piperidinyl-methyl)piperazine trifluoroacetate and the indicated aldehyde or ketone.

Example 268
1-(4-Methoxybenzoyl-D-phenylglycinyl)-4-(1-methylpiperidin-4-ylmethyl)piperazine hydrochloride Prepared from paraformaldehyde using Method A (56%).
IR (KBr)
1H-NMR(CD$_3$OD)
CI-MS, m/e=465 (M+1)

Example 269
1-(4-Methoxybenzoyl-D-phenylglycinyl)-4-(1-isopropylpiperidin-4-ylmethyl)piperazine hydrochloride Prepared from acetone using Method A (72%).
Melting Point=172–180° C. with decomposition
IR (KBr)
1H-NMR(CD$_3$OD)
CI-MS, m/e=493 (M+1)
Analysis for C$_{29}$H$_{40}$N$_4$O$_3$·3HCl:
Calcd: C, 55.85; H, 7.34; N. 8.98;
Found: C, 55.63; H, 7.32; N, 8.66.
HPLC Analysis (Method B): 98.2% RT=14.4 min.

Example 270
1-(4-Methoxybenzoyl-D-phenylglycinyl)-4-[3-(3-pyridinyl)propyl]piperazine hydrochloride Prepared from pyridine-3-propionaldehyde (prepared as described below) using Method B (72%).
1H-NMR(CD$_3$OD)
CI-MS, m/e=473 (M+1)

Pyridine-3-propionaldehyde
(Oxidation Method A) 1,1,1-Triacetoxy-1,1-dihydro-1,2-benziodoxol-3(1H)-one (5.4 g, 12.7 mmol) was suspended in dichloromethane (45 mL). 3-Pyridinepropanol (1.59 g, 11.6 mmol) as a solution in dichloromethane (35 mL) was added slowly. The mixture stirred for 3 h at room temperature.

The mixture was diluted with saturated aqueous NaHCO$_3$ and ether. The mixture was stirred for 10 min and was diluted with sodium thiosulfate (2 N) and stirred until the solids dissolved. The layers were separated, and the water layer was extracted with ether. The organic layers were combined, washed with water and brine, dried (Na$_2$SO$_4$), filtered and concentrated to provide pyridine-3-propionaldehyde (1.03 g, 66%) as a yellow oil.
1H-NMR(CDCl$_3$)

Example 271
1-(4-Methoxybenzoyl-D-phenylglycinyl)-4-[3-(4-pyridinyl)propyl]piperazine hydrochloride.

Prepared from pyridine-4-propionaldehyde (prepared as described below) using Method A; the hydrochloride salt was prepared using HCl (2 M) in diethyl ether (76%).
1H-NMR(CD$_3$OD)
CI-MS, m/e=473 (M+1)

Pyridine-4-propionaldehyde
Prepared from 4-pyridinepropanol using Oxidation Method A (80%).
1H-NMR(CDCl$_3$)

Example 272
1-(4-Methoxybenzoyl-D-phenylglycinyl)-4-(2-cyclopentylethyl)piperazine hydrochloride hydrate The free base was prepared from cyclopentylacetaldehyde (prepared as described below) using Method B (58%).
$^1$H NMR (CDCl$_3$)

To a stirred solution of 1-(4-methoxybenzyl-D-phenylglycinyl)-4-(2-cyclopentylethyl)piperazine (260 mg, 0.58 mmol) in ether (10 mL) and methylene chloride (1 mL) was added hydrogen chloride as a 2 N solution in ether (about 2 mL), and the resulting precipitate was filtered to give 1-(4-methoxybenzoyl-D-phenylglycinyl)-4-(2-cyclopentylethyl)piperazine hydrochloride as a pale yellow solid.
1H NMR (CD$_3$OD)
IS-MS, m/e=450 (M+1)
Analysis for C$_{27}$H$_{35}$N$_3$O$_3$·HCl·0.5H$_2$O:
Calcd: C, 65.51; H, 7.53; N, 8.49;
Found: C, 65.67; H, 7.58; N, 8.13.
HPLC Analysis (Method E): >99%, RT=15.84
Melting Point=190–192° C.

Cyclopentylacetaldehyde
Using Oxidation Method A, the title compound was prepared from 2-cyclopentylethanol and used with trace amounts of ether and methylene chloride present due to volatility of product.
1H NMR (CDCl$_3$)

Example 273
1-(4-Methoxybenzoyl-D-phenylglycinyl)-4-(3-pyrrolidinyl)piperazine trifluoroacetate (R)-(+)-1-Boc-3-pyrrolidinol
To a stirred solution of (R)-(+)-3-pyrrolidinol (2 g, 22.96 mmol) in tetrahydrofuran (60 mL) and water (30 mL) was added di-tert-butyl dicarbonate (5.27 g, 24.15 nmol) and 3 N sodium hydroxide (16 mL), and the resulting solution was stirred for 6 h. Another portion of di-tert-butyl dicarbonate (0.74 g, 0.34 mmol) was added and the solution was stirred overnight. The reaction was diluted with water (40 mL) and extracted with ethyl acetate (2×150 mL). The combined organic extracts were washed with 2 N potassium hydrogen sulfate (200 mL), saturated sodium bicarbonate (2×150 mL), brine (150 mL) and dried over magnesium sulfate.

Removal of solvent in vacuo gave (R)-(+)-1-Boc-3-pyrrolidinol (4.21 g, 98%) as a yellow oil.
1H-NMR (CDCl$_3$)

1-Boc-3-pyrrolidinone
Using Oxidation Method A, the title compound was prepared from (R)-(+)-1-Boc-3-pyrrolidinol (85%).
$^1$H NMR (CDCl$_3$)

1-(4-Methoxybenzyl-D-phenylglycinyl)-4-(1-Boc-3-pyrrolidinyl)piperazine
Using Alkylation Method B, the title compound was prepared (69%) from 1-(4-methoxybenzyl-D-phenylglycinyl)piperazine trifluoroacetate and 1-Boc-3-pyrrolidinone.
$^1$H NMR (CDCl$_3$)

1-(4-Methoxybenzoyl-D-phenylglycinyl)-4-(3-pyrrolidinyl)piperazine trifluoroacetate.
Using Deprotection Method A, the title compound was prepared from 1-(4-methoxybenzyl-D-phenylglycinyl)-4-(1-Boc-3-pyrrolidinyl)piperazine
$^1$H NMR (CD$_3$OD)

Example 274
1-(4-Methoxybenzoyl-D-phenylglycinyl)-4-[2-(4-pyridinyl)ethyl]piperazine 1-Boc-4-[2-(4-pyridinyl)ethyl]piperazine
1-Boc-piperazine (4.0 g, 21.5 mmol), 4-vinylpyridine (2.94 g, 27.9 mmol), and acetic acid (1.29 g, 21.5 mmol) were mixed in ethanol and heated to reflux for 48 h. The mixture was cooled to room temperature and concentrated under vacuum to provide 1-Boc-4-[2-(4-pyridinyl)ethyl]piperazine (2.9 g, 45%) as an off white solid. The product was used without further purification.
1H-NMR(CDCl$_3$)
CI-MS, m/e=292 (M+1)

1-[2-(4-Pyridinyl)ethyl]piperazine hydrochloride
(Deprotection Method B) 1-Boc-4-[2-(4-pyridinyl)ethyl]piperazine (1.0 g, 3.43 mmol) was dissolved in ethyl ether.

Ethyl acetate (15 mL) saturated with HCl was added, and the mixture stirred for 30 min at room temperature. The mixture was concentrated under vacuum and provided 1-[2-(4-pyridinyl)ethyl]piperazine hydrochloride (900 mg, 87%) as a tan solid.
1H-NMR(CD$_3$OD)
CI-MS, m/e=192 (M+1)

1-(D-Boc-phenylglycinyl)-4-[2-(4-pyridinyl)ethyl]piperazine

Using Coupling Method A, the title compound was prepared from 1-[2-(4-pyridinyl)ethyl]piperazine and Boc-D-phenylglycine (95%).
1H-NMR(CDCl$_3$)
CI-MS, m/e=425 (M+1)

1-(D-Phenylglycinyl)-4-[2-(4-pyridinyl)ethyl]piperazine hydrochloride

Using Deprotection Method B, the title compound was prepared from 1-(D-Boc-phenylglycinyl)-4-[2-(4-pyridinyl)ethyl]-piperazine (89%).
1H-NMR(CD$_3$OD)
CI-MS, m/e=325 (M+1)

1-(4-Methoxybenzoyl-D-phenylglycinyl)-4-[2-(4-pyridinyl)ethyl]piperazine

Using Acylation Method B, the title compound was prepared from 1-(D-phenylglycinyl)-4-[2-(4-pyridinyl)ethyl]piperazine hydrochloride and p-anisoyl chloride (70%).
1H-NMR(CDCl$_3$)
CI-MS, m/e=459 (M+1)
HPLC Analysis (Method E): 99.7%, RT=10.98 min.

Examples 275 to 276

Using Alkylation Method B, the title compounds were prepared from 1-(4-methoxybenzoyl-D-phenylglycinyl)-4-(3-pyrrolidinyl)piperazine trifluoroacetate and the indicated aldehyde or ketone.

Example 275
1-(4-Methoxybenzoyl-D-phenylglycinyl)-4-(1-methylpyrrolidin-3-yl)piperazine
Prepared from paraformaldehyde (20%).
1H-NMR(CDCl$_3$)

Example 276
1-(4-Methoxybenzoyl-D-phenylglycinyl)-4-(1-isopropylpyrrolidin-3-yl)piperazine.
Prepared from acetone (59%).
1H-NMR(CDCl$_3$)

The following analytical methods apply to Examples 277–336.
Analytical RPHPLC Method 1=Vydac C18, linear gradient of 90/10–50/50 (0.1% TFA in water/0.1% TFA in acetonitrile) over 40 min, 1 mL/min.
Analytical RPHPLC Method 2=Vydac C18, linear gradient of 85/20–40/60 (0.1% TFA in water/0.1% TFA in acetonitrile) over 40 min, 1 mL/min.

Examples 277 to 290

Unless otherwise indicated, the products of Examples 277 through 290 were obtained from the indicated acid and 1-D-phenylglycinyl-1'-methyl-4,4'-bispiperidine using the procedure described in Example 277 (Coupling Method B).

Example 277
1-(2-Chloropyridine-5-carbonyl-D-phenylglycinyl)-1'-methyl-4,4'-bispiperidine
(Coupling Method B) To a stirring solution of 1-[3-(dimethylamino)propyl]-3-ethylcarbodiimide hydrochloride (0.20 g, 1.0 mmol) and 1-hydroxybenzotriazole hydrate (0.15 g, 1.1 mmol) in DMF (3 mL) was added 2-chloropyridine-5-carboxylic acid (0.14 g, 0.89 mmol) followed by a solution of 1-D-phenylglycinyl-1'-methyl-4,4'-bispiperidine (0.25 g, 0.80 mmol) in DMF (2 mL). After stirring for 18 h, the solvent was removed in vacuo and the residue was partitioned between dichloromethane and 1 N sodium hydroxide. The aqueous phase was separated, extracted twice with dichloromethane, and the combined organic phases were dried with MgSO$_4$, filtered and concentrated in vacuo. The resulting solid was dissolved in a minimum amount of dichloromethane and chromatographed over silica gel, eluting with 10% methanol (containing 2 N ammonia) in dichloromethane through 15% methanol (containing 2 N ammonia) in dichloromethane. The product containing fractions were combined and concentrated in vacuo to give 0.258 g (71%) of a white solid
1H-NMR
IS-MS, m/e 455.0 (M+1)
Analysis for C$_{25}$H$_{31}$N$_4$O$_2$Cl·0.4H$_2$O:
Calcd: C, 64.96; H, 6.93; N, 12.13;
Found: C, 64.68; H, 6.72; N, 12.02.
Analytical RPHPLC, Method 1, RT=21.28 min (98%)

Example 278
1-(5-Chloropyridine-2-carbonyl-D-phenylglycinyl)-1'-methyl-4,4'-bispiperidine
Prepared from 2-chloropyridine-5-carboxylic acid (61%)
1H-NMR
IS-MS, m/e 454.9 (M+1)
Analysis for C$_{25}$H$_{31}$N$_4$O$_2$Cl·0.4H$_2$O:
Calcd: C, 64.96; H. 6.93; N, 12.12;
Found: C, 64.75; H, 6.64; N, 12.00.
Analytical RPHPLC, Method 1, RT=27.23 min (100%)

Example 279
1-(3-Cyano-4-fluorobenzoyl-D-phenylglycinyl)-1'-methyl-4,4'-bispiperidine
Prepared from 3-cyano-4-fluorobenzoic acid (66%).
1H-NMR
IS-MS, m/e 463.0 (M+1)
Analysis for C$_{27}$H$_{31}$N$_4$O$_2$F·0.3H$_2$O:
Calcd: C, 69.30; H, 6.81; N, 11.97;
Found: C, 68.91; H, 6.58; N, 11.77.
Analytical RPHPLC [Vydac C18, linear gradient of 85/15–45/55 (0.1% TFA in water/0.1% TFA in acetonitrile) over 40 min, 1 mL/min] RT=21.54 (99%)

Example 280
1-(5-Chlorobenzo[b]thiophene-2-carbonyl-D-phenylglycinyl)-1'-methyl-4,4'-bispiperidine
Prepared from 5-chlorobenzo[b]thiophene-2-carboxylic acid (38%).
1H-NMR
IS-MS, m/e 509.9 (M+1)
Analysis for C$_{28}$H$_{32}$N$_3$O$_2$SCl·0.3H$_2$O:
Calcd: C, 65.24; H, 6.37; N, 8.15;
Found: C, 65.01; H, 6.12; N, 8.07.
Analytical RPHPLC, Method 1, RT=36.08 min (99%)

Example 281
1-(2-Benzo[b]thiophenecarbonyl-D-phenylglycinyl)-1'-methyl-4,4'-bispiperidine
Prepared from 2-benzo[b]thiophenecarboxylic acid (82%).
1H-NMR
IS-MS, m/e 475.9 (M+1)
Analysis for C$_{28}$H$_{33}$N$_3$O$_2$S·0.4H$_2$O:

Calcd: C, 69.65; H, 7.06; N, 8.70;
Found: C, 69.45; H, 6.90; N, 8.58.
Analytical RPHPLC, Method 2, RT=22.30 min (100%)

Example 282
1-(6-Chlorobenzo[b]thiophene-2-carbonyl-D-phenylglycinyl)- 1'-methyl-4,4'-bispiperidine Prepared from 6-chlorobenzo[b]thiophene-2-carboxylic acid (77).
1H-NMR
IS-MS, m/e 509.9 (M+1)
Analysis for $C_{28}H_{32}N_3O_2SCl \cdot 0.3H_2O$:
Calcd: C, 65.24; H, 6.37; N, 8.15;
Found: C, 64.97; H, 6.23; N, 8.07.

Example 283
1-(Indole-2-carbonyl-D-phenylglycinyl)-1'-methyl-4,4'-bispiperidine

Prepared from 2-indolecarboxylic acid (57%).
1H-NMR
IS-MS, m/e 459.0 (M+1)
Analysis for $C_{28}H_{34}N_4O_2 \cdot 0.4H_2O$:
Calcd: C, 71.10; H, 7.59; N, 11.85;
Found: C, 70.82; H, 7.25; N, 11.74.
Analytical RPHPLC, Method 1, RT=29.60 min (99%)

Example 284
1-(1-Methylindole-2-carbonyl-D-phenylglycinyl)-1'-methyl-4,4'-bispiperidine Prepared from 1-methylindole-2-carboxylic acid (43%).
1H-NMR
IS-MS, m/e 473.0 (M+1)
Analytical RPHPLC, Method 2, RT=22.20 min (98%)

Example 285
1-(Benzofuran-2-carbonyl-D-phenylglycinyl)-1'-methyl-4,4'-bispiperidine Prepared from 2-benzofurancarboxylic acid (50%).
1H-NMR
IS-MS, m/e 460.0 (M+1)
Analytical RPHPLC, Method 1, RT=27.59 min (100%)

Example 286
1-(3-Methylbenzofuran-2-carbonyl-D-phenylglycinyl)-1'-methyl-4,4'-bispiperidine Prepared from 3-methylbenzofuran-2-carboxylic acid (47%).
1H-NMR
IS-MS, m/e 474.1 (M+1)
Analytical RPHPLC, Method 1, RT=31.31 min (95%)

Example 287
1-(5-Methylbenzofuran-2-carbonyl-D-phenylglycinyl)-1'-methyl-4,4'-bispiperidine Prepared from 5-methylbenzofuran-2-carboxylic acid (45%).
1H-NMR
IS-MS, m/e 474.3 (M+1)
Analytical RPHPLC, Method 1, RT=30.91 min (100%)

Example 288
1-(6-Methoxybenzofuran-2-carbonyl-D-phenylglycinyl)-1'-methyl-4,4'-bispiperidine Prepared from 6-methoxybenzofuran-2-carboxylic acid (50%).
1H-NMR
IS-MS, m/e 490.0 (M+1)
Analytical RPHPLC, Method 1, RT=29.26 min (100%)

Example 289
1-(5-Chlorobenzofuran-2-carbonyl-D-phenylglycinyl)-1'-methyl-4,4'-bispiperidine Prepared from 5-chlorobenzofuran-2-carboxylic acid (59%)
1H-NMR
IS-MS, m/e 493.9 (M+1)
Analysis for $C_{28}H_{32}N_3O_3Cl \cdot 0.5H_2O$:
Calcd: C, 66.85; H, 6.61; N, 8.35;
Found; C, 66.46; H, 6.28; N, 8.25.
Analytical RPHPLC, Method 1, RT=34.86 min (100%)

Example 290
1-(2-Aminobenzimidazole-5-carbonyl-D-phenylglycinyl)-1'-methyl-4,4'-bispiperidine Prepared from 2-amino-5-carboxybenzimidazole hydrochloride (32%).
1H-NMR
IS-MS, m/e 475.2 (M+1)
Analytical RPHPLC [Vydac C18, linear gradient of 98/2-58/42 (0.1% TFA in water/0.1% TFA in acetonitrile) over 40 min, 1 mL/min] RT=24.56 (90%)

Example 291
1-(3-Aminobenzisoxazole-5-carbonyl-D-phenylglycine)-1'-methyl-4,4'-bispiperidine To a stirring solution of acetoxime (98 mg, 7.1 mmol) in DMF (5 mL) was added a 1 M solution of potassium tert-butoxide (1.3 mL, 1.3 mmol) in THF. After 2 min, 1-(3-cyano-4-fluorobenzoyl-D-phenylglycinyl)-1'-methyl-4,4'-bispiperidine (303 mg, 0.65 mmol) was added; and, after another hour, the solvent was partially removed and the residue was partitioned between brine and dichloromethane. The layers were separated and the aqueous phase was extracted another two times with dichloromethane. The combined organics were dried (MgSO$_4$), filtered and concentrated in vacuo.

IS-MS, m/e 516.0 (M+1)

The residue was then dissolved in ethanol (3.6 mL) and 1 N HCl was added. The stirring solution was heated to reflux.

After 5 h, the heating mantle was removed and after cooling, the solution was diluted ethyl acetate and water. The pH of the aqueous phase was adjusted to 11 with 2 N sodium hydroxide and extracted twice with dichloromethane. The combined dichloromethane extracts were dried (MgSO$_4$), filtered and concentrated in vacuo. The resulting solid was dissolved in a minimum amount of dichloromethane and chromatographed over silica gel, eluting with 2% methanol (containing 2 N ammonia) in dichloromethane through 10% methanol (containing 2 N ammonia) in dichloromethane. The product containing fractions were combined and concentrated in vacuo to give 89 mg (29%) of an off-white solid.
1H-NMR
IS-MS, m/e 476.3 (M+1)
Analytical RPHPLC, Method 1, RT=19.55 min (99%).

Examples 292 to 303
Preparation of Starting Materials
1-(Boc-D-phenylglycinyl)-4-hydroxypiperidine (Coupling Method C) To a stirring solution of 1-hydroxy-7-azabenzotriazole (10.24 g, 75.2 mmol) and EDCI (14.42 g, 75.2 mmol) in DMF (160 mL) was added a solution of Boc-D-phenylglycine (18.9 g, 75.2 mmol) in DMF (80 mL). After 10 min, 4-hydroxypiperidine (6.85 g, 67.7 mmol) was added.

After stirring over night, the solvent was evaporated in vacuo and the residue was partitioned between ethyl acetate and water. The organic phase separated and washed with saturated aqueous NaHCO$_3$, followed by brine, dried over MgSO$_4$, filtered and concentrated in vacuo. Two-thirds of this material was dissolved in a minimum amount of dichloromethane and chromatographed over silica gel, eluting with a gradient of dichloromethane through 1:1 dichloromethane/ethyl acetate. The product containing fractions were combined and concentrated in vacuo to give 15.71 g (94%) of a white foam.

1H-NMR
IS-MS, m/e 335.1 (M+1)
Analysis for C$_{18}$H$_{26}$N$_2$O$_4$O:
Calcd: C, 64.65; H, 7.84; N, 8.37;
Found: C, 64.40; H, 7.77; N, 8.12.

1-(D-phenylglycinyl)-4-hydroxypiperidine (Deprotection Method D) To a stirring solution of 1-(Boc-D-phenylglycinyl)-4-hydroxypiperidine (5 g, 15 mmol) in dichloromethane (290 mL) was added anisole, (8 mL) followed by trifluoroacetic acid (29 mL). After stirring for 4 h, the solvent was concentrated in vacuo and the residue was suspended with stirring in diethyl ether. After 1 h, the mixture was filtered and the solid was partitioned between ethyl acetate and saturated aqueous NaHCO$_3$. The organic phase was washed with brine, dried with MgSO$_4$, filtered and concentrated to give 0.41 g of white solid. The combined aqueous phase was back extracted with 3:1 chloroform/isopropanol and this organic phase was separated, dried with MgSO$_4$, filtered and concentrated in vacuo to give 1.6 g of white solid. The two crops of solid were combined to give 2.02 g (90%) of the title compound.

1H-NMR
IS-MS, m/e 235.1 (M+1)

1-(4-Methoxybenzoyl-D-phenylglycinyl)-4-hydroxypiperidine

To a stirring solution of 1-[3-(dimethylamino)propyl]-3-ethylcarbodiimide hydrochloride (1.4 g, 7.4 mmol), 1-hydroxybenzotriazole hydrate (1.0 g, 7.4 mmol) and N,N-diisopropylethylamine (1.4 mL) in DMF (20 mL) was added a solution of 1-(D-phenylglycinyl)-4-hydroxypiperidine (2.0 g, 7.38 mmol) in DMF (10 mL) followed by a solution of 4-methoxybenzoic acid (1.0 g, 6.7 mmol) in DMF (10 mL).

After stirring overnight at room temperature, the solvent was removed in vacuo and the residue was partitioned between ethyl acetate and water. The organic phase was washed again with water followed by saturated aqueous NaHCO$_3$ (2×) and brine, then dried with MgSO$_4$, filtered and concentrated in vacuo to give 2.4 g of off-white solid. A portion of this material (2.0 g) was dissolved in a minimal amount of dichloromethane and chromatographed over silica gel, eluting with a gradient of dichloromethane through 50% ethyl acetate/dichloromethane. The product-containing fractions were combined and concentrated in vacuo to give 1.3 g (60%) of a white foam.

1H-NMR
IS-MS, m/e 369.2 (M+1)
Analysis for C$_{21}$H$_{24}$N$_2$O$_4$:
Calcd: C, 68.46; H, 6.57; N, 7.60;
Found: C, 67.88; H, 6.73; N, 7.33.
Analytical RPHPLC, Method 1, RT=24.24 min (100%)

1-(4-Methoxybenzoyl-D-phenylglycinyl)-4-oxopiperidine (Oxidation Method B) To a stirring solution of oxalyl chloride (0.26 mL, 3 mmol) in dichloromethane (6.5 mL) at −50° C., was added a solution of DMSO (0.43 mL, 6 mmol) in dichloromethane (1.3 mL). After 3 min, a solution of 1-(4-methoxybenzoyl-D-phenylglycinyl)-4-hydroxypiperidine (1.0 g, 2.7 mmol) in dichloromethane (4 mL) was added and the solution was allowed to warm to −20° C. over 45 min.

Triethylamine (2 mL) was then added and the solution was allowed to warm to room temperature. The solution was then diluted with dichloromethane and water and the layers were separated. The organic phase was washed with brine, dried over MgSO$_4$, filtered and concentrated in vacuo. The residue was dissolved in a minimum amount of dichloromethane and chromatographed over silica gel, eluting with a gradient of dichloromethane through 50% ethyl acetate/dichloromethane.

The product containing fractions were combined and concentrated in vacuo to give 0.77 g (78%) of a white foam.

1H-NMR
IS-MS, m/e 367.2 (M+1)
Analysis for C$_{21}$H$_{22}$N$_2$O$_4$:
Calcd: C, 68.84; H, 6.05; N, 7.65;
Found: C, 68.33; H, 6.01; N, 7.27.
Analytical RPHPLC, Method 1, RT=25.52 min (100%)

General Procedure: Unless otherwise indicated, the product of Examples 292–303 was obtained from 1-(4-methoxybenzoyl-D-phenylglycinyl)-4-oxopiperidine and the indicated amine using the alkylation procedure described for Example 292 (Alkylation Method C).

Example 292

1-(4-Methoxybenzoyl-D-phenylglycinyl)-4-(1-pyrrolidinyl)piperidine (Alkylation Method C) To a stirring solution of 1-(4-methoxybenzoyl-D-phenylglycinyl)-4-oxopiperidine (50 mg, 0.14 mmol) and pyrrolidine (0.011 mL, 0.13 mmol) in 1,2-dichloroethane (1 mL) was added sodium triacetoxyborohydride (45 mg, 0.21 mmol). After stirring overnight, the mixture was loaded onto an SCX column (pretreated with a 5% glacial acetic acid in methanol solution), rinsed with methanol (2 column volumes) and eluted with a 30% 2 N ammonia/methanol in dichloromethane solution. The solution was concentrated in vacuo. The product containing fractions were combined and concentrated in vacuo to give 48 mg (87%) of the title compound.

1H-NMR
IS-MS, m/e 422.0 (M+1)
Analytical RPHPLC, Method 1, RT=21.02 min (100%)

Example 293

1-(4-Methoxybenzoyl-D-phenylglycinyl)-4-(1-piperidinyl)piperidine

Prepared from piperidine (49%).
1H-NMR
IS-MS, m/e 436.0 (M+1)
Analytical RPHPLC, Method 1, RT=22.14 min (100%)

Example 294

1-(4-Methoxybenzoyl-D-phenylglycinyl)-4-(4-methylpiperidin-1-yl)piperidine

Prepared from 4-methylpiperidine (78%).
1H-NMR
IS-MS, m/e 450.0 (M+1)
Analytical RPHPLC, Method 1, RT=24.06 min (100%)

Example 295

1-(4-Methoxybenzoyl-D-phenylglycinyl)-4-(4-methylpiperazin-1-yl)piperidine

Prepared from 1-methylpiperazine (98%).
1H-NMR
IS-MS, m/e 451.0 (M+1)
Analytical RPHPLC, Method 1, RT=18.66 min (99%)

Example 296
1-(4-Methoxybenzoyl-D-phenylglycinyl)-4-(4-ethylpiperazin-1-yl)piperidine
Prepared from 1-ethylpiperazine (76%).
1H-NMR
IS-MS, m/e 465.0 (M+1)
Analytical RPHPLC, Method 1, RT=19.11 min (100%)

Example 297
1-(4-Methoxybenzoyl-D-phenylglycinyl)-4-(4-isopropylpiperazin-1-yl)piperidine
Prepared from 1-isopropylpiperazine (83%).
1H-NMR
IS-MS, m/e 479.2 (M+1)
Analysis for $C_{28}H_{38}N_4O_3 \cdot 0.3H_2O$:
Calcd: C, 69.48; H, 8.04; N, 11.58;
Found: C, 69.22; H, 7.91; N, 11.34.
Analytical RPHPLC, Method 1, RT=19.56 min (99%)

Example 298
1-(4-Methoxybenzoyl-D-phenylglycinyl)-4-(hexahydro-1,4-diazapin-1-yl)piperidine hydrochloride
1H-NMR
IS-MS, m/e 451.0 (M+1)
Analytical RPHPLC, Method 1, RT=16.86 min (100%)

Example 299
1-(4-Methoxybenzoyl-D-phenylglycinyl)-4-[4-methyl(hexahydro-1,4-diazapin-1-yl)]1-piperidine
Prepared from 4-methyl-hexahydro-1,4-diazapine (63%).
1H-NMR
IS-MS, m/e 465.0 (M+1)
Analytical RPHPLC, Method 1, RT=18.86 min (98%)

Example 300
1-(4-Methoxybenzoyl-D-phenylglycinyl)-4-(3-pyridylamino)piperidine
Prepared from 3-aminopyridine (25%).
1H-NMR
IS-MS, m/e 445.0 (M+1)
Analytical RPHPLC, Method 1, RT=23.87 min (100%)

Example 301
1-(4-Methoxybenzoyl-D-phenylglycinyl)-4-[(N-methyl-N-benzyl)amino]piperidine
Prepared from N-methylbenzylamine (89%).
1H-NMR
IS-MS, m/e 472.0 (M+1)
Analysis for $C_{29}H_{33}N_3O_3 \cdot 0.1H_2O$:
Calcd: C, 73.58; H, 7.07; N, 8.88;
Found: C, 73.39; H, 7.19; N, 9.06.
Analytical RPHPLC, Method 1, RT=26.27 min (98%)

Example 302
1-(4-Methoxybenzoyl-D-phenylglycinyl)-4-[(3-pyridylmethyl)amino]piperidine
Prepared from 3-aminomethylpyridine (72%).
1H-NMR
IS-MS, m/e 459.0 (M+1)
Analysis for $C_{27}H_{30}N_4O_3 \cdot 0.2H_2O$:
Calcd: C, 70.17; H, 6.63; N, 12.12;
Found: C, 70.00; H, 6.53; N, 12.13.
Analytical RPHPLC, Method 1, RT=16.38 min (100%)

Example 303
1-(4-Methoxybenzoyl-D-phenylglycinyl)-4-[(4-pyridylmethyl)amino]piperidine
Prepared from 4-aminomethylpyridine (46%).
1H-NMR
IS-MS, m/e 459.0 (M+1)
Analysis for $C_{27}H_{30}N_4O_3 \cdot 0.9H_2O$:
Calcd: C, 68.30; H, 6.75; N, 11.80;
Found: C, 67.99; H, 6.42; N, 11.59.
Analytical RPHPLC, Method 1, RT=18.36 min (100%)

Examples 304 to 314
General Procedure: Unless otherwise indicated, the product of Examples 304–314 was obtained from 1-(4-methoxybenzoyl-D-phenylglycinyl)piperazine and the indicated aldehyde or ketone using the alkylation procedure described for Example 304 (Alkylation Method D).

Example 304
1-(4-Methoxybenzoyl-D-phenylglycinyl)-4-(2-pyridylmethyl)piperazine (Alkylation Method D) To a stirring solution of 1-(4-methoxybenzoyl-D-phenylglycinyl)piperazine (50 mg, 0.14 mmol) and 2-pyridinecarboxaldehyde (0.020 mL, 23 mg, 0.21 mmol) in 5% acetic acid/methanol (1 mL) was added $NaBH_3CN$ (20 mg, 0.32 mmol). After 4 h, the solution was loaded onto an SCX column (pretreated with a 5% glacial acetic acid in methanol solution), rinsed with methanol (2 column volumes) and eluted with a 30% 2N ammonia/methanol in dichloromethane solution. The solution was concentrated in vacuo and the residue was dissolved in a minimum amount of dichloromethane and chromatographed over silica gel, eluting with dichloromethane, followed by 50% ethyl acetate/dichloromethane, and finally with a gradient of 2%–10% (2 N $NH_3$ in MeOH) in dichloromethane. The product containing fractions were combined and concentrated in vacuo to give 30 mg (48%) of the title compound.
1H-NMR
IS-MS, m/e 444.9 (M+1)
Analytical RPHPLC, Method 1, RT=21.70 min (100)

Example 305
1-(4-Methoxybenzoyl-D-phenylglycinyl)-4-(3-pyridylmethyl)piperazine
Prepared from 3-pyridine carboxaldehyde (42%).
1H-NMR
IS-MS, m/e 444.9 (M+1)
Analytical RPHPLC, Method 1, RT=17.84 min (99%)

Example 306
1-(4-Methoxybenzoyl-D-phenylglycinyl)-4-(4-pyridylmethyl)piperazine
Prepared from 4-pyridine carboxaldehyde (45%).
1H-NMR
IS-MS, m/e 444.9 (M+1)
Analytical RPHPLC, Method 1, RT=18.36 min (99%)

Example 307
1-(4-Methoxybenzoyl-D-phenylglycinyl)-4-phenethylpiperazine
Prepared from phenylacetaldehyde (34%).
1H-NMR
IS-MS, m/e 458.0 (M+1)
Analytical RPHPLC, Method 1, RT=27.44 min (100%)

Example 308
1-(4-Methoxybenzoyl-D-phenylglycinyl)-4-(3-pentyl)piperazine

Prepared from 3-pentanone (88%).
1H-NMR
IS-MS, m/e 424.0 (M+1)
Analytical RPHPLC, Method 1, RT=23.62 min (100%)

Example 309
1-(4-Methoxybenzoyl-D-phenylglycinyl)-4-cyclopentylpiperazine

Prepared from cyclopentanone (95%).
1H-NMR
IS-MS, m/e 422.0 (M+1)
Analytical RPHPLC, Method 1, RT=20.76 min (100%)

Example 310
1-(4-Methoxybenzoyl-D-phenylglycinyl)-4-(4-methylcyclohexyl)piperazine Prepared from 4-methylcyclohexanone (46%).
1H-NMR
IS-MS, m/e 450.0 (M+1)
Analytical RPHPLC, Method 1, RT=27.07 min (isomer 1), 27.74 min (isomer 2)

Example 311
1-(4-Methoxybenzoyl-D-phenylglycinyl)-4-(tetrahydrothiopyran-4-yl)piperazine Prepared from tetrahydro-4H-thiopyran-4-one (86%).
1H-NMR
IS-MS, m/e 453.9 (M+1)
Analytical RPHPLC, Method 1, RT=22.96 min (100%)

Example 312
1-(4-Methoxybenzoyl-D-phenylglycinyl)-4-(2-indanyl)piperazine

Prepared from 2-indanone (92%).
1H-NMR
IS-MS, m/e 469.9 (M+1)
Analytical RPHPLC, Method 1, RT=26.32 min (100%)

Example 313
1-(4-Methoxybenzoyl-D-phenylglycinyl)-4-benzylpiperazine

Prepared from benzaldehyde (87%).
1H-NMR
IS-MS, m/e 444.0 (M+1)
Analytical RPHPLC, Method 1, RT=25.78 min (96%)

Example 314
1-(4-Methoxybenzoyl-D-phenylglycinyl)-4-(cyclohexylmethyl)piperazine Prepared from cyclohexanecarboxaldehyde (86%).
1H-NMR
IS-MS, m/e 450.2 (M+1)
Analytical RPHPLC, Method 1, RT=28.07 min (94%)

Examples 315 to 316
Preparation of Starting Materials
1-(Boc-D-Phenylglycinyl)-4-oxopiperidine Using Oxidation Method B, the title compound was prepared from 1-(Boc-D-phenylglycinyl)-4-hydroxypiperidine (44%).
1H-NMR
IS-MS, m/e 333.0 (M+1)
1-(Boc-D-Phenylglycinyl)-4-(4-methylpiperazin-1-yl)piperidine Using Alkylation Method C, the title compound was prepared from 1-(Boc-D-phenylglycinyl)-4-oxopiperidine and methylpiperazine (65%).
1H-NMR
IS-MS, m/e 417.3 (M+1)
Analysis for $C_{23}H_{36}N_4O_3$:
Calcd: C, 66.32; H, 8.71; N, 13.45;
Found: C, 66.25; H, 8.58; N, 13.42.
1-D-Phenylglycinyl-4-(4-methylpiperazin-1-yl)piperidine HCl gas was bubbled through a stirring solution of 1-(Boc-D-phenylglycinyl)-4-(4-methylpiperazin-1-yl)piperidine (1.36 g, 3.26 mmol) in ethyl acetate (150 mL). A white precipitate was formed immediately, but then went back into solution. After about 5 min, a white precipitate again fell out of solution. After 10 min, the addition of HCl was discontinued and after stirring for a total of 1 h, the mixture was filtered to give 1.38 g (quantitative) of white solid.
1H-NMR
IS-MS, m/e 317.3 (M+1)
Analysis for $C_{18}H_{28}N_4O \cdot 2.9HCl \cdot 2.5H_2O$:
Calcd: C, 46.27; H, 7.74; N, 11.99; Cl, 22.01;
Found: C, 46.06; H, 7.51; N, 11.63; Cl, 21.78.
General Procedure: The product of Examples 315–316 was prepared from 1-(D-phenylglycinyl)-4-(4-methylpiperazin-1-yl) piperidine and the indicated acid using Coupling Method B.

Example 315
1-(Indole-6-carbonyl-D-phenylglycinyl)-4-(4-methylpiperazin-1-yl)piperidine Prepared from indole-6-carboxylic acid (66%).
1H-NMR
IS-MS, m/e 460.2 (M+1)
Analytical RPHPLC, Method 1, RT=17.83 min (99%)

Example 316
1-(3-Chloroindole-6-carbonyl-D-phenylglycinyl)-4-(4-methylpiperazinyl)piperidine Prepared from 3-chloroindole-6-carboxylic acid (69%).
1H-NMR
IS-MS, m/e 494.3 (M+1)
Analytical RPHPLC, Method 1, RT=22.99 min (99%)

Examples 317 to 320
Preparation of Starting Materials
(Cbz-D-phenylglycinyl)piperazine.

Using Deprotection Method D, the title compound was prepared from 1-(Cbz-D-phenylglycinyl)-4-Boc-piperazine (85%)
1H-NMR
IS-MS, m/e 354.2 (M+1)
Analysis for $C_{20}H_{23}N_3O_3 \cdot 0.2H_2O$:
Calcd: C, 67.28; H, 6.61; N, 11.77;
Found: C, 67.10; H, 6.46; N, 11.63.
1-(Cbz-D-phenylglycinyl)-4-(1-methylpiperidin-4-yl)piperazine Using Alkylation Method C, the title compound was prepared from (Cbz-D-phenylglycinyl)piperazine and 1-methylpiperidin-4-one (49%). The product was purified using silica gel chromatography, eluting with a gradient of dichloromethane through 10% (2 N ammonia in methanol)/dichloromethane.
1H-NMR
IS-MS, m/e 451.3 (M+1)
Analysis for $C_{26}H_{34}N_4O_3$:
Calcd: C, 69.31; H, 7.61; N, 12.43;
Found: C, 69.36; H, 7.71; N, 13.14.

1-D-Phenylglycinyl-4-(1-methylpiperidin-4-yl)piperazine dihydrochloride.

To a stirring suspension of 5% Pd/C (0.6 g) in ethanol (25 mL) under nitrogen was added a solution of 1-(Cbz-D-phenylglycinyl)-4-(1-methylpiperidin-4-yl)piperazine (2.6 g, 5.77 mmol) and acetic acid (1.6 mL) in ethanol (50 mL). The flask was placed under vacuum and the atmosphere was replaced with hydrogen (balloon). After 4 h, diatomaceous earth was added and the mixture was filtered through a pad of diatomaceous earth and concentrated in vacuo. The residue was dissolved in ethyl acetate and HCl gas was bubbled through the stirring solution to precipitate the dihydrochloride salt. The mixture was filtered and the solid was dried in vacuo to give 2.6 g (quantitative) of the title compound.
1H-NMR
IS-MS, m/e 317.3 (M+1)
General Procedure: The product of Examples 317–320 was prepared from 1-(D-phenylglycinyl)-4-(1-methylpiperidin-4-yl)piperazine dihydrochloride and the indicated acid using Coupling Method B.

Example 317
1-(4-Methoxybenzoyl-D-phenylglycinyl)-4-(1-methylpiperidin-4-yl)piperazine
Prepared from 4-methoxybenzoic acid (19%).
1H-NMR
IS-MS, m/e 451.0 (M+1)
Analytical RPHPLC, Method 1, RT=16.76 min (100%)

Example 318
1-(Indole-6-carbonyl-D-phenylglycinyl)-4-(1-methylpiperidin-4-yl)piperazine
Prepared from indole-6-carboxylic acid (65%).
1H-NMR
IS-MS, m/e 460.2 (M+1)
Analytical RPHPLC, Method 1, RT=16.68 min (100%)

Example 319
1-(3-Methylindole-6-carbonyl-D-phenylglycinyl)-4-(1-methylpiperidin-4-yl)piperazine
Prepared from 3-methylindole-6-carboxylic acid (50%).
1H-NMR
IS-MS, m/e 474.3 (M+1)
Analytical RPHPLC, Method 1, RT=22.20 min (98%)

Example 320
1-(3-Chloroindole-6-carbonyl-D-phenylglycinyl)-4-(1-methylpiperidin-4-yl)piperazine
Prepared from 3-chloroindole-6-carboxylic acid (76%).
1H-NMR
IS-MS, m/e 493.9 (M+1)
Analytical RPHPLC, Method 1, RT=22.66 min (100%)

Examples 321 to 324
Preparation of Starting Materials
Ethyl hydroxyimino-pyridine-2-acetate To a stirring solution of ethyl pyridine-2-acetate (12.6 g, 76.3 mmol) in acetic acid (19 mL) at 5° C. was added a solution of sodium nitrite (6.05 g, 87.7 mmol) in water (12 mL) at a rate sufficient to maintain the internal temperature below 15° C. After complete addition and an additional 30 min, an additional 30 mL of water was added. The resulting white precipitate was filtered, washed with water, saturated aqueous NaHCO$_3$, and again with water. The solid was then dried under vacuum to give 14.1 g (95%) of the title compound.
1H-NMR
IS-MS, m/e 194.9 (M+1)
Analysis for C$_9$H$_{10}$N$_2$O$_3$:
Calcd: C, 55.67; H, 5.19; N. 14.43;
Found: C, 55.79; H, 5.14; N, 14.13.
Boc-D,L-(2-Pyridinyl)glycine ethyl ester To a solution of ethyl hydroxyimino-pyridine-2-acetate (7.8 g, 40.15 g) in ethanol (175 mL) and glacial acetic acid (20 mL) was added 5% Pd/C, and the mixture was shaken in a hydrogenation apparatus under an atmosphere of hydrogen at 3.1 bar for 4 h. The mixture was filtered through diatomaceous earth and concentrated in vacuo. The residue was dissolved in THF/H$_2$O (1:1, 240 mL) and treated with di-tert-butyl dicarbonate (14.23 g, 65.2 mmol) and sodium bicarbonate (27.4 g, 326 mmol). After stirring at room temperature for 2 h, the solution was concentrated in vacuo and the residue was partitioned between EtOAc and water. The organic phase was washed with brine, dried over magnesium sulfate, filtered and concentrated in vacuo. The crude material was purified via chromatography over silica gel, eluting with a stepwise gradient of 10–20% ethyl acetate in dichloromethane, to give 8.11 g (72%) of a yellow oil.
1H-NMR
IS-MS, m/e 281.1 (M+1)
1-[Boc-D,L-(2-Pyridinyl)glycinyl]-1'-methyl-4,4'-bispiperidine To a stirring solution of Boc-D,L-(2-pyridinyl)glycine ethyl ester (3.89 g, 13.88 mmol) in 1,4-dioxane (20 mL) was added a solution of lithium hydroxide hydrate (0.64 g, 15.27 mmol) in water (20 mL). After stirring for 2 h, the solution was concentrated in vacuo. The residue was dried under vacuum for 15 h then dissolved in DMF (50 mL). The solution was cooled to 0° C., purged with nitrogen, and diethyl cyanophosphonate (2.5 g, 16.66 mmol) was slowly added. After 2 min, the solution was treated with a solution of 1-methyl-4,4'-bispiperidine dihydrochloride (3.9 g, 15.27 mmol) and triethylamine (6.8 mL, 48.58 mmol) in DMF (50 mL). After 2 h, the cold bath was removed and the solution was allowed to stir overnight. The next morning, the solvent was evaporated in vacuo and the resulting oil was partitioned between 3:1 chloroform:isopropyl alcohol and saturated aqueous sodium bicarbonate. The organic phase was dried over magnesium sulfate, filtered and concentrated in vacuo. The crude material was purified via chromatography over silica gel, eluting with a stepwise gradient of 5–9% (2 N ammonia in methanol) in dichloromethane to give 2.6 g (45%) of a clear oil.
1H-NMR
IS-MS, m/e 417.2 (M+1)
1-[D,L-(2-Pyridinyl)glycinyl]-1'-methyl-4,4'-bispiperidine (Deprotection Method E) To a stirring solution of 1-[Boc-D,L-(2-pyridinyl)glycinyl]-1'-methyl-4,4'-bispiperidine (1.8 g, 4.32 mmol) in dichloromethane (90 mL) was added anisole (2.3 mL, 21.6 mmol), followed by trifluoroacetic acid (8.3 mL, 108 mmol). After 4 h, the solvents were evaporated in vacuo, the crude product was dissolved in methanol and loaded onto an SCX column (pretreated with a 5% glacial acetic acid in methanol solution), rinsed with methanol (2 column volumes) and eluted with a 30% 2 N ammonia/methanol in dichloromethane solution. The product containing fractions were combined and concentrated in vacuo to give 1.08 g (77%) of a yellow oil.
1H-NMR
IS-MS, m/e 317.2 (M+1)
Analysis for C$_{18}$H$_{28}$N$_4$O·0.55H$_2$O:
Calcd: C, 66.25; H, 8.99; N, 17.17;
Found: C, 66.07; H, 8.49; N, 16.66.

General Procedure: The product of Examples 321–324 was prepared from 1-(D,L-(2-pyridinyl)glycinyl]-1'-methyl-4,4'-bispiperidine and the indicated acid using the procedure described for Example 321 (Coupling Method D).

Example 321
1-[Indole-6-carbonyl-D,L-(2-pyridinyl)glycinyl]-1'-methyl-4,4'-bispiperidine
(Coupling Method D) To a stirring solution of 1-[D,L-(2-pyridinyl)glycinyl]-1'-methyl-4,4'-bispiperidine (0.3 g, 0.95 mmol) in N,N-dimethylformamide (3 mL) was added indole-6-carboxylic acid (0.15 g, 0.95 mmol) and 1-hydroxy-benzotriazole hydrate (0.13 g, 0.95 mmol), followed by 1,3-dicyclohexylcarbodiimide (0.19 g, 0.95 mmol). After stirring overnight, the mixture was filtered and the filtrate was loaded onto an SCX column (pretreated with a 5% glacial acetic acid in methanol solution), rinsed with methanol (2 column volumes) and eluted with a 30% (2 N ammonia in methanol) in dichloromethane solution. The product containing fractions were concentrated in vacuo and the residue was was chromatographed over silica gel, eluting with a stepwise gradient of 5–9% (2 N ammonia in methanol) in dichloromethane to give 255 mg (58%) of a tan foam.
1H-NMR
IS-MS, m/e 460.3 (M+1)
Analytical RPHPLC, Method 1, RT=14.90 min (100%)

Example 322
1-[4-Methoxybenzoyl-D,L-(2-pyridinyl)glycinyl]-1'-methyl-4,4'-bispiperidine
Prepared from 4-methoxybenzoic acid (53%).
1H-NMR
IS-MS, m/e 451.2 (M+1)
Analytical RPHPLC, Method 1, RT=14.79 min (98%)

Example 323
1-[3-Methylindol-6-carbonyl-D,L-(2-pyridinyl)glycinyl]-1'-methyl-4,4'-bispiperidine
Prepared from 3-methyl-6-carboxyindole (40%).
1H-NMR
IS-MS, m/e 474.3 (M+1)
Analytical RPHPLC, Method 1, RT=18.28 min (97%)

Example 324
1-3-Chloroindole-6-carbonyl-D,L-(2-pyridinyl)glycinyl]-1'-methyl-4,4'-bispiperidine
Prepared from 3-chloro-6-carboxyindole (71%).
1H-NMR
IS-MS, m/e 494.0 (M+1)
Analysis for $C_{27}H_{32}N_5O_2Cl \cdot 0.2H_2O$:
Calcd: C, 65.17; H, 6.56; N, 14.07;
Found: C, 65.57; H, 6.56; N, 13.23.
Analytical RPHPLC, Method 1, RT=20.96 min (99%)

Examples 325 to 328
Preparation of Starting Materials
Ethyl hydroxyimino-pyridine-3-acetate
Using the procedure of Tikk et al. [Acta. Chimica Hungarica, 114(3–4), 355], a mixture of ethyl hydroxyimino-pyridine-3-acetate and n-butyl hydroxyimino-pyridine-3-acetate was prepared from ethyl pyridine-3-acetate and n-butyl nitrite.
1H-NMR
IS-MS, m/e 195 (M+1), 223.1 (M+1)
Boc-D,L-(3-Pyridinyl)glycine ethyl ester
Using methods substantially equivalent to those described above in preparation of Boc-D,L-(2-pyridinyl)glycine ethyl ester, the title compound was prepared from the above ethyl hydroxyimino-pyridine-3-acetate (57%).
1H-NMR
IS-MS, m/e 281.1(M+1)
1-[Boc-D,L-(3-Pyridinyl)glycinyl]-1'-methyl-4,4'-bispiperidine
Using methods substantially equivalent to those described in preparation of 1-[Boc-D,L-(2-pyridinyl)glycinyl]-1'-methyl-4,4'-bispiperidine, the title compound was prepared from Boc-D,L-(3-pyridinyl)glycine ethyl ester (20%).
¹H-NMR
IS-MS, m/e 417.2 (M+1)
1-[D,L-(3-Pyridinyl)glycinyl]-1'-methyl-4,4'-bispiperidine
Using methods substantially equivalent to those described in preparation of 1-[D,L-(2-pyridinyl)glycinyl]-1'-methyl-4,4'-bispiperidine, the title compound was prepared from 1-[Boc-D,L-(3-pyridinyl)glycinyl]-1'-methyl-4,4'-bispiperidine (75%).
1H-NMR
IS-MS, m/e 317.2 (M+1)
General Procedure: The product of Examples 325–328 was prepared from 1-[D,L-(3-pyridinyl)glycinyl]-1'-methyl-4,4'-bispiperidine and the indicated acid using the procedure described for Example 325 (Coupling Method D).

Example 325
1-[4-Methoxybenzoyl-D,L-(3-pyridinyl)glycinyl]-1'-methyl-4,4'-bispiperidine
Prepared from 4-methoxybenzoic acid (45%).
1H-NMR
IS-MS, m/e 451.2 (M+1)
Analysis for $C_{26}H_{34}N_4O_3 \cdot 1.2H_2O$:
Calcd: C, 66.13; H, 7.77; N, 11.87;
Found: C, 66.61; H, 7.27; N, 11.87.
Analytical RPHPLC, Method 1, RT=12.98 min (98%)

Example 326
1-[Indole-6-carbonyl-D,L-(3-pyridinyl)glycinyl]-1'-methyl-4,4'-bispiperidine
Prepared from indole-6-carboxylic acid (36%).
1H-NMR
IS-MS, m/e 460.3 (M+1)
Analysis for $C_{27}H_{33}N_5O_2 \cdot 1.5H_2O$:
Calcd: C, 66.64; H, 7.46; N, 14.39;
Found: C, 66.71; H, 6.87; N, 13.89.
Analytical RPHPLC, Method 1, RT=14.39 min (100%)

Example 327
1-[3-Methylindole-6-carbonyl-D,L-(3-pyridinyl)glycinyl]-1'-methyl-4,4'-bispiperidine
Prepared from 3-methylindole-6-carboxylic acid (40%).
1H-NMR
IS-MS, m/e 474.3(M+1)
Analysis for $C_{28}H_{35}N_5O_2 \cdot 1.6H_2O$:
Calcd: C, 66.93; H, 7.66; N, 13.94;
Found: C, 66.63; H, 6.99; N, 13.52.
Analytical RPHPLC, Method 1, RT=16.98 min (98%)

Example 328
1-[3-Chloroindole-6-carbonyl-D,L-(3-pyridinyl)glycinyl]-1'-methyl-4,4'-bispiperidine
Prepared from 3-chloroindole-6-carboxylic acid (46%).
1H-NMR
IS-MS, m/e 494.2 (M+1)
Analysis for $C_{27}H_{32}ClN_5O_2 \cdot 1.1H_2O$:
Calcd: C, 63.11; H, 6.71; N, 13.63;

Found: C, 62.84; H, 6.32; N, 13.26.
Analytical RPHPLC, Method 1, RT=19.63 min (100%)

Examples 329 to 330

Preparation of Starting Materials

Boc-D-[3-(ethanesulfonylamino)phenyl]glycine

To a stirring solution of D-3-(ethanesulfonylamino)-phenylglycine (20 g, 77.43 mmol) and sodium carbonate (8.2 g, 77.43 mmol) in 3:1 THF/water (200 mL) at 0° C., was added di-tert-butyl dicarbonate (18.5 g, 85.17 mmol). After stirring for 30 min, the cold bath was removed; and after an additional 30 min at room temperature, the solvent was removed and the residue was partitioned between ethyl acetate and water. The aqueous layer was acidified to pH 2 with $KHSO_4$ and extracted twice with ethyl acetate. The combined ethyl acetate extracts were washed with water, dried with $Na_2SO_4$, filtered and concentrated in vacuo to give 17.51 g (63%) of a white solid.

1H-NMR

IS-MS, m/e 357.0 (M−1)

1-[Boc-D-(3-(ethanesulfonylamino)phenyl]glycinyl]-1'-methyl-4,4'-bispiperidine

To a stirring solution of Boc-D-[3-(ethanesulfonylamino) phenyl]glycine (5 g, 13.95 mmol) in dichloromethane at 0° C., diethyl cyanophosphonate (2.12 mL, 13.95 mmol) and diisopropylethylamine (4.86 mL, 27.91 mmol) and then N-methylbispiperidine dihydrobromide (4.32 g, 12.56 mmol) were added; and the mixture was stirred at 0° C. for 3 h. The reaction mixture was then stirred at room temperature overnight, filtered, washed with saturated aqueous sodium bicarbonate and water, dried over sodium sulfate, filtered and concentrated in vacuo to give 5 g (76%) of a tan foam.

1H-NMR

IS-MS, m/e (M+1)

1-[D-[3-(Ethanesulfonylamino)phenyl]glycinyl]-1'-methyl-4,4'-bispiperidine

Using Deprotection Method E, the title compound was prepared from 1-[Boc-D-[3-(ethanesulfonylamino)phenyl] glycinyl]-1'-methyl-4,4'-bispiperidine (74%).

1H-NMR

IS-MS, m/e 423.1(M+1)

Analysis for $C_{21}H_{34}N_4O_3S·1.3H_2O$:

Calcd: C, 56.55; H, 8.27; N, 12.56;

Found: C, 56.68; H, 7.87; N, 11.97.

General Procedure: The product of Examples 329–330 was prepared from 1-[D-[3-(ethanesulfonylamino)phenyl] glycinyl]- 1'-methyl-4,4'-bispiperidine and the indicated acid using the procedure described for Example 321 (Coupling Method D).

Example 329

1-[4-Methoxybenzoyl-D[3-(ethanesulfonylamino)phenyl] glycinyl]-1'-methyl-4,4'-bispiperidine Prepared from 4-methoxybenzoic acid (43%).

1H-NMR

IS-MS, m/e 557.3(M+1)

Analysis for $C_{29}H_{40}N_4O_5S·0.9H_2O$:

Calcd: C, 60.79; H, 7.35; N, 9.78;

Found: C, 60.49; H, 7.08; N, 9.62.

Analytical RPHPLC, Method 1, RT=22.68 min (98%)

Example 330

1-[Indole-6-carbonyl-D-[3-(ethanesulfonylamino)phenyl] glycinyl]-1'-methyl-4,4'-bispiperidine Prepared from indole-6-carboxylic acid (58%)

1H-NMR

IS-MS, m/e (M+1)

Analysis for $C_{30}H_{39}N_5O_4S·2H_2O$:

Calcd: C, 59.88; H, 7.20; N, 11.64;

Found: C, 59.97; H, 6.65; N, 11.43.

Analytical RPHPLC, Method 1, RT=29.02 min (98%)

Example 331

1-(3-Aminoindazole-5-carbonyl-D-phenylglycinyl)-1'-methyl-4,4'-bispiperidine

To a stirring solution of 1-(3-cyano-4-fluorobenzoyl-D-phenylglycinyl)-1'-methyl-4,4'-bispiperidine (120 mg, 0.259 mmol) in p-dioxane (6 mL) was added hydrazine hydrate (26 mg, 0.518 mmol), and the solution was heated to reflux. After 2 h, the heat was removed and the solvent was evaporated in vacuo. The residue was dissolved in ethanol and heated to reflux. After 12 h, the solution was cooled and concentrated in vacuo. The residue was chromatographed over silica gel, eluting with 10% (2 N ammonia in methanol) in dichloromethane. The product containing fractions were combined and concentrated in vacuo to give 75 mg (62%) of an off white solid.

1H-NMR

IS-MS, m/e 475.3 (M+1)

Analytical RPHPLC, Method 1, RT=14.72 min (100%)

Example 332

1-(1-Methyl-3-aminoindazole-5-carbonyl-D-phenylglycinyl)-1'-methyl-4,4'-bispiperidine Using methods substantially equivalent to those described in Example 331, the title compound was prepared from methylhydrazine and 1-(3-cyano-4-fluorobenzoyl-D-phenylglycinyl)-1'-methyl-4,4'-bispiperidine (31%).

1H-NMR

IS-MS, m/e 489.2 (M+1)

Analytical RPHPLC [Vydac C18, linear gradient of 98/2-80/20 (0.1% TFA in water/0.1% TFA in acetonitrile) over 40 min, 1 mL/min] RT=38.99 min (100%).

Example 333

1-(Imidazo[1,2-a]pyrimidine-2-carbonyl-D-phenylglycinyl)-1'-methyl-4,4'-bispiperidine Imidazo[1,2-a]pyrimidine-2-carboxylic acid To a stirring solution of ethyl 1-(imidazo[1,2-a] pyrimidine-2-carboxylate (1 g, 5.2 mmol) [Abignente, et al. Eur. J. Med. Chem. (1994) 29, 279] in ethanol (30 mL) was added 2 N aqueous KOH (10 mL, 20 mmol). The solution was heated to reflux; and after 2 h, the heating mantle was removed, the solution was allowed to cool and the solvent was removed by rotary evaporation. The residue was dissolved in water (20 mL) and acidified to pH 3 with 5 N HCl. The resulting precipitate was filtered, washed with water and dried in vacuo to give 700 mg (83%) of a tan solid.

1H-NMR

FD-MS, m/e 163.2 (M+1)

Analysis for $C_7H_5N_3O_2$:

Calcd: C, 51.54; H, 3.09; N, 25.76;

Found: C, 51.12; H, 3.25; N, 25.25.

1-(Imidazo[1,2-a]pyrimidine-2-carbonyl-D-phenylglycinyl)-1'-methyl-4,4'-bispiperidine Using Coupling Method B, the title compound was prepared from imidazo[1,2-a]pyrimidine-2-carboxylic acid and 1-D-phenylglycinyl-1'-methyl-4,4'-bispiperidine (56%).

1H-NMR

IS-MS, m/e 461.2 (M+1)

Analytical RPHPLC [Vydac C18, linear gradient of 98/2-80/20 (0.1% TFA in water/0.1% TFA in acetonitrile) over 40 min, 1 mL/min] RT=32.72 min (96%).

Example 334
1-(5,6,7,8-Tetrahydro-imidazo[1,2-a]pyrimdine-2-carbonyl-D-phenylglycinyl)-1'-methyl-4,4'-bispiperidine To a stirring solution of 1-(imidazo[1,2-a]pyrimidine-2-carbonyl-D-phenylglycinyl)-1'-methyl-4,4'-bispiperidine (250 mg, 0.542 mmol) in ethanol (5 mL) was added sodium borohydride (103 mg, 2.71 mmol). After 24 h, the mixture was diluted with water and extracted 3 times with dichloromethane. The organic phase was dried ($MgSO_4$), filtered and concentrated in vacuo. The residue was dissolved in dichloromethane and chromatographed over silica gel, eluting with 5% through 10% (2 N $NH_3$ in MeOH) in dichloromethane. The product containing fractions were combined and concentrated in vacuo to give 55 mg (20%) of the title compound.

1H-NMR
IS-MS, m/e 465.2 (M+1)

Analytical RPHPLC [Vydac C18, linear gradient of 98/2-80/20 (0.1% TFA in water/0.1% TFA in acetonitrile) over 40 min, 1 mL/min) RT=28.44 min (97%).

Examples 335 to 338
Preparation of Starting Materials
Ethyl hydroxyimino-pyridine-4-acetate The oxime was prepared in 82% yield from ethyl pyridine-4-acetate using a procedure similar to that described above under Examples 321–324 for the preparation of ethyl hydroxyimino-pyridine-2-acetate.

1H-NMR (DMSO)
IS-MS, m/e 194.9 (M+1)

Boc-D,L-(4-Pyridinyl)glycine ethyl ester

The protected amino ester is prepared from ethyl hydroxyimino-pyridine-4-acetate using a procedure similar to that described above under Examples 321–324 for the preparation of Boc-D,L-(2-pyridinyl)glycine ethyl ester.

1-[Boc-D,L-(4-Pyridinyl)glycinyl]-1'-methyl-4,4'-bispiperidine

The protected amide is prepared from Boc-D,L-(4-pyridinyl)glycine ethyl ester and 1-methyl-4,4'-bispiperidine dihydrochloride using a procedure similar to that described above under Examples 321–324 for the preparation of 1-[Boc-D, L-(2-pyridinyl)glycinyl]-1'-methyl-4,4'-bispiperidine.

1-[D,L-(4-Pyridinyl)glycinyl]-1'-methyl-4,4'-bispiperidine

The amine is prepared from 1-[Boc-D,L-(4-pyridinyl)-glycinyl]-1'-methyl-4,4'-bispiperidine using a procedure similar to that described above under Examples 321–324 for the preparation of 1-[D,L-(2-pyridinyl)glycinyl]-1'-methyl-4,4'-bispiperidine.

General Procedure: The product of Examples 335–338 is prepared from 1-[D,L-(4-pyridinyl)glycinyl]-1'-methyl-4,4'-bispiperidine and the indicated acid using Coupling Method D.

Example 335
1-[4-Methoxybenzoyl-D,L-(4-pyridinyl)glycinyl]-1'-methyl-4,4'-bispiperidine From 4-methoxybenzoic acid.

Example 336
1-(Indole-6-carbonyl-D,L-(4-pyridinyl)glycinyl]-1'-methyl-4,4'-bispiperidine From indole-6-carboxylic acid.

Example 337
1-[3-Methylindole-6-carbonyl-D,L-(4-pyridinyl)glycinyl]-1'-methyl-4,4'-bispiperidine From 3-methylindole-6-carboxylic acid.

Example 338
1-[3-Chloroindole-6-carbonyl-D,L-(4-pyridinyl)glycinyl]-1'-methyl-4,4'-bispiperidine From 3-chloroindole-6-carboxylic acid.

Assay protocols
Enzyme Inhibition assays:

The ability of a test compound to inhibit factor Xa may be evaluated in one or more of the following Enzyme Inhibition assays, or in other standard assays known to those skilled in the art.

Enzyme Inhibition Assay 1

Enzyme assays were carried out at room temperature in 0.1M phosphate buffer, pH7.4 according to the method of Tapparelli et al (J. Biol. Chem. 1993,268,4734–4741). Purified human factor Xa, trypsin, thrombin and plasmin were purchased from Alexis Corporation, Nottingham, UK. Urokinase was purchased from Calbiochem, Nottingham, UK. Chromogenic substrates for these enzymes; pefachrome-FXA, pefachrome-TRY, pefachrome-TH, pefachrome-PL and pefachrome-UK were purchased from Pentapharm AG, Basel, Switzerland. Product (p-nitroaniline) was quantified by adsorption at 405 nm in 96 well microplates using a Dynatech MR5000 reader (Dynex Ltd, Billingshurst, UK). Km and Ki were calculated using SAS PROC NLIN (SAS Institute, Cary, N.C., USA, Release 6.11) $K_m$ values were determined as 100.9 µM for factor Xa/pefachrome-FXA and 81.6 µM for trypsin/pefachrome-TRY. Inhibitor stock solutions were prepared at 40 mM in Me2SO and tested at 500 µM, 50 µM and 5 µM. Accuracy of Ki measurements was confirmed by comparison with Ki values of known inhibitors of factor Xa and trypsin.

In agreement with published data, benzamidine inhibited factor Xa, trypsin, thrombin, plasmin and urokinase with Ki values of 155 µM, 21 µM, 330 nM, 200 nM and 100 nM respectively. NAPAP inhibited thrombin with a Ki value of 3 nM. Compounds of the invention were found to have activity in these assays.

Enzyme Inhibition Assay 2

Human factor Xa and human thrombin were purchased from Enzyme Research Laboratories (South Bend, Ind., USA). Other proteases were from other commercial sources. Chromogenic para-nitroanilide peptide protease substrates were purchased from Midwest Biotech (Fishers, Ind., USA).

The binding affinities for human factor Xa were measured as apparent association constants (Kass) derived from protease inhibition kinetics as described previously.[a,b,c,d] The apparent Kass values were obtained using automated (BioMek-1000) dilutions of inhibitors (Kass determinations are performed in triplicate at each of four-eight inhibitor concentrations) into 96-well plates and chromogenic substrate hydrolysis rates determined at 405 nm using a Thermomax plate reader from Molecular Devices (San Francisco). For factor Xa inhibition, the assay protocol was: 50 µl buffer (0.06 M tris, 0.3 M NaCl, pH 7.4); 25 µl inhibitor test solution (in MeOH); 25 µl human factor Xa (32 nM in 0.03 M tris, 0.15 M NaCl, 1 mg/ml HSA); finally, 150 µl BzIleGluGlyArgpNA (0.3 mM in water) added within 2 min to start hydrolysis. Final factor Xa was 3.2 nM. Free [Xa] and bound [Xa] were determined from linear standard curves on the same plate by use of SoftmaxPro software for each inhibitor concentration and apparent Kass calculated for each inhibitor concentration which produced hydrolysis inhibition between 20% and 80% of the control (3.2 nM factor Xa): apparent Kass=$[E:I]/[E_f]$ $[I_f]$=$[E_b]/[E_f]$ $[I°-I_b]$. The apparent Kass values so obtained are approximately the inverse of the Ki for the respective inhibitors [1/appKass= app Ki]. The variability of mean apparent Kass values determined at the single substrate concentration was +/−15%. The assay system Km was measured as 0.347+/−0.031 mM [n=4]; and Vmax was 13.11+/−0.76 µM/min.

Kass values were determined with thrombin and other proteases using the same protocol with the following enzyme and substrate concentrations: thrombin 5.9 nM with 0.2 mM BzPheValArgpNA; XIa 1.2 nM with 0.4 mM pyroGluProArgpNA; XIIa 10 nM with 0.2 mM HDProPheArgpNA; plasmin 3.4 nM with 0.5 mM HDValLeuLyspNA; nt-PA 1.2 nM with 0.8 mM HDIleProArgpNA; and urokinase 0.4 nM with 0.4 mM pyroGluGlyArgpNA; aPC 3 nM with 0.174 mM pyroGluProArgpNA; plasma kallikrein 1.9 nM with D-ProPheArgpNA; bovine trypsin 1.4 nM with 0.18 mM BzPheValArgpNA.

Citations (a) Sall D J, J A Bastian, S L Briggs, J A Buben, N Y Chirgadze, D K Clawson, M L Denny, D D Giera, D S Gifford-Moore, R W Harper, K L Hauser, V J Klimkowski, T J Kohn, H-S Lin, J R McCowan, A D Palkowitz, G F Smith, M E Richett, K Takeuchi, K J Thrasher, J M Tinsley, B G Utterback, S-CB Yan, M Zhang. Dibasic Benzo[b]thiophenes Derivatives as a Novel Class of Active Site Directed Thrombin Inhibitors. 1. Determination of the Serine Protease Selectivity, Structure-Activity Relationships and Binding Orientation. *J Med Chem* 40 3489–3493 (1997).

(b) Smith G F, T J Craft, D S Gifford-Moore, W J Coffman, K D Kurz, E Roberts, R T Shuman, G E Sandusky, N D Jones, N Chirgadze, and C V Jackson. A Family of Arginal Thrombin Inhibitors Related to Efegatran. Sem. Thrombos. Hemost. 22, 173–183 (1996).

(c) Smith G F, D S Gifford-Moore, T J Craft, N Chirgadze, K J Ruterbories, T D Lindstrom, J H Satterwhite. Efegatran: A New Cardiovascular Anticoagulant. In New Anticoagulants for the Cardiovascular Patient. Ed. R Pifarre. Hanley & Belfus, Inc., Philadelphia (1997) pp 265–300.

(d) Sall D J, J A Bastian, N Y Chirgadze, M L Denny, M J Fisher, D S Gifford-Moore, R W Harper, V J Klimkowski, T J Kohn, H S Lin, J R McCowan, M E Richett, GF Smith, K Takeuchi, J E Toth, M Zhang. Diamino Benzo[b]thiophene Derivatives as a Novel Class of Active Site Directed Thrombin Inhibitors: 5. Potency, Efficacy and Pharmacokinetic Properties of Modified C-3 Side Chain Derivatives. In press, *J Med Chem* (1999).

In general, the compounds of formula (I) exemplified herein have been found to exhibit a Ki of 10 µM or less in Assay 1 and/or a Kass of at least 0.1×10⁶ L/mole in Assay 2.

The ability of a test compound to elongate Partial Thromboplastin Time (Prothrombin Time) may be evaluated in the following test protocols.

Partial Thromboplastin Time (Prothrombin) Test Protocol

Venous blood was collected into 3.2% (0.109 m) trisodium citrate vacutainer tubes at 1 volume of anticoagulant to nine volumes of blood. The blood cells were separated by centrifugation at 700 g for ten minutes to yield plasma, which was frozen at 70° C. until required.

To perform the test, 100 µl of plasma was pipetted into in a glass test tube, 1 µl of test compound in DMSO was added, and allowed to warm to 37° over two minutes. 100 µl of warm (37°) Manchester (tissue thromboplasin) reagent (Helena Biosciences, UK) was added, allowed to equilibrate for two minutes. 100 µl of warm (37°) 25 mM calcium chloride solution was added to initiate clotting. The test tube was tilted three times through a 90° angle every five seconds to mix the reagents and the time to clot formation recorded. Data from a series of observations and test compound concentrations are analysed by a SAS statistical analysis program and a CT2 (Concentration required to double clotting time) for each compound is generated.

Compounds of the invention were found to significantly elongate the partial thromboplastin time (Prothrombin time).

| Example No. | Conc. necessary to double the prothrombin time (µM)[a] |
|---|---|
| 8 | 26 |
| 27 | 6.7 |
| 30 | 7.8 |
| 32 | 11 |
| 35 | 8.8 |
| 38 | 9.0 |
| 39 | 12 |
| 40 | 12 |
| 62 | 8.6 |
| 63 | 2.1 |
| 64 | 4.4 |
| 65 | 6.1 |
| 66 | 2.1 |
| | (average of 3 tests) |
| 68 | 3.6 |
| 69 | 5.8 |
| 70 | 4.0 |

[a]The concentration quoted is that of the solution which, when added to the other reagents in the assay, doubles prothrombin time. The final concentration in the assay mixture is one third of this value.

By way of comparison with the result for the compound of Example 66, the compound of Example 75 of WO99/11657 was found to double prothrombin time at a concentration of 11.4 µM (average of 3 tests).

By way of comparison with the result for the compound of Example 35, 1-aminoisoquinolin-7-oyl-D-phenylglycine-4-(4-fluoro-2-methanesulfonylphenyl)-piperazinamide ditrifluoroactetate salt (a compound within the scope of WO99/11657) was found to double prothrombin time at a concentration of 45 µM (average of 3 tests).

Alternative Prothrombin Time and APTT Protocols

Coagulation Determinations. Prothrombin Times and APTT values were determined in HUMAN PLASMA with a STA instrument (Stago). BioPT is a special non-plasma clotting assay triggered with human tissue factor (Innovin). Possible binding to albumen or to lipid was assessed by comparing the BioPT effects in the presence/absence of 30 mg/ml human albumen (HSA) and 1 mg/ml phosphatidyl choline (PC).

Inhibitors were delivered in 50% MeOH vehicle.

APTT ASSAY

75 µl plasma Citrol Baxter-Dade Citrated Normal Human Plasma

25 µl test sol'n

75 µl Agtin Baxter-Dade Activated Cephaloplastin incubate 2 min min. @37°

75 µl CaCl₂ (0.02 M)

PT ASSAY

75 µl plasma

25 µl test sol'n

75 µl saline incubate 1 min. @ 37° C.

75 µl Innovin Baxter-Dade Recombinant Human Tissue Factor

Compounds of the invention were found to be potent inhibitors of factor Xa.

What is claimed is:

1. A compound of formula (I)

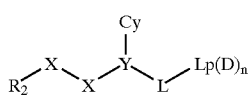

where $R_2$ represents (i) phenyl optionally being substituted in the 3 and/or 4 position by halo, nitro, thiol, haloalkoxy, hydrazido, alkylhydrazido, amino, haloalkyl, alkylthio, alkenyl, alkynyl, acylamino, tri or difluoromethoxy, carboxy, acyloxy, $MeSO_2$— or $R_1$, and optionally substituted at the 6 position by amino, hydroxy, halo, alkyl, carboxy, alkoxycarbonyl, cyano, amido, aminoalkyl, alkoxy or alkylthio; or (ii) naphth-2-yl optionally substituted at the 6 or 7 position by halo, haloalkoxy, haloalkyl, cyano, nitro, amino, hydrazido, alkylthio, alkenyl, alkynyl or $R_{1j}$ and optionally substituted at the 3 position by amino, hydroxy, halo, alkyl, carboxy, cyano, amido, aminoalkyl, alkoxy or alkylthio;

—X—X— is CONH;

$R_{1j}$ represents hydrogen or hydroxyl, alkoxy, alkyl, aminoalkyl, hydroxyalkyl, alkoxyalkyl, alkoxycarbonyl, alkylaminocarbonyl, alkoxycarbonylamino, acyloxymethoxycarbonyl or alkylamino optionally substituted by hydroxy, alkylamino, alkoxy, oxo, aryl or cycloalkyl;

$R_1$ is as defined for $R_{1j}$, provided that $R_1$ is not unsubstituted aminoalkyl;

L is CO;

Y is a CH group;

Cy is a saturated or unsaturated, mono or poly cyclic, homocyclic group optionally substituted by groups $R_{3a}$ or phenyl optionally substituted by $R_{3a}$;

each $R_{3a}$ independently is $R_{1c}$, amino, halo, cyano, nitro, thiol, alkylthio, alkylsulphonyl, alkylsulphenyl, triazolyl, imidazolyl, tetrazolyl, hydrazido, alkyl iymidazolyl, thiazolyl, alkyl thiazolyl, alkyl oxazolyl, oxazolyl, alkylsulphonamido, alkylaminosulphonyl, aminosulphonyl, haloalkoxy and haloalkyl;

$Lp(D)_n$ is a lipophilic organic group selected from

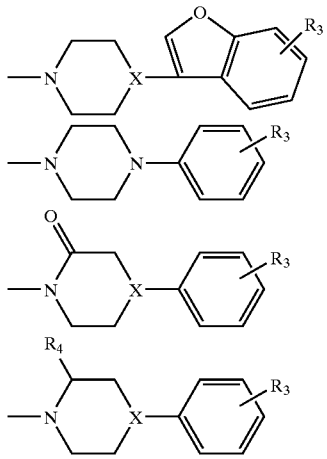

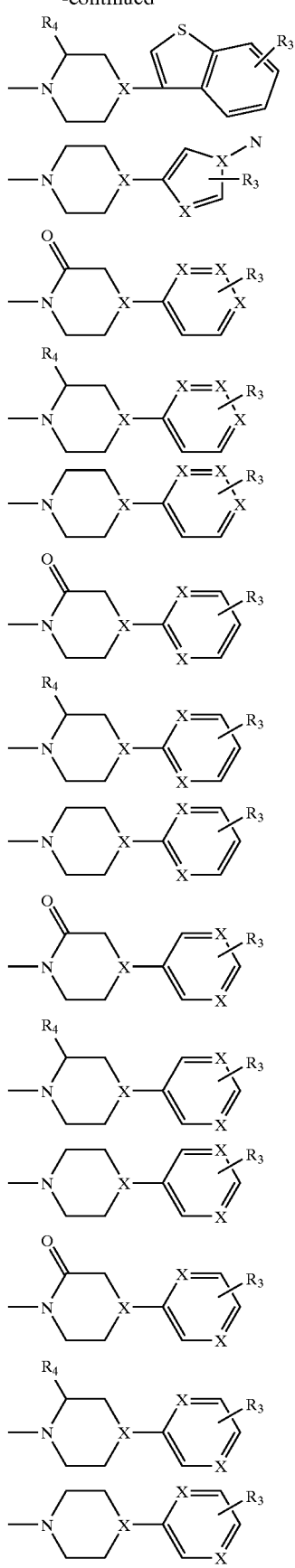

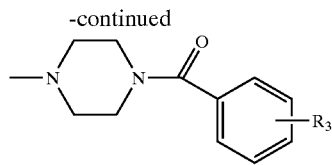

wherein $R_3$ is as defined for $R_{3a}$;
$R_4$ represents hydrogen, $(CH_2)_wCOOH$ or $(CH_2)_wCONH_2$;
w represents an integer from 0 to 4; and
when X is in the ring bonded to L, X is N and, otherwise X represents CH or N; and
$R_{1c}$ is as defined for $R_{1j}$, or a physioloqically tolerable salt thereof.

2. A compound as claimed in claim 1, in which Y has the conformation that would result from construction from a D-α-aminoacid $NH_2$—CH(Cy)-COOH where the $NH_2$ represents part of X—X.

3. A compound as claimed in claim 1, in which Cy represents an optionally $R_{3a}$ substituted phenyl, naphthyl or cycloalkyl group.

4. A compound as claimed in claim 3, in which $R_{3a}$ is selected from hydrogen, hydroxyl, methoxy, ethoxy, methyl, ethyl, methylaminomethyl, dimethylaminomethyl, hydroxymethyl, carboxy, methoxymethyl, methoxycarbonyl, ethoxycarbonyl, methylaminocarbonyl, dimethylinino-carbonyl, aminomethyl, $CONH_2$, $CH_2CONH_2$, acetylamino, methoxycarbonylamino, ethoxycarbonylamino, t-butoxycarbonylamino, amino, fluoro, chloro, cyano, nitro, thiol, methylthio, methylsulphonyl, ethylsulphonyl, methylsulphenyl, methylsulphonylamido, ethylsulphonylamido, methylaminosulphonyl, ethylaminosulphonyl, aminosulphonyl, trifluoromethoxy and trifluoromethyl.

5. A compound as claimed in claim 1, in which Cy is phenyl, 4-aminophenyl, 4-amidophenyl, 4-(N-methyl)amidophenyl, 4-(N,N-dimethyl)amidophenyl, 2-chlorophenyl, 2-methylphenyl, 2-fluorophenyl, 3-fluorophenyl, 4-fluorophenyl, 4-hydroxphenyl, 2-methoxyphenyl, 4-methoxyphenyl, 4-carboxyphenyl, 3-ethylsulphonylaminophenyl, cyclohexyl or naphth-1-yl.

6. A compound as claimed in claim 1, in which $R_3$ is selected from hydrogen, hydroxyl, methoxy, ethoxy, methyl, ethyl, propyl, 2-propyl, butyl, 2-butyl, t-butyl, pentyl, 2-pentyl or 3-pentyl, isopropylaminomethyl, dimethylaminomethyl, diethylaminomethyl, dimethylaminoethyl, acetyl, hydroxymethyl, hydroxyethyl, carboxy, methoxymethyl, methoxycarbonyl, ethoxycarbonyl, methylaminocarbonyl, dimethylaminocarbonyl, aminomethyl, aminocarbonyl, methylamino, dimethylamino, ethylamino, formylamino, acetylamino, amino, fluoro, chloro, cyano, nitro, thiol, methylthio, methylsulphonyl, ethylsulphonyl, isopropylsulphonyl, methylsulphenyl, 1,2,4-triazol-2-yl, 1,2,4-triazol-4-yl, 1,2,3-triazol-4-yl, 1,3-imidazol-1-yl or 1,3-imidazol-4-yl, tetrazol-1-yl, tetrazol-5-yl;
methylsulphonamido, ethylsulphonamido, propylsulphonamido, methyl aminosulphonyl, ethylaminosulphonyl, propylaminosulphonyl, aminosulphonyl, trifluoromethoxy, trifluoromethyl and trichloromethyl.

7. A compound as claimed in claim 1, in which $Lp(D)_n$ is selected from

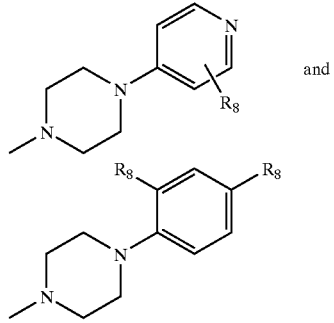

where $R_8$ represents H, OMe, $SO_2Me$, F, cyano, amido, amino, $NO_2$, Cl or OH.

8. A compound as claimed in claim 1, in which $Lp(D)_n$ represents

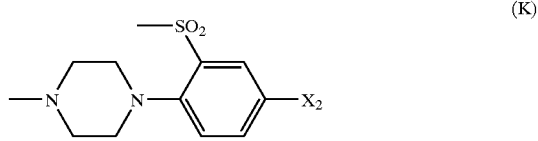

(K)

wherein $x_2$ ids halo, hydrogen, amino, nitro or $CONH_2$.

9. A compound as claimed in claim 1, in which $R_2$ represents:

(i) phenyl optionally being substituted in the 3 and/or 4 position by fluoro, chloro, bromo, iodo, nitro, difluoromethoxy, trifluoromethoxy, amino, trifluoromethyl, methylthio, vinyl, carboxy, acetoxy, $MeSO_2$—, hydroxy, methoxy, ethoxy, methyl, methoxycarbonyl, methylamino, ethylamino or amido, and optionally substituted at the 6 position by amino, hydroxy, fluoro, methoxycarbonyl, cyano or aminomethyl; or (ii) naphth-2-yl optionally substituted at the 6, position by hydroxy and optionally substituted at the 3 position by amino or hydroxy.

10. A pharmaceutical composition, which comprises a compound as claimed in claim 1 together with at least one pharmaceutically acceptable carrier or excipient.

11. A compound as claimed in claim 9, in which $R_2$ represents phenyl substituted in the 4 position by chloro, amino, vinyl, methylamino, methyl or methoxy, optionally at the 3 position with amino or hydroxy, and optionally at the 6 position with amino or hydroxy.

12. A compound as claimed in claim 1, which is selected from:
1-(3-Amino-4-chlorobenzoyl-D-phenylglycinyl)-4-(4-fluoro-2-methylsulphonylphenyl)piperazine;
1-(3-Amino-4-chlorobenzoyl-D-phenylglycinyl)-4-(2-methylsulphonylphenyl)piperazine;
and physiologically tolerable salts thereof.

13. A pharmaceutical composition, which comprises a compound as claimed in claim 12 together with at least one pharmaceutically acceptable carrier or excipient.

* * * * *